(12) United States Patent
Yao et al.

(10) Patent No.: US 11,021,457 B2
(45) Date of Patent: Jun. 1, 2021

(54) CLASS OF ISOINDOLONE-IMIDE RING-1,3-DIONE-2-ENE COMPOUNDS, COMPOSITION AND USE THEREOF

(71) Applicant: WIGEN BIOMEDICINE TECHNOLOGY (SHANGHAI) CO., LTD., Shanghai (CN)

(72) Inventors: Zhiyi Yao, Shanghai (CN); Cheng Luo, Shanghai (CN); Yuli Xie, Shanghai (CN); Liyan Yue, Shanghai (CN); Wei Wan, Shanghai (CN); Yuanyuan Zhang, Shanghai (CN); Hualiang Jiang, Shanghai (CN); Kaixian Chen, Shanghai (CN)

(73) Assignee: WIGEN BIOMEDICINE TECHNOLOGY (SHANGHAI) CO., LTD., Shanghai (CN)

( * ) Notice: Subject to any disclaimer, the term of this patent is extended or adjusted under 35 U.S.C. 154(b) by 45 days.

(21) Appl. No.: 16/614,493

(22) PCT Filed: May 17, 2018

(86) PCT No.: PCT/CN2018/087241
§ 371 (c)(1),
(2) Date: Nov. 18, 2019

(87) PCT Pub. No.: WO2018/214796
PCT Pub. Date: Nov. 29, 2018

(65) Prior Publication Data
US 2020/0071291 A1  Mar. 5, 2020

(30) Foreign Application Priority Data
May 22, 2017  (CN) .......................... 201710365494.7

(51) Int. Cl.
| | | |
|---|---|---|
| *C07D 401/04* | (2006.01) | |
| *C07D 401/14* | (2006.01) | |
| *C07D 409/14* | (2006.01) | |
| *C07D 417/14* | (2006.01) | |
| *C07D 495/04* | (2006.01) | |

(52) U.S. Cl.
CPC ......... *C07D 401/04* (2013.01); *C07D 401/14* (2013.01); *C07D 409/14* (2013.01); *C07D 417/14* (2013.01); *C07D 495/04* (2013.01)

(58) Field of Classification Search
CPC .. C07D 401/04; C07D 401/14; C07D 409/14; C07D 417/14; C07D 495/04
See application file for complete search history.

(56) References Cited

FOREIGN PATENT DOCUMENTS

| | | |
|---|---|---|
| CN | 102822165 A | 12/2012 |
| CN | 103396397 A | 11/2013 |
| CN | 105566290 A | 5/2016 |

*Primary Examiner* — John Mabry
(74) *Attorney, Agent, or Firm* — SZDC Law P.C.

(57) ABSTRACT

The present invention provides an isoindolone-imide ring-1,3-dione-2-ene compound, and a preparation method, a pharmaceutical composition and use thereof. Specifically, the present invention provides a compound of Formula (I) below or a pharmaceutically acceptable salt thereof, wherein Ar is an isoindolinone-imide group represented by Formula (II), L is absent or is a divalent, trivalent or tetravalent linking group, and X is a group represented by Formula (III). Definitions of the other groups are as described in the specification. The compound of Formula (I) is an autophagy modulators, particularly a mammalian ATG8 homolog modulator.

Ar—L(—X)p   (I)

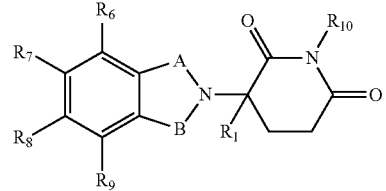

(II)

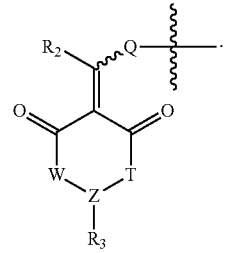

(III)

9 Claims, 2 Drawing Sheets
Specification includes a Sequence Listing.

SEQUENCE LISTING

<160> NUMBER OF SEQ ID NOS: 2

<210> SEQ ID NO 1
<211> LENGTH: 356
<212> TYPE: PRT
<213> ORGANISM: Artificial Sequence
<220> FEATURE:
<223> OTHER INFORMATION: GST-LC3B

<400> SEQUENCE: 1

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Met Pro Ser Glu Lys Thr Phe Lys Gln
225                 230                 235                 240
```

```
Arg Arg Thr Phe Glu Gln Arg Val Glu Asp Val Arg Leu Ile Arg Glu
            245                 250                 255

Gln His Pro Thr Lys Ile Pro Val Ile Ile Glu Arg Tyr Lys Gly Glu
            260                 265                 270

Lys Gln Leu Pro Val Leu Asp Lys Thr Lys Phe Leu Val Pro Asp His
        275                 280                 285

Val Asn Met Ser Glu Leu Ile Lys Ile Ile Arg Arg Arg Leu Gln Leu
        290                 295                 300

Asn Ala Asn Gln Ala Phe Phe Leu Leu Val Asn Gly His Ser Met Val
305                 310                 315                 320

Ser Val Ser Thr Pro Ile Ser Glu Val Tyr Glu Ser Glu Lys Asp Glu
            325                 330                 335

Asp Gly Phe Leu Tyr Met Val Tyr Ala Ser Gln Glu Thr Phe Gly Met
            340                 345                 350

Lys Leu Ser Val
        355

<210> SEQ ID NO 2
<211> LENGTH: 15
<212> TYPE: PRT
<213> ORGANISM: Artificial Sequence
<220> FEATURE:
<223> OTHER INFORMATION: N-terminal FITC-labeled peptide

<400> SEQUENCE: 2

Gly Gly Asp Asp Asp Trp Thr His Leu Ser Ser Lys Glu Val Asp
1               5                   10                  15
```

CLASS OF ISOINDOLONE-IMIDE RING-1,3-DIONE-2-ENE COMPOUNDS, COMPOSITION AND USE THEREOF

This application is the National Stage Application of PCT/CN2018/087241, filed on May 17, 2018, which claims priority to Chinese Patent Application No.: 2017-10365494.7, filed on May 22, 2017, which is incorporated by reference for all purposes as if fully set forth herein.

FIELD OF THE INVENTION

The present invention relates to the field of biomedicine, and in particular to an autophagy modulator, particularly a mammalian ATG8 homolog modulator, and a preparation method, a pharmaceutical composition and use thereof.

DESCRIPTION OF THE RELATED ART

Autophagy is a cellular degradative pathway whereby dysfunctional proteins or organelles are transported to lysosome and then digested and degraded. It is a universal and conservative process amongst yeast, plants and mammals.

Current studies demonstrate that autophagy plays an important role in maintaining physiological functions, such as providing nutrients during hunger, eliminating cell contents, antigen presentation.

The diseases associated with autophagy include liver cancer, lung cancer, pancreatic cancer, breast cancer, cervical cancer, endometrial cancer, colorectal cancer, gastric cancer, lung cancer, nasopharyngeal carcinoma, ovarian cancer, prostate cancer, leukemia, lymphoma, myeloma, and the other relevant diseases include cardiovascular diseases, autoimmune diseases, neurodegenerative diseases, hypertension, bone tissue cell and bone diseases, Crohn's disease, acute kidney injury, cerebral ischemia, retinal disease, bronchial asthma, Vici syndrome, amyotrophic lateral sclerosis and various infectious diseases.

Currently, there are about 30 clinical trials about autophagy regulation, for example, using hydroxychloroquine alone, chloroquine alone or combined with other anti-tumor drugs to assess the therapeutic effects of autophagy inhibition mainly on refractory or relapsed solid tumors. Relevant results can be retrieved on the clinicaltrial.gov website. However, the side effects of antilysosomal agents and undetermined directions of chemical space optimization may severely limit further development of these types of autophagy inhibitors, because of a lack of definite molecular targets. There is an urgent need to develop a new modulator which directly acts on important proteins on autophagy pathway for treating related diseases, particularly the development prospect of the modulator of mammalian ATG8 homologous proteins targeting LC3B is promising.

Lenalidomide, as an immunomodulator, has been approved for use in multiple myeloma, myelodysplastic syndrome and mantle cell lymphoma. Indications for clinical studies also include non-Hodgkin's lymphoma, large B lymphoma, follicular lymphoma, T-cell lymphoma, mucosa-associated lymphoid tumors, plasma cell myeloma, chronic lymphocytic leukemia (CLL), acute myelogenous leukemia (AML), non-small cell lung cancer, liver cancer, renal cancer, ovarian cancer, squamous cell carcinoma, spongioblastoma, thyroid tumor, POEMS syndrome, neurofibomatosis-1, prostatic cancer, carcinoma of urinary bladder, systemic lupus erythematosus, anemia, HIV-1 infection, autism, primary cutaneous amyloidosis, Crohn's disease, and pain syndrome-1 and the like.

Since the indications for autophagy regulators and the indications for lenalidomide cover a wide range, and are overlapped considerably, the development of a small molecule inhibitor having the activity of lenalidomide and its analogues and the activity of autophagy-related proteins, such as mammalian ATG8 homologous family proteins, may have a wide range of application and promising prospect.

SUMMARY OF THE INVENTION

The present invention provides an autophagy modulator, particularly a mammalian ATG8 homolog modulator, and a preparation method, a pharmaceutical composition and use thereof.

In an aspect, the present invention provides a compound of General Formula (I) below or a pharmaceutically acceptable salt thereof:

where p is 1, 2 or 3;

Ar is an isoindolinone-imide group represented by Formula (II):

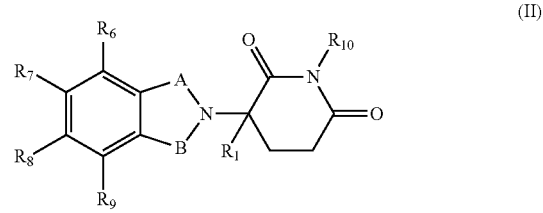

wherein one of A and B is C=O, and the other is C=O or $CH_2$;

$R_1$ is selected from hydrogen, deuterium, halo, and C1-C4 alkyl;

one of $R_6$, $R_7$, $R_8$ and $R_9$ is a divalent group selected from O, S, $SO_2$, and NH, which is attached to L or directly to X, and the remaining three of $R_6$, $R_7$, $R_8$ and $R_9$ are each independently selected from the group consisting of hydrogen, deuterium, halo, C1-C4 alkyl, unsubstituted or substituted phenyl, and unsubstituted or substituted 5-10 membered heteroaryl; and $R_{10}$ is hydrogen; or $R_6$, $R_7$, $R_8$ and $R_9$ are each independently selected from the group consisting of hydrogen, deuterium, halo, C1-C4 alkyl, unsubstituted or substituted phenyl, unsubstituted or substituted 5-10 membered heteroaryl, and $NR_{b1}R_{b'}$, in which $R_{b1}$ and $R_{b'}$ are each independently selected from the group consisting of hydrogen, C1-C4 alkyl, unsubstituted or substituted phenyl, and unsubstituted or substituted 5-10 membered heteroaryl; and $R_{10}$ is absent, and the nitrogen attached to $R_{10}$ is directly attached to L or X;

L is absent, or is a divalent, trivalent or tetravalent linking group, where when L is absent or is a divalent linking group, p is 1; when L is a trivalent linking group, p is 2; when L is a tetravalent linking group, p is 3; and when p is 2 or 3, the 2 or 3 Xs linked to L are the same or different; and X is a group represented by General Formula (III):

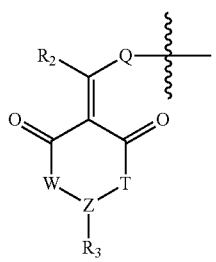

(III)

wherein

R$_2$ is selected from hydrogen, deuterium, halo, C1-C6 alkyl, unsubstituted or substituted phenyl, and unsubstituted or substituted 5-10 membered heteroaryl;

W and T are each independently absent, —C(R$_{a1}$)(R$_{a1'}$)—, —C(R$_{a1}$)(R$_{a1'}$) C(R$_{a2}$)(R$_{a2'}$))—, —O—, —S— or —NR$_{a3}$—, where R$_{a1}$, R$_{a1'}$, R$_{a2}$, R$_{a2'}$ and R$_{a3}$ are each independently selected from the group consisting of hydrogen, deuterium, hydroxyl, amino, halo, CN, CO$_2$R$_{a4'}$, CONR$_{a5}$R$_{a5'}$, C1-C6 alkyl, C1-C10 heteroalkyl, C2-C4 alkenyl, C2-C4 alkynyl, unsubstituted or substituted —CONH—(C6-C10) aryl, unsubstituted or substituted —CH=CH—(C6-C10) aryl, unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-C10 aryl-C1-C6 alkyl, unsubstituted or substituted C1-C6 alkyl-C6-C10 aryl, unsubstituted or substituted 5-10 membered heteroaryl-C1-C6 alkyl or unsubstituted or substituted C1-C6 alkyl-5-10 membered heteroaryl;

Z is selected from N, O or CR$_d$, in which R$_d$ is hydrogen, deuterium, halo, C1-C4 alkyl or C6-C12 aryl; and when Z is O, R$_3$ is absent;

R$_3$ is selected from the group consisting of hydrogen, deuterium, hydroxyl, amino, halo, CN, CO$_2$R$_{e1'}$, CONR$_{e2}$R$_{e2'}$, C1-C6 alkyl, C1-C10 heteroalkyl, C2-C4 alkenyl, C2-C4 alkynyl, —O(C6-C10) aryl, unsubstituted or substituted —S(C6-C10) aryl, unsubstituted or substituted —NH(C6-C10) aryl, unsubstituted or substituted —NHC(=O)(C6-C10) aryl, unsubstituted or substituted —CONH—(C6-C10) aryl, unsubstituted or substituted —CH=CH—(C6-C10) aryl, unsubstituted or substituted C6-10 aryl, unsubstituted or substituted 5-10 membered heteroaryl, unsubstituted or substituted C3-C10 cycloalkyl, unsubstituted or substituted 3-10 membered heterocycloalkyl, unsubstituted or substituted 3-7 membered heterocycloalkenyl, unsubstituted or substituted C6-C10 aryl-C1-6 alkyl, unsubstituted or substituted C1-6 alkyl-C6-C10 aryl, unsubstituted or substituted 5-10 membered heteroaryl-C1-C6 alkyl or unsubstituted or substituted C1-C6 alkyl-5-10 membered heteroaryl; and R$_3$ may form, together with the adjacent W and T, unsubstituted or substituted C6-C10 aryl, unsubstituted or substituted 5-10 membered heteroaryl, 5-10 membered cycloalkyl or 5-10 membered heterocycloalkyl, where R$_{e1}$, R$_{e1'}$ and R$_{e2'}$ are each independently hydrogen, hydroxyl, and C1-C6 alkyl; and Q is absent, O, N(R$_f$), S or SO$_2$, where R$_f$ is selected from hydrogen or C1-C4 alkyl, where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl and C1-C6 hydroxyalkyl; and

represents me point or attachment.

In a specific embodiment, in General Formula (I), Ar is a group represented by General Formula (IIa):

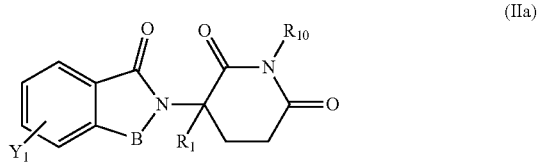

(IIa)

where

B is C=O or CH$_2$;

R$_1$ is selected from hydrogen, deuterium, halo, and C1-C4 alkyl;

R$_{10}$ is H, and Y$_1$ is NH or O, and is attached to L or directly to X; or

R$_{10}$ is absent, and the N attached to R$_{10}$ is directly attached to L or X; and Y$_1$ is H, NH$_2$ or halo; or Ar is selected from the groups of:

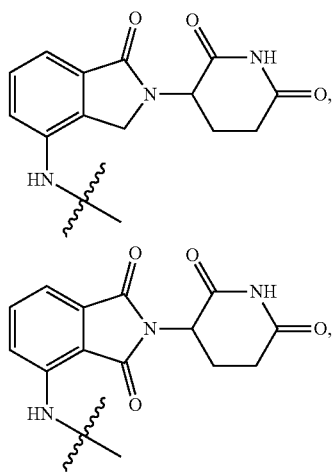

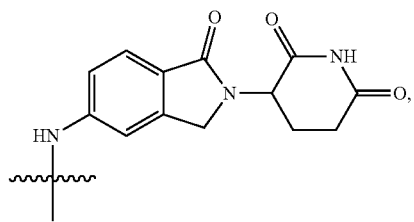

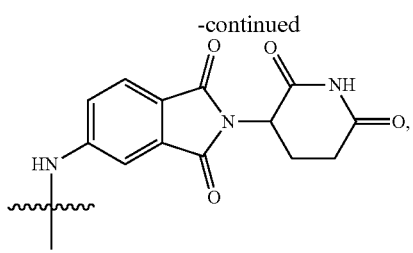

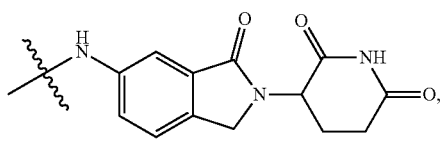

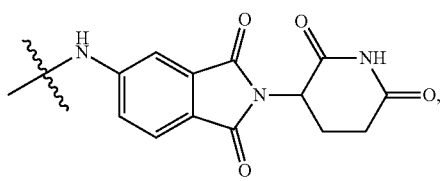

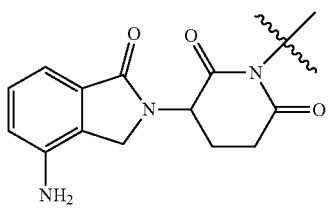

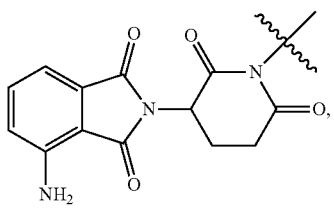

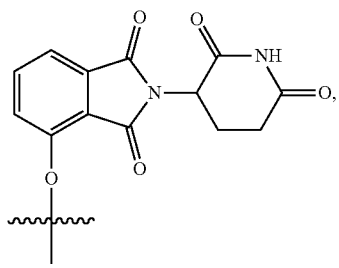

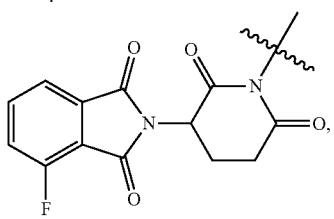

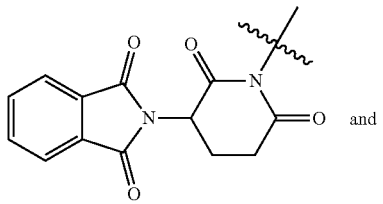

and

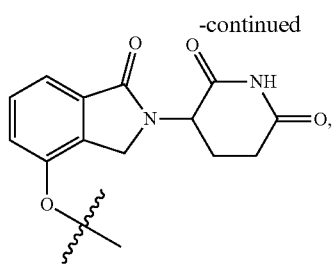

wherein

represents the point of attachment.

In another specific embodiment, in General Formula (I), X is selected from the groups represented by General Formulas (IIIa) and (IIIb):

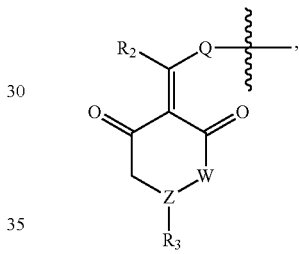

(IIIa)

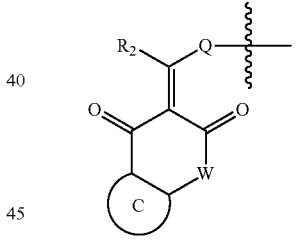

(IIIb)

wherein $R_2$ is selected from hydrogen, deuterium, halo, C1-C4 alkyl, and unsubstituted or substituted phenyl;

Q is absent, or selected from NH, or O;

W is selected from $CR_{g1}R_{g1'}$, O, and $NR_{g2}$, in which $R_{g1}$, $R_{g1'}$ and $R_{g2}$ are each independently hydrogen, C1-C6 alkyl, $CO_2R_{g3}$ or $CONR_{g4}R_{g4'}$; where $R_{g3}$, $R_{g4}$ and $R_{g4'}$ are each independently hydrogen or C1-C6 alkyl;

$R_3$ is selected from the group consisting of unsubstituted or substituted —CONH—(C6-C10) aryl, —CO$_2$—(C6-C10) aryl, unsubstituted or substituted —CH═CH—(C6-C10) aryl, unsubstituted or substituted C6-C10 aryl, unsubstituted or substituted 5-10 membered heteroaryl, unsubstituted or substituted C3-C10 cycloalkyl, unsubstituted or substituted 3-10 membered heterocycloalkyl, unsubstituted or substituted 3-7 membered heterocycloalkenyl, unsubstituted or substituted C1-C6 alkyl-C6-C10 aryl, unsubstituted or substituted —O(C6-C10) aryl, unsubstituted or substituted —S(C6-C10) aryl, unsubstituted or substituted —NH(C6-C10) aryl, unsubstituted or substituted —NHC(=O)(C6-C10) aryl, or unsubstituted or substituted C1-C6 alkyl-5-10 membered heteroaryl;

Z is selected from $CR_{e3}$ and N, in which $R_{e3}$ is selected from hydrogen, C1-C6 alkyl, C1-C10 heteroalkyl, C2-C4 alkenyl, C2-C4 alkynyl, and unsubstituted or substituted C6-C10 aryl; and the ring C is unsubstituted or substituted C6-C10 aryl, or unsubstituted or substituted 5-10 membered heteroaryl;

where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl, and C1-C6 hydroxyl alkyl, and

represents the point of attachment.

In another specific embodiment, in General Formula (I), $R_3$ is selected from the following groups:

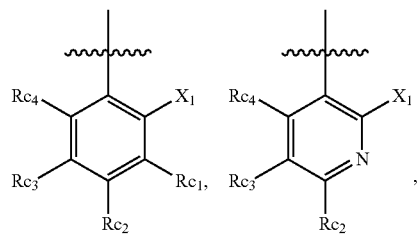

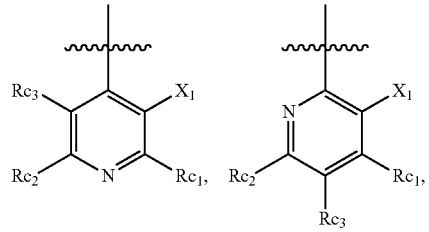

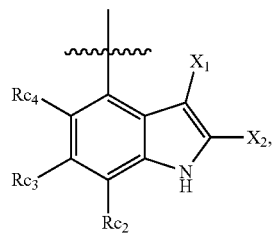

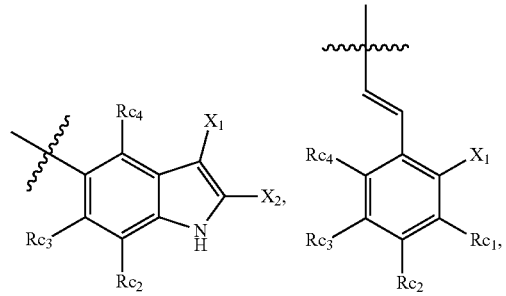

-continued

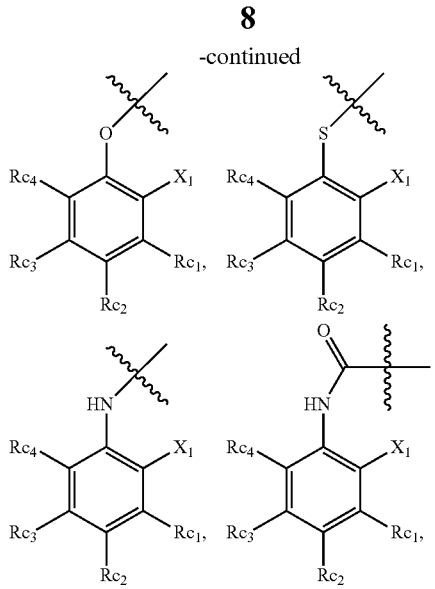

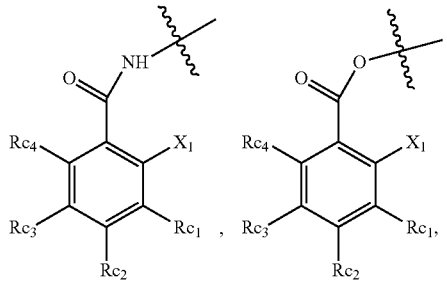

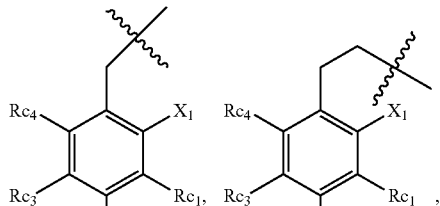

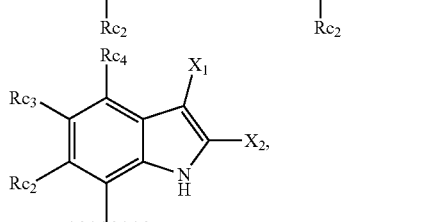

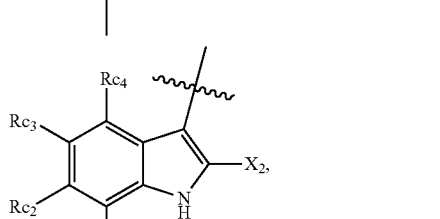

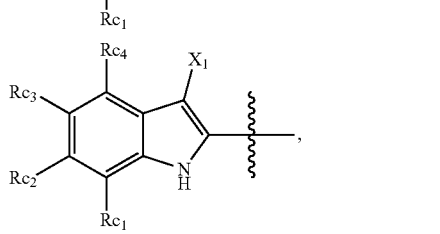

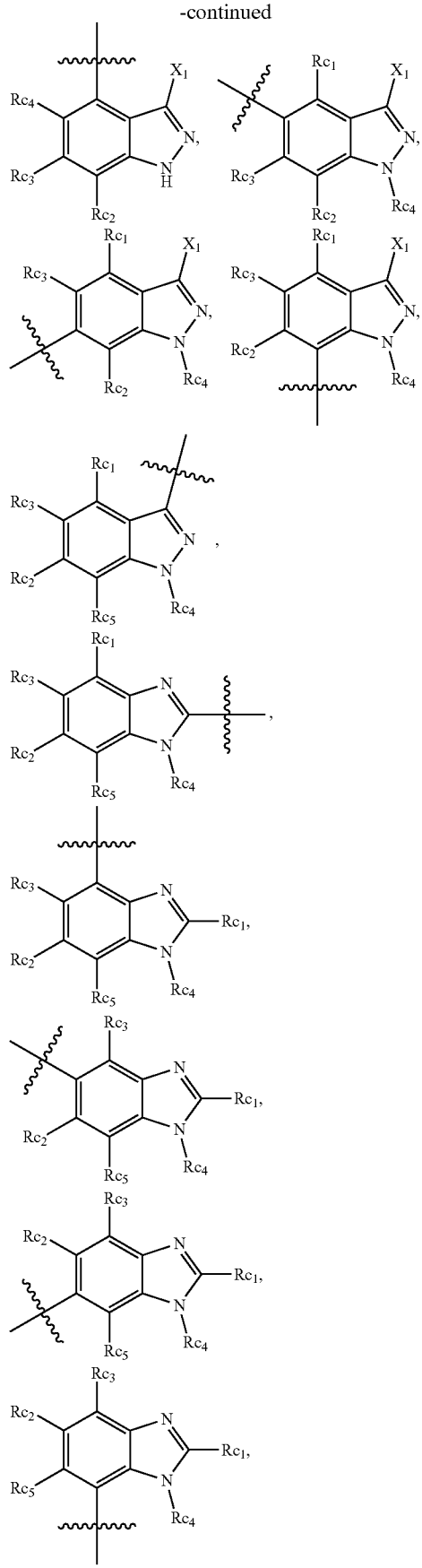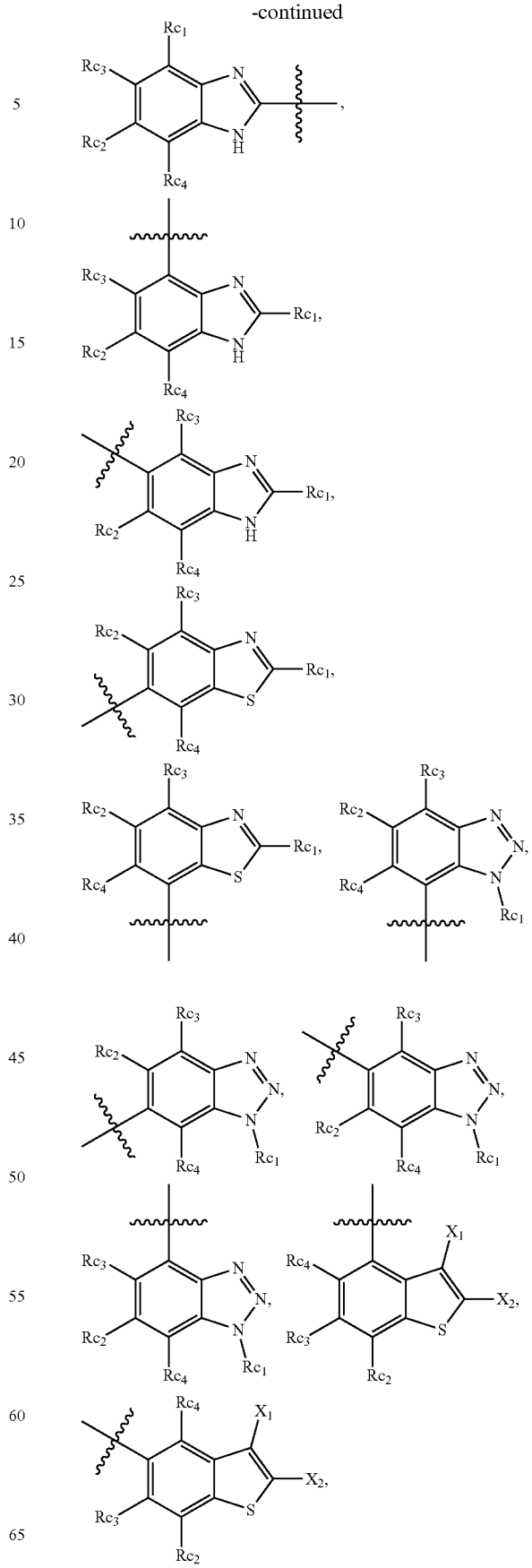

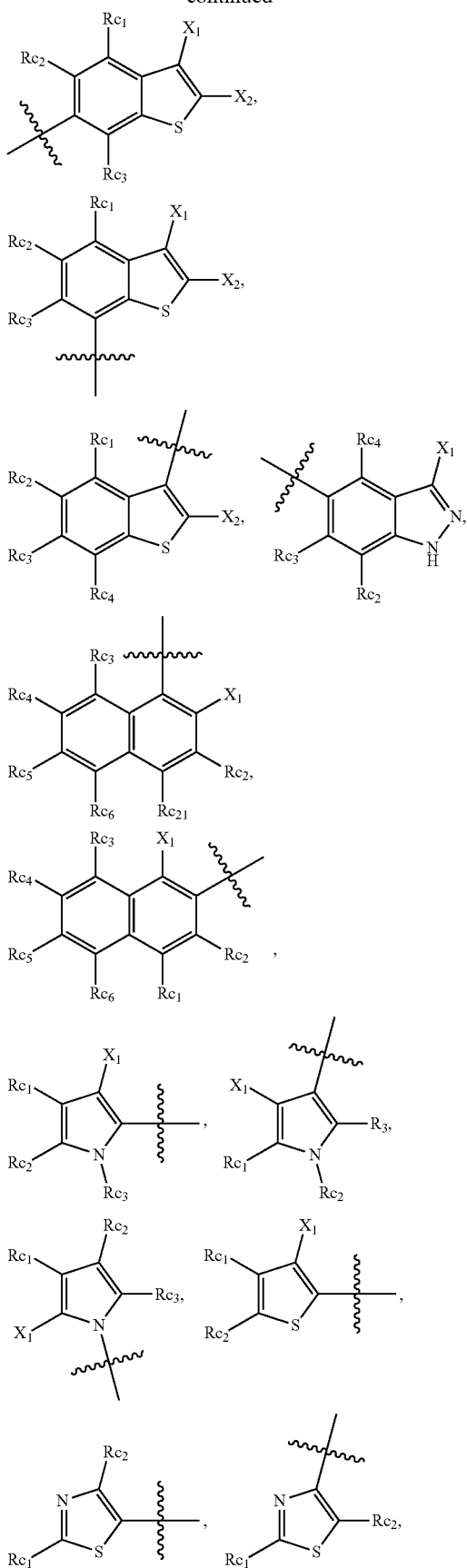
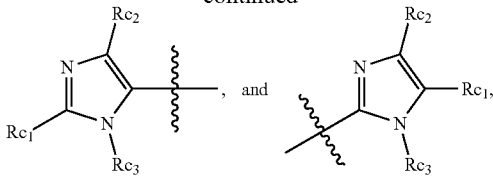

wherein $X_1$ is hydrogen, halo or $CF_3$;

$X_2$ is hydrogen, halo or $CF_3$;

$R_{c1}$, $R_{c2}$, $R_{c3}$, $R_{c4}$, $R_{c5}$ and $R_{c6}$ are each independently selected from the group consisting of hydrogen, deuterium, hydroxyl, halo, cyano, nitro, formyl, $CO_2R_h$, $CONR_{h1}R_{h1'}$, $NR_{h2}R_{h2'}$, C1-C4 alkyl, C1-C10 heteroalkyl, C2-C4 alkenyl, C2-C4 alkynyl, unsubstituted or substituted C6-C10 aryl, unsubstituted or substituted 5-10 membered heteroaryl, unsubstituted or substituted C3-C10 cycloalkyl, unsubstituted or substituted 3-10 membered heterocycloalkyl, unsubstituted or substituted 3-7 membered heterocycloalkenyl, unsubstituted or substituted C6-C10 aryl-C1-6 alkyl, unsubstituted or substituted C1-6 alkyl-C6-C10 aryl, unsubstituted or substituted 5-10 membered heteroaryl-C1-C6 alkyl, and unsubstituted or substituted C1-C6 alkyl-5-10 membered heteroaryl, in which $R_h$, $R_{h1}$, $R_{h1'}$, $R_{h2}$ and $R_{h2'}$ are each independently selected from hydrogen and C1-C4 alkyl; or $R_{c1}$ and $R_{c2}$, or $R_{c2}$ and $R_{c3}$, or $R_{c3}$ and $R_{c4}$, or $R_{c5}$ and $R_{c6}$ form, together with the ring atoms in the ring to which they are attached, unsubstituted or substituted C6-10 aryl, or unsubstituted or substituted 5-10 membered heteroaryl, where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl and C1-C6 hydroxyl alkyl; or $R_3$ is selected from the groups of:

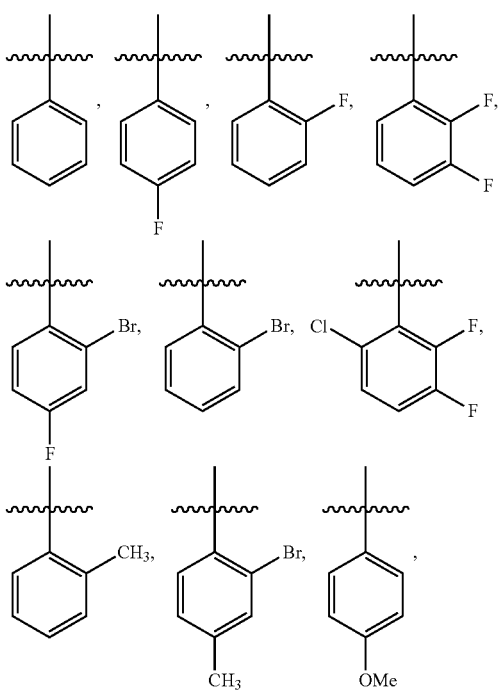

-continued
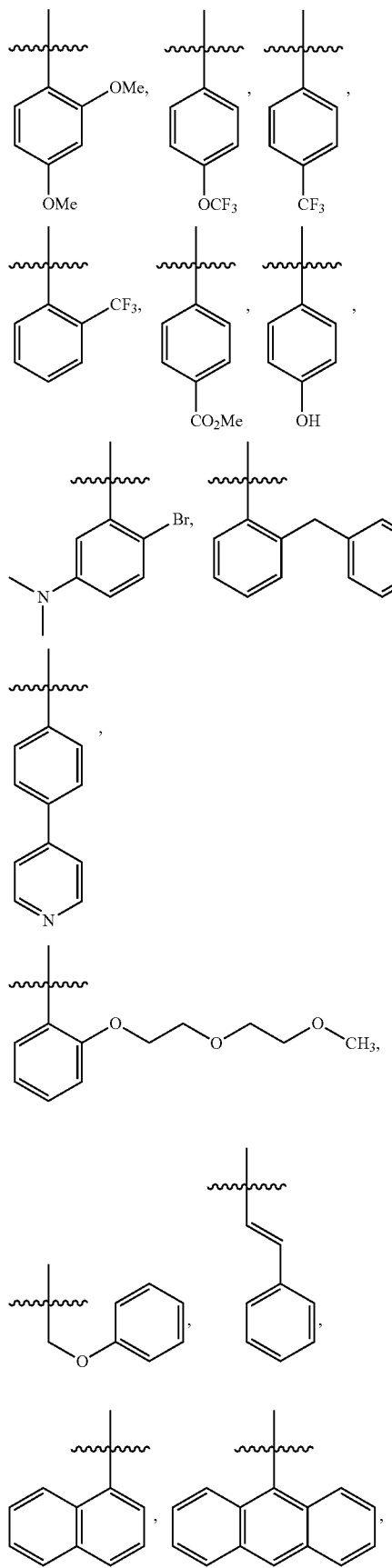
-continued
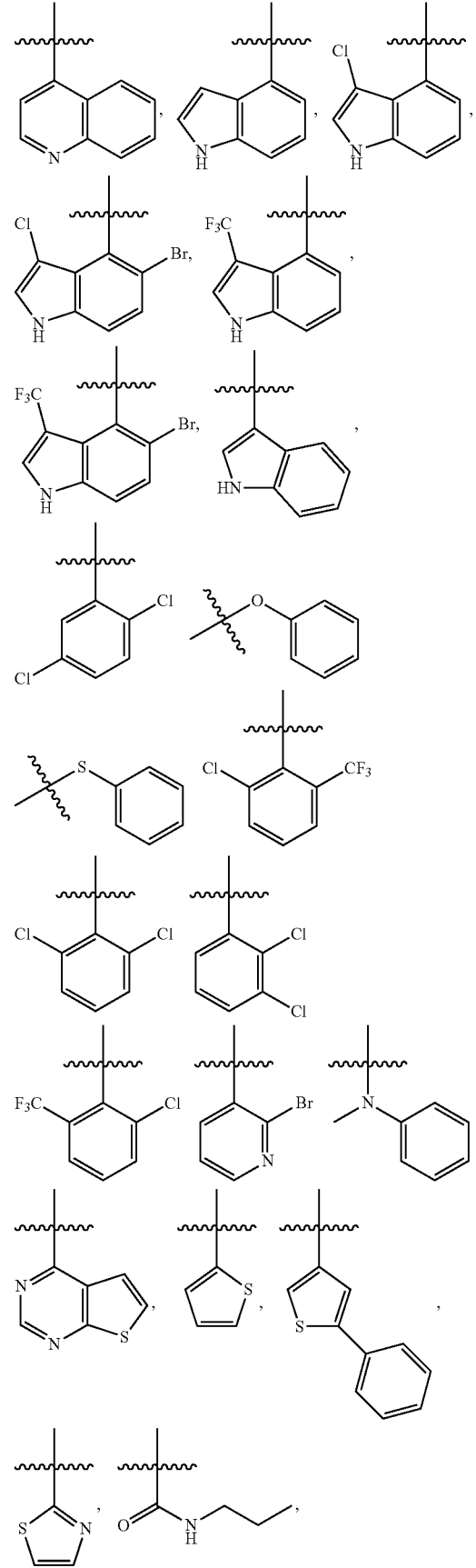

-continued
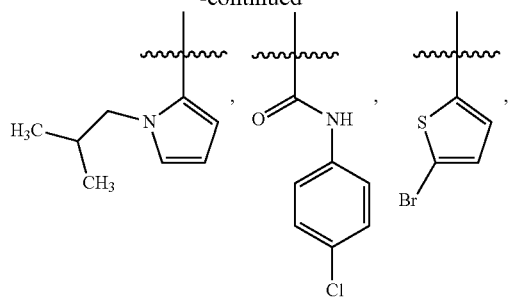
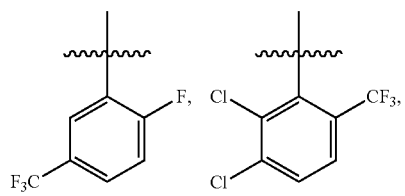
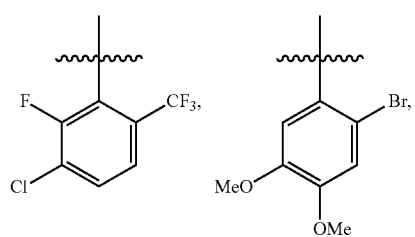
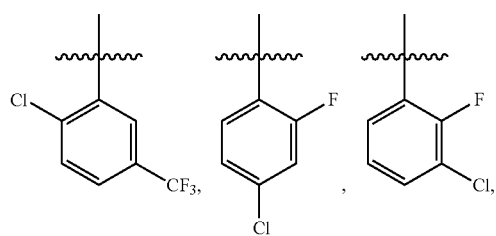
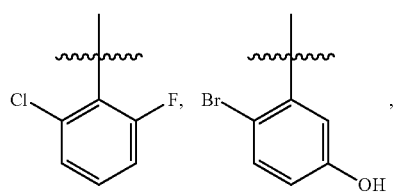
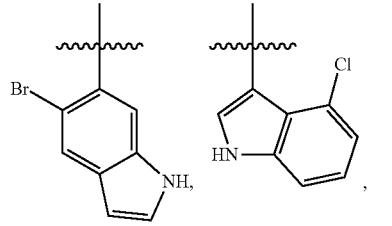
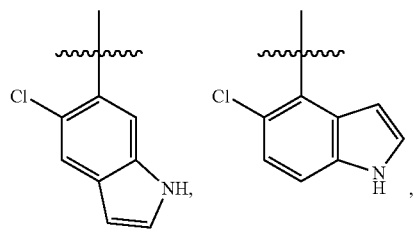
-continued
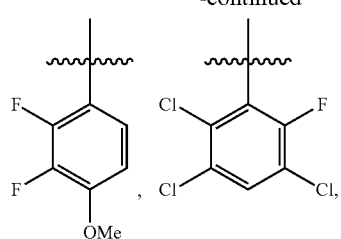
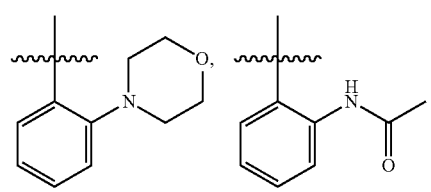
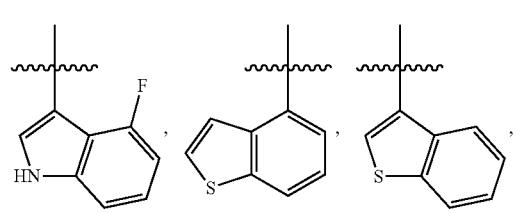
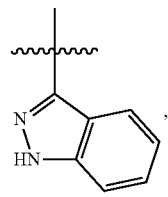
and H,
wherein
represents the point of attachment.
In another specific embodiment, in General Formula (I), X is selected from the groups of:
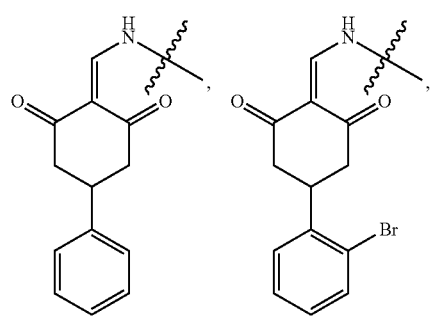

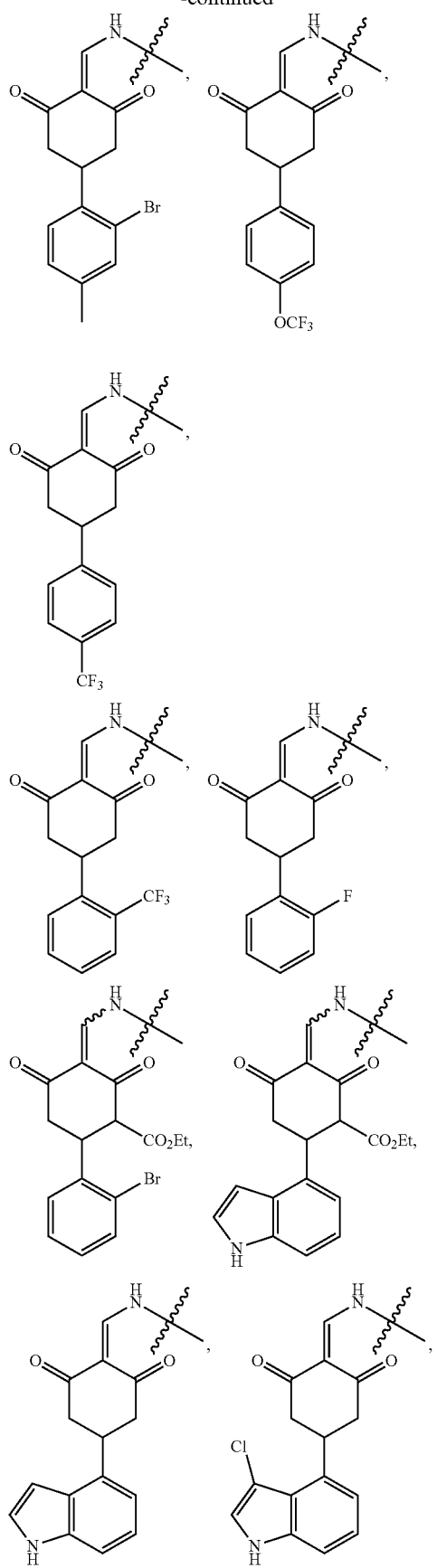
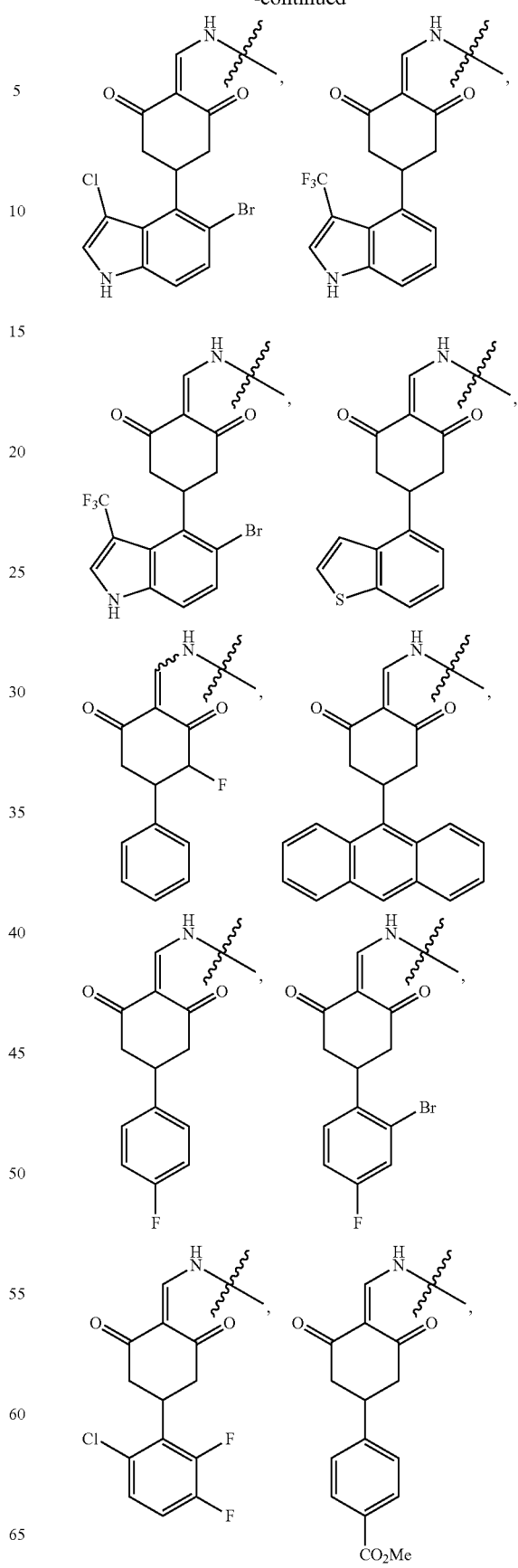

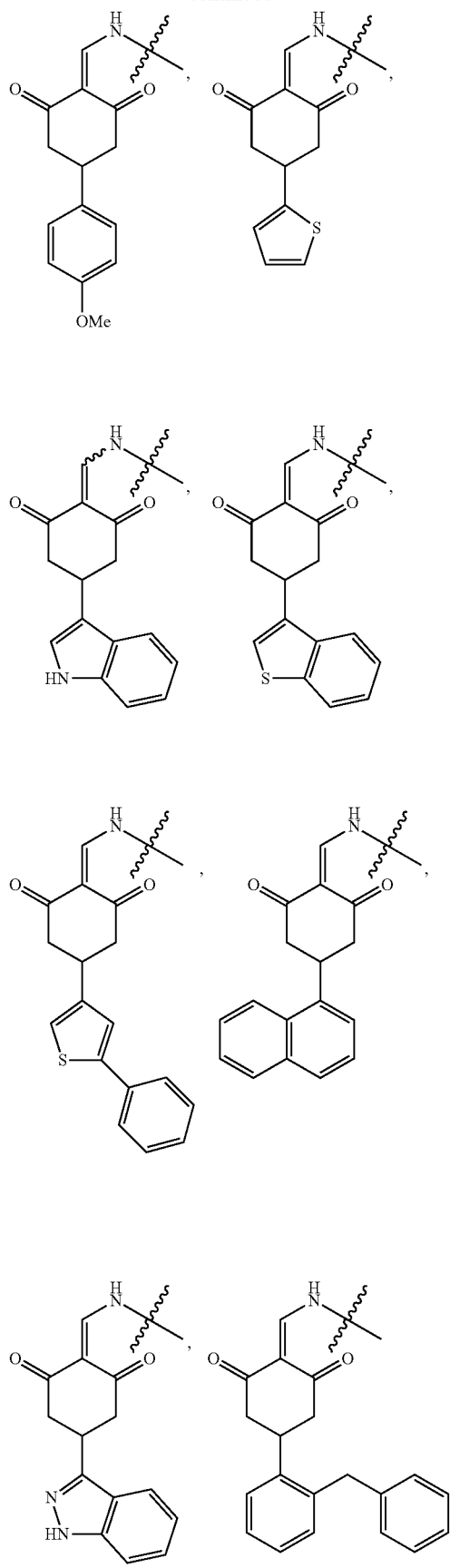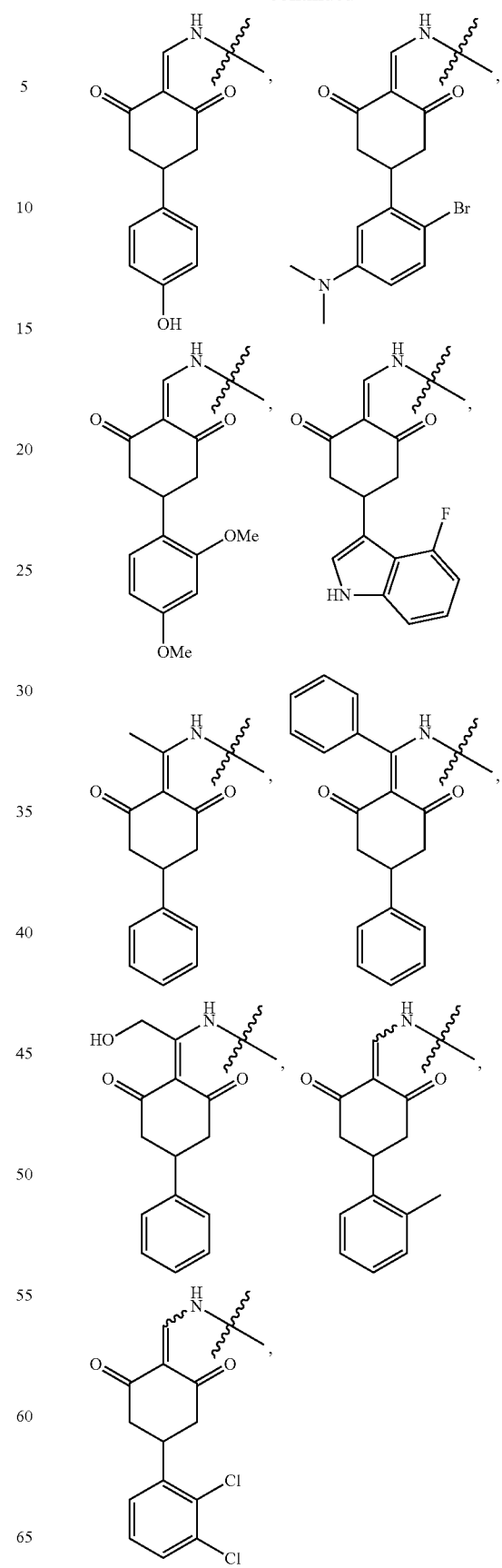

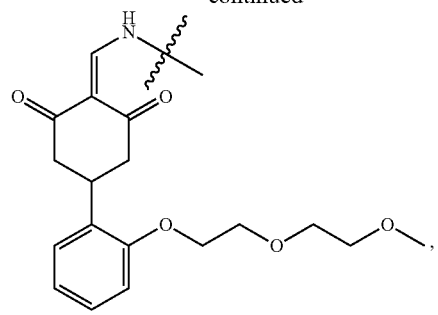
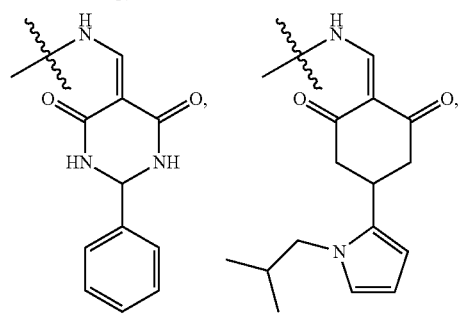
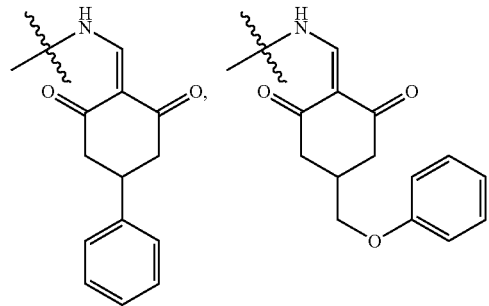
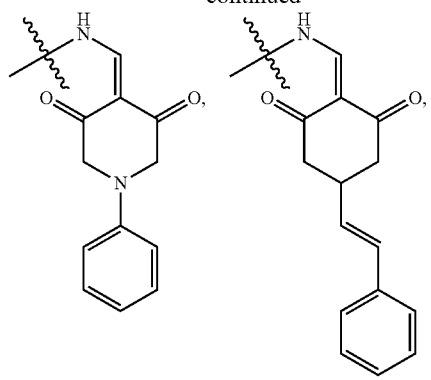
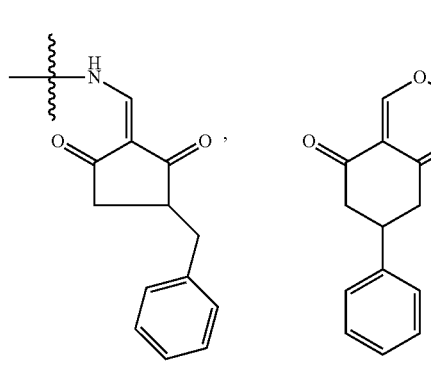
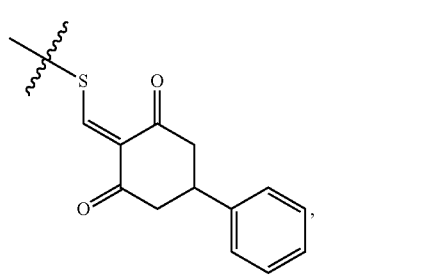
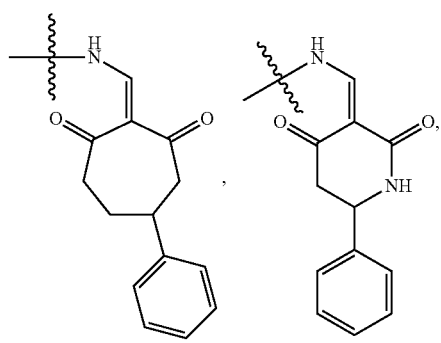
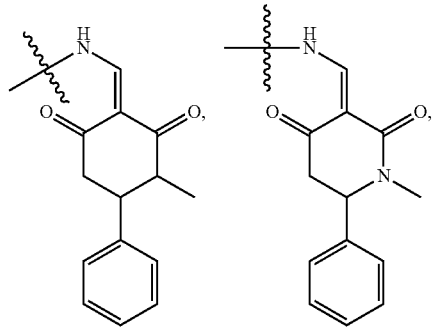

-continued
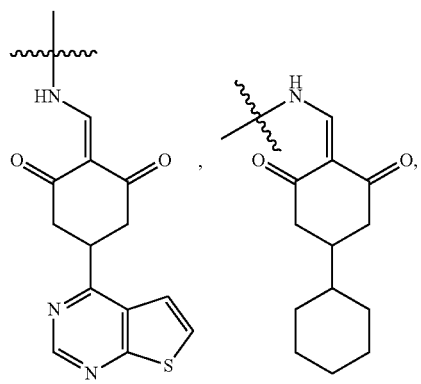 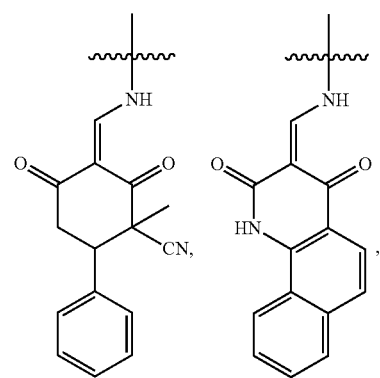
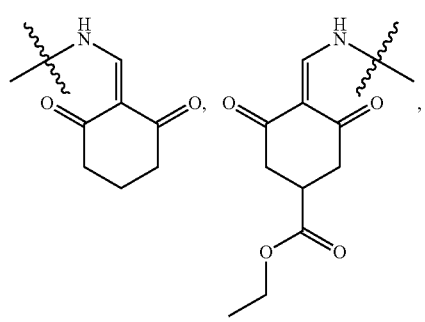 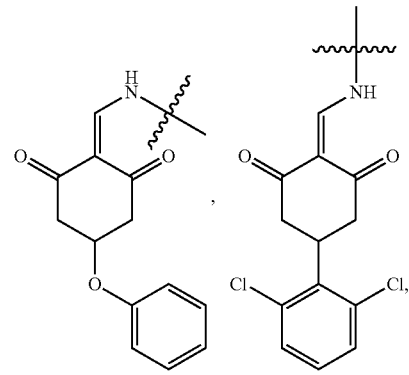
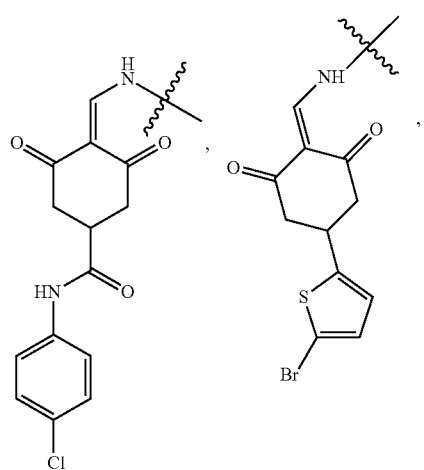 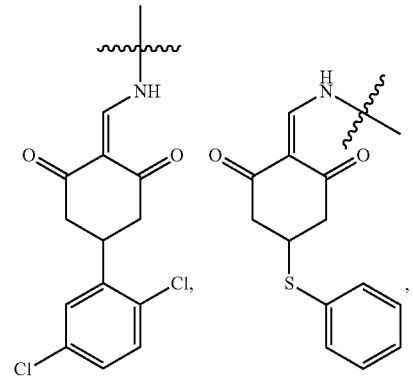
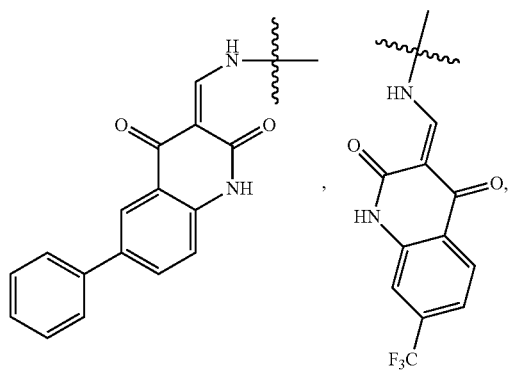 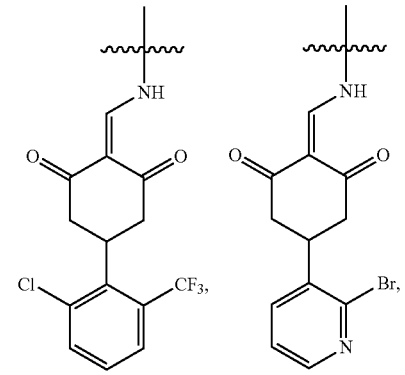

-continued
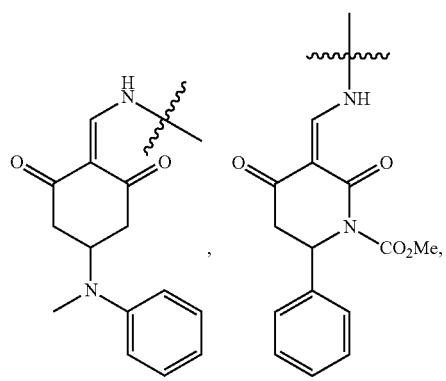
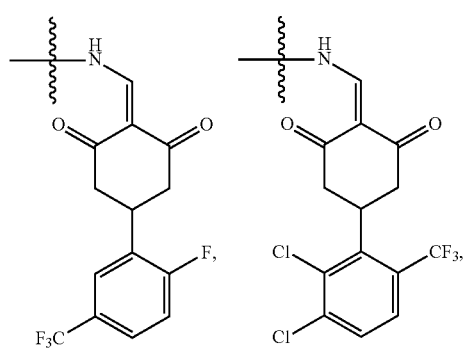
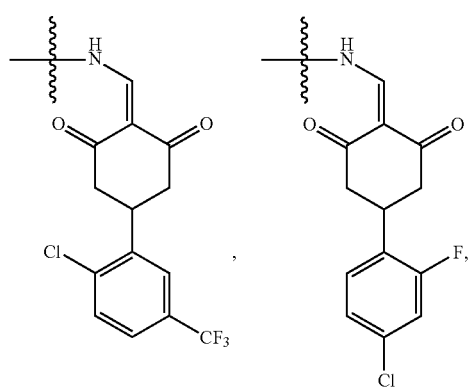
-continued
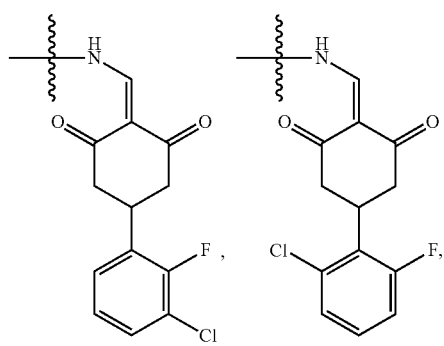
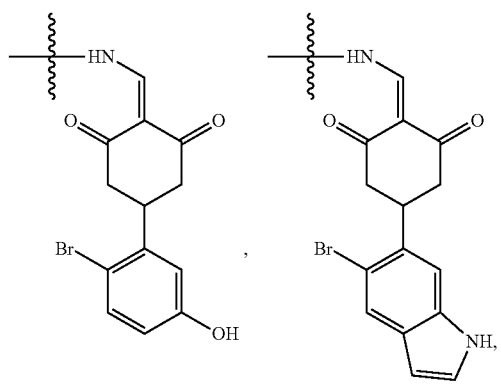
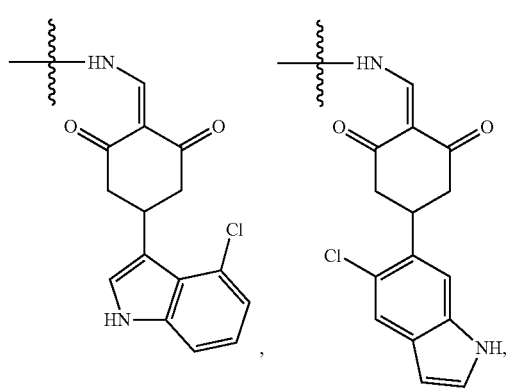
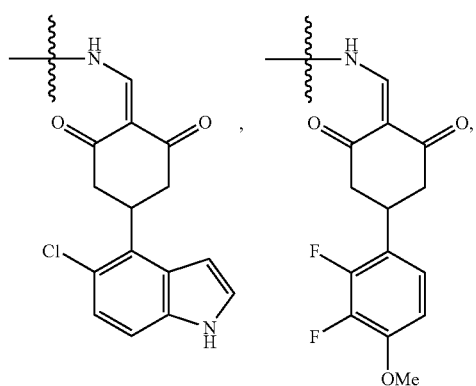

-continued

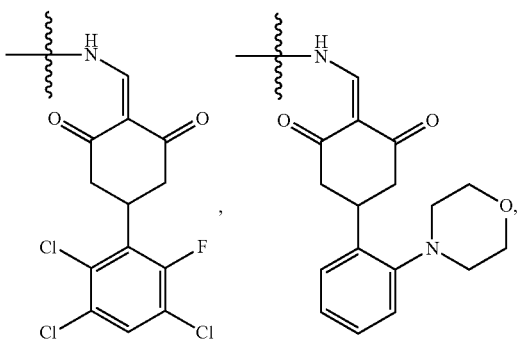

,

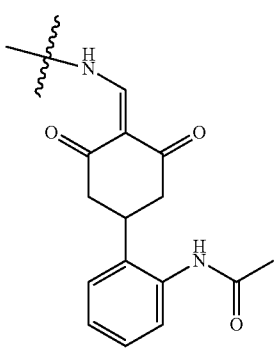

,

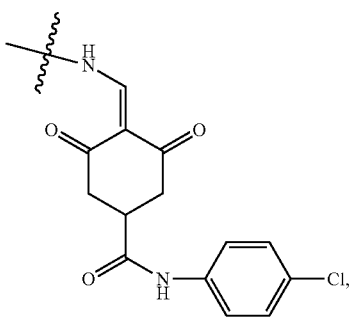

,

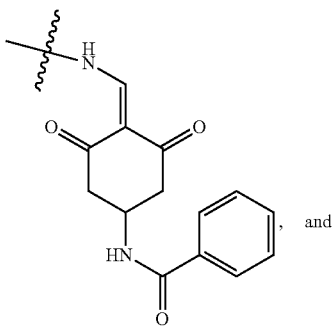

, and

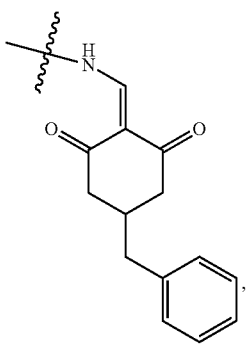

, wherein

represents the point of attachment.

In another specific embodiment, in General Formula (I), L is absent or is a divalent group represented by General Formula (IV) or a trivalent group represented by General Formula (V):

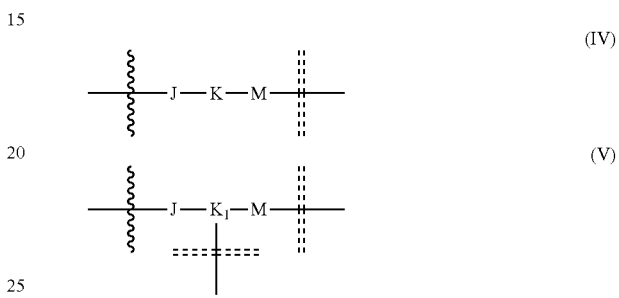

wherein

J and M are each independently absent, $NR_i$, O, S, $SO_2$, $C(=O)$ or $C(=S)$, in which $R_i$ is hydrogen, C1-C4 alkyl or C6-C10 aryl;

K is absent, C1-C10 alkylene, C3-C10 cycloalkylene, C1-C6 heteroalkylene, C2-C6 alkenylene, C2-C6 alkynylene, unsubstituted or substituted C6-C10 arylene, unsubstituted or substituted 5-10 membered heteroarylene, unsubstituted or substituted C3-C8 cycloalkylene, unsubstituted or substituted 3-10 membered non-aromatic heterocyclylene, peptidylene consisting of 2 to 8 identical or different amino acids, or any combination of two, three, or four identical or different groups thereof; and $K_1$ is a trivalent group, selected from the group consisting of C1-C10 alkyl, C3-C10 cycloalkyl, C1-C6 heteroalkyl, C2-C6 alkenyl, C2-C6 alkynyl, unsubstituted or substituted C6-C10 aryl, unsubstituted or substituted 5-10 membered heteroaryl, unsubstituted or substituted C3-C8 cycloalkyl, unsubstituted or substituted 3-10 membered non-aromatic heterocyclyl, peptidyl consisting of 2 to 8 identical or different amino acids, and any combination of two, three, or four identical or different groups thereof;

where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl, and C1-C6 hydroxyalkyl.

Preferably, the divalent and trivalent groups represented by General Formulas (IV) and (V) are selected from the following groups or any combinations of identical or different groups thereof:

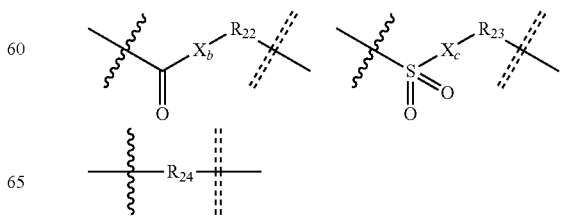

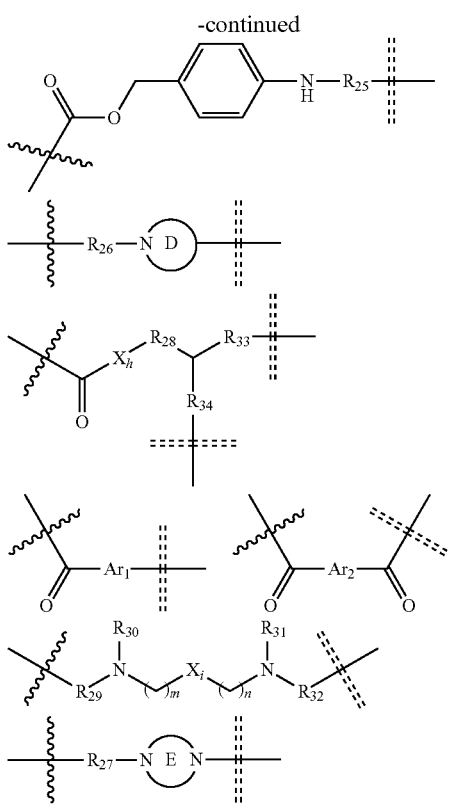

where m and n are each independently 0, 1, 2, 3, 4 or 5;

$X_b$, $X_c$, $X_h$ and $X_i$ are each independently absent, O, S or NH;

$R_{22}$, $R_{23}$, $R_{24}$, $R_{25}$, $R_{26}$, $R_{27}$, $R_{29}$, $R_{32}$, $R_{33}$ and $R_{34}$ are each independently absent, C1-C10 alkylene, C3-C10 cycloalkylene, C1-C6 heteroalkylene, C2-C6 alkenylene, C2-C6 alkynylene, unsubstituted or substituted C6-C10 arylene, unsubstituted or substituted 5-10 membered heteroarylene, unsubstituted or substituted C3-C8 cycloalkylene, unsubstituted or substituted 3-10 membered non-aromatic heterocyclylene, or any combination of two, three, or four identical or different groups thereof;

$R_{30}$ and $R_{31}$ are each independently H, C1-C10 alkyl, C3-C10 cycloalkyl, C1-C6 heteroalkyl, C2-C6 alkenyl, C2-C6 alkynyl, unsubstituted or substituted C6-C10 aryl, unsubstituted or substituted 5-10 membered heteroaryl, unsubstituted or substituted C3-C8 cycloalkyl, unsubstituted or substituted 3-10 membered non-aromatic heterocyclyl, or any combination of two, three, or four identical or different groups thereof;

$Ar_1$ and $Ar_2$ are each independently unsubstituted or substituted C6-C10 arylene, or unsubstituted or substituted 5-10 membered heteroarylene; and the rings D and E are each independently unsubstituted or substituted 3-10 membered nitrogen-containing heterocyclic ring, where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl or C1-C6 hydroxylalkyl.

Preferably, the divalent and trivalent groups represented by General Formulas IV and V are selected from the groups of:

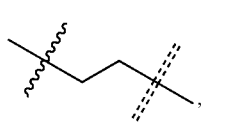

L-1

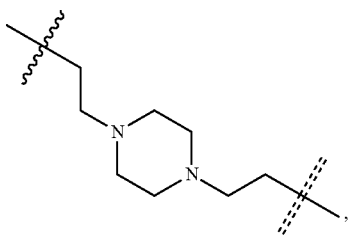

L-2

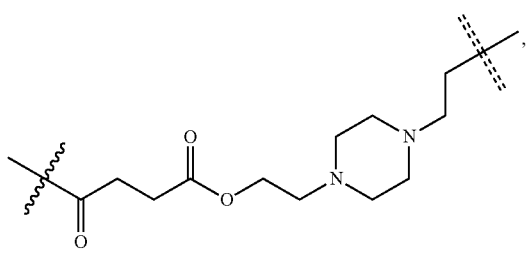

L-3

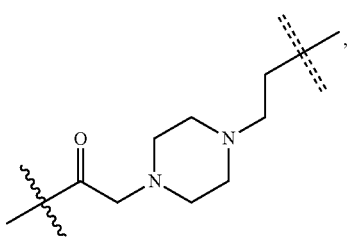

L-4

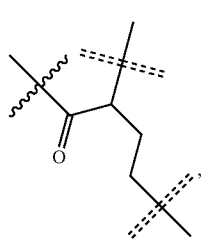

L-5

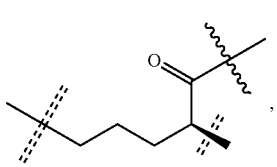

L-6

-continued
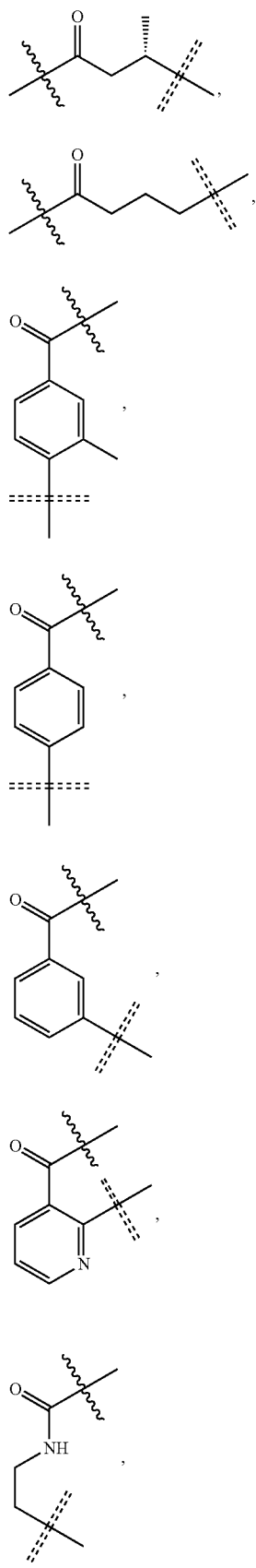
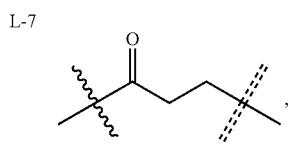
L-7
L-8
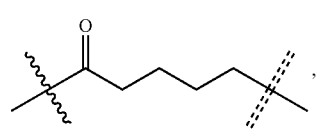
L-9
L-10
L-11
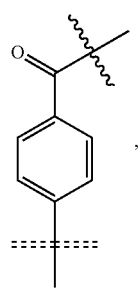
L-12
L-13
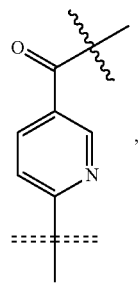
L-14
L-15
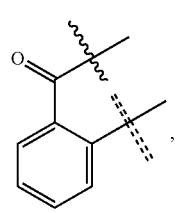
L-16
L-17
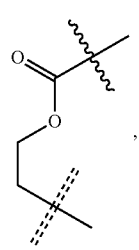
L-18
L-19
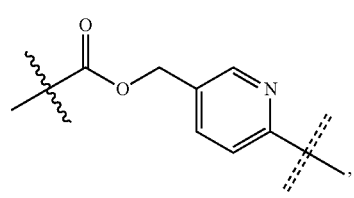
L-20

-continued
L-21
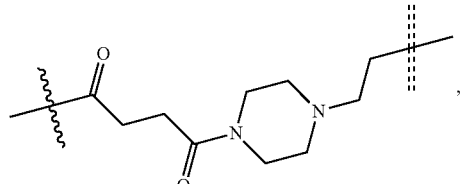
L-22
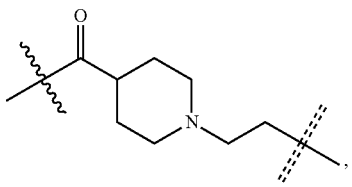
L-23
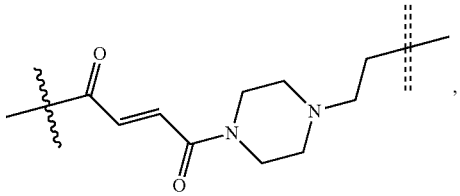
L-24
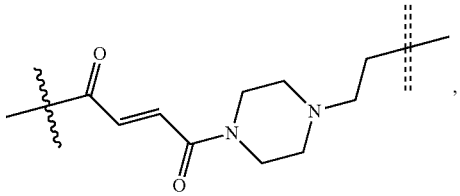
L-25
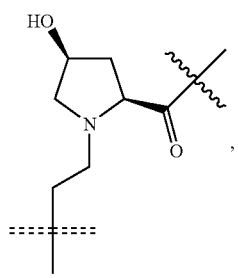
L-26
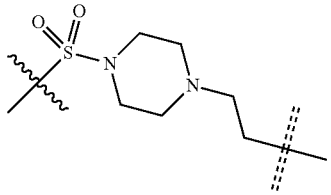
L-27
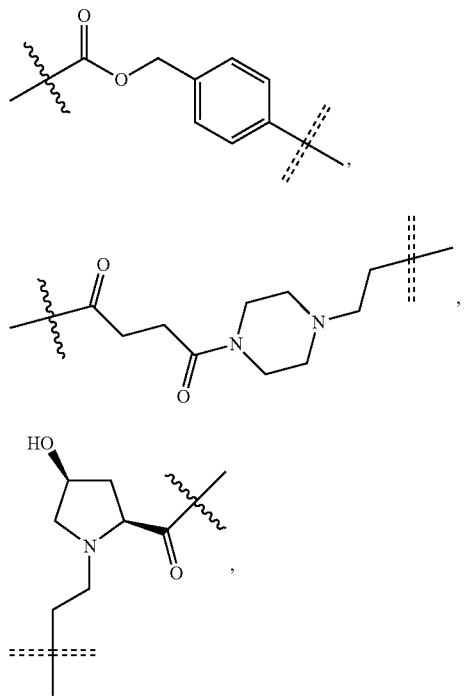
L-28
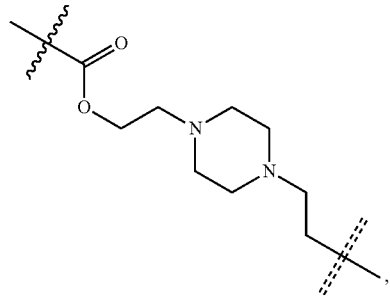
L-30
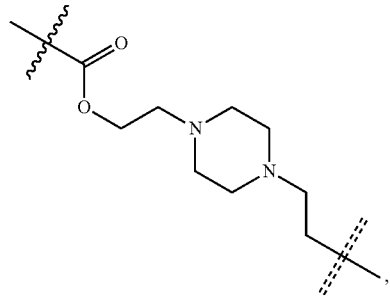
L-40
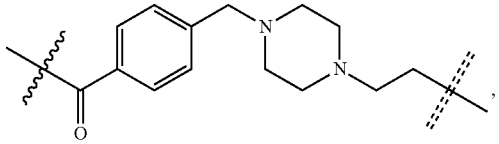
L-41
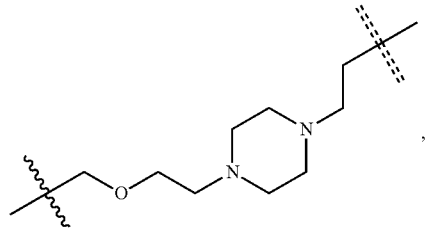
L-42
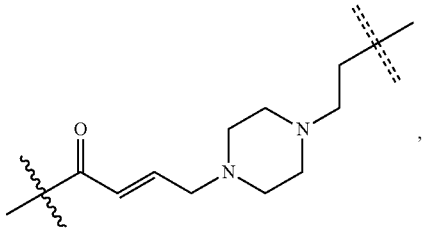
L-43
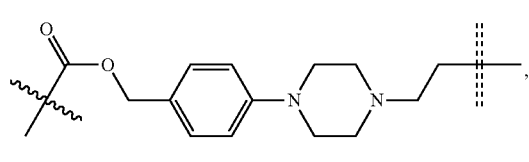
L-44
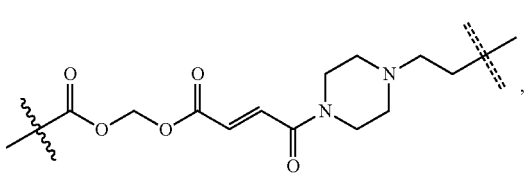

L-46
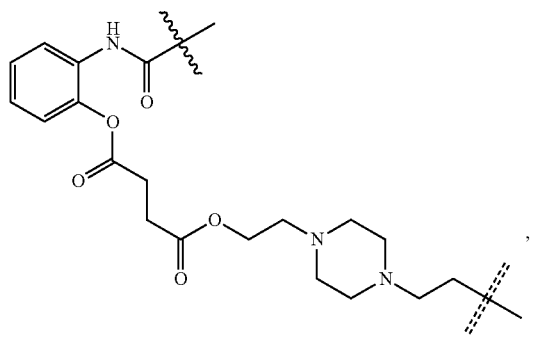
L-47
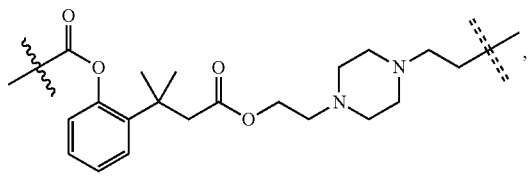
L-48
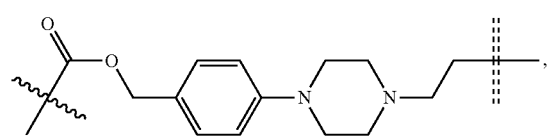
L-49
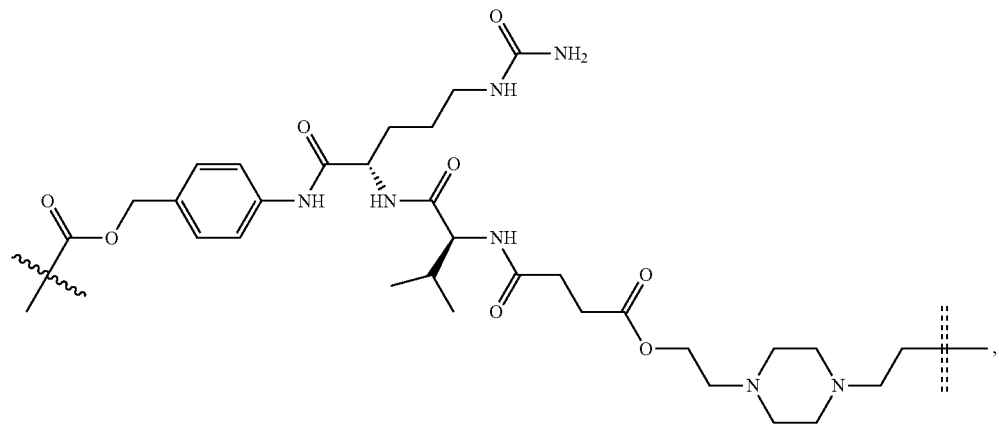
L-50
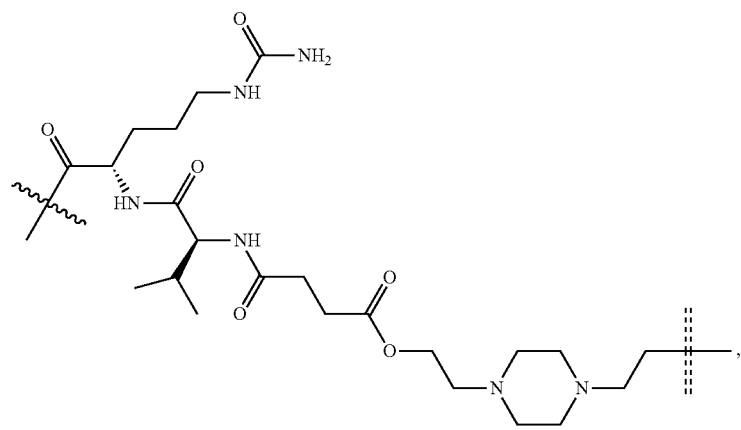

-continued
L-51
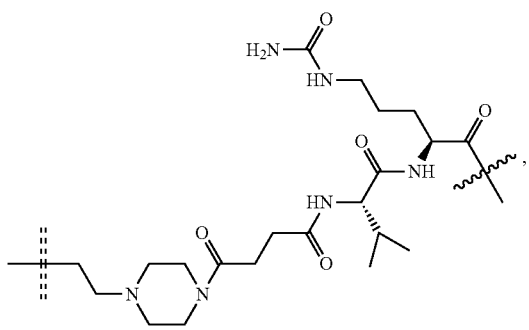
L-52
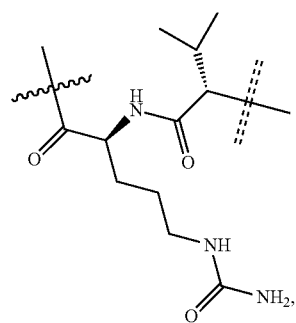
L-53
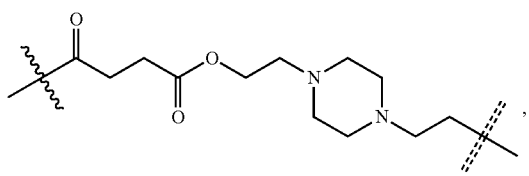
L-54
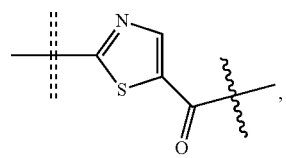
L-55
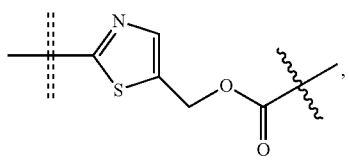
L-56
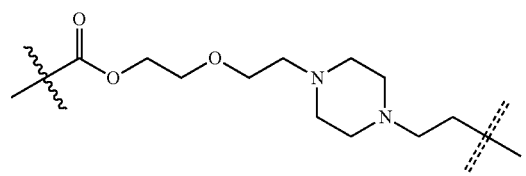
L-57
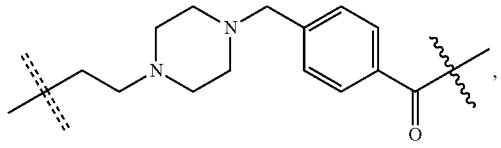
L-58
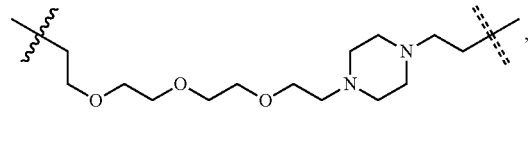
L-59
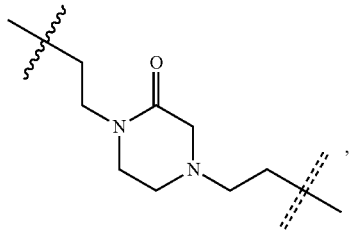
L-60
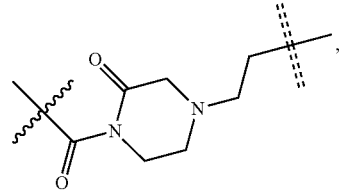
L-61
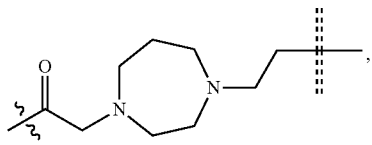
L-62
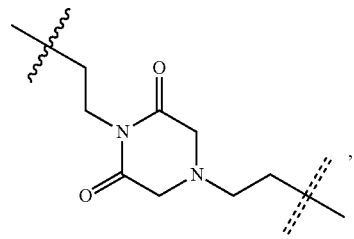

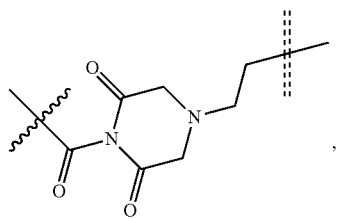
L-63
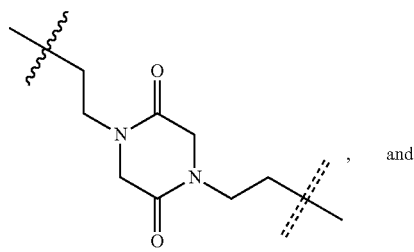
L-64
, and
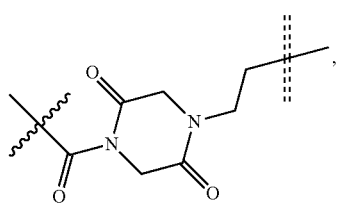
where the group is attached to Ar at the end
and to the fragment X at the end
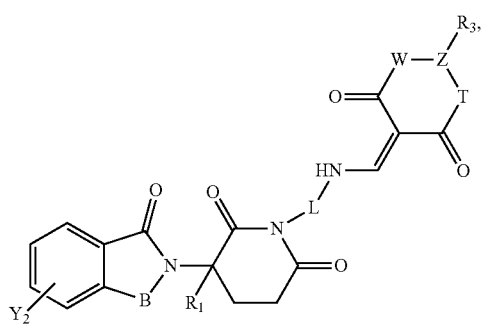
In another specific embodiment, the compound of General Formula (I) is selected from the compounds of General Formulas (VI), (VII), (VIII), (IX), (X) and (XI):
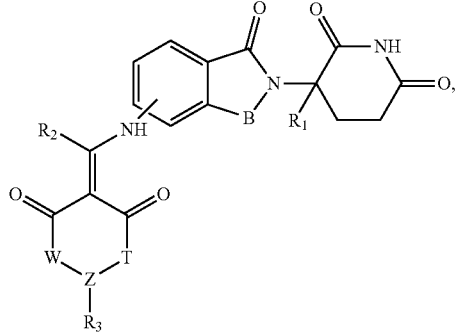
(VI)
(VII)

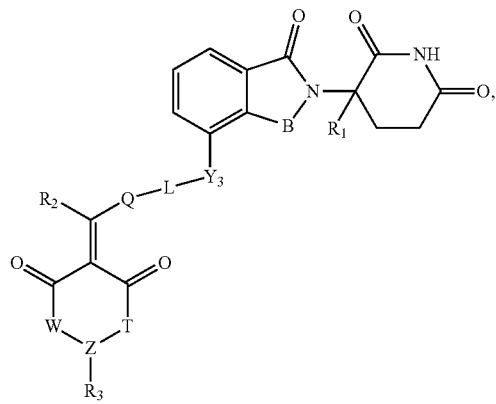
(VIII)
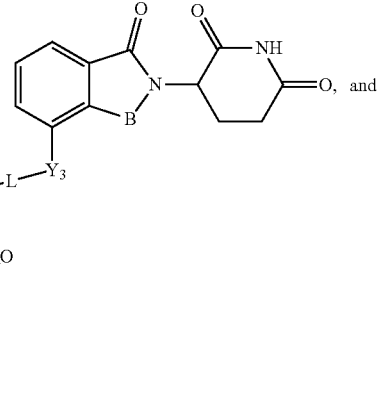
(X)
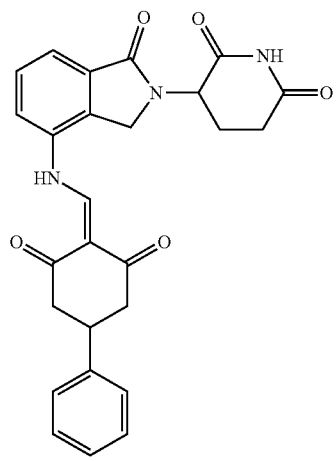 [SMILES: O=C1CCC(N2Cc3c(NC=C4C(=O)CC(c5ccccc5)CC4=O)cccc3C2=O)C(=O)N1]
(IX)
(XI)
where A, B, R$_1$, R$_2$, R$_3$, Q, L, W, T, and Z are as defined in corresponding claims;
Y$_2$ is H, NH$_2$ or halo; and
Y$_3$ is NH or O.
In another specific embodiment, the compound of General Formula (I) is selected from:
| Compound |
|---|
| 1 |

-continued
| Compound | |
|---|---|
| 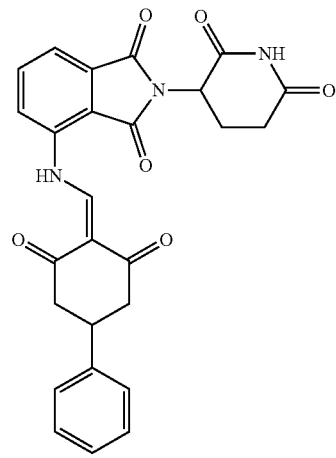 [SMILES: O=C1CCC(N2C(=O)c3cccc(NC=C4C(=O)CC(c5ccccc5)CC4=O)c3C2=O)C(=O)N1] | 2 |
| 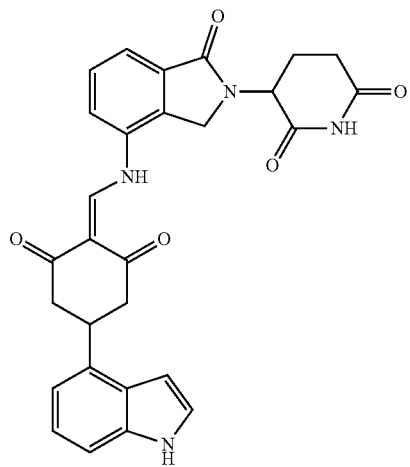 [SMILES: O=C1CCC(N2Cc3c(NC=C4C(=O)CC(c5cccc6[nH]ccc56)CC4=O)cccc3C2=O)C(=O)N1] | 3 |
| 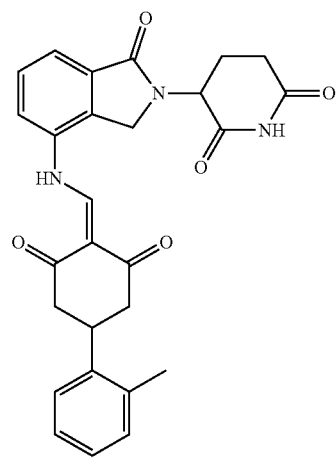 [SMILES: Cc1ccccc1C1CC(=O)C(=CNc2cccc3c2CN(C2CCC(=O)NC2=O)C3=O)C(=O)C1] | 4 |

-continued
| Compound | |
|---|---|
| 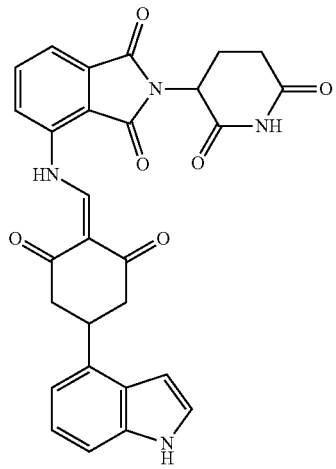 [SMILES: O=C1CCC(N2C(=O)c3cccc(NC=C4C(=O)CC(c5cccc6[nH]ccc56)CC4=O)c3C2=O)C(=O)N1] | 5 |
| 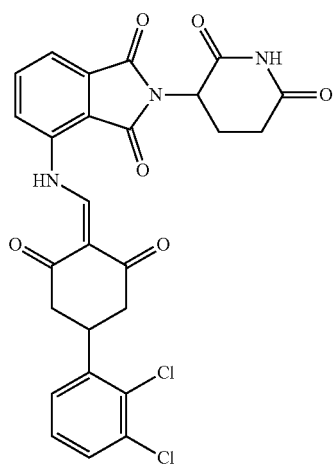 [SMILES: O=C1CCC(N2C(=O)c3cccc(NC=C4C(=O)CC(c5cccc(Cl)c5Cl)CC4=O)c3C2=O)C(=O)N1] | 6 |
| 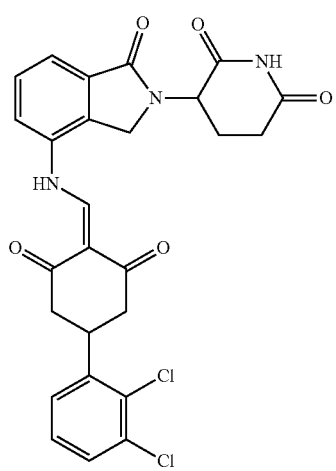 [SMILES: O=C1CCC(N2Cc3c(NC=C4C(=O)CC(c5cccc(Cl)c5Cl)CC4=O)cccc3C2=O)C(=O)N1] | 7 |

-continued
| Compound | |
|---|---|
| 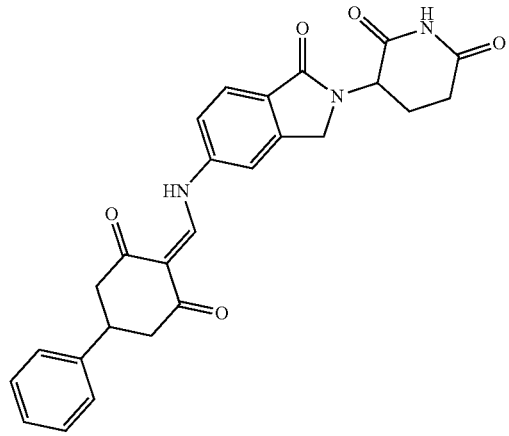 [SMILES: O=C1CCC(N2Cc3cc(NC=C4C(=O)CC(c5ccccc5)CC4=O)ccc3C2=O)C(=O)N1] | 8 |
| 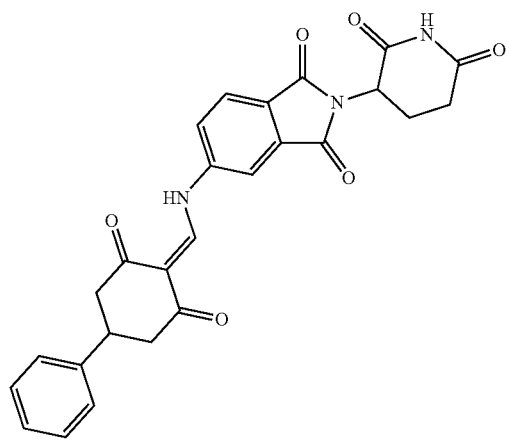 [SMILES: O=C1CCC(N2C(=O)c3ccc(NC=C4C(=O)CC(c5ccccc5)CC4=O)cc3C2=O)C(=O)N1] | 9 |
| 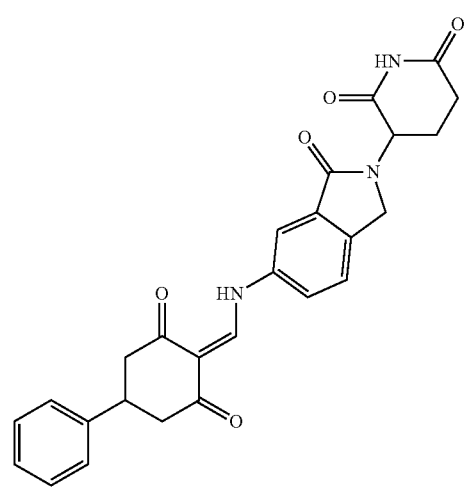 [SMILES: O=C1CCC(N2Cc3ccc(NC=C4C(=O)CC(c5ccccc5)CC4=O)cc3C2=O)C(=O)N1] | 10 |

-continued
| Compound | |
|---|---|
| 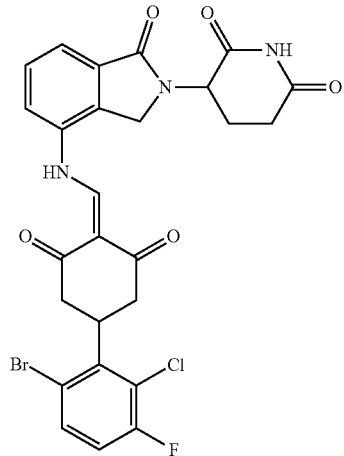 | 11 |
| 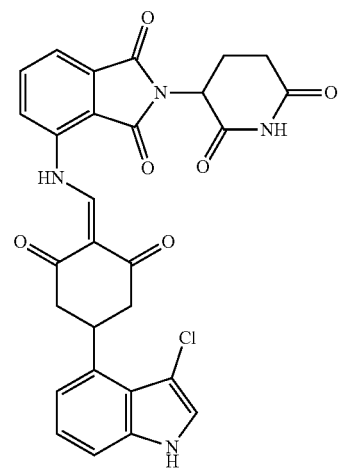 [SMILES: O=C1CCC(N2C(=O)c3cccc(NC=C4C(=O)CC(c5cccc6[nH]cc(Cl)c56)CC4=O)c3C2=O)C(=O)N1] | 12 |
| 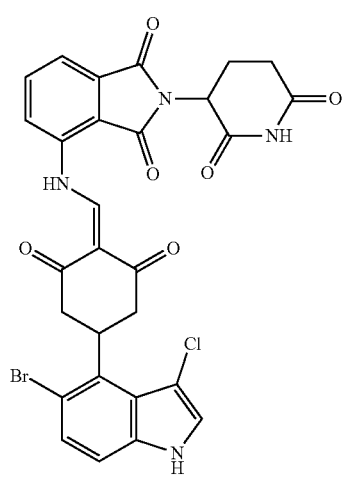 [SMILES: O=C1CCC(N2C(=O)c3cccc(NC=C4C(=O)CC(c5c(Br)ccc6[nH]cc(Cl)c56)CC4=O)c3C2=O)C(=O)N1] | 13 |

-continued
| Compound | |
|---|---|
| 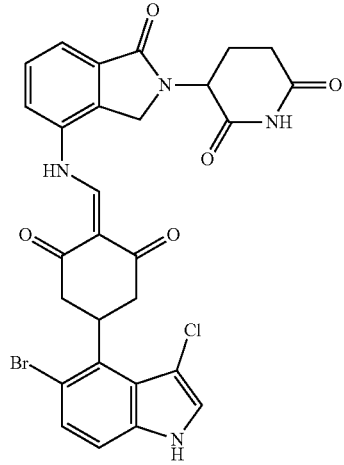 [SMILES: O=C1CCC(N2Cc3c(NC=C4C(=O)CC(c5c(Br)ccc6[nH]cc(Cl)c56)CC4=O)cccc3C2=O)C(=O)N1] | 14 |
| 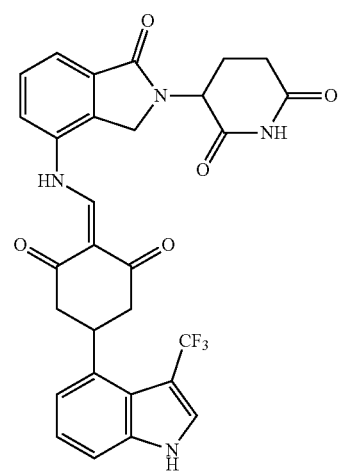 [SMILES: O=C1CCC(N2Cc3c(NC=C4C(=O)CC(c5cccc6[nH]cc(C(F)(F)F)c56)CC4=O)cccc3C2=O)C(=O)N1] | 15 |
| 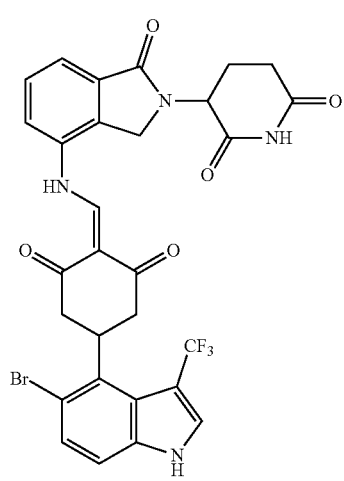 | 16 |

-continued
| Compound | |
|---|---|
| 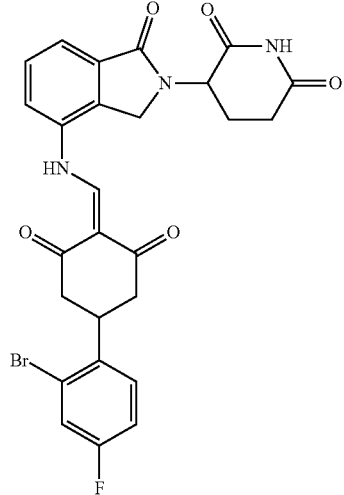 | 17 |
| 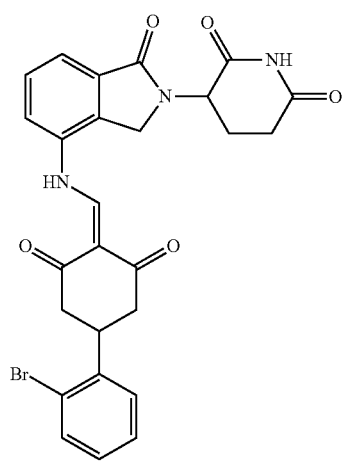 | 18 |
| 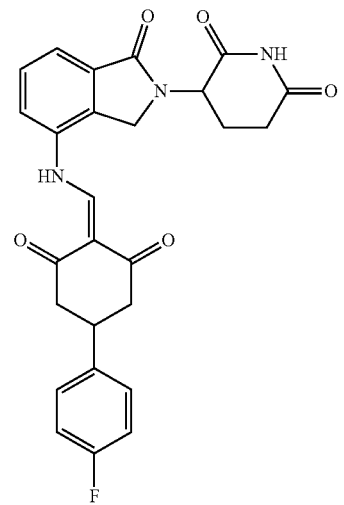 [SMILES: O=C1CCC(N2Cc3c(NC=C4C(=O)CC(c5ccc(F)cc5)CC4=O)cccc3C2=O)C(=O)N1] | 19 |

-continued
| Compound | |
|---|---|
| 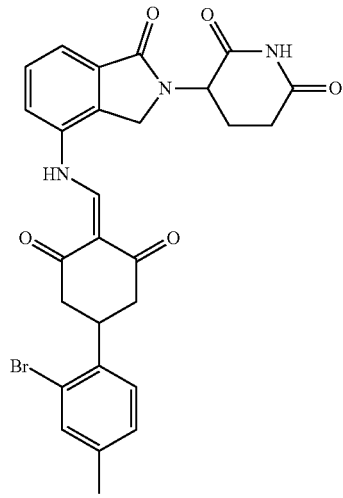 | 20 |
| 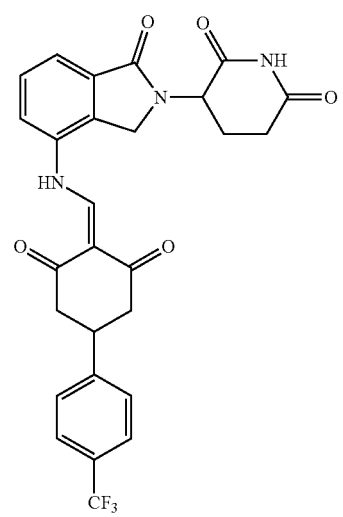 [SMILES: O=C1CCC(N2Cc3c(NC=C4C(=O)CC(c5ccc(C(F)(F)F)cc5)CC4=O)cccc3C2=O)C(=O)N1] | 21 |
| 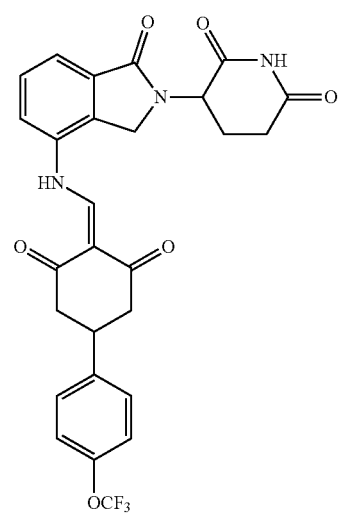 [SMILES: O=C1CCC(N2Cc3c(NC=C4C(=O)CC(c5ccc(OC(F)(F)F)cc5)CC4=O)cccc3C2=O)C(=O)N1] | 22 |

-continued
| Compound | |
|---|---|
| 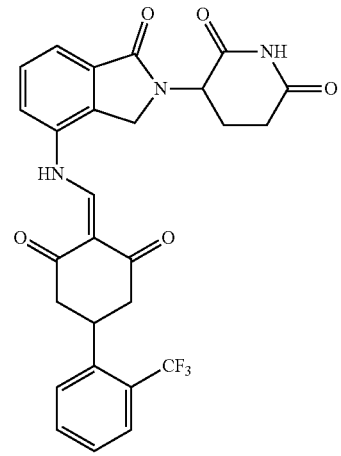 [SMILES: O=C1CCC(N2Cc3c(NC=C4C(=O)CC(c5ccccc5C(F)(F)F)CC4=O)cccc3C2=O)C(=O)N1] | 23 |
| 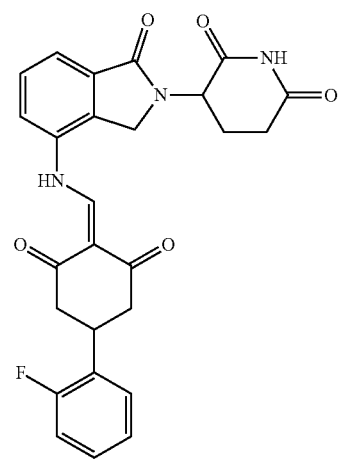 [SMILES: O=C1CCC(N2Cc3c(NC=C4C(=O)CC(c5ccccc5F)CC4=O)cccc3C2=O)C(=O)N1] | 24 |
| 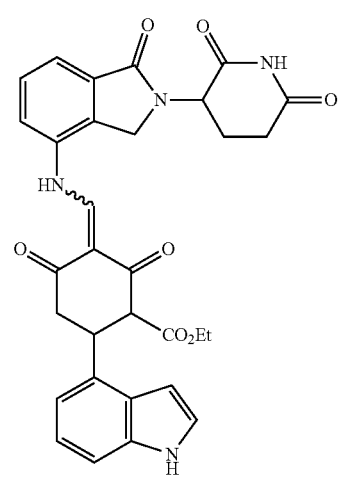 [SMILES: CCOC(=O)C1C(=O)C(=CNc2cccc3c2CN(C2CCC(=O)NC2=O)C3=O)C(=O)CC1c1cccc2[nH]ccc12] | 25 |

-continued
| Compound | |
|---|---|
| 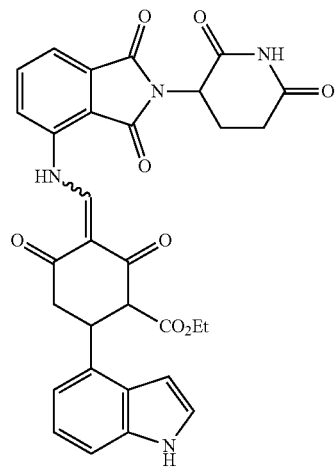 [SMILES: CCOC(=O)C1C(=O)C(=CNc2cccc3c2C(=O)N(C2CCC(=O)NC2=O)C3=O)C(=O)CC1c1cccc2[nH]ccc12] | 26 |
| 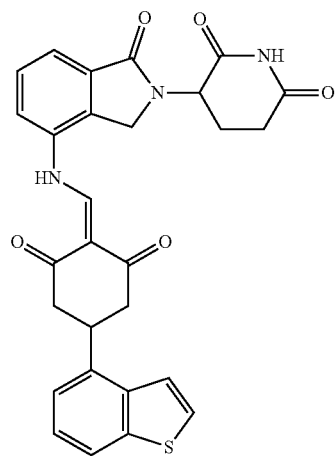 [SMILES: O=C1CCC(N2Cc3c(NC=C4C(=O)CC(c5cccc6sccc56)CC4=O)cccc3C2=O)C(=O)N1] | 27 |
| 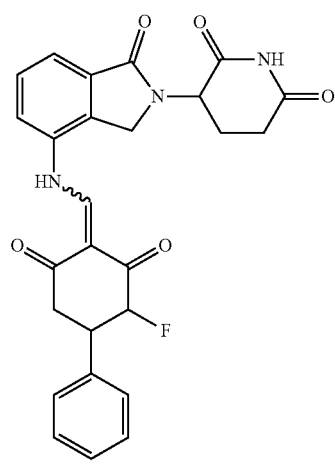 [SMILES: O=C1CCC(N2Cc3c(NC=C4C(=O)CC(c5ccccc5)C(F)C4=O)cccc3C2=O)C(=O)N1] | 28 |

-continued
| Compound |
|---|
| 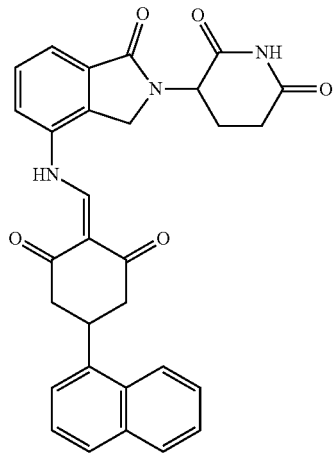 [SMILES: O=C1CCC(N2Cc3c(NC=C4C(=O)CC(c5cccc6ccccc56)CC4=O)cccc3C2=O)C(=O)N1] 29 |
| 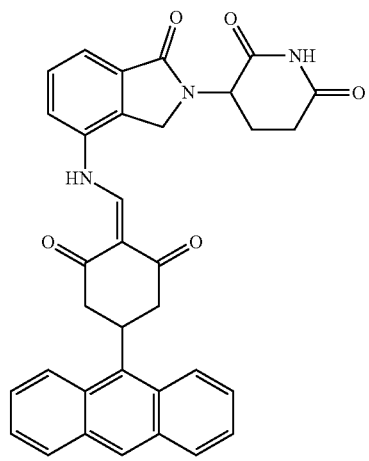 [SMILES: O=C1CCC(N2Cc3c(NC=C4C(=O)CC(c5c6ccccc6cc6ccccc56)CC4=O)cccc3C2=O)C(=O)N1] 30 |
| 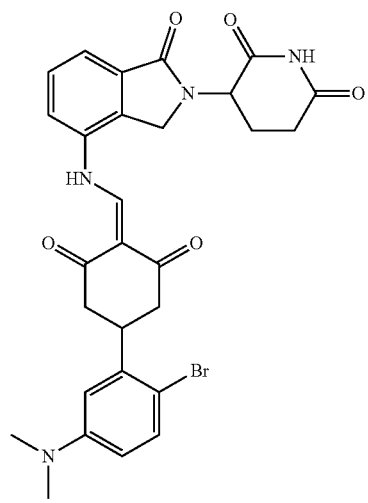 [SMILES: CN(C)c1ccc(Br)c(C2CC(=O)C(=CNc3cccc4c3CN(C3CCC(=O)NC3=O)C4=O)C(=O)C2)c1] 31 |

-continued

| Compound | |
|---|---|
| (structure of compound 32) | 32 |
| (structure of compound 33) | 33 |
| (structure of compound 34) | 34 |

| Compound | |
|---|---|
| 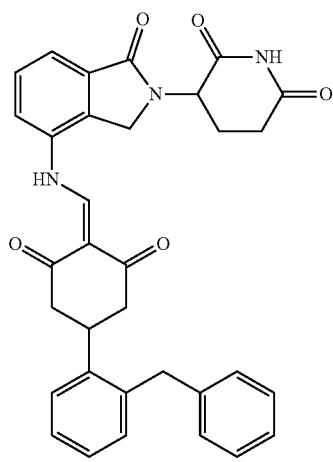 [SMILES: O=C1CCC(N2Cc3c(NC=C4C(=O)CC(c5ccccc5Cc5ccccc5)CC4=O)cccc3C2=O)C(=O)N1] | 35 |
| 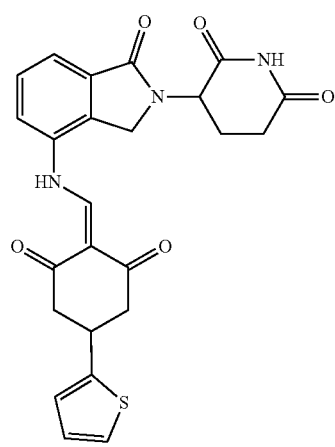 [SMILES: O=C1CCC(N2Cc3c(NC=C4C(=O)CC(c5cccs5)CC4=O)cccc3C2=O)C(=O)N1] | 36 |
| 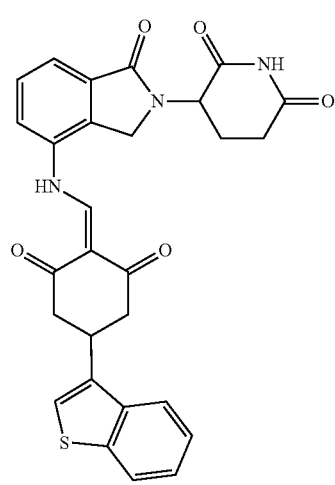 [SMILES: O=C1CCC(N2Cc3c(NC=C4C(=O)CC(c5csc6ccccc56)CC4=O)cccc3C2=O)C(=O)N1] | 37 |

| Compound | |
|---|---|
| 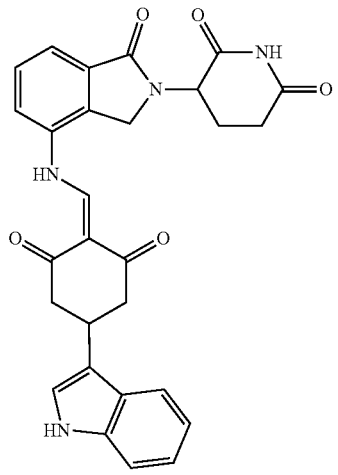 [SMILES: O=C1CCC(N2Cc3c(NC=C4C(=O)CC(c5c[nH]c6ccccc56)CC4=O)cccc3C2=O)C(=O)N1] | 38 |
| 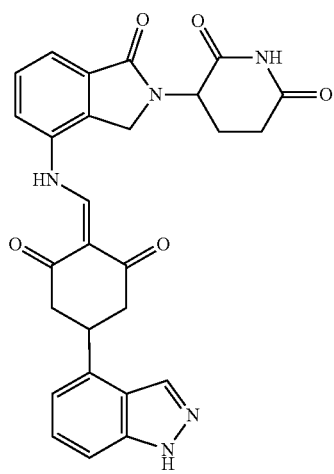 [SMILES: O=C1CCC(N2Cc3c(NC=C4C(=O)CC(c5cccc6[nH]ncc56)CC4=O)cccc3C2=O)C(=O)N1] | 39 |
| 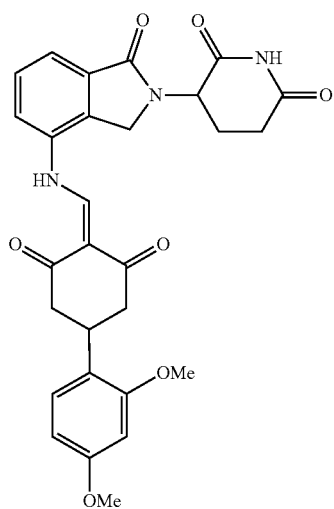 [SMILES: COc1ccc(C2CC(=O)C(=CNc3cccc4c3CN(C3CCC(=O)NC3=O)C4=O)C(=O)C2)c(OC)c1] | 40 |

-continued
| Compound | |
|---|---|
| 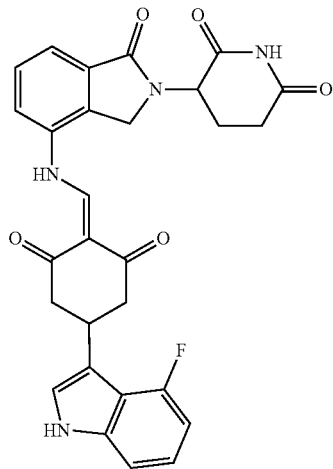 [SMILES: O=C1CCC(N2Cc3c(NC=C4C(=O)CC(c5c[nH]c6cccc(F)c56)CC4=O)cccc3C2=O)C(=O)N1] | 41 |
| 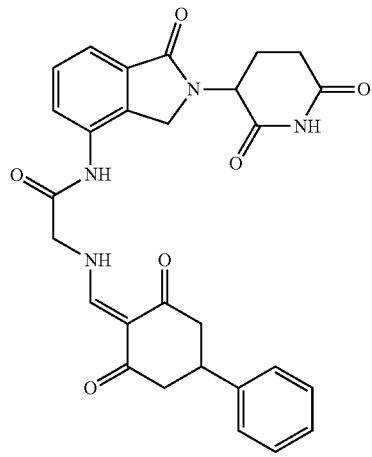 [SMILES: O=C1CCC(N2Cc3c(NC(=O)CNC=C4C(=O)CC(c5ccccc5)CC4=O)cccc3C2=O)C(=O)N1] | 42 |
| 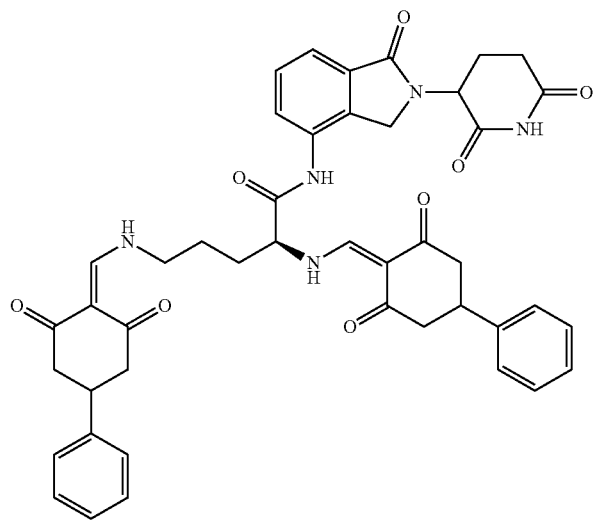 [SMILES: O=C1CCC(N2Cc3c(NC(=O)[C@H](CCCNC=C4C(=O)CC(c5ccccc5)CC4=O)NC=C4C(=O)CC(c5ccccc5)CC4=O)cccc3C2=O)C(=O)N1] | 43 |

| Compound | |
|---|---|
| 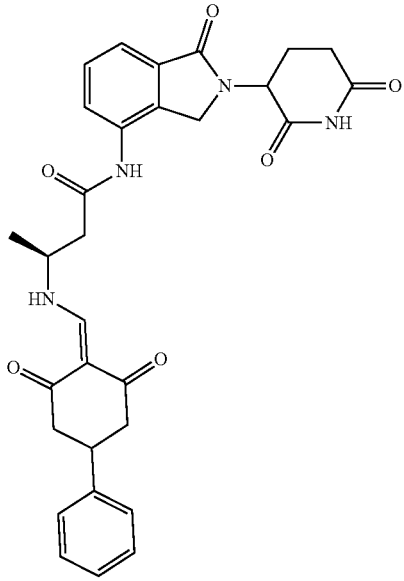 [SMILES: C[C@@H](CC(=O)Nc1cccc2c1CN(C1CCC(=O)NC1=O)C2=O)NC=C1C(=O)CC(c2ccccc2)CC1=O] | 44 |
| 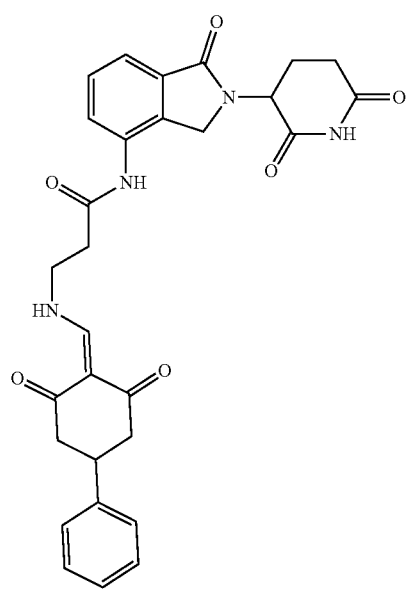 [SMILES: O=C1CCC(N2Cc3c(NC(=O)CCNC=C4C(=O)CC(c5ccccc5)CC4=O)cccc3C2=O)C(=O)N1] | 45 |

-continued
| Compound | |
|---|---|
| 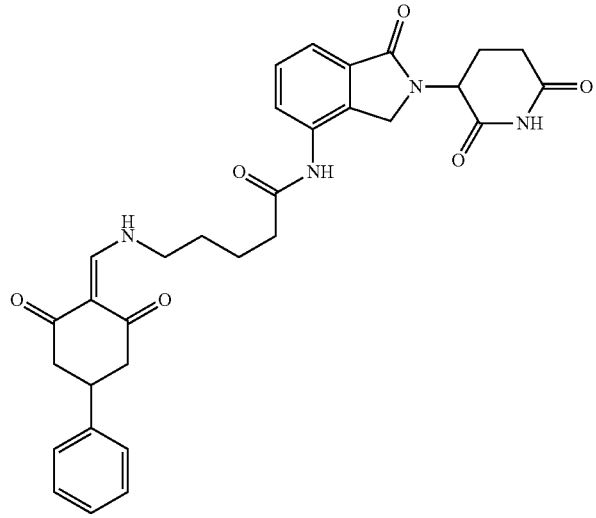 [SMILES: O=C1CCC(N2Cc3c(NC(=O)CCCCNC=C4C(=O)CC(c5ccccc5)CC4=O)cccc3C2=O)C(=O)N1] | 46 |
| 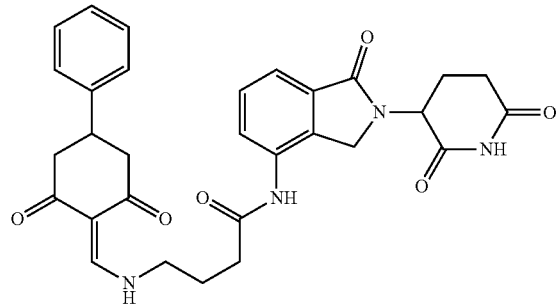 [SMILES: O=C1CCC(N2Cc3c(NC(=O)CCCNC=C4C(=O)CC(c5ccccc5)CC4=O)cccc3C2=O)C(=O)N1] | 47 |
| 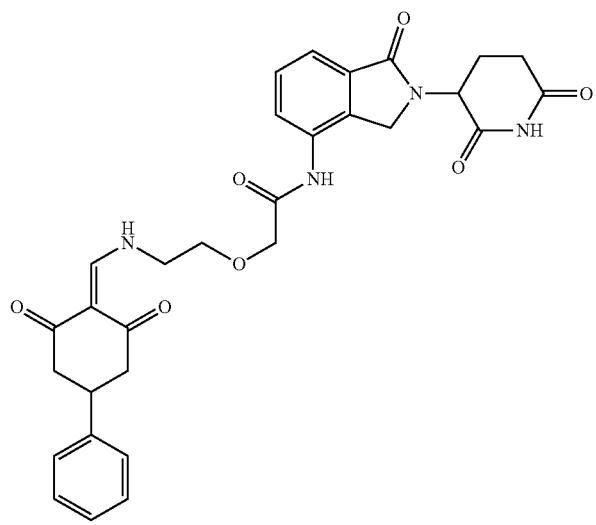 [SMILES: O=C1CCC(N2Cc3c(NC(=O)COCCNC=C4C(=O)CC(c5ccccc5)CC4=O)cccc3C2=O)C(=O)N1] | 48 |

-continued
| Compound | |
|---|---|
| 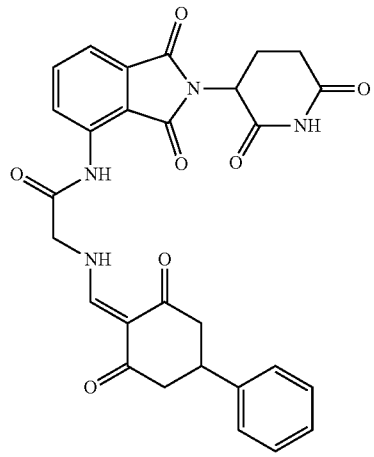 [SMILES: O=C1CCC(N2C(=O)c3cccc(NC(=O)CNC=C4C(=O)CC(c5ccccc5)CC4=O)c3C2=O)C(=O)N1] | 49 |
| 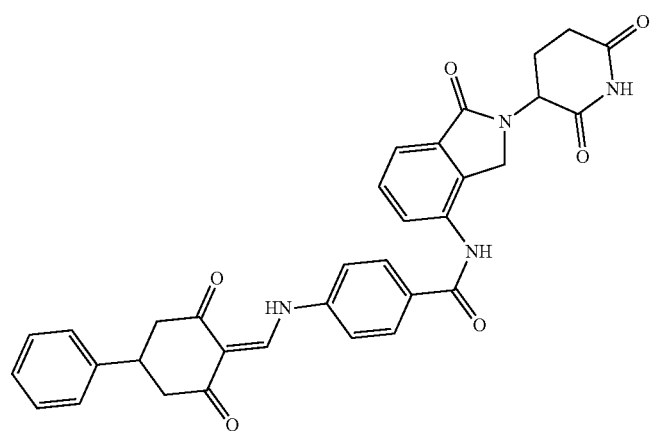 [SMILES: O=C1CCC(N2Cc3c(NC(=O)c4ccc(NC=C5C(=O)CC(c6ccccc6)CC5=O)cc4)cccc3C2=O)C(=O)N1] | 50 |
| 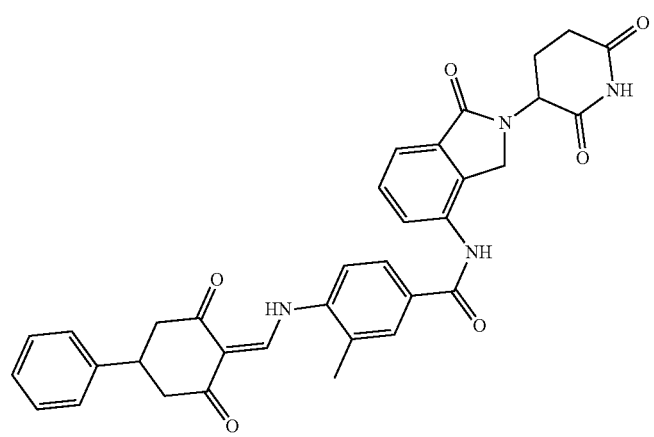 [SMILES: Cc1cc(C(=O)Nc2cccc3c2CN(C2CCC(=O)NC2=O)C3=O)ccc1NC=C1C(=O)CC(c2ccccc2)CC1=O] | 51 |

| Compound | |
|---|---|
| 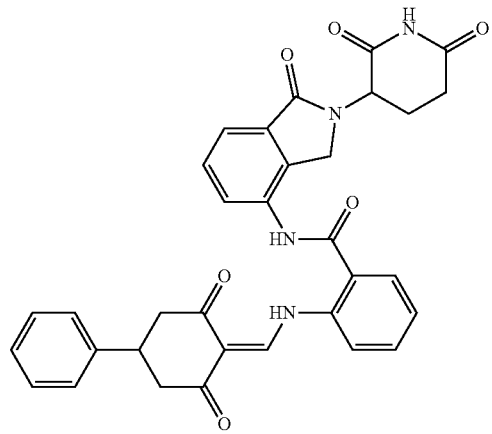 [SMILES: O=C1CCC(N2Cc3c(NC(=O)c4ccccc4NC=C4C(=O)CC(c5ccccc5)CC4=O)cccc3C2=O)C(=O)N1] | 52 |
| 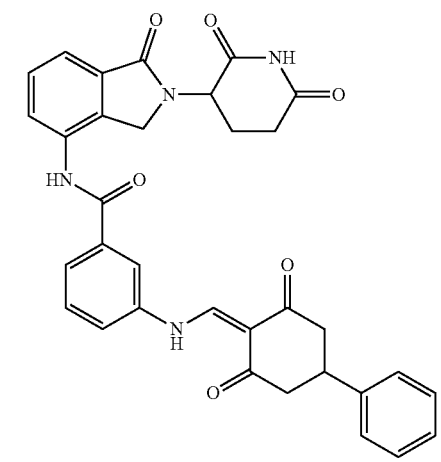 [SMILES: O=C1CCC(N2Cc3c(NC(=O)c4cccc(NC=C5C(=O)CC(c6ccccc6)CC5=O)c4)cccc3C2=O)C(=O)N1] | 53 |
| 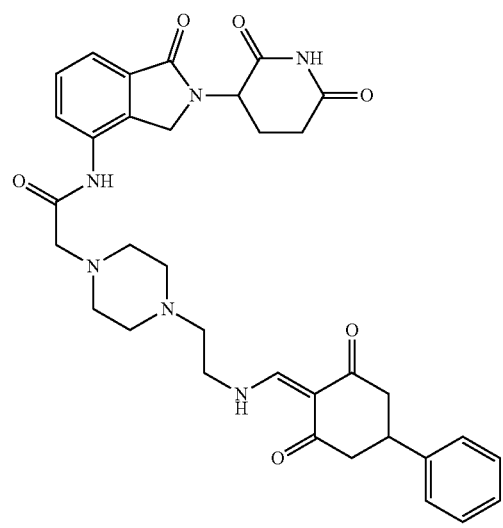 [SMILES: O=C1CCC(N2Cc3c(NC(=O)CN4CCN(CCNC=C5C(=O)CC(c6ccccc6)CC5=O)CC4)cccc3C2=O)C(=O)N1] | 54 |

-continued
| Compound | |
|---|---|
| 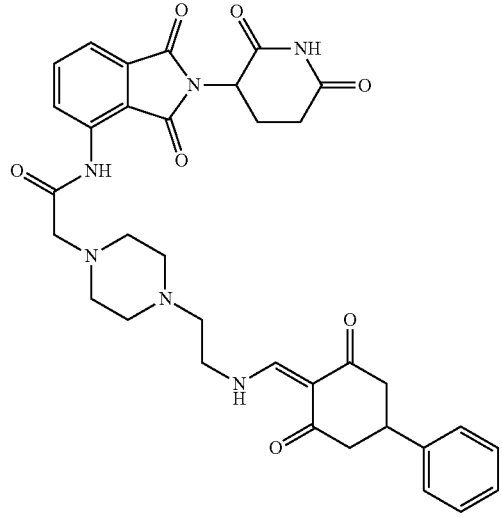 [SMILES: O=C1CCC(N2C(=O)c3cccc(NC(=O)CN4CCN(CCNC=C5C(=O)CC(c6ccccc6)CC5=O)CC4)c3C2=O)C(=O)N1] | 55 |
| 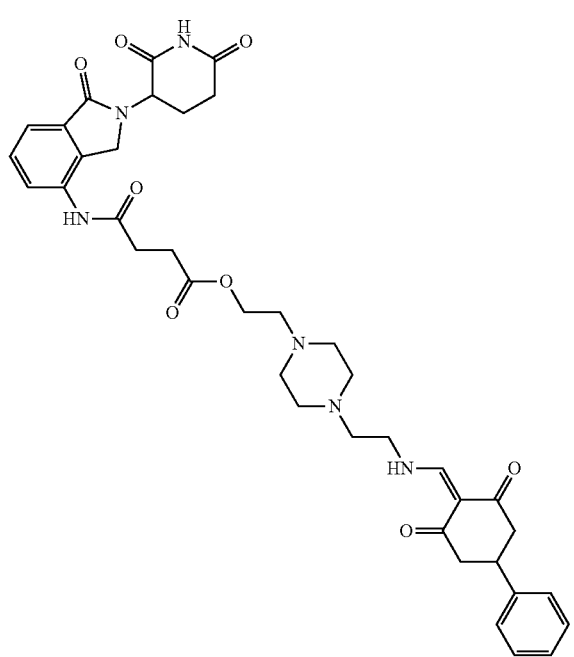 [SMILES: O=C1CCC(N2Cc3c(NC(=O)CCC(=O)OCCN4CCN(CCNC=C5C(=O)CC(c6ccccc6)CC5=O)CC4)cccc3C2=O)C(=O)N1] | 56 |

-continued
| Compound | |
|---|---|
| 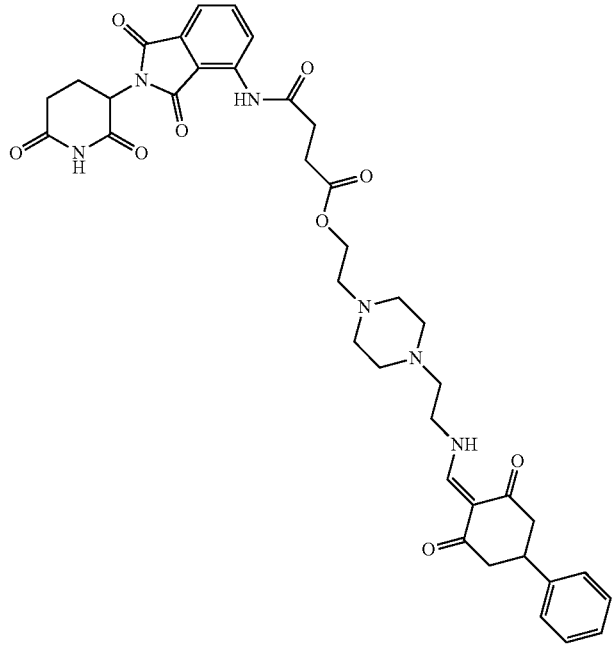 [SMILES: O=C1CCC(N2C(=O)c3cccc(NC(=O)CCC(=O)OCCN4CCN(CCNC=C5C(=O)CC(c6ccccc6)CC5=O)CC4)c3C2=O)C(=O)N1] | 57 |
| 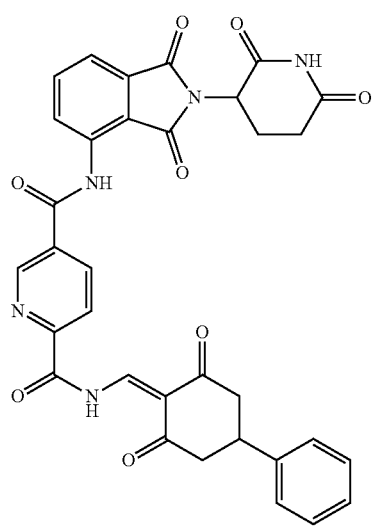 [SMILES: O=C1CCC(N2C(=O)c3cccc(NC(=O)c4ccc(C(=O)NC=C5C(=O)CC(c6ccccc6)CC5=O)nc4)c3C2=O)C(=O)N1] | 58 |

| Compound |
|---|
| 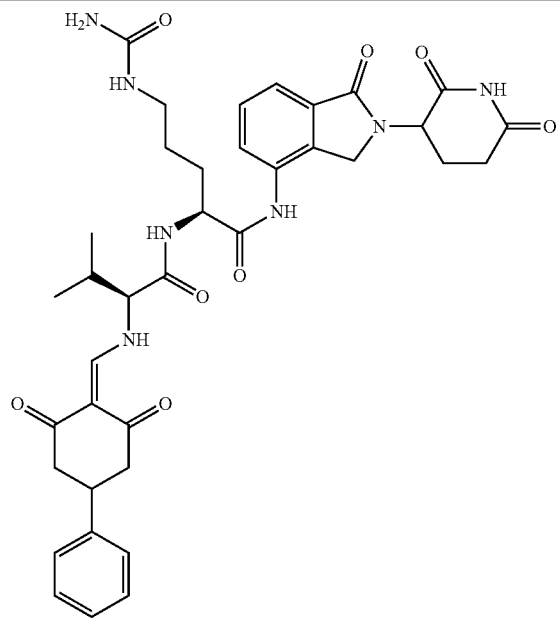 [SMILES: CC(C)[C@H](NC=C1C(=O)CC(c2ccccc2)CC1=O)C(=O)N[C@@H](CCCNC(N)=O)C(=O)Nc1cccc2c1CN(C1CCC(=O)NC1=O)C2=O] 59 |
| 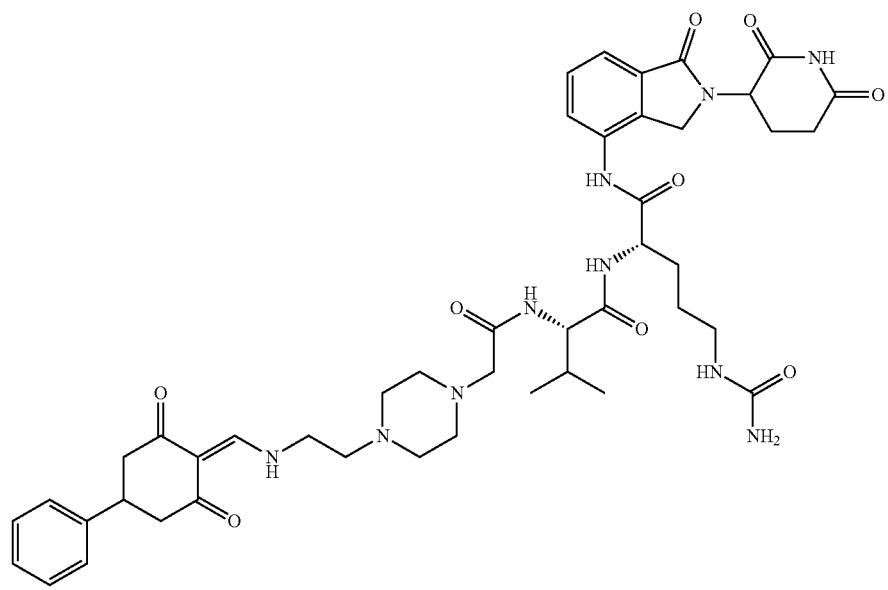 [SMILES: CC(C)[C@H](NC(=O)CN1CCN(CCNC=C2C(=O)CC(c3ccccc3)CC2=O)CC1)C(=O)N[C@@H](CCCNC(N)=O)C(=O)Nc1cccc2c1CN(C1CCC(=O)NC1=O)C2=O] 60 |

-continued
| Compound |
|---|
| 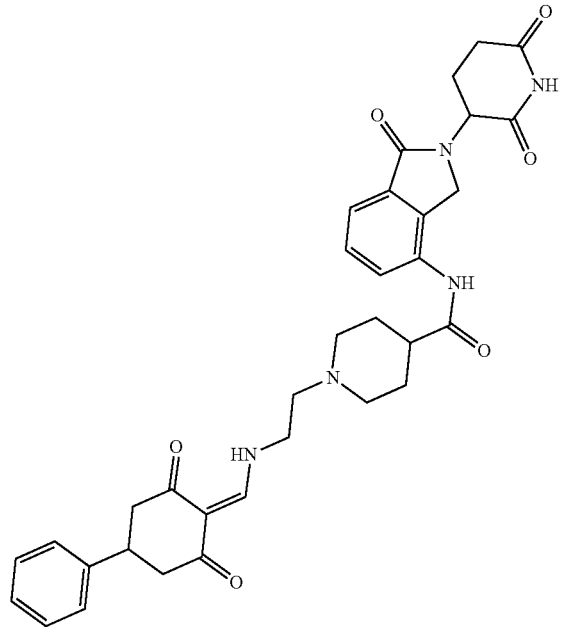 [SMILES: O=C1CCC(N2Cc3c(NC(=O)C4CCN(CCNC=C5C(=O)CC(c6ccccc6)CC5=O)CC4)cccc3C2=O)C(=O)N1] 61 |
| 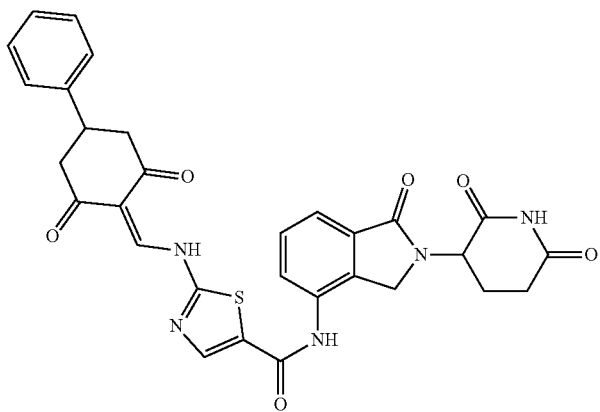 [SMILES: O=C1CCC(N2Cc3c(NC(=O)c4cnc(NC=C5C(=O)CC(c6ccccc6)CC5=O)s4)cccc3C2=O)C(=O)N1] 62 |
| 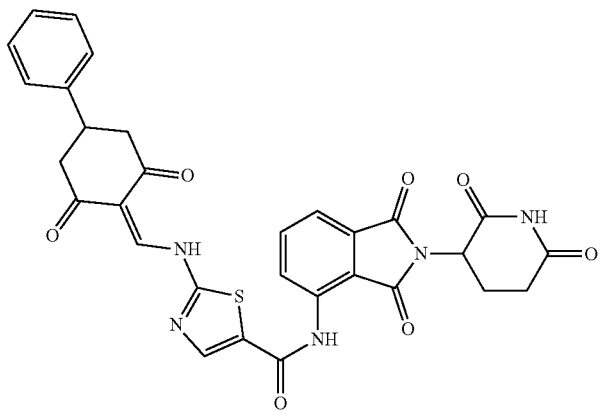 [SMILES: O=C1CCC(N2C(=O)c3cccc(NC(=O)c4cnc(NC=C5C(=O)CC(c6ccccc6)CC5=O)s4)c3C2=O)C(=O)N1] 63 |

| Compound |
|---|
| 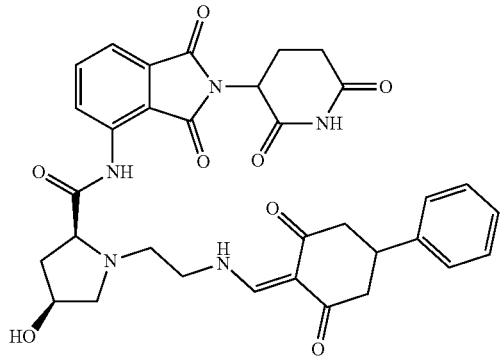 [SMILES: O=C1CCC(N2C(=O)c3cccc(NC(=O)[C@@H]4C[C@H](O)CN4CCNC=C4C(=O)CC(c5ccccc5)CC4=O)c3C2=O)C(=O)N1] 64 |
| 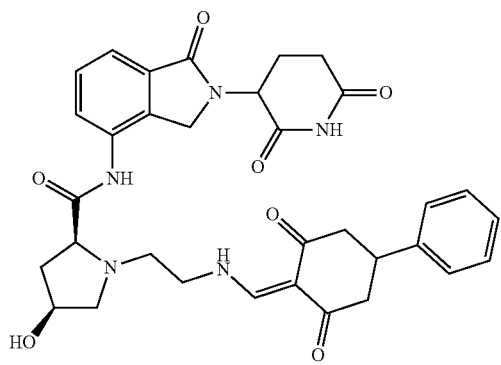 [SMILES: O=C1CCC(N2Cc3c(NC(=O)[C@@H]4C[C@H](O)CN4CCNC=C4C(=O)CC(c5ccccc5)CC4=O)cccc3C2=O)C(=O)N1] 65 |
| 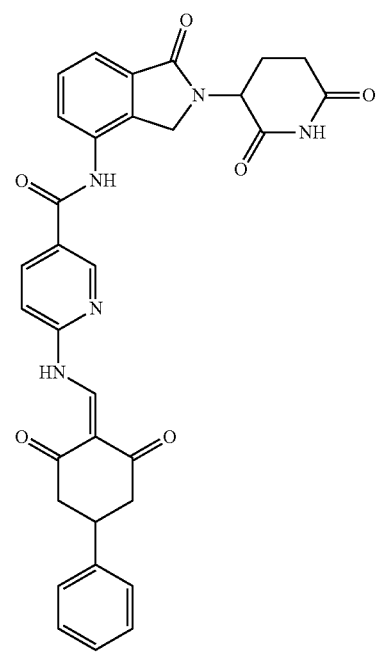 [SMILES: O=C1CCC(N2Cc3c(NC(=O)c4ccc(NC=C5C(=O)CC(c6ccccc6)CC5=O)nc4)cccc3C2=O)C(=O)N1] 66 |

-continued
| Compound | |
|---|---|
| 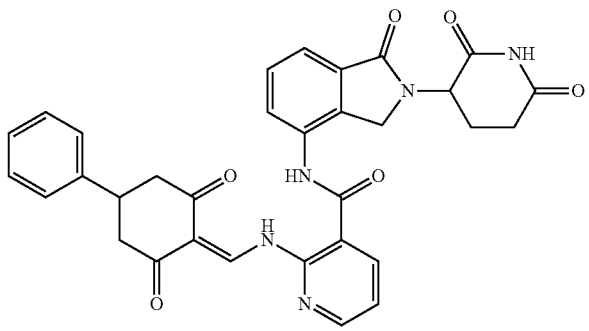 [SMILES: O=C1CCC(N2Cc3c(NC(=O)c4cccnc4NC=C4C(=O)CC(c5ccccc5)CC4=O)cccc3C2=O)C(=O)N1] | 67 |
| 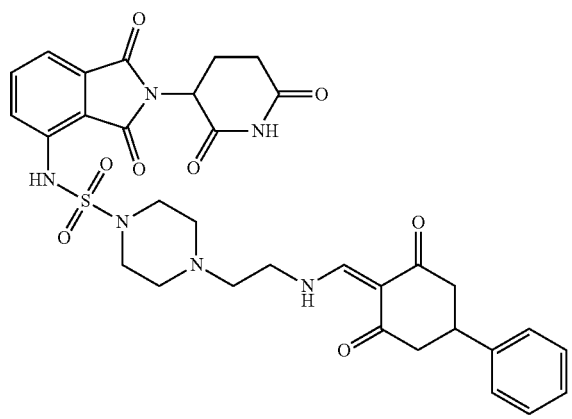 [SMILES: O=C1CCC(N2C(=O)c3cccc(NS(=O)(=O)N4CCN(CCNC=C5C(=O)CC(c6ccccc6)CC5=O)CC4)c3C2=O)C(=O)N1] | 71 |
| 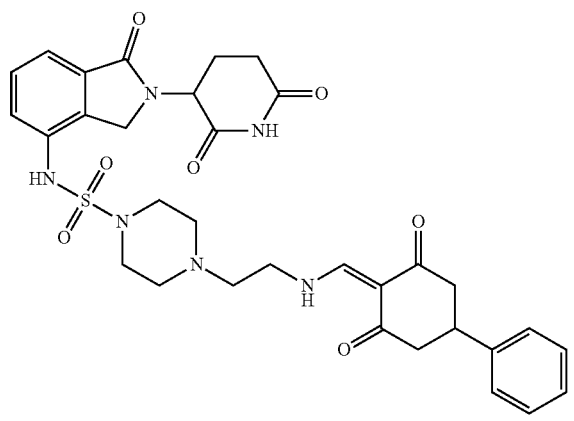 [SMILES: O=C1CCC(N2Cc3c(NS(=O)(=O)N4CCN(CCNC=C5C(=O)CC(c6ccccc6)CC5=O)CC4)cccc3C2=O)C(=O)N1] | 72 |
| 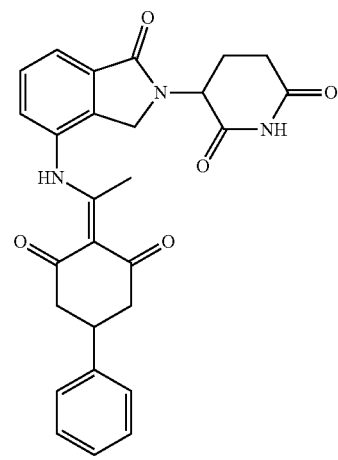 [SMILES: CC(Nc1cccc2c1CN(C1CCC(=O)NC1=O)C2=O)=C1C(=O)CC(c2ccccc2)CC1=O] | 73 |

| Compound | |
|---|---|
| 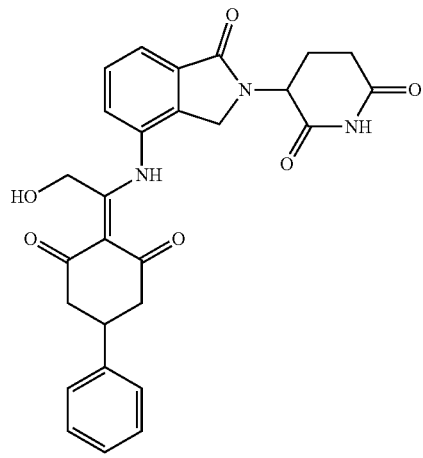 [SMILES: O=C1CCC(N2Cc3c(NC(CO)=C4C(=O)CC(c5ccccc5)CC4=O)cccc3C2=O)C(=O)N1] | 74 |
| 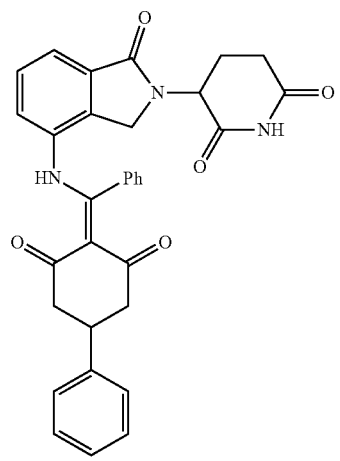 | 75 |
| 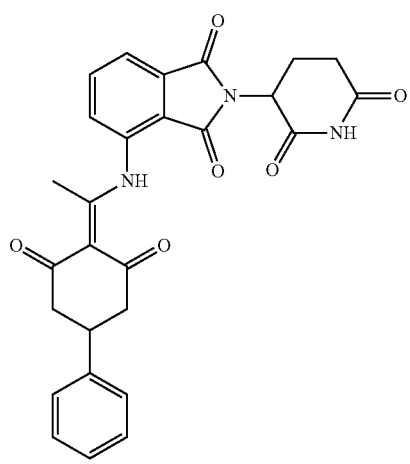 [SMILES: CC(Nc1cccc2c1C(=O)N(C1CCC(=O)NC1=O)C2=O)=C1C(=O)CC(c2ccccc2)CC1=O] | 76 |

-continued
| Compound |
|---|
| 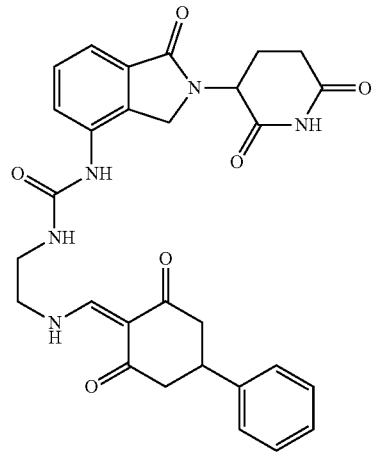 [SMILES: O=C1CCC(N2Cc3c(NC(=O)NCCNC=C4C(=O)CC(c5ccccc5)CC4=O)cccc3C2=O)C(=O)N1] 77 |
| 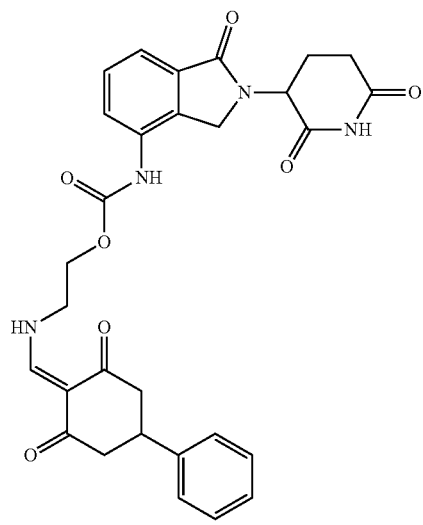 [SMILES: O=C1CCC(N2Cc3c(NC(=O)OCCNC=C4C(=O)CC(c5ccccc5)CC4=O)cccc3C2=O)C(=O)N1] 78 |
| 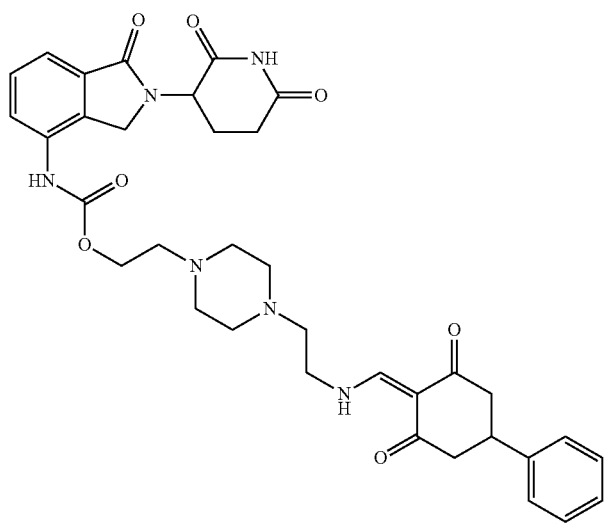 [SMILES: O=C1CCC(N2Cc3c(NC(=O)OCCN4CCN(CCNC=C5C(=O)CC(c6ccccc6)CC5=O)CC4)cccc3C2=O)C(=O)N1] 79 |

| Compound | |
|---|---|
| 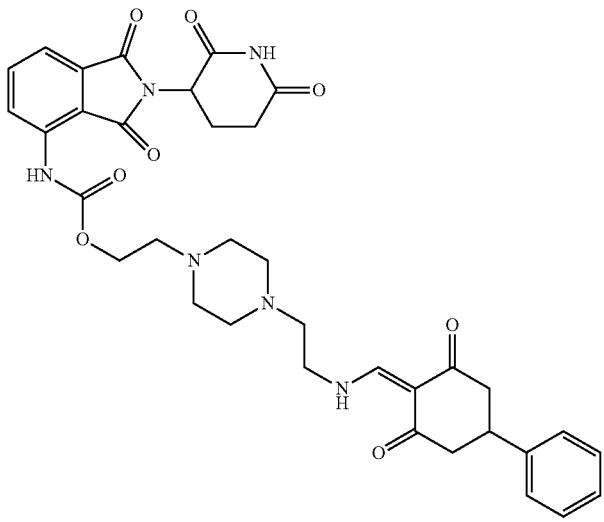 [SMILES: O=C1CCC(N2C(=O)c3cccc(NC(=O)OCCN4CCN(CCNC=C5C(=O)CC(c6ccccc6)CC5=O)CC4)c3C2=O)C(=O)N1] | 80 |
| 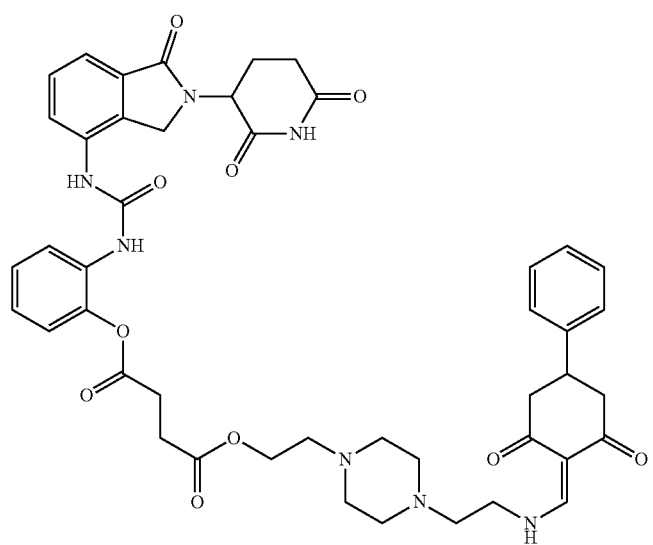 [SMILES: O=C1CCC(N2Cc3c(NC(=O)Nc4ccccc4OC(=O)CCC(=O)OCCN4CCN(CCNC=C5C(=O)CC(c6ccccc6)CC5=O)CC4)cccc3C2=O)C(=O)N1] | 81 |
| 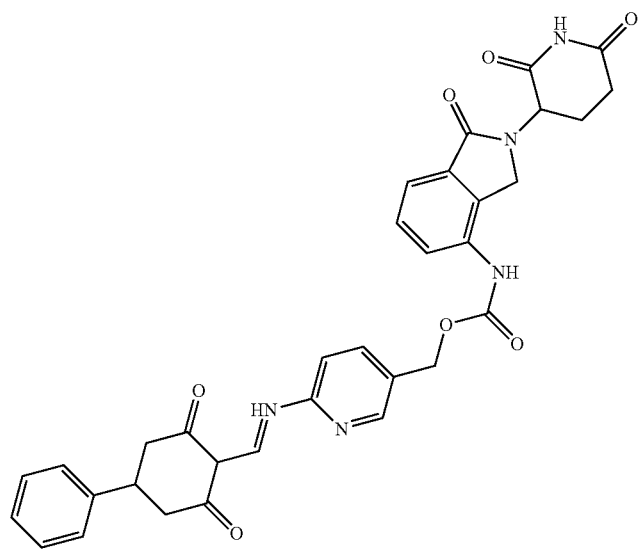 [SMILES: O=C1CCC(N2Cc3c(NC(=O)OCc4ccc(/N=C/C5C(=O)CC(c6ccccc6)CC5=O)nc4)cccc3C2=O)C(=O)N1] | 82 |

| Compound |
|---|
| 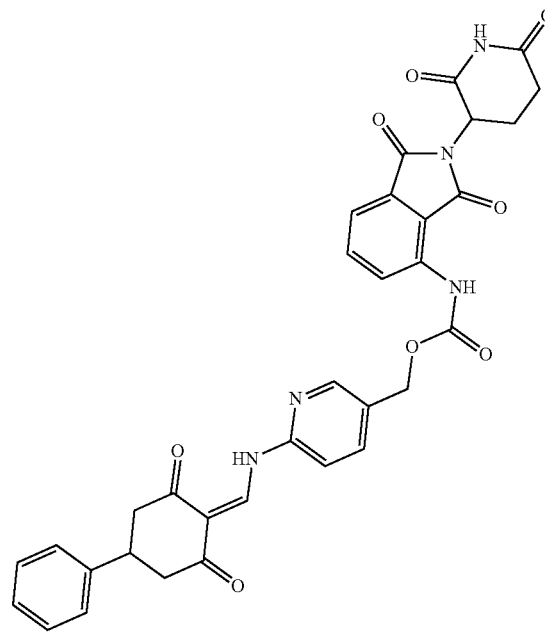 83 |
| 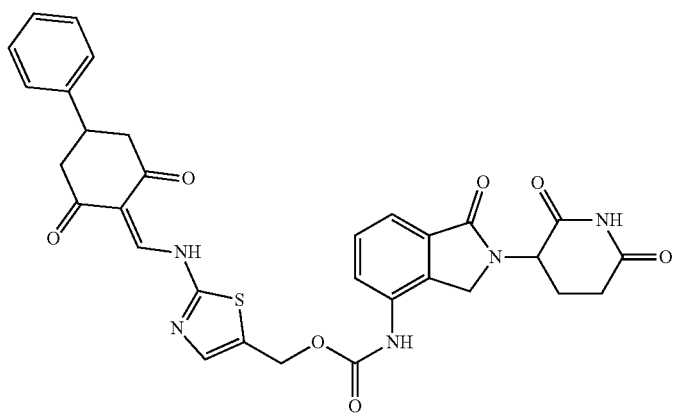 [SMILES: O=C1CCC(N2Cc3c(NC(=O)OCc4cnc(NC=C5C(=O)CC(c6ccccc6)CC5=O)s4)cccc3C2=O)C(=O)N1] 84 |
| 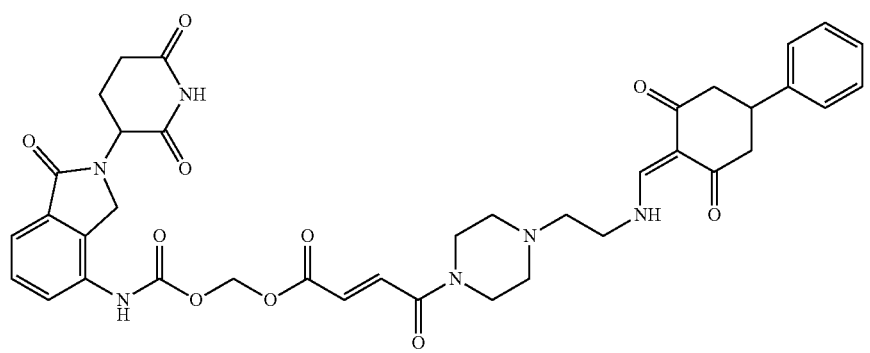 [SMILES: O=C1CCC(N2Cc3c(NC(=O)OCOC(=O)/C=C/C(=O)N4CCN(CCNC=C5C(=O)CC(c6ccccc6)CC5=O)CC4)cccc3C2=O)C(=O)N1] 85 |

| Compound | |
|---|---|
| 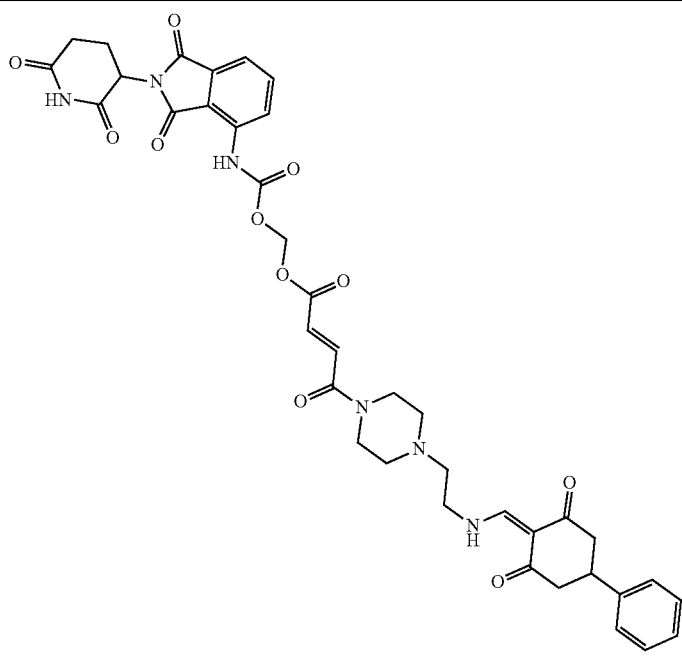 | 86 |
| 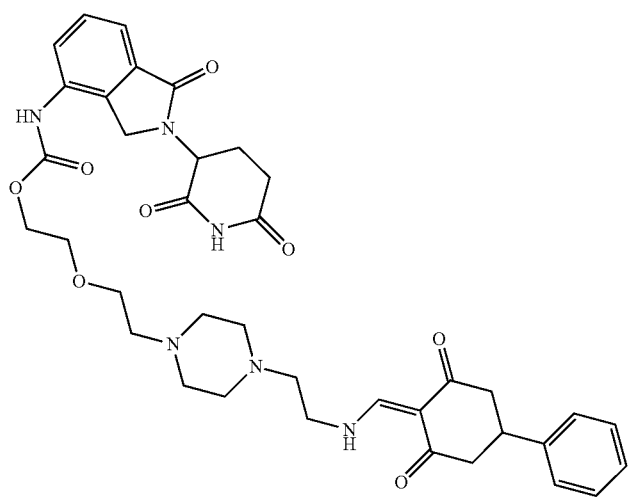 [SMILES: O=C1CCC(N2Cc3c(NC(=O)OCCOCCN4CCN(CCNC=C5C(=O)CC(c6ccccc6)CC5=O)CC4)cccc3C2=O)C(=O)N1] | 87 |
| 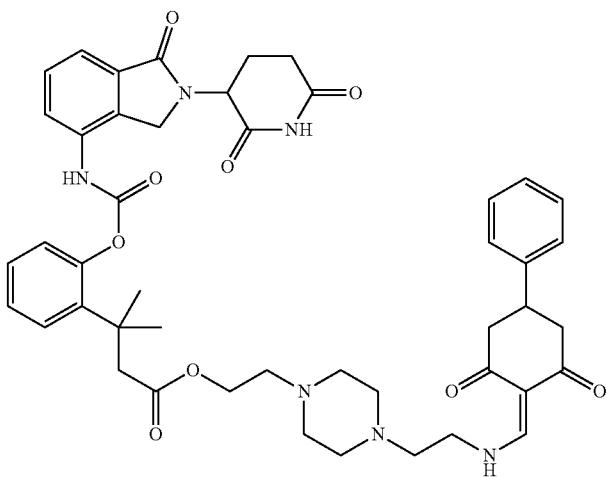 [SMILES: CC(C)(CC(=O)OCCN1CCN(CCNC=C2C(=O)CC(c3ccccc3)CC2=O)CC1)c1ccccc1OC(=O)Nc1cccc2c1CN(C1CCC(=O)NC1=O)C2=O] | 88 |

| Compound |
|---|
| 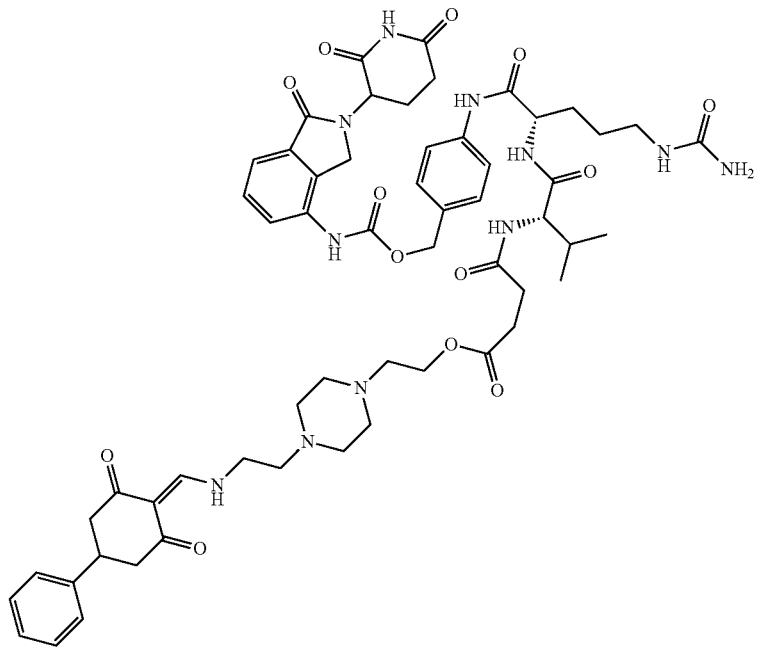 [SMILES: CC(C)[C@H](NC(=O)CCC(=O)OCCN1CCN(CCNC=C2C(=O)CC(c3ccccc3)CC2=O)CC1)C(=O)N[C@@H](CCCNC(N)=O)C(=O)Nc1ccc(COC(=O)Nc2cccc3c2CN(C2CCC(=O)NC2=O)C3=O)cc1] 89 |
| 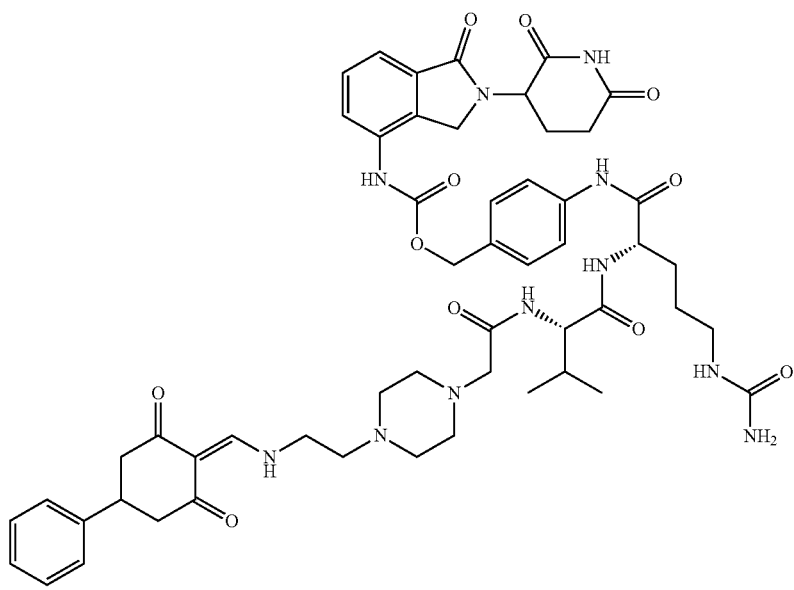 [SMILES: CC(C)[C@H](NC(=O)CN1CCN(CCNC=C2C(=O)CC(c3ccccc3)CC2=O)CC1)C(=O)N[C@@H](CCCNC(N)=O)C(=O)Nc1ccc(COC(=O)Nc2cccc3c2CN(C2CCC(=O)NC2=O)C3=O)cc1] 90 |
| 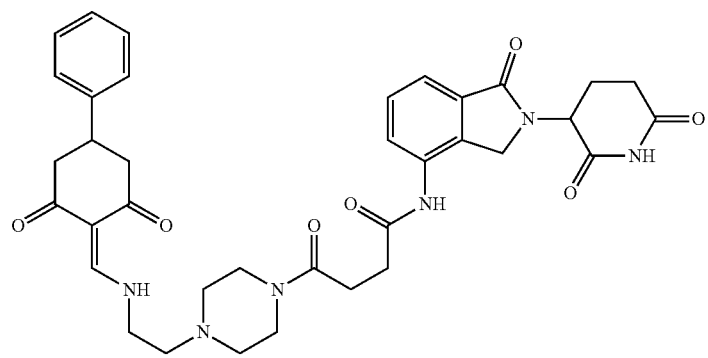 [SMILES: O=C1CCC(N2Cc3c(NC(=O)CCC(=O)N4CCN(CCNC=C5C(=O)CC(c6ccccc6)CC5=O)CC4)cccc3C2=O)C(=O)N1] 91 |

-continued
Compound
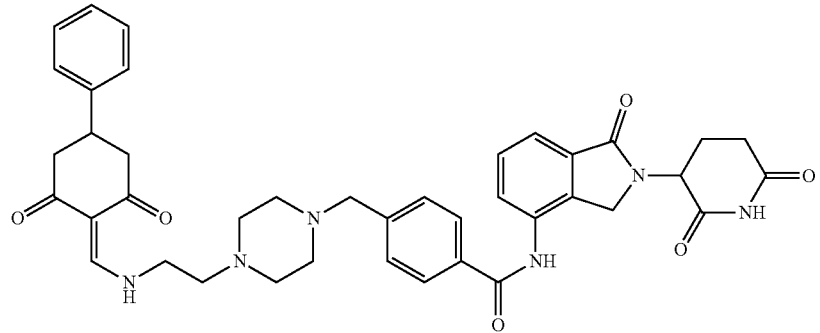 [SMILES: O=C1CCC(N2Cc3c(NC(=O)c4ccc(CN5CCN(CCNC=C6C(=O)CC(c7ccccc7)CC6=O)CC5)cc4)cccc3C2=O)C(=O)N1]
92
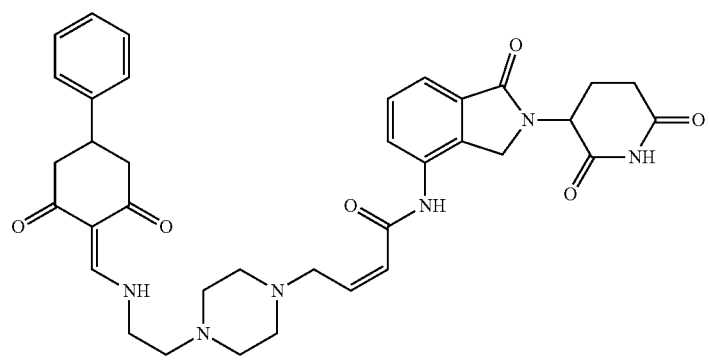 [SMILES: O=C(/C=C\CN1CCN(CCNC=C2C(=O)CC(c3ccccc3)CC2=O)CC1)Nc1cccc2c1CN(C1CCC(=O)NC1=O)C2=O]
93
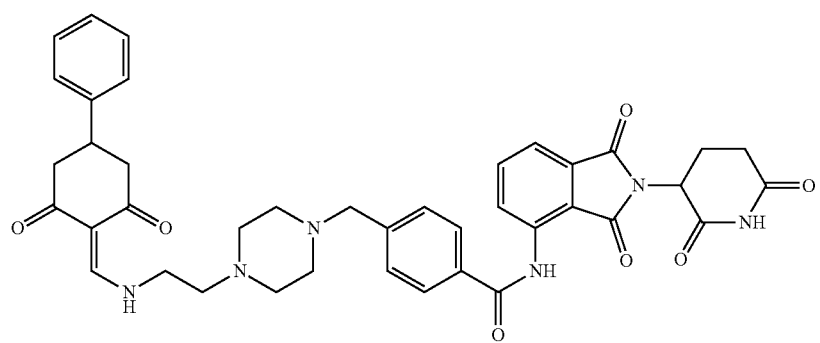 [SMILES: O=C1CCC(N2C(=O)c3cccc(NC(=O)c4ccc(CN5CCN(CCNC=C6C(=O)CC(c7ccccc7)CC6=O)CC5)cc4)c3C2=O)C(=O)N1]
94

| Compound | |
|---|---|
| 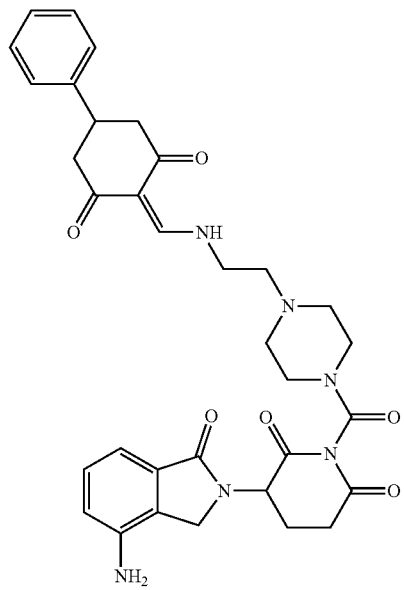 [SMILES: Nc1cccc2c1CN(C1CCC(=O)N(C(=O)N3CCN(CCNC=C4C(=O)CC(c5ccccc5)CC4=O)CC3)C1=O)C2=O] | 100 |
| 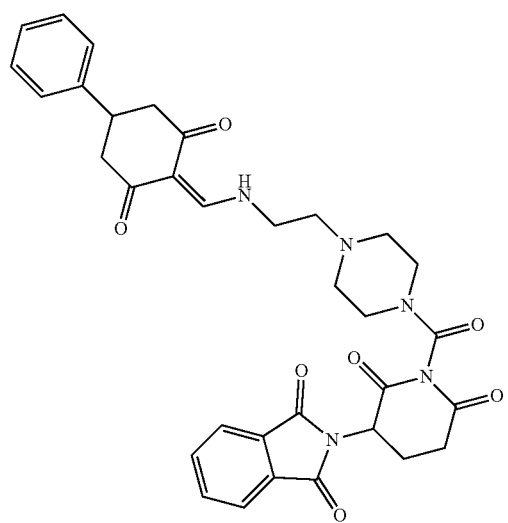 [SMILES: O=C1CC(c2ccccc2)CC(=O)C1=CNCCN1CCN(C(=O)N2C(=O)CCC(N3C(=O)c4ccccc4C3=O)C2=O)CC1] | 101 |
| 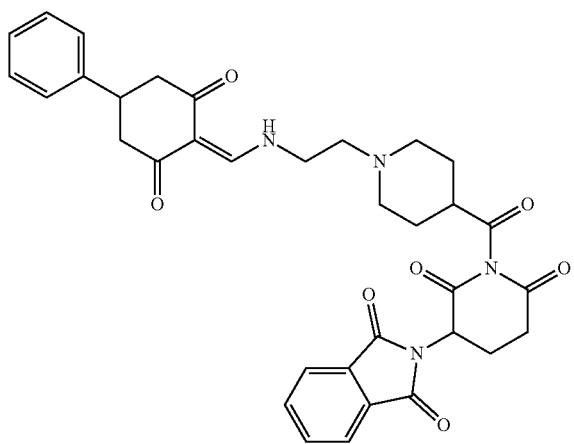 [SMILES: O=C1CC(c2ccccc2)CC(=O)C1=CNCCN1CCC(C(=O)N2C(=O)CCC(N3C(=O)c4ccccc4C3=O)C2=O)CC1] | 102 |

-continued
| Compound |
|---|
| 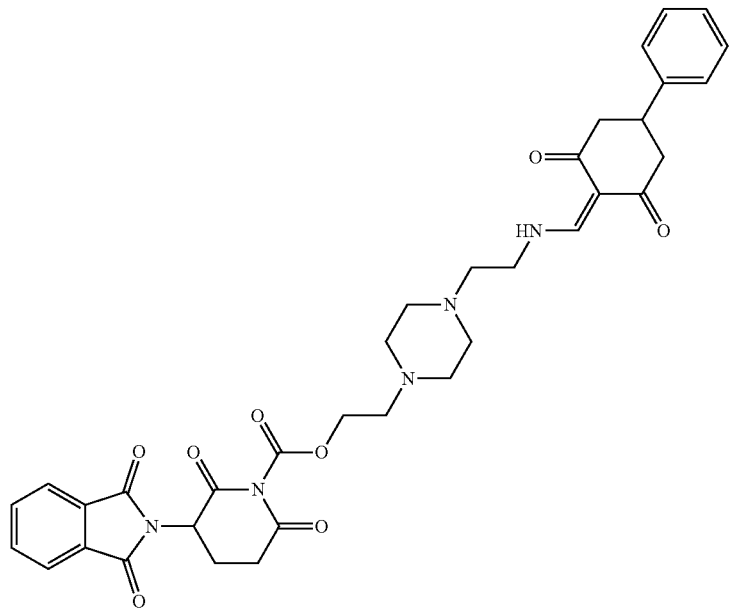 [SMILES: O=C1CC(c2ccccc2)CC(=O)C1=CNCCN1CCN(CCOC(=O)N2C(=O)CCC(N3C(=O)c4ccccc4C3=O)C2=O)CC1] 103 |
| 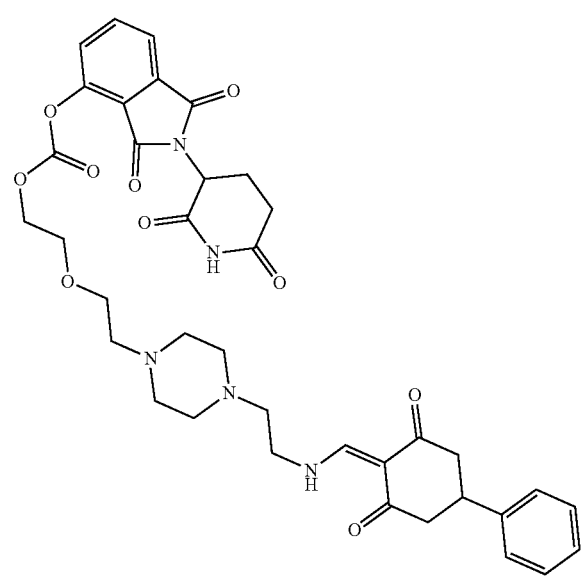 [SMILES: O=C1CCC(N2C(=O)c3cccc(OC(=O)OCCOCCN4CCN(CCNC=C5C(=O)CC(c6ccccc6)CC5=O)CC4)c3C2=O)C(=O)N1] 104 |

-continued
| Compound |
|---|
| 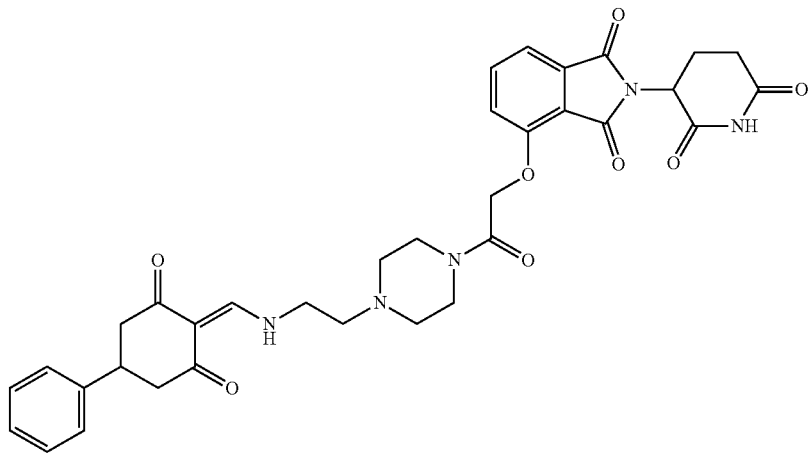 [SMILES: O=C1CCC(N2C(=O)c3cccc(OCC(=O)N4CCN(CCNC=C5C(=O)CC(c6ccccc6)CC5=O)CC4)c3C2=O)C(=O)N1] 105 |
| 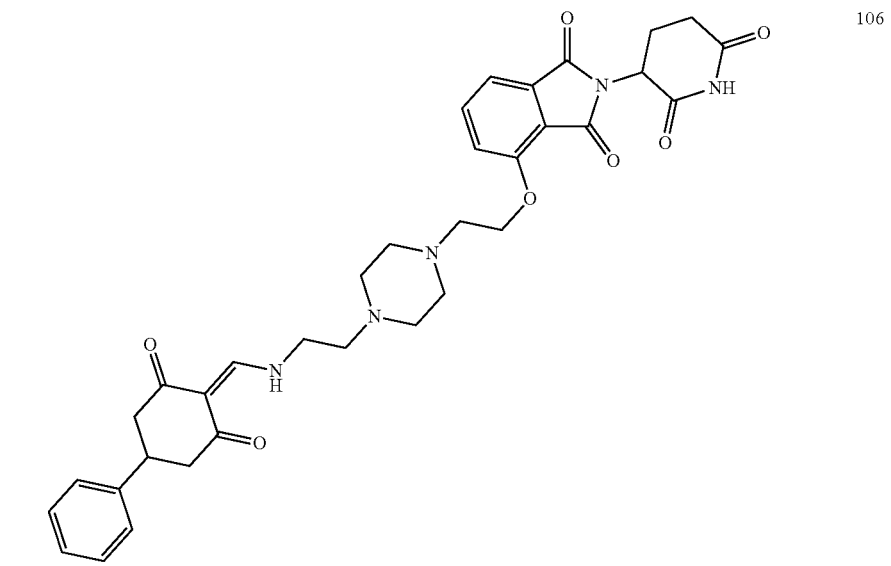 106 |
| 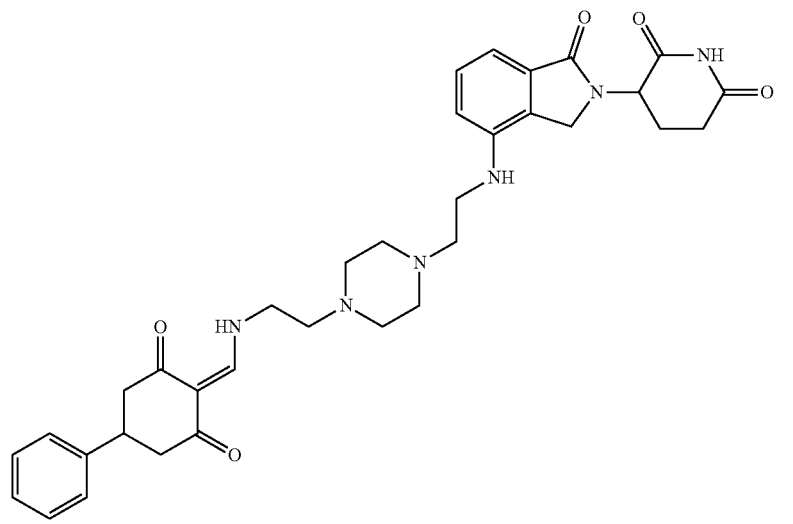 [SMILES: O=C1CCC(N2Cc3c(NCCN4CCN(CCNC=C5C(=O)CC(c6ccccc6)CC5=O)CC4)cccc3C2=O)C(=O)N1] 107 |

-continued
| Compound |
|---|
| 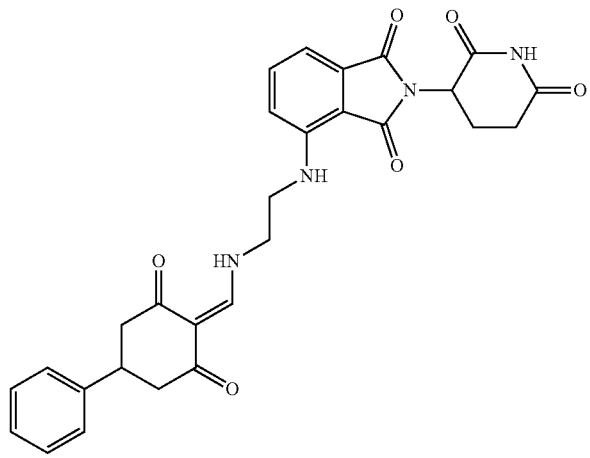 [SMILES: O=C1CCC(N2C(=O)c3cccc(NCCNC=C4C(=O)CC(c5ccccc5)CC4=O)c3C2=O)C(=O)N1] 108 |
| 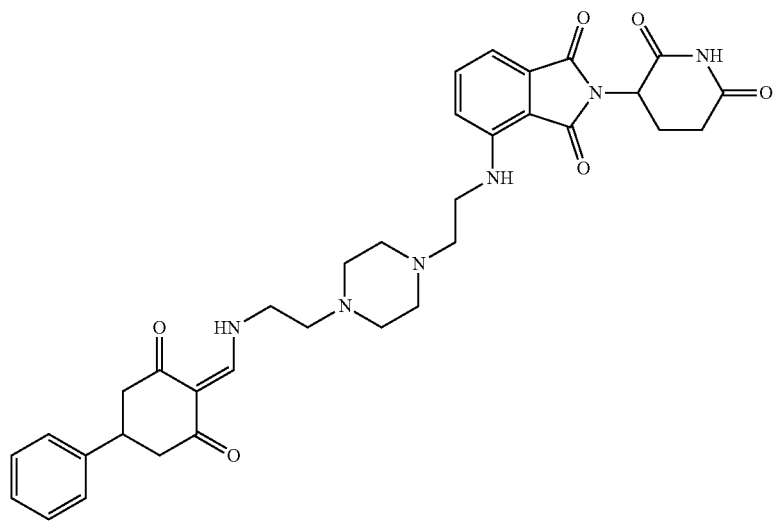 [SMILES: O=C1CCC(N2C(=O)c3cccc(NCCN4CCN(CCNC=C5C(=O)CC(c6ccccc6)CC5=O)CC4)c3C2=O)C(=O)N1] 109 |
| 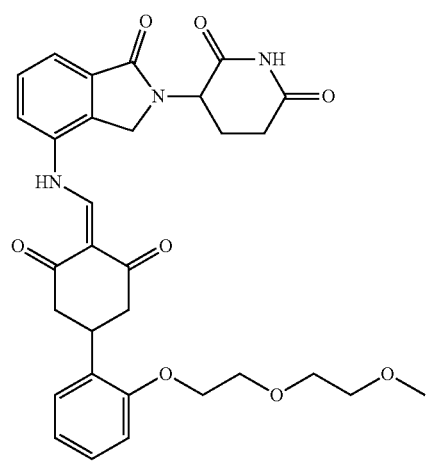 [SMILES: COCCOCCOc1ccccc1C1CC(=O)C(=CNc2cccc3c2CN(C2CCC(=O)NC2=O)C3=O)C(=O)C1] 110 |

-continued
| Compound | |
|---|---|
| 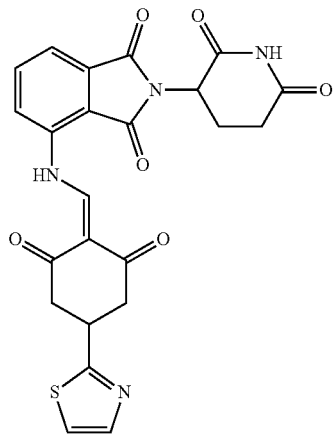 [SMILES: O=C1CCC(N2C(=O)c3cccc(NC=C4C(=O)CC(c5nccs5)CC4=O)c3C2=O)C(=O)N1] | 111 |
| 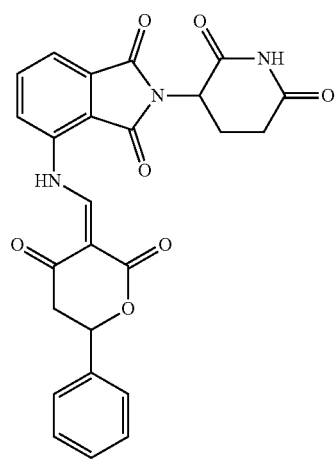 | 112 |
| 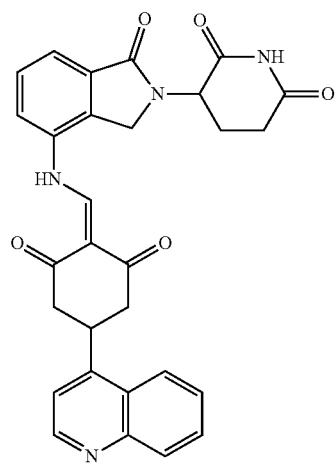 [SMILES: O=C1CCC(N2Cc3c(NC=C4C(=O)CC(c5ccnc6ccccc56)CC4=O)cccc3C2=O)C(=O)N1] | 113 |

| Compound | |
|---|---|
| 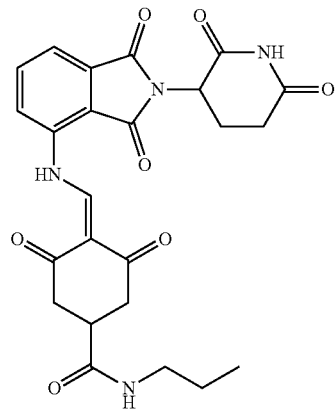 [SMILES: CCCNC(=O)C1CC(=O)C(=CNc2cccc3c2C(=O)N(C2CCC(=O)NC2=O)C3=O)C(=O)C1] | 114 |
| 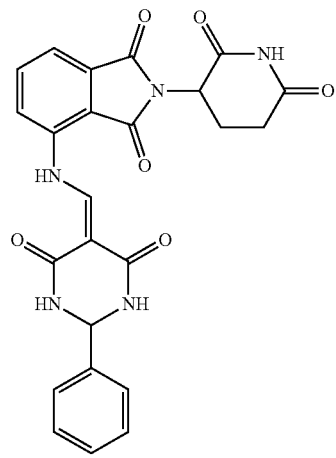 | 115 |
| 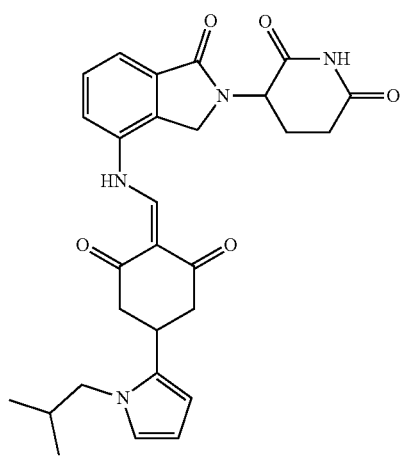 [SMILES: CC(C)Cn1cccc1C1CC(=O)C(=CNc2cccc3c2CN(C2CCC(=O)NC2=O)C3=O)C(=O)C1] | 116 |

| Compound | |
|---|---|
| 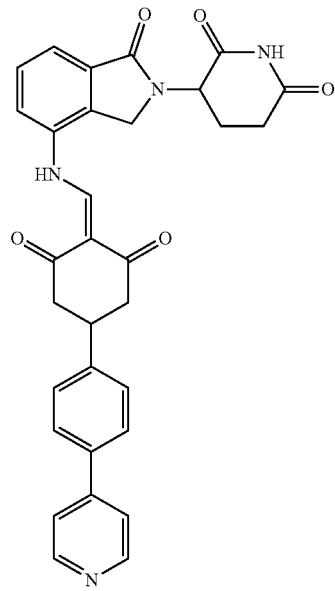 [SMILES: O=C1CCC(N2Cc3c(NC=C4C(=O)CC(c5ccc(-c6ccncc6)cc5)CC4=O)cccc3C2=O)C(=O)N1] | 117 |
| 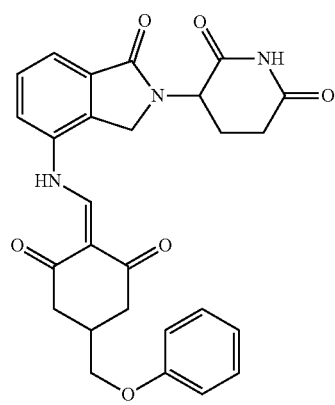 [SMILES: O=C1CCC(N2Cc3c(NC=C4C(=O)CC(COc5ccccc5)CC4=O)cccc3C2=O)C(=O)N1] | 118 |
| 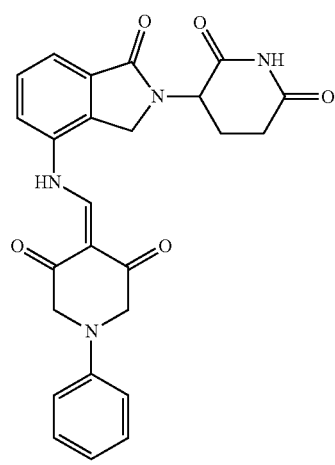 [SMILES: O=C1CCC(N2Cc3c(NC=C4C(=O)CN(c5ccccc5)CC4=O)cccc3C2=O)C(=O)N1] | 119 |

| Compound | |
|---|---|
| 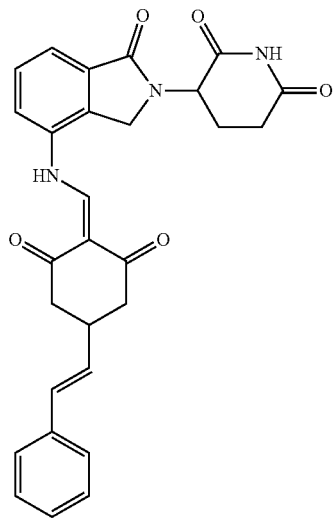 [SMILES: O=C1CCC(N2Cc3c(NC=C4C(=O)CC(/C=C/c5ccccc5)CC4=O)cccc3C2=O)C(=O)N1] | 120 |
| 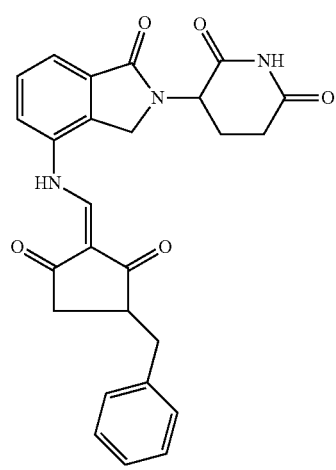 [SMILES: O=C1CCC(N2Cc3c(N/C=C4\C(=O)CC(Cc5ccccc5)C4=O)cccc3C2=O)C(=O)N1] | 121 |
| 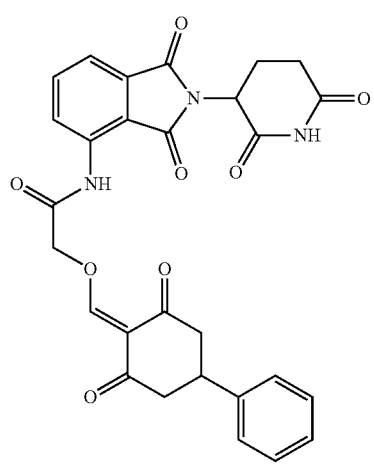 | 122 |

| Compound | |
|---|---|
| 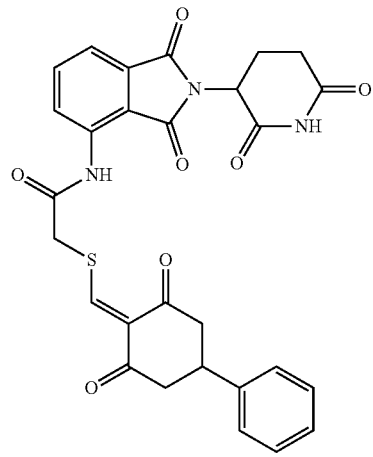 | 123 |
| 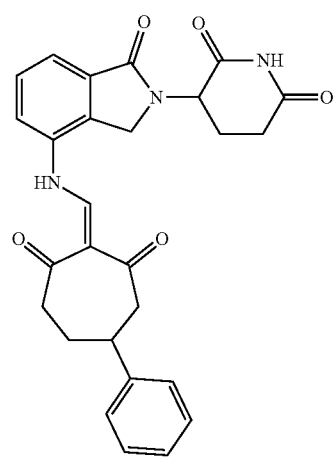 [SMILES: O=C1CCC(N2Cc3c(N/C=C4\C(=O)CCC(c5ccccc5)CC4=O)cccc3C2=O)C(=O)N1] | 124 |
| 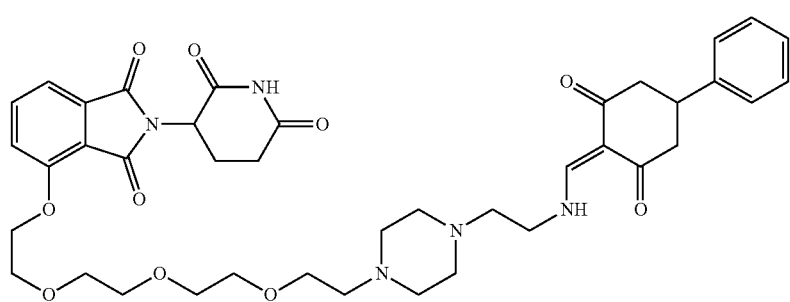 [SMILES: O=C1CCC(N2C(=O)c3cccc(OCCOCCOCCOCCN4CCN(CCNC=C5C(=O)CC(c6ccccc6)CC5=O)CC4)c3C2=O)C(=O)N1] | 125 |

-continued
| Compound |
|---|
| 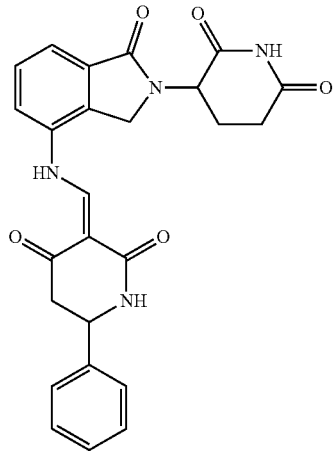 [SMILES: O=C1CCC(N2Cc3c(N/C=C4\C(=O)CC(c5ccccc5)NC4=O)cccc3C2=O)C(=O)N1] 126 |
| 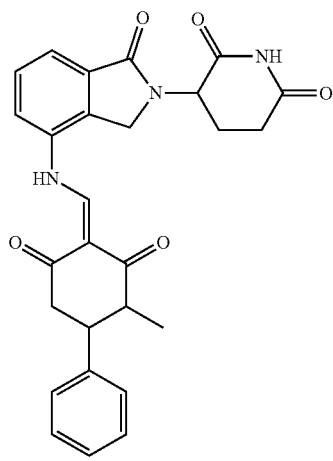 [SMILES: CC1C(=O)/C(=C/Nc2cccc3c2CN(C2CCC(=O)NC2=O)C3=O)C(=O)CC1c1ccccc1] 127 |
| 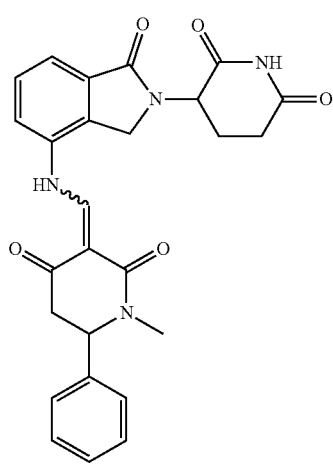 [SMILES: CN1C(=O)C(=CNc2cccc3c2CN(C2CCC(=O)NC2=O)C3=O)C(=O)CC1c1ccccc1] 128 |

| Compound | |
|---|---|
| 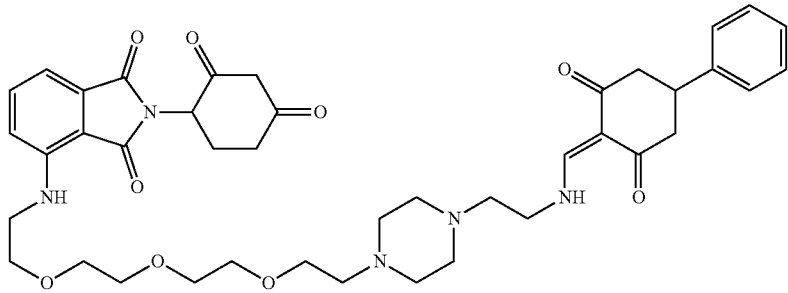 [SMILES: O=C1CCC(N2C(=O)c3cccc(NCCOCCOCCOCCN4CCN(CCNC=C5C(=O)CC(c6ccccc6)CC5=O)CC4)c3C2=O)C(=O)C1] | 129 |
| 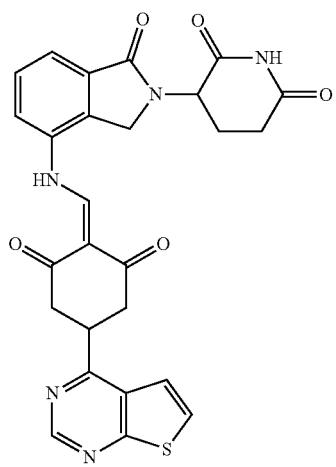 [SMILES: O=C1CCC(N2Cc3c(NC=C4C(=O)CC(c5ncnc6sccc56)CC4=O)cccc3C2=O)C(=O)N1] | 130 |
| 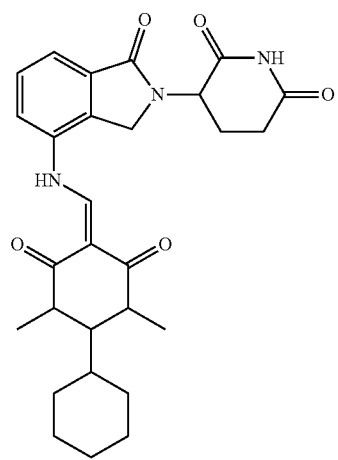 [SMILES: CC1C(=O)C(=CNc2cccc3c2CN(C2CCC(=O)NC2=O)C3=O)C(=O)C(C)C1C1CCCCC1] | 131 |
| 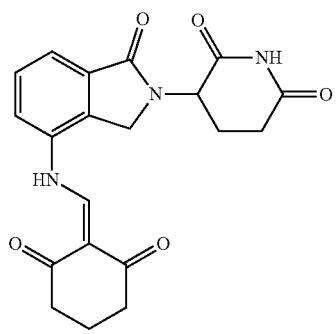 [SMILES: O=C1CCC(N2Cc3c(NC=C4C(=O)CCCC4=O)cccc3C2=O)C(=O)N1] | 132 |

| Compound |
|---|
| 133 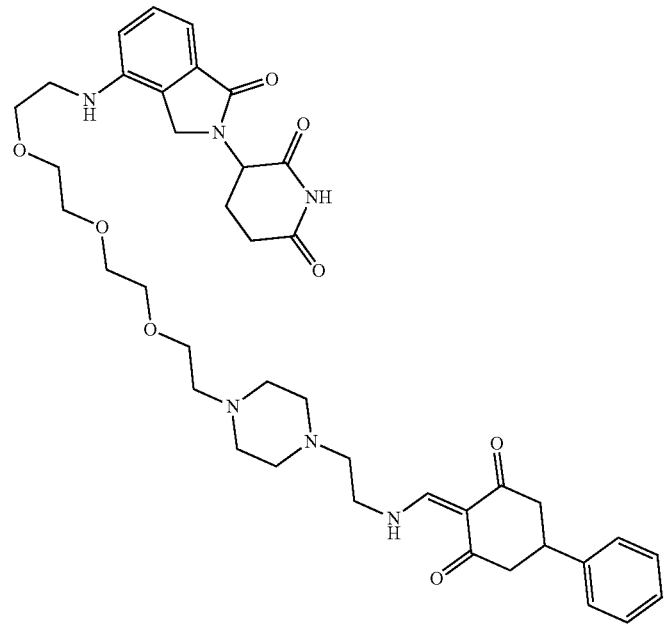 [SMILES: O=C1CCC(N2Cc3c(NCCOCCOCCOCCN4CCN(CCNC=C5C(=O)CC(c6ccccc6)CC5=O)CC4)cccc3C2=O)C(=O)N1] |
| 134 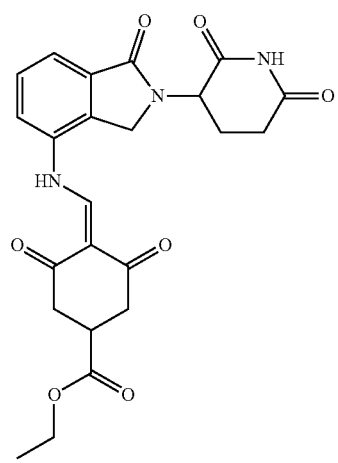 [SMILES: CCOC(=O)C1CC(=O)C(=CNc2cccc3c2CN(C2CCC(=O)NC2=O)C3=O)C(=O)C1] |
| 135 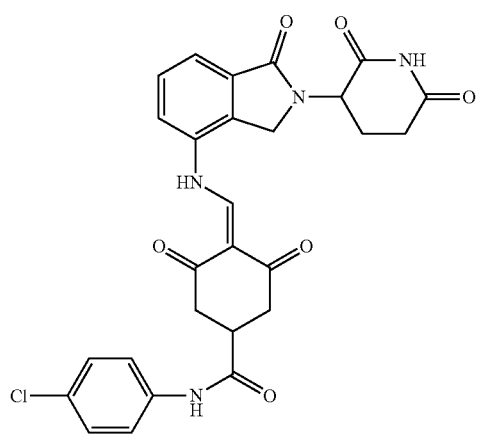 [SMILES: O=C1CCC(N2Cc3c(NC=C4C(=O)CC(C(=O)Nc5ccc(Cl)cc5)CC4=O)cccc3C2=O)C(=O)N1] |

| Compound | |
|---|---|
| 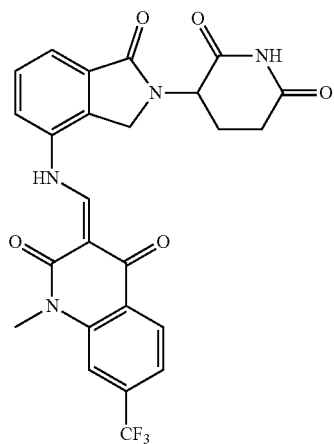 [SMILES: CN1C(=O)/C(=C\Nc2cccc3c2CN(C2CCC(=O)NC2=O)C3=O)C(=O)c2ccc(C(F)(F)F)cc21] | 136 |
| 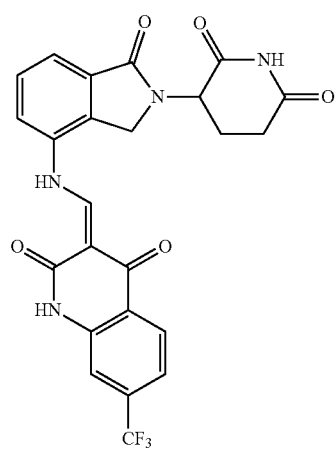 [SMILES: O=C1CCC(N2Cc3c(N/C=C4\C(=O)Nc5cc(C(F)(F)F)ccc5C4=O)cccc3C2=O)C(=O)N1] | 137 |
| 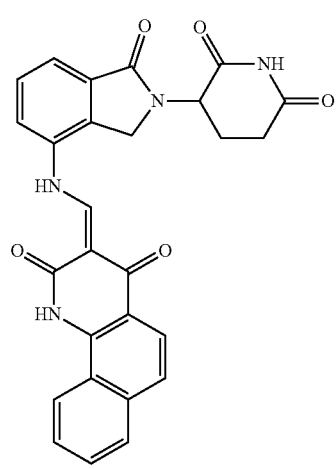 [SMILES: O=C1CCC(N2Cc3c(N/C=C4\C(=O)Nc5c(ccc6ccccc56)C4=O)cccc3C2=O)C(=O)N1] | 138 |

-continued
| Compound | |
|---|---|
| 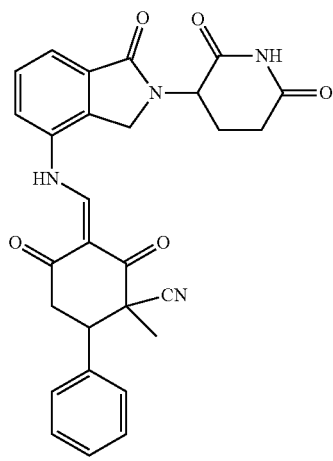 [SMILES: CC1(C#N)C(=O)/C(=C/Nc2cccc3c2CN(C2CCC(=O)NC2=O)C3=O)C(=O)CC1c1ccccc1] | 139 |
| 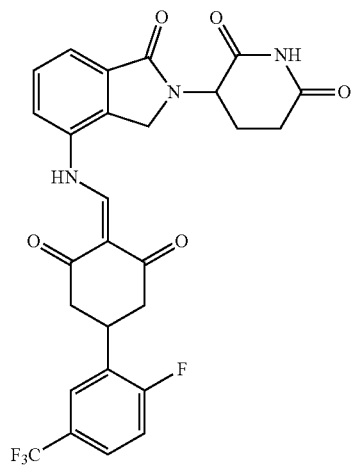 [SMILES: O=C1CCC(N2Cc3c(NC=C4C(=O)CC(c5cc(C(F)(F)F)ccc5F)CC4=O)cccc3C2=O)C(=O)N1] | 140 |
| 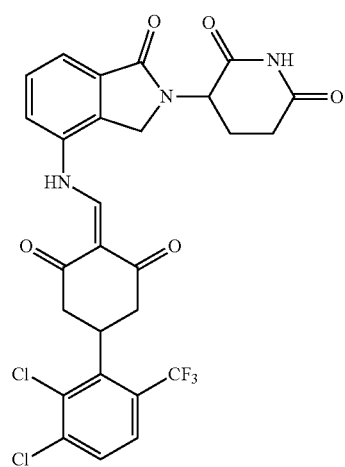 [SMILES: O=C1CCC(N2Cc3c(NC=C4C(=O)CC(c5c(C(F)(F)F)ccc(Cl)c5Cl)CC4=O)cccc3C2=O)C(=O)N1] | 141 |

-continued
| Compound | |
|---|---|
| 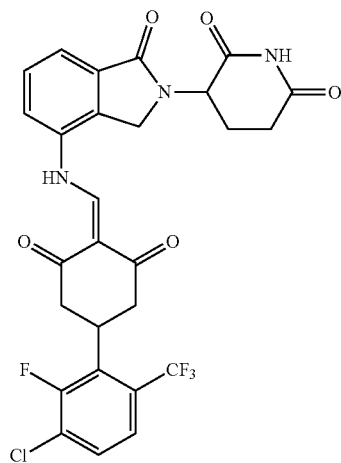 [SMILES: O=C1CCC(N2Cc3c(NC=C4C(=O)CC(c5c(C(F)(F)F)ccc(Cl)c5F)CC4=O)cccc3C2=O)C(=O)N1] | 142 |
| 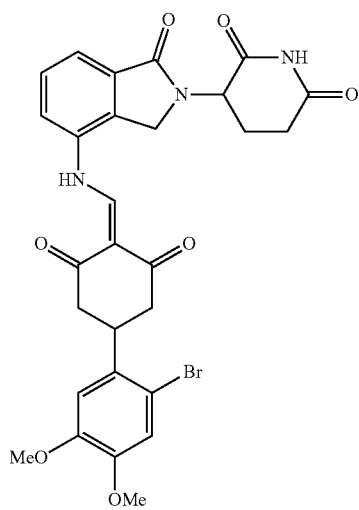 [SMILES: COc1cc(Br)c(C2CC(=O)C(=CNc3cccc4c3CN(C3CCC(=O)NC3=O)C4=O)C(=O)C2)cc1OC] | 143 |
| 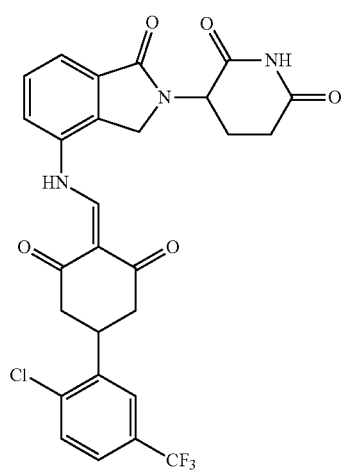 [SMILES: O=C1CCC(N2Cc3c(NC=C4C(=O)CC(c5cc(C(F)(F)F)ccc5Cl)CC4=O)cccc3C2=O)C(=O)N1] | 144 |

| Compound | |
|---|---|
| 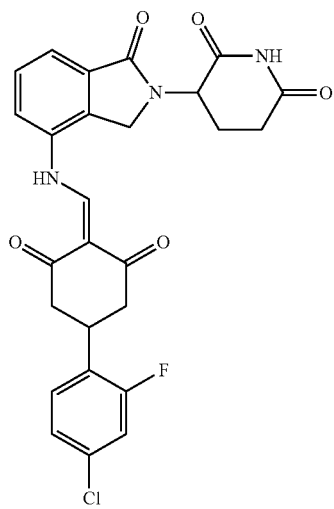 [SMILES: O=C1CCC(N2Cc3c(NC=C4C(=O)CC(c5ccc(Cl)cc5F)CC4=O)cccc3C2=O)C(=O)N1] | 145 |
| 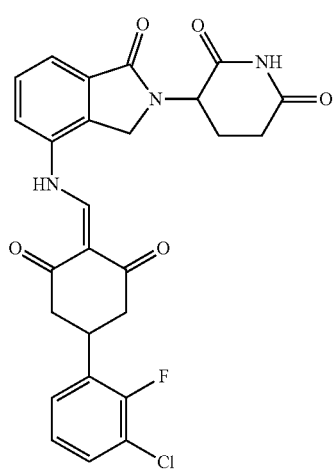 [SMILES: O=C1CCC(N2Cc3c(NC=C4C(=O)CC(c5cccc(Cl)c5F)CC4=O)cccc3C2=O)C(=O)N1] | 146 |
| 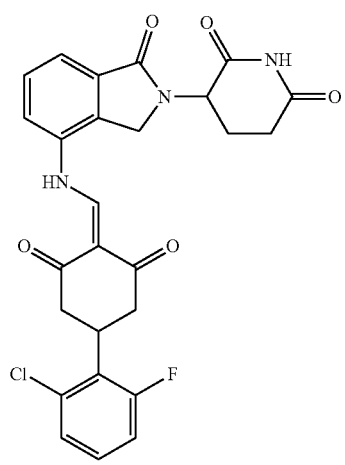 [SMILES: O=C1CCC(N2Cc3c(NC=C4C(=O)CC(c5c(F)cccc5Cl)CC4=O)cccc3C2=O)C(=O)N1] | 147 |

-continued
| Compound | |
|---|---|
| 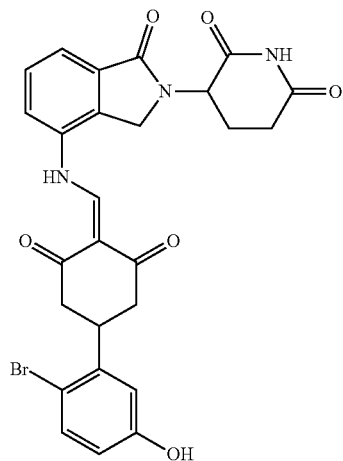 | 148 |
| 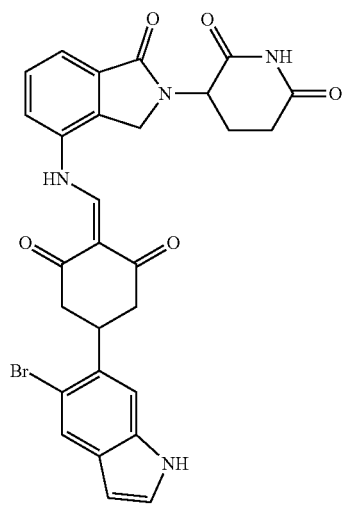 | 149 |
| 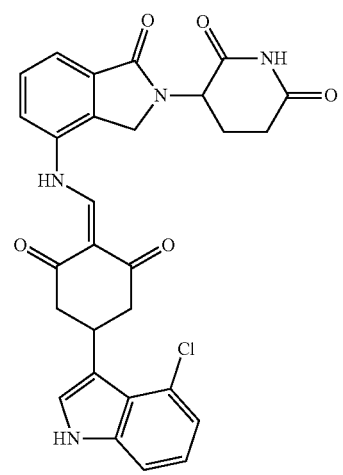 [SMILES: O=C1CCC(N2Cc3c(NC=C4C(=O)CC(c5c[nH]c6cccc(Cl)c56)CC4=O)cccc3C2=O)C(=O)N1] | 150 |

-continued
| Compound | |
|---|---|
| 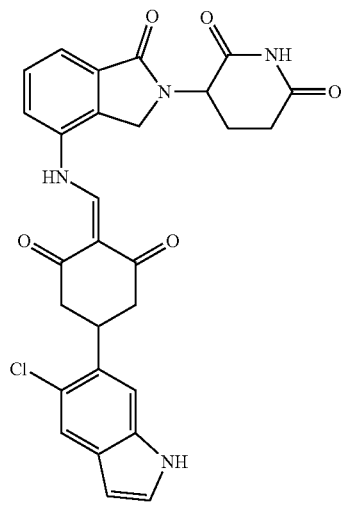 [SMILES: O=C1CCC(N2Cc3c(NC=C4C(=O)CC(c5cc6[nH]ccc6cc5Cl)CC4=O)cccc3C2=O)C(=O)N1] | 151 |
| 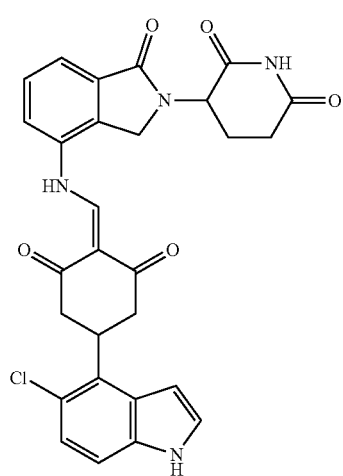 [SMILES: O=C1CCC(N2Cc3c(NC=C4C(=O)CC(c5c(Cl)ccc6[nH]ccc56)CC4=O)cccc3C2=O)C(=O)N1] | 152 |
| 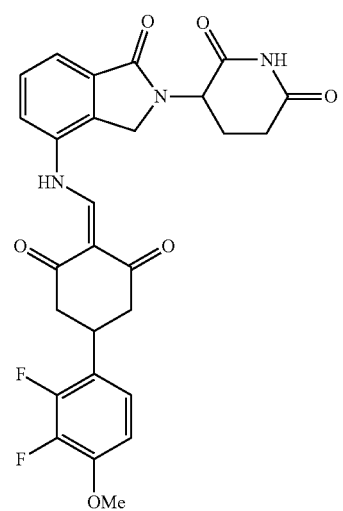 [SMILES: COc1ccc(C2CC(=O)C(=CNc3cccc4c3CN(C3CCC(=O)NC3=O)C4=O)C(=O)C2)c(F)c1F] | 153 |

-continued
| Compound | |
|---|---|
| 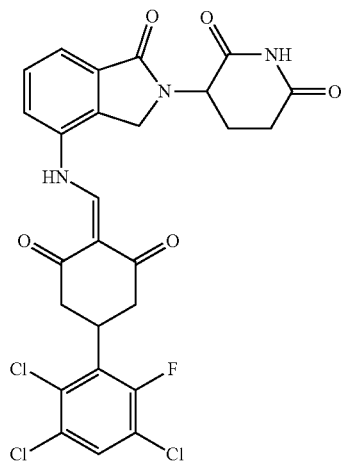 [SMILES: O=C1CCC(N2Cc3c(NC=C4C(=O)CC(c5c(F)c(Cl)cc(Cl)c5Cl)CC4=O)cccc3C2=O)C(=O)N1] | 154 |
| 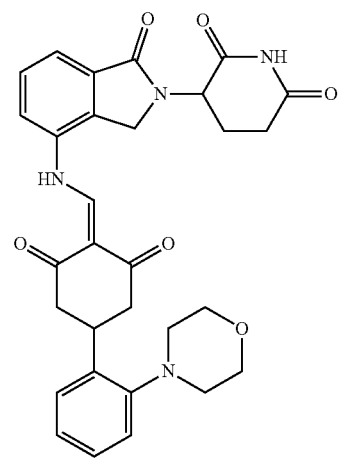 [SMILES: O=C1CCC(N2Cc3c(NC=C4C(=O)CC(c5ccccc5N5CCOCC5)CC4=O)cccc3C2=O)C(=O)N1] | 155 |
| 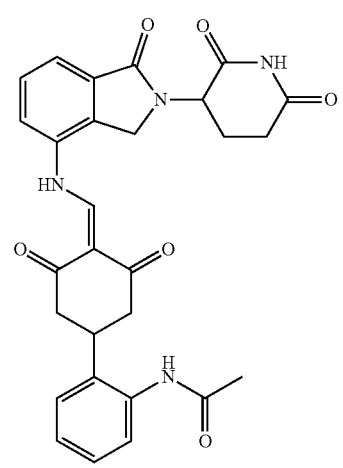 [SMILES: CC(=O)Nc1ccccc1C1CC(=O)C(=CNc2cccc3c2CN(C2CCC(=O)NC2=O)C3=O)C(=O)C1] | 156 |

| Compound | |
|---|---|
| 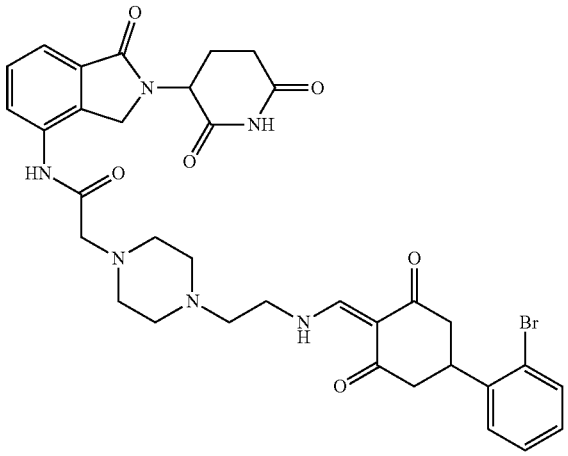 [SMILES: O=C1CCC(N2Cc3c(NC(=O)CN4CCN(CCNC=C5C(=O)CC(c6ccccc6Br)CC5=O)CC4)cccc3C2=O)C(=O)N1] | 157 |
| 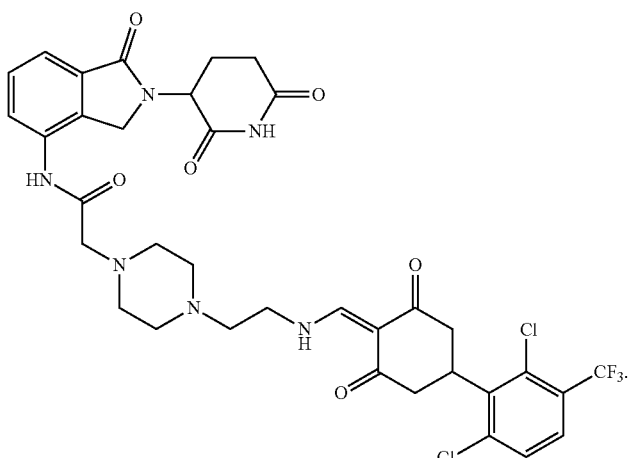 | 158 |

The present invention also provides a pharmaceutical composition comprising the compound or a pharmaceutically acceptable salt thereof of the present invention, and optionally a pharmaceutically acceptable excipient.

The present invention also provides the use of the compound or a pharmaceutically acceptable salt thereof of the present invention in the preparation of an autophagy modulator, particularly a mammalian ATG8 homolog modulator, for preventing or treating a disease associated with autophagy.

The present invention also provides a method for modulating autophagy, comprising administering, to a subject in need thereof, the compound or a pharmaceutically acceptable salt thereof according to the present invention, or the pharmaceutical composition according to the present invention.

The present invention also provides a method for modulating a mammalian ATG8 homolog, comprising administering, to a subject in need thereof, the compound or a pharmaceutically acceptable salt thereof according to the present invention, or the pharmaceutical composition according to the present invention.

The present invention also provides a method for preventing or treating a disease associated with autophagy, comprising administering, to a subject in need thereof, the compound or a pharmaceutically acceptable salt thereof according to the present invention, or the pharmaceutical composition according to the present invention.

The diseases associated with autophagy are selected from the group consisting of tumors, cancers, cardiovascular diseases, autoimmune diseases, neurodegenerative diseases, hypertension, bone tissue cell and bone diseases, Crohn's disease, acute kidney injury, cerebral ischemia, retinal disease, bronchial asthma, Vici syndrome, amyotrophic lateral sclerosis and infectious diseases, where the cancers are selected from the group consisting of liver cancer, lung cancer, pancreatic cancer, breast cancer, cervical cancer, endometrial cancer, colorectal cancer, gastric cancer, lung cancer, nasopharyngeal carcinoma, ovarian cancer, prostate cancer, leukemia, lymphoma, myeloma, and preferably lymphoma, multiple myeloma, leukemia, lung cancer, breast cancer and pancreatic cancer.

DETAILED DESCRIPTION OF THE PREFERRED EMBODIMENTS

Figure 1:
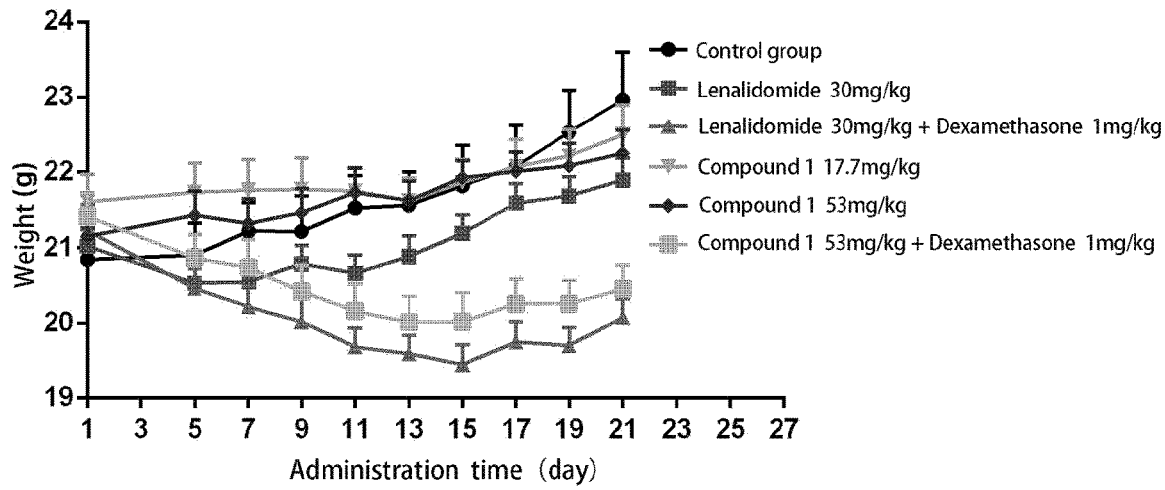
FIG. 1 shows the body weight vs time of each group of mice in the in-vivo pharmacodynamic test in Example 25 of the present invention.

The present invention will be described in detail below. Of course, various corresponding changes and modifications can be made by those skilled in the art based on the disclosure of the present invention without departing from the spirit and the essence of the present invention, which are contemplated in the scope of protection as defined by the appended claims of the present invention.

The terms used in the present invention have their general meaning in the art, and in the case of conflict, the definitions in this application apply. The chemical names, generic names and chemical structures are used interchangeably to describe the same structure. These definitions apply regardless of whether they are used alone or in combination with other terms. Thus, the definition of "alkyl" applies to the "alkyl" and the "alkyl" moiety of "hydroxyl alkyl", "haloalkyl", "aryl alkyl", "alkyl aryl", "alkoxy" and the like.

"Pharmaceutical composition" means a composition suitable for administration to a patient. The composition may contain a single compound of the present invention, a mixture of the compounds of the present invention, a salt, a solvate, a prodrug, an isomer or a tautomer of the compound of the present invention, or the compound of the present invention in combination with one or more pharmaceutically acceptable carriers or excipients. The "subjects" include humans and non-human animals. The pharmaceutical composition may be in various forms such as tablets, capsules, powders, syrups, solutions, suspensions, aerosols, and the like, and may be present in a suitable solid or liquid carrier or diluent and in a sterilized container suitable for injection or infusion.

Various dosage forms of the pharmaceutical composition of the present invention can be prepared according to conventional preparation methods in the pharmaceutical field. The formulation of the preparation comprises, in a unit dosage, 0.05-200 mg of the compound of General Formula (I), and preferably 0.1-100 mg of the compound of General Formula (I).

The compound and pharmaceutical composition of the present invention can be used clinically in mammals, including humans and animals, and can be given through the routes of administration including oral, intranasal, transdermal, transpulmonary, or gastrointestinal tract administration, and most preferably oral administration. The most preferred daily dose is 0.01-200 mg/kg body weight in a single dose, or 0.01-100 mg/kg body weight in divided doses. Regardless of the route of administration, the optimal dosage for an individual depends on the particular treatment. Generally, the most suitable dose is found by starting with a small dose, and then gradually increasing the dose.

"Halo" refers to fluoro, chloro, bromo, or iodo.

"Alkyl" refers to an aliphatic saturated hydrocarbon group, and is preferably a linear or branched alkyl group having 1 to 10 carbon atoms, preferably a linear or branched alkyl group having 1 to 6 carbon atoms, and more preferably a linear or branched alkyl group having 1 to 4 carbon atoms. "Branched" means that one or more alkyl groups having 1 to 4 carbon atoms such as methyl, ethyl or propyl is/are attached to a linear alkyl group. Preferred alkyl groups include, but are not limited to, methyl, ethyl, n-propyl, isopropyl, n-butyl, isobutyl, t-butyl groups and the like.

"Haloalkyl" refers to an alkyl group as defined above, where one or more hydrogen atoms in the alkyl group are substituted with halo as defined above.

"Heteroalkyl" means an alkyl group as defined above, where one or more carbon atoms in the alkyl group are replaced by groups independently selected from —O—, —S—, —(S=O)—, —(O=S=O)—, —N(H) and —N—. Preferably heteroalkyl groups include, but are not limited to, —O— alkyl, —S— alkyl, —(S=O)— alkyl, —(O=S=O)— alkyl, —N(H) alkyl, —N(alkyl)$_2$, and the like.

"Alkenyl" means an aliphatic hydrocarbon group containing at least one carbon-carbon double bond, which may be linear or branched and comprises 2 to 10 carbon atoms, preferably 2 to 6 carbon atoms, and more preferably 2 to 4 carbon atoms in a linear or branched chain. "Branched" means that one or more lower alkyl groups is/are attached to a linear alkenyl chain. Preferably alkenyl groups include, but are not limited to, ethenyl, propenyl, n-butenyl, 3-methyl-but-2-enyl, n-pentenyl, octenyl, and decenyl, and the like.

"Alkylene" refers to a divalent group obtained by removing a hydrogen atom from the alkyl group defined above. Preferably alkylene groups include, but are not limited to, methylene, ethylene, propylene, and the like. In general, they can be optionally and equivalently represented herein as -(alkyl)-, for example —CH$_2$CH$_2$— is ethylene.

"Alkynyl" refers to an aliphatic hydrocarbon group containing at least one carbon-carbon triple bond, which may be linear or branched and contains 2 to 10 carbon atoms, preferably 2 to 6 carbon atoms, and more preferably 2 to 4 carbon atoms in the chain. "Branched" means that one or more alkyl groups having 2 to 4 carbon atoms is/are attached to a linear alkynyl group. Preferably alkynyl groups include, but are not limited to, ethynyl, propynyl, 2-butynyl, and 3-methyl butynyl.

"Alkenylene" refers to a difunctional group obtained by removing a hydrogen atom from the above-defined alkenyl group. Preferably alkenylene groups include, but are not limited to, —CH=CH—, —C(CH$_3$)=CH—, —CH=CHCH$_2$—, and the like.

"Aryl" refers to a carbocyclic aromatic monocyclic or polycyclic ring system having 6 to 14 carbon atoms, and preferably 6 to 10 carbon atoms in the ring. The aryl may be optionally substituted with one or more identical or different "substituents" as defined herein. Preferably aryl groups include, but are not limited to, phenyl and naphthyl. The "monocyclic aryl" means phenyl.

"Arylene" refers to a divalent functional group obtained by removing a hydrogen atom from the above-defined aryl group. For example,

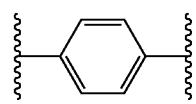

is p-phenylene.

"Heteroaryl" refers to an aromatic monocyclic or polycyclic ring system having 5 to 14 ring atoms and preferably 5 to 10 ring atoms in the ring, where one or more ring atoms are elements other than carbon, such as nitrogen, oxygen, or sulfur, used alone or in combination. Preferably heteroaryl groups contain 5 to 6 ring atoms. "Heteroaryl" may be optionally substituted with one or more substituents as defined herein which may be the same or different. The prefix aza, oxa or thia before the root name heteroaryl means containing at least one nitrogen, oxygen or sulfur atom independently acting as a ring atom. The nitrogen atom in the heteroaryl group can be optionally oxidized into the corresponding N-oxide. The term "heteroaryl" also includes a heteroaryl as defined above, which is fused to an aryl as defined above. Preferably heteroaryl groups include, but are not limited to, pyridyl, pyrazinyl, furyl, thienyl, pyrimidinyl, pyridone (including N-substituted pyridone), isoxazolyl, isothiazolyl, oxazolyl, oxadiazolyl, thiazolyl, thiadiazolyl, pyrazolyl, furazanyl, pyrrolyl, triazolyl, 1,2,4-thiadiazolyl, pyridazinyl, quinoxalinyl, phthalazinyl, hydroxyindolyl, imidazo[1,2-a]pyridyl, imidazo[2,1-b]thiazolyl, benzofurazanyl, indolyl, azaindolyl, benzimidazolyl, benzothienyl, quinolyl, imidazolyl, thienopyridyl, quinazolinyl, thienopyrimidinyl, pyrrolopyridyl, imidazopyridine, isoquinolinyl, benzoazinyl, 1,2,4-triazinyl, benzothiazolyl, and the like. The term "heteroaryl" also refers to partially saturated heteroaryl groups, such as tetrahydroisoquinolyl, tetrahydroquinolinyl and the like. The term "monocyclic heteroaryl" refers to a monocyclic form of a heterocycle as described above, and includes 4- to 7-membered monocyclic heteroaryl groups having from 1 to 4 ring heteroatoms independently selected from N, O and S and oxides thereof. The point of attachment to the parent moiety is any available ring carbon atom or ring heteroatom. Preferably monocyclic heteroaryl groups include, but are not limited to, pyridyl, pyrazinyl, furyl, thienyl, pyrimidinyl, pyridazinyl, pyridonyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g. 1,2,4-thiadiazolyl), imidazolyl, triazinyl (e.g. 1,2,4-triazinyl) and oxides thereof "Cycloalkyl" refers to a non-aromatic monocyclic or polycyclic ring system containing from 3 to 10 carbon atoms, and preferably from 3 to 6 carbon atoms. The cycloalkyl may be optionally substituted with one or more substituents as described in the present invention which are the same or different. Monocyclic cycloalkyl refers to a monocyclic form of the cycloalkyl described in the present invention. Preferably monocyclic cycloalkyl groups include, but are not limited to, cyclopropyl, cyclopentyl, cyclohexyl, cycloheptyl and the like. Preferably polycyclic cycloalkyl groups include, but are not limited to, [1.1.1]-bicyclopentyl, 1-decanoyl, norbornyl, adamantyl and the like.

"Cycloalkenyl" refers to a non-aromatic monocyclic or polycyclic ring system having from 3 to 10 carbon atoms and containing at least one cyclic carbon-carbon double bond. Preferably cycloalkenyl rings contain from 3 to 7 ring atoms. The cycloalkenyl may be optionally substituted with one or more substituents as described in the present invention, which may be the same or different. The term "monocyclic cycloalkenyl" refers to a monocyclic form of the cycloalkenyl as described in the present invention and includes non-aromatic 3- to 7-membered monocyclic cycloalkenyl groups containing one or more carbon-carbon double bonds. Preferably monocyclic cycloalkenyl groups include, but are not limited to, cyclopropenyl, cyclobutenyl, cyclopentenyl, cyclohexenyl, cycloheptane-1,3-dienyl, and the like. Preferably polycyclic cycloalkenyl groups include, but are not limited to, norbornenyl.

"Heterocycloalkyl" (or "heterocyclyl") refers to a non-aromatic saturated monocyclic or polycyclic ring system containing from 3 to 10 ring atoms and preferably from 5 to 10 ring atoms, where one or more atoms in the ring system are elements other than carbon, such as nitrogen, oxygen or sulfur, alone or a combination thereof. No adjacent oxygen and/or sulfur atoms are present in the ring system. Preferably heterocyclyl groups contain from 5 to 6 ring atoms. The heterocyclyl may be optionally substituted with one or more substituents as described in the present invention, which are the same or different. The nitrogen or sulfur atom in the heterocyclyl group can be optionally oxidized into the corresponding N-oxide, S-oxide or S,S-dioxide. Thus the term "oxide" in the present invention refers to the corresponding N-oxide, S-oxide or S, S-dioxide. "Heterocyclyl" also includes a group in which two available hydrogen atoms on the same carbon atom of the ring system are replaced by a single group =O (e.g., carbonyl), which may be referred to as "oxo" in the present invention. The term "monocyclic heterocycloalkyl" refers to a monocyclic form of the heterocycloalkyl group described in the present invention, including 4 to 7 membered monocyclic heterocycloalkyl groups having from 1 to 4 ring heteroatoms independently selected from N, N-oxide, O, S, S-oxide, S(O) and S(O)$_2$. Preferably monocyclic heterocycloalkyl groups include, but are not limited to, piperidinyl, oxetanyl, pyrrolyl, piperazinyl, morpholinyl, thiomorpholinyl, thiazolidinyl, 1,4-dioxanyl, tetrahydrofuryl, tetrahydrothiophenyl, a lactam group (such as pyrrolidinonyl), a lactone group and oxides thereof.

"Heterocycloalkenyl" refers to a non-aromatic monocyclic or polycyclic ring system containing from 3 to 10 ring atoms and preferably from 3 to 7 ring atoms, where one or more atoms in the ring system are elements other than carbon, for example, nitrogen, oxygen or sulfur, alone or a combination thereof; and containing at least one carbon-carbon double bond or carbon-nitrogen double bond. No adjacent oxygen and/or sulfur atoms are present in the ring system. Preferably heterocycloalkenyl groups contain from 5 to 6 ring atoms. The prefix aza, oxa or thia before the root name heterocycloalkenyl means containing at least one nitrogen, oxygen or sulfur atom independently acting as a ring atom. The heterocycloalkenyl may be optionally substituted with one or more substituents as described in the present invention, which are the same or different. The nitrogen or sulfur atom in the heterocycloalkenyl group can be optionally oxidized into the corresponding N-oxide, S-oxide or S,S-dioxide. Preferably heterocycloalkenyl groups include, but are not limited to, 1,2,3,4-tetrahydropyridyl, 1,2-dihydropyridyl, 1,4-dihydropyridyl, 1,2,3,6-tetrahydropyridyl, 1,4,5,6-tetrahydropyrimidinyl, 2-pyrrolinyl, 3-pyrrolinyl, 2-imidazolinyl, 2-pyrazolinyl, dihydroimidazolyl, dihydroxazolyl, dihydroxadiazolyl, dihydrothiazolyl, 3,4-dihydro-2H-pyranyl, dihydrofuranyl, fluorodihydrofuranyl and the like. "Heterocycloalkenyl" may also be a substituted ring system where two available hydrogen atoms on the same carbon atom are replaced by a single group =O (e.g., carbonyl). The term "monocyclic heterocycloalkenyl" refers to a monocyclic form of the heterocycloalkenyl group as described in the present invention, including 4- to 7-membered monocyclic heterocycloalkenyl groups having from 1 to 4 ring heteroatoms independently selected from N,N-dioxide, O, S, S-oxide, S(O), and S(O)$_2$. Preferably monocyclic heterocycloalkenyl groups include, but are not limited to, 1,2,3,4-tetrahydropyridyl, 1,2-dihydropyridyl, 1,4-dihydropyridyl, 1,2,3,6-tetrahydropyridyl, 1,4,5,6-tetrahydropyrimidinyl, 2-pyrrolinyl, 3-pyrrolinyl, 2-imidazolinyl, 2-pyrazolinyl, dihydroimidazolyl, dihydroxazolyl, dihydroxadiazolyl, dihydrothiazolyl, 3,4-dihydro-2H-pyranyl, dihydrofuranyl, fluorodihydrofuranyl, dihydrothiophenyl, dihydrothiopyranyl and oxides thereof.

"Arylalkyl" (or "aralkyl") refers to an aryl-alkyl- group in which the aryl and alkyl are as defined above. Unless otherwise stated, the alkyl group in the definition "arylalkyl" (or "-alkyl-aryl") refers to a linear or branched lower alkyl group. Preferably, the arylalkyl includes a lower alkyl group. Preferably arylalkyl groups include, but are not limited to, benzyl, 2-phenethyl and naphthylmethyl. The group is attached to the parent moiety via the alkyl group. The term (and like terms) can be written as "arylalkyl" (or "-alkyl-aryl"), to indicate the point of attachment to the parent moiety. Similarly, "heteroaryl alkyl", "cycloalkyl alkyl", "cycloalkenyl alkyl", "heterocycloalkyl alkyl", "heterocycloalkenyl alkyl" and the like refer to the heteroaryl, cycloalkenyl, heterocycloalkyl, heterocycloalkenyl and the like as described in the present invention, which are attached to the parent moiety via the alkyl group.

"Alkylaryl" (or "alkaryl") refers to an alkyl-aryl group where the alkyl and aryl are as described above. Preferably, the alkylaryl group comprises a lower alkyl group. Prefer- Substitutions on groups such as cycloalkylalkyl, heterocycloalkylalkyl, arylalkyl, heteroarylalkyl, and aryl fused cycloalkylalkyl include substitutions on any of the ring moieties and/or alkyl moieties of the groups.

A tautomer refers to a compound produced by the transfer of a proton from one atom to another atom in a molecule. The tautomer also refers to two or more isomeric forms in equilibrium that trend to convert from one isomeric form to another. One of ordinary skill in the art will recognize the possibility of all tautomeric ring atom arrangements. All such isomeric forms of these compounds are expressly embraced in the disclosure of the present invention.

In particular, the compound of the present invention includes all tautomers thereof, such as keto-enol tautomers. For convenience, in the detailed description and claims of the present invention, some structures of these tautomers and the mixtures thereof (Example 1) are shown below.

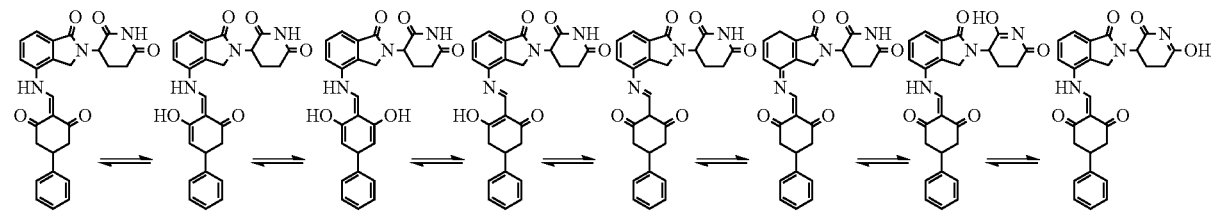

ably alkylaryl includes, but is not limited to, tolyl. The group is attached to the parent moiety via the aryl group.

"Heteroaralkyl" (or "heteroarylalkyl") refers to a heteroaryl-alkyl- group in which the heteroaryl and alkyl are as described above. Preferably, the heteroaralkyl contains a lower alkyl group. Preferably aralkyl groups include, but are not limited to, pyridylmethyl and quinolin-3-ylmethyl. The group is attached to the parent moiety via the alkyl group.

"Hydroxyalkyl" refers to a HO-alkyl- group in which the alkyl group is as defined above. Preferably, the hydroxyalkyl contains a lower alkyl group. Preferably hydroxyalkyl groups include, but are not limited to, hydroxymethyl and 2-hydroxyethyl. "Alkoxy" refers to an alkyl-O— group in which the alkyl is as defined above. Preferably alkoxy groups include, but are not limited to, methoxy, ethoxy, n-propoxy, isopropoxy and n-butoxy. The group is attached to the parent moiety via oxygen. "Alkoxyalkyl" refers to a group derived from an alkoxy group and an alkyl group as defined in the present invention. The group is attached to the parent moiety via the alkyl group.

Any of the foregoing functional groups mentioned in the present invention may be unsubstituted or substituted with the substituents described in the present invention. The term "substituted" (or substitution) means that one or more hydrogen atoms on a given atom is/are replaced by a group selected from specified groups, provided that the normal valence of the given atom is not exceeded and that the substitution results in a stable compound. The combination of the substituents and/or variables is permissible only when the combination results in a stable compound. "Stable compound" or "stable structure" means a compound having stability sufficient to be separated from the reaction mixture to a useful purity and prepared into an effective therapeutic agent.

The term "unsubstituted or substituted" means that a particular group is unsubstituted or substituted with one or more substituents.

For convenience, only one tautomer of each compound is exemplified in the present invention. It should be noted that the compound of the present invention includes all tautomers.

A stereoisomer refers to an isomer of a compound having the same molecular formula and having the same joining order, but different spatial arrangement of atoms in the molecule. Stereoisomerism includes cis-trans isomerism, conformational isomerism, enantiomerism and diastereomerism, etc. The cis-trans isomerism is caused by the inability of two carbon atoms connected by a double bond to rotate relatively freely around a sigma bond, and generally refers to the cis-trans isomerism of a double bond of an olefin and also a C═N double bond, a N═N double bond, and a cyclic compound. Enantiomers refer to stereoisomers that are mirror images of each other. Diastereomers refer to stereoisomers in which the molecule has two or more chiral centers and the molecules are in a non-mirror relationship. Unless otherwise indicated, the specification is intended to include individual stereoisomers and mixtures thereof.

In particular, the compound of the present invention includes all isomers thereof, such as diastereomers and cis/trans (Z/E) isomers.

For convenience, only one isomer of each compound is exemplified in the present invention. It should be noted that the compound of the present invention includes all stereoisomers.

The compound of the present invention can form a metal chelate with one or more metal ions, including, but not limited to, copper, iron, magnesium, calcium, zinc, nickel, and platinum. The compound of the present invention includes all metal chelates.

The term "pharmaceutically acceptable salt" refers to a substance that is suitable for use in humans and/or animals without undue adverse side effects (e.g., toxicity, irritation, and allergies), i.e., having a reasonable benefit/risk ratio.

Pharmaceutically acceptable salts include inorganic and organic salts that can be obtained during the final separation and purification of the compound of the present invention, or by reaction of the free acid or base functional group with a suitable base or acid. Acids suitable for salt formation include, but are not limited to, inorganic acids such as hydrochloric acid, phosphoric acid or sulfuric acid, or organic acids such as citric acid, ascorbic acid, tartaric acid, lactic acid, maleic acid, malonic acid, fumaric acid, glycolic acid, succinic acid, propionic acid, acetic acid or methanesulfonic acid. Bases suitable for salt formation include, but are not limited to, inorganic bases such as sodium carbonate, sodium hydroxide, potassium carbonate, potassium hydroxide, lithium hydroxide, calcium acetate, calcium chloride or magnesium chloride, and organic bases such as aminoethanol.

The term "effective amount" means that the amount of the compound of present invention contained in the administered composition is sufficient to modulate (e.g., inhibit or activate) a mammalian ATG8 homolog.

The compound of the present invention can be prepared by various similar known methods in the art, and the following reaction schemes are an alternative to the preparation of the compound of the present invention. Those skilled in the art will readily appreciate that these compounds can be prepared using known variations of the conditions and procedures in the following preparative methods. The starting reactants used in the present invention are commercially available unless otherwise stated.

For example, the compound of the present invention can be synthesized using one of the following general synthesis methods:

General Synthesis Method I:

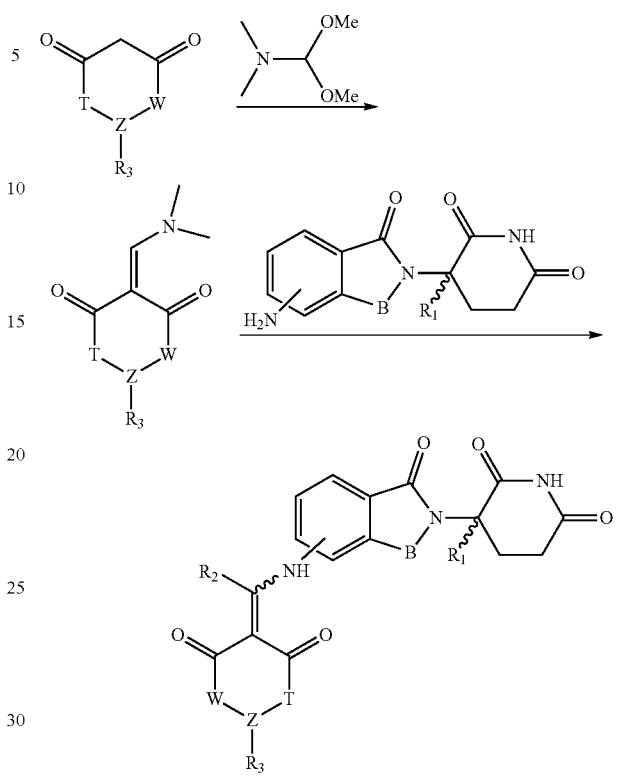

General Synthesis Method II:

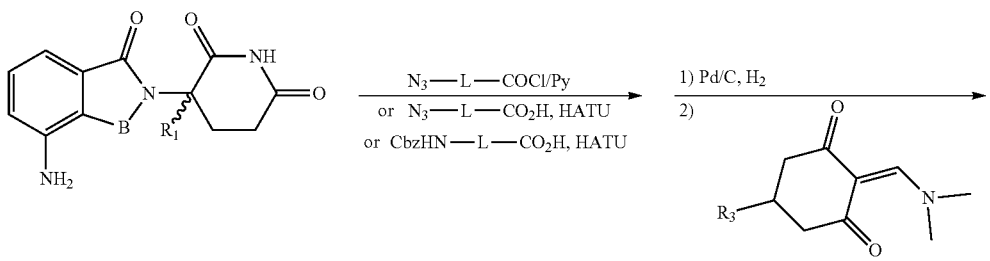

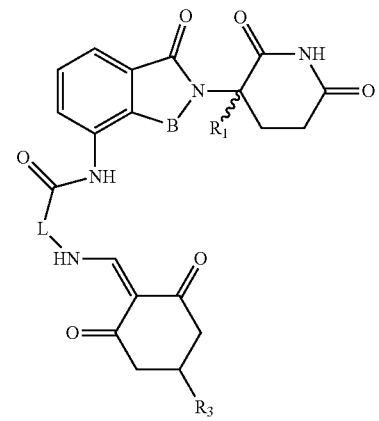

General Synthesis Method III:
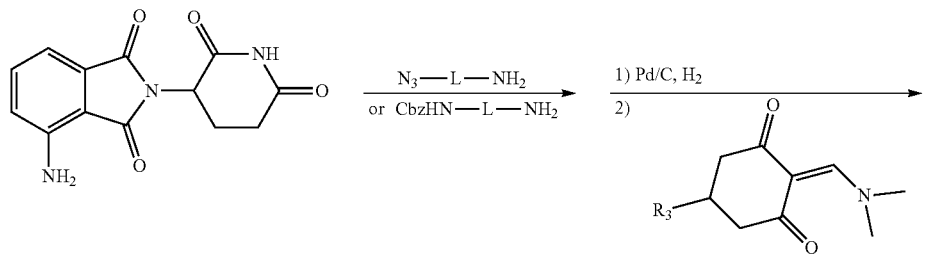

General Synthesis Method IV:
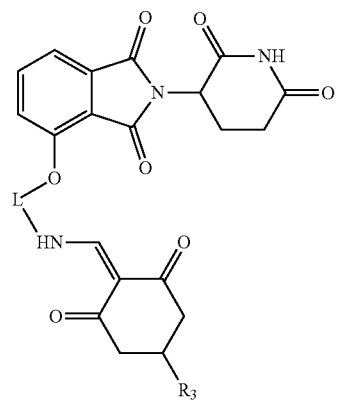

General Synthesis Method V:

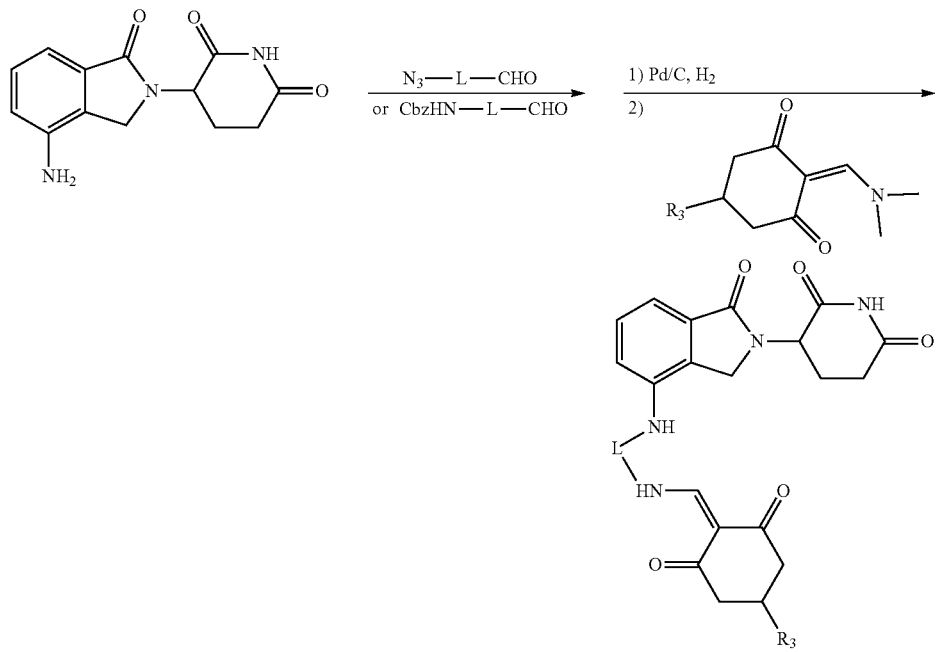

General Synthesis Method VI:

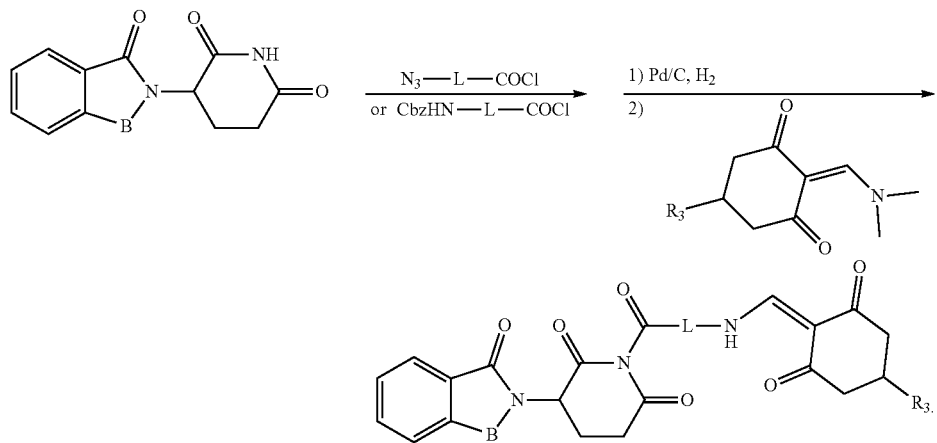

The groups or substituents in the above general synthesis method are as defined above. The intermediates can be prepared by methods described in some of the references known to those of ordinary skill in the art. These references include, for example:

Bioorganic & Medicinal Chemistry Letters, 24(16), 3764-3771, 2014;
Chemistry—A European Journal, 20(9), 2445-2448, 2014;
Bioorganic & Medicinal Chemistry, 20(2), 1029-1045, 2012;
Journal of Organic Chemistry, 82(5), 2630-2640, 2017;
Tetrahedron Letters, 49 (2008), 4725-4727; Journal of Organic Chemistry, 78(9), 4563-4567, 2013;
Heterocycles, 28(2), 1015-35, 1989; Journal of Medicinal Chemistry, 57(10), 3924-3938, 2014;
Journal of Organic Chemistry, 66(24), 8000-8009, 2001; and Tetrahedron Letters, 56(45), 6287-6289, 2015;
The Journal of Immunology, pp. 380-386, 1999; J. Org. Chem., vol. 53, pp. 1167-1170, 1988;
Progress in Medicinal Chemistry, vol. 22, pp. 166-242 (1985); J. Med. Chem., pp. 2858-2865 (1997);
Chem. Pharm. Bull., 46(7), pp. 1165-1168 (1998);
Bioorganic & Medicinal Chem. Letters 9, pp. 1625-1630 (1999);
J. Med. Chem., pp. 3044-3045 (1996);
Journal of Medicinal Chemistry, vol. 39, No. 17, pp. 3238-3240 (1996);
Bioorganic & Medicinal Chemistry Letters 8, pp. 2669-2674 (1998);
Bioorganic & Medicinal Chemistry Letters 7, pp. 1071-1076 (1998);
Immunopharmacology 35, pp. 203-212 (1997).

EXAMPLES

The present invention is further elaborated below in conjunction with specific examples. It should be understood that these examples are only used to illustrate the present invention and are not intended to limit the scope of the present invention.

Abbreviations: Nuclear magnetic resonance (NMR); triethylamine (TEA); mass spectrometry (MS); dimethylformamide (DMF); N,N-dimethylformamide dimethylacetal (DMF-DMA); diisopropyl ethylamine (DIPEA); N-methylpyrrolidone (NMP); Lenalidomide; benzyl formate (Cbz); sodium sulfate (Na$_2$SO$_4$); tert-butyl formate (Boc); 2-(7-azabenzotriazol-1-yl)-N,N,N',N'-tetramethyluronium hexafluorophosphate (HATU)

Liquid chromatography-mass spectrometry (LCMS); thin layer chromatography (TLC); mg/g/kg; mol/mmol; ml/L; equivalent (eq).

General Synthesis Conditions:

Unless otherwise stated, all reactions are carried out under an inert gas atmosphere (such as argon or nitrogen), and the commercially available reagents and anhydrous solvents are used without further treatment.

The liquid chromatograph-mass spectrometer (LC-MS) is an Agilent 6120B single quadrupole liquid chromatograph-mass spectrometer. Gradient of solvent system: 2 to 98% B over 1.5 min, flow rate 1.2 mL/min; eluent A: water/0.1% TFA, eluent B: ACN/0.1% TFA. Column: Kinetex C18 2.6 μm 2.1×50 mm (Phenomenex), column temperature: 50° C. LC/MS UPLC system (column: Acquity C18 BEH 1.7 μm, 2.1×50 mm at 50° C.; eluent A: water+0.1% formic acid; eluent B: ACN. Gradient: 2 to 98% B over 1.4 min, flow rate 1.0 mL/min. HPLC: method group: 10 to 95%; run time: 10 min.

Nuclear magnetic resonance (NMR) spectra (such as hydrogen spectrum ($^1$H), carbon spectrum ($^{13}$C), phosphorus spectrum ($^{31}$P) and fluorine spectrum ($^{19}$F)) are recorded on Bruker AMX-400, Gemini-300 or AMX-600 NMR Spectrometer, in a deuterated solvent such as deuterated chloroform, deuterated methanol, deuterated water or deuterated dimethyl sulfoxide, with the deuterated solvent peaks as a reference. The chemical shift δ is in ppm, the coupling constant (J or J) is in Hertz (Hz), and the coupling and split peaks in the NMR spectrum are expressed as: broad singlet (brs), singlet (s), doublet (d), doublet of doublets (dd), triplet (t), quartet (q) and multiplet (m).

Example 1: Synthesis of Compound 1

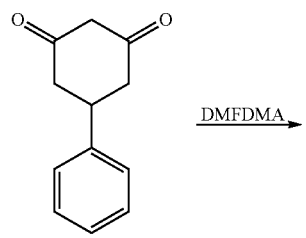

DMFDMA

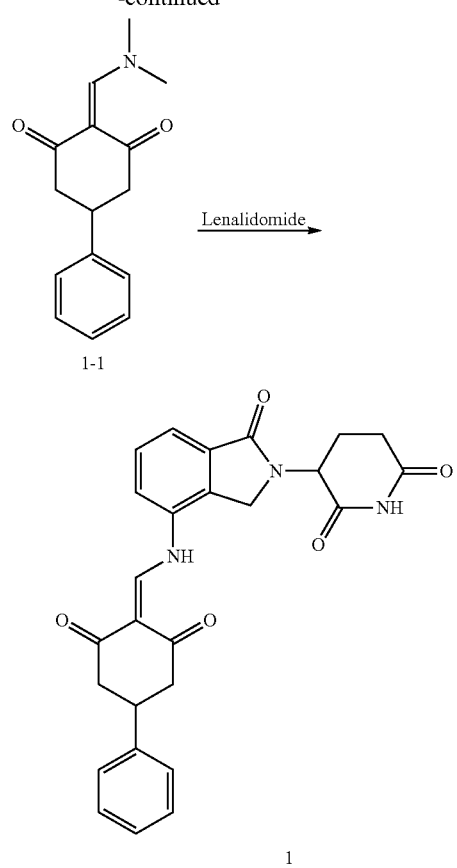

Step 1: 5-phenyl-1,3-cyclohexandione (30.0 g, 159.4 mmol) was dissolved in chloroform (100 mL). N, N-dimethylformamide dimethyl acetal (DMFDMA, 20 mL) was added slowly at room temperature and stirred for 1 hr, until TLC showed the reaction was complete. The reaction solution was poured into iced water, the chloroform phase was separated, and the aqueous phase was extracted with dichloromethane. The combined organic phase was washed with water and brine, dried (Na$_2$SO$_4$), and concentrated. The crude product was separated by column chromatography to afford the target intermediate 1-1 (30.4 g, yield 78.4%).

Step 2: Lenalidomide (910 mg, 3.5 mmol) and the intermediate 1-1 (1.10 g, 4.5 mmol) were dissolved in a mixture of ethanol (20 mL)/dichloromethane (15 mL). The reaction solution was heated and refluxed for 1 hr, until TLC showed the reaction was complete. The reaction solution was filtered while hot, and the solid was washed with ethanol (10 mL×3), dried under suction, beaten in methanol (20 mL), and stirred for 2 hrs. After filtering, the crude product was dissolved in dichloromethane (20 mL), beaten for 1 hr, filtered, and dried to obtain the target compound 1 (1.42 g, yield 89%).

$^1$H NMR (400 MHz, DMSO_d6): δ 12.87 (d, J=13.6 Hz, 1H), 10.99 (s, 1H), 8.58 (d, J=13.6 Hz, 1H), 7.89 (dd, J=6.8, 1.2 Hz, 1H), 7.63-7.57 (m, 2H), 7.32-7.29 (m, 4H), 7.23-7.20 (m, 1H), 5.17-5.12 (m, 1H), 4.62-4.44 (m, 2H), 3.43-3.38 (m, 1H), 2.95-2.78 (m, 3H), 2.68-2.55 (m, 3H), 2.45-2.40 (m, 1H), 1.99-1.96 (m, 1H). MS: 458.5 (M+1).

Example 2: Synthesis of Compounds 2-41, 110-121, 124, 126-128, 130-132, and 134-156

The synthesis method of the compounds 2-41, 110-121, 124, 126-128, 130-132, and 134-156 was the same as that for the compound 1. The details of these compounds are shown in Table 1:

TABLE 1

| Compound | Structure | $^1$HNMR, MS (m/z) |
|---|---|---|
| 2 | 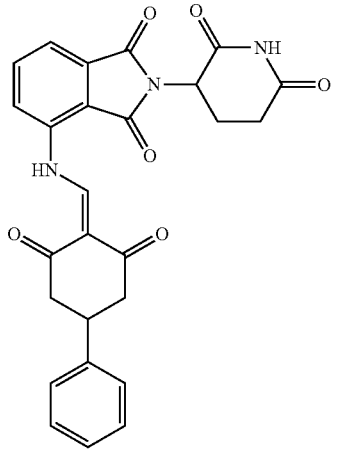 [SMILES: O=C1CCC(N2C(=O)c3cccc(NC=C4C(=O)CC(c5ccccc5)CC4=O)c3C2=O)C(=O)N1] | $^1$H NMR (400 MHz, DMSO-d$_6$) δ 13.42 (s, 1H), 11.18 (s, 1H), 8.74 (d, J = 13.6 Hz, 1H), 8.24 (s, 1H), 7.91 (s, 1H), 7.73 (s, 1H), 7.30 (d, J = 42.2 Hz, 5H), 5.18 (s, 1H), 3.46 (s, 1H), 2.89 (s, 3H), 2.68 (d, J = 19.2 Hz, 4H), 2.10 (s, 1H). MS: 472.1 (M + 1) |
| 3 | 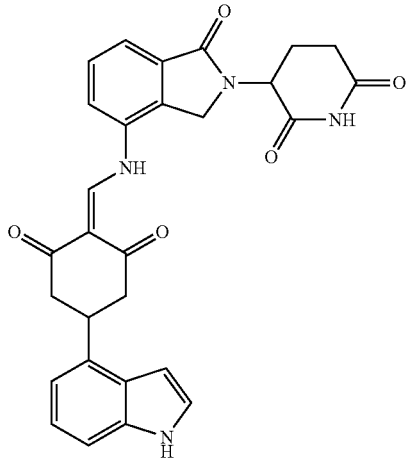 [SMILES: O=C1CCC(N2Cc3c(NC=C4C(=O)CC(c5cccc6[nH]ccc56)CC4=O)cccc3C2=O)C(=O)N1] | $^1$H NMR (400 MHz, DMSO_d6) δ: 12.91 (d, J = 13.2 Hz, 1H), 7.91-7.93 (m, 1H), 7.56-7.63 (m, 2H), 7.33 (t, J = 2.4 Hz, 1H), 7.27 (d, J = 8.4 Hz, 1H), 7.03 (t, J = 8.0 Hz, 1H), 6.88 (d, J = 8.0 Hz, 1H), 6.56 (s, 1H), 5.17 (dd, J = 14.0, 5.2 Hz, 1H), 4.64-4.45 (m, 2H), 3.77-3.85 (m, 1H), 2.60-2.94 (m, 7H), 1.97-1.99 (m, 1H). MS: 497.3 (M + 1) |
| 4 | 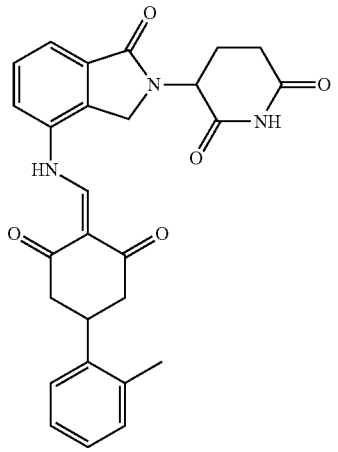 [SMILES: Cc1ccccc1C1CC(=O)C(=CNc2cccc3c2CN(C2CCC(=O)NC2=O)C3=O)C(=O)C1] | $^1$H NMR (400 MHz, DMSO_d6) δ 12.91 (d, J = 16.0 Hz, 1H), 11.01 (s, 1H), 8.61 (d, J = 12.8 Hz, 1H), 7.92 (dd, J$_1$ = 6.8 Hz, J$_2$ = 1.6 Hz, 1H), 7.61-7.65 (m, 2H), 7.11-7.33 (m, 4H), 5.16 (J = 12.8, 4.8 Hz, 1H), 4.64-4.45 (m, 2H), 3.55-3.62 (m, 1H), 2.72-2.93 (m, 3H), 2.50-2.61 (m, 3H), 2.41-2.45 (m, 1H), 2.27-2.29 (m, 3H), 1.97-2.00 (m, 1H). MS: 472.1 (M + 1) |

TABLE 1-continued
| Compound | Structure | ¹HNMR, MS (m/z) |
|---|---|---|
| 5 | 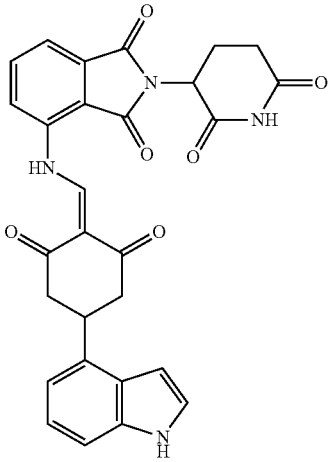 [SMILES: O=C1CCC(N2C(=O)c3cccc(NC=C4C(=O)CC(c5cccc6[nH]ccc56)CC4=O)c3C2=O)C(=O)N1] | ¹H NMR (400 MHz, DMSO_d6) δ 13.40 (d, J = 13.2 Hz, 1H), 11.14-11.18 (m, 2H), 8.74 (d, J = 13.2 Hz, 1H), 8.22 (d, J = 8.8 Hz, 1H), 7.89 (t, J = 8.0 Hz, 1H), 7.70 (d, J = 7.2 Hz, 1H), 7.26-7.34 (m, 2H), 7.01 (t, J = 8.0 Hz, 2H), 6.87 (d, J = 6.8 Hz, 1H), 6.57-6.58 (m, 1H), 5.19-5.14 (m, 3H), 3.80-3.86 (m, 1H), 2.73-3.07 (m, 5H), 2.50-2.63 (m, 2H), 2.05-2.09 (m, 1H).<br>MS: 511.1 (M + 1) |
| 6 | 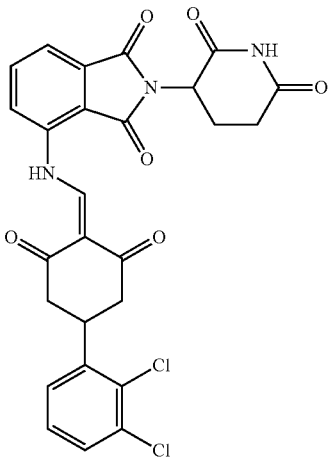 [SMILES: O=C1CCC(N2C(=O)c3cccc(NC=C4C(=O)CC(c5cccc(Cl)c5Cl)CC4=O)c3C2=O)C(=O)N1] | MS: 540.3 (M + 1) |
| 7 | 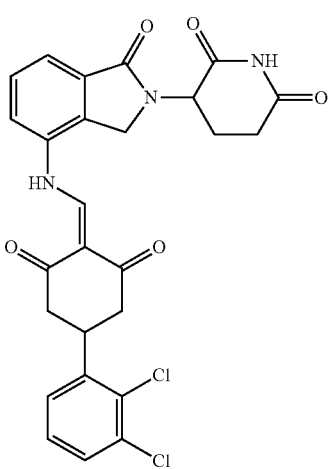 [SMILES: O=C1CCC(N2Cc3c(NC=C4C(=O)CC(c5cccc(Cl)c5Cl)CC4=O)cccc3C2=O)C(=O)N1] | MS: 526.3 (M + 1) |

TABLE 1-continued
| Compound | Structure | ¹HNMR, MS (m/z) |
|---|---|---|
| 8 | 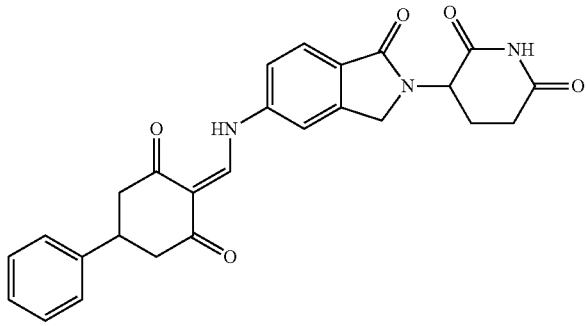 [SMILES: O=C1CCC(N2Cc3cc(NC=C4C(=O)CC(c5ccccc5)CC4=O)ccc3C2=O)C(=O)N1] | MS: 458.2 (M + 1) |
| 9 | 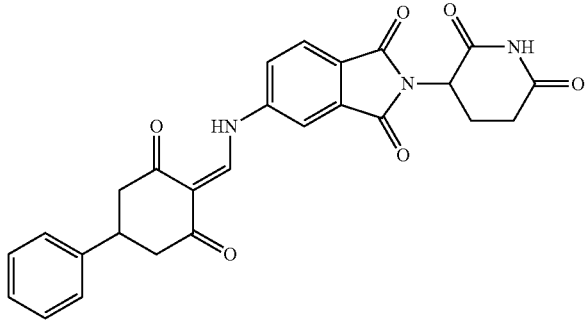 [SMILES: O=C1CCC(N2C(=O)c3ccc(NC=C4C(=O)CC(c5ccccc5)CC4=O)cc3C2=O)C(=O)N1] | MS: 472.3 (M + 1) |
| 10 | 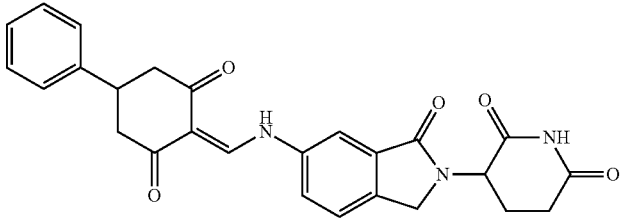 [SMILES: O=C1CCC(N2Cc3ccc(NC=C4C(=O)CC(c5ccccc5)CC4=O)cc3C2=O)C(=O)N1] | MS: 458.3 (M + 1) |
| 11 | 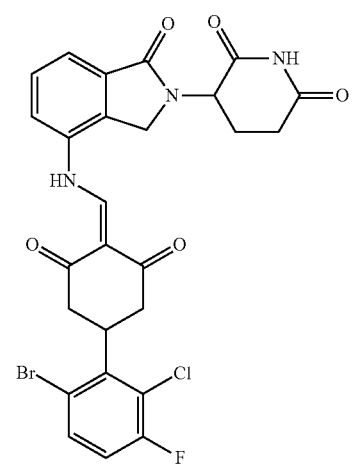 | MS: 588.2 (M + 1) |

TABLE 1-continued
| Compound | Structure | ¹HNMR, MS (m/z) |
| --- | --- | --- |
| 12 | 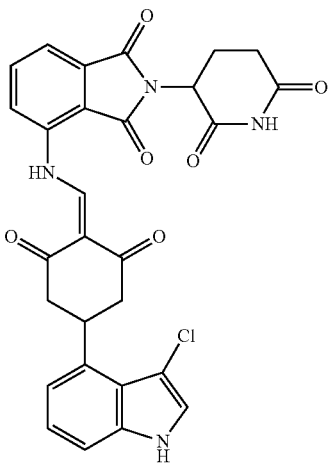 [SMILES: O=C1CCC(N2C(=O)c3cccc(NC=C4C(=O)CC(c5cccc6[nH]cc(Cl)c56)CC4=O)c3C2=O)C(=O)N1] | MS: 545.3 (M + 1) |
| 13 | 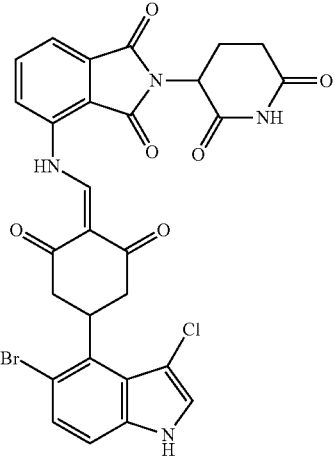 [SMILES: O=C1CCC(N2C(=O)c3cccc(NC=C4C(=O)CC(c5c(Br)ccc6[nH]cc(Cl)c56)CC4=O)c3C2=O)C(=O)N1] | MS: 623.1 (M + 1) |
| 14 | 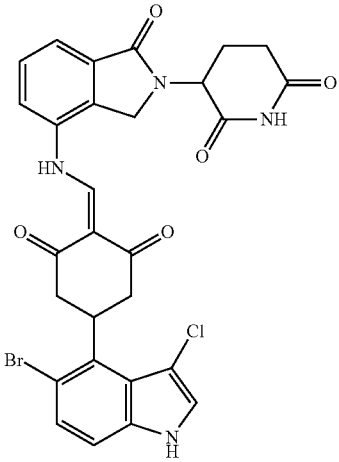 | MS: 609.2 (M + 1). |

TABLE 1-continued
| Compound | Structure | ¹HNMR, MS (m/z) |
|---|---|---|
| 15 | 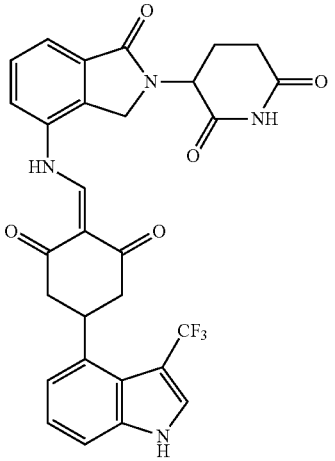 [SMILES: O=C1CCC(N2Cc3c(NC=C4C(=O)CC(c5cccc6[nH]cc(C(F)(F)F)c56)CC4=O)cccc3C2=O)C(=O)N1] | MS: 565.3 (M + 1) |
| 16 | 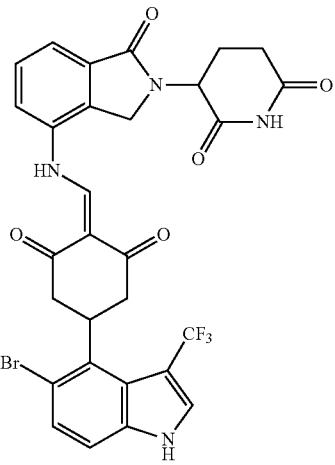 [SMILES: O=C1CCC(N2Cc3c(NC=C4C(=O)CC(c5c(Br)ccc6[nH]cc(C(F)(F)F)c56)CC4=O)cccc3C2=O)C(=O)N1] | MS: 643.2 (M + 1) |
| 17 | 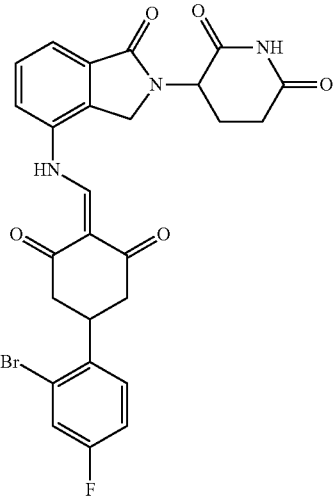 [SMILES: O=C1CCC(N2Cc3c(NC=C4C(=O)CC(c5ccc(F)cc5Br)CC4=O)cccc3C2=O)C(=O)N1] | MS: 554.3 (M + 1) |

TABLE 1-continued

| Compound | Structure | ¹HNMR, MS (m/z) |
| --- | --- | --- |
| 18 | 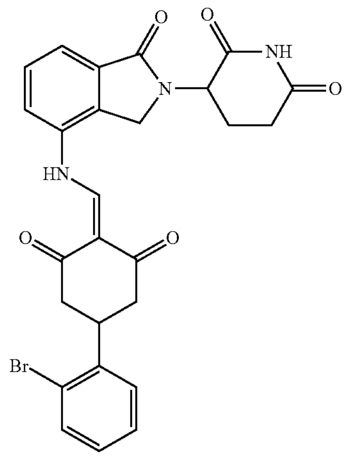 | MS: 536.3 (M + 1) |
| 19 | 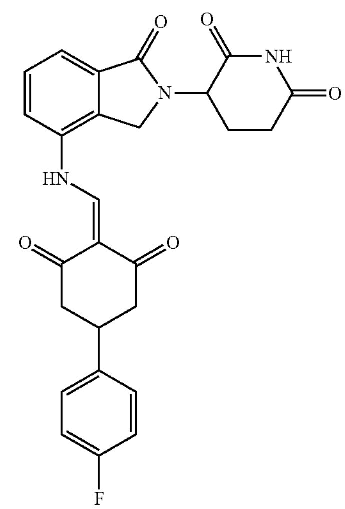 [SMILES: O=C1CCC(N2Cc3c(NC=C4C(=O)CC(c5ccc(F)cc5)CC4=O)cccc3C2=O)C(=O)N1] | MS: 476.3 (M + 1) |
| 20 | 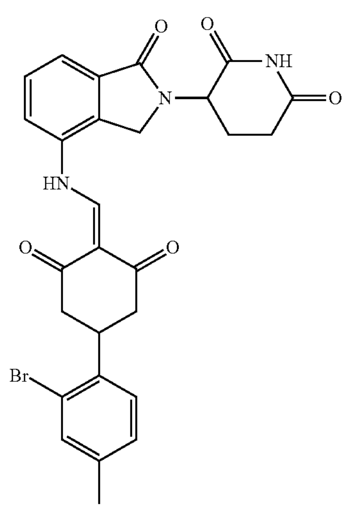 [SMILES: Cc1ccc(C2CC(=O)C(=CNc3cccc4c3CN(C3CCC(=O)NC3=O)C4=O)C(=O)C2)c(Br)c1] | MS: 550.3 (M + 1) |

TABLE 1-continued

| Compound | Structure | ¹HNMR, MS (m/z) |
|---|---|---|
| 21 | 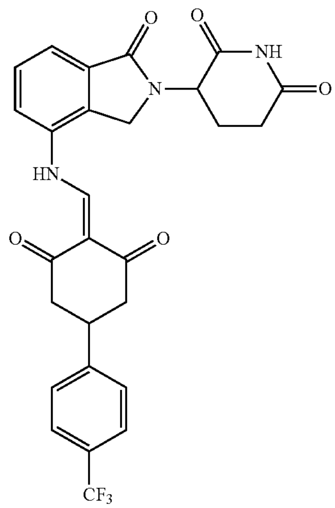 [SMILES: O=C1CCC(N2Cc3c(NC=C4C(=O)CC(c5ccc(C(F)(F)F)cc5)CC4=O)cccc3C2=O)C(=O)N1] | MS: 526.3 (M + 1) |
| 22 | 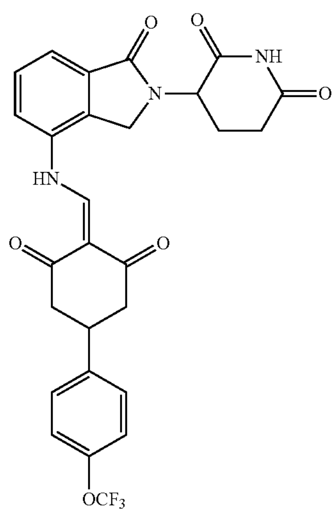 [SMILES: O=C1CCC(N2Cc3c(NC=C4C(=O)CC(c5ccc(OC(F)(F)F)cc5)CC4=O)cccc3C2=O)C(=O)N1] | MS: 542.3 (M + 1) |
| 23 | 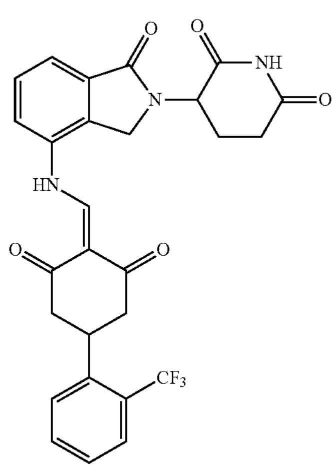 [SMILES: O=C1CCC(N2Cc3c(NC=C4C(=O)CC(c5ccccc5C(F)(F)F)CC4=O)cccc3C2=O)C(=O)N1] | .MS: 526.3 (M + 1) |

TABLE 1-continued

| Compound | Structure | ¹HNMR, MS (m/z) |
| --- | --- | --- |
| 24 | 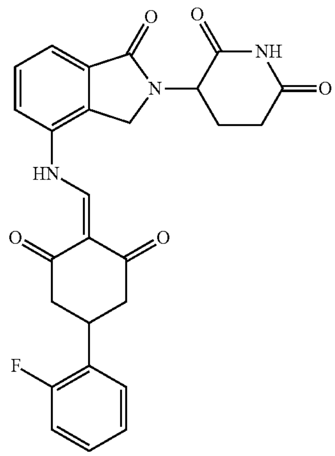 [SMILES: O=C1CCC(N2Cc3c(NC=C4C(=O)CC(c5ccccc5F)CC4=O)cccc3C2=O)C(=O)N1] | MS: 476.3 (M + 1) |
| 25 | 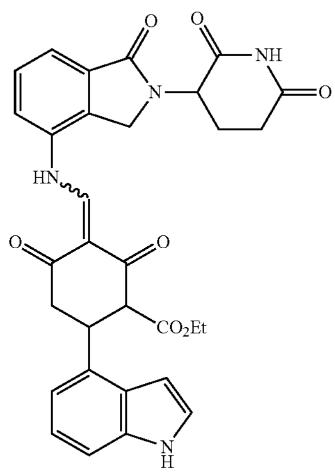 [SMILES: CCOC(=O)C1C(=O)C(=CNc2cccc3c2CN(C2CCC(=O)NC2=O)C3=O)C(=O)CC1c1cccc2[nH]ccc12] | MS: 569.4 (M + 1) |
| 26 | 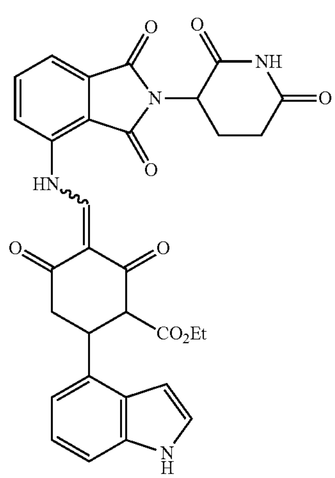 [SMILES: CCOC(=O)C1C(=O)C(=CNc2cccc3c2C(=O)N(C2CCC(=O)NC2=O)C3=O)C(=O)CC1c1cccc2[nH]ccc12] | MS: 583.3 (M + 1) |

TABLE 1-continued

| Compound | Structure | ¹HNMR, MS (m/z) |
|---|---|---|
| 27 | 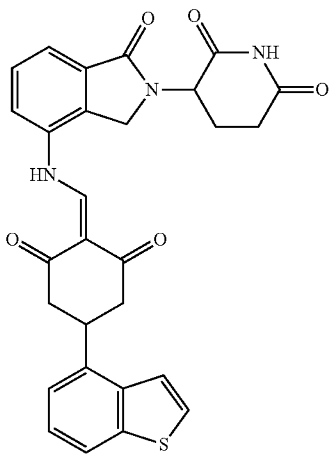 [SMILES: O=C1CCC(N2Cc3c(NC=C4C(=O)CC(c5cccc6sccc56)CC4=O)cccc3C2=O)C(=O)N1] | MS: 514.3 (M + 1) |
| 28 | 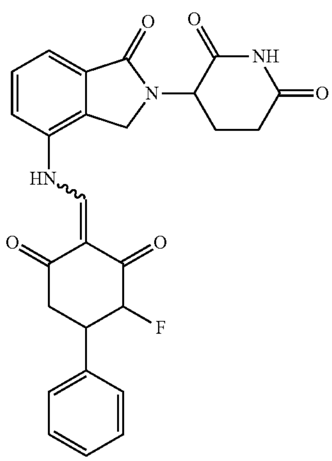 [SMILES: O=C1CCC(N2Cc3c(NC=C4C(=O)CC(c5ccccc5)C(F)C4=O)cccc3C2=O)C(=O)N1] | MS: 476.3 (M + 1) |
| 29 | 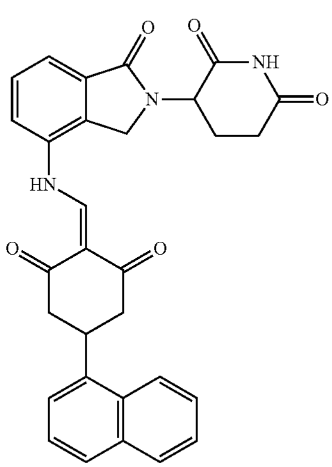 [SMILES: O=C1CCC(N2Cc3c(NC=C4C(=O)CC(c5cccc6ccccc56)CC4=O)cccc3C2=O)C(=O)N1] | MS: 508.3 (M + 1) |

TABLE 1-continued
| Compound | Structure | ¹HNMR, MS (m/z) |
|---|---|---|
| 30 | 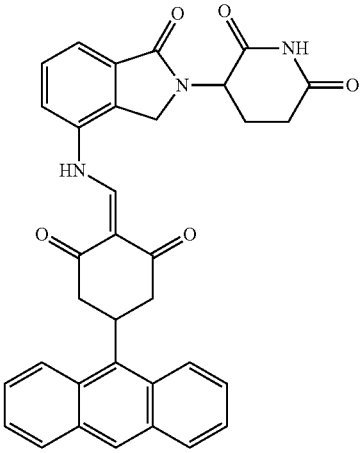 [SMILES: O=C1CCC(N2Cc3c(NC=C4C(=O)CC(c5c6ccccc6cc6ccccc56)CC4=O)cccc3C2=O)C(=O)N1] | MS: 558.4 (M + 1) |
| 31 | 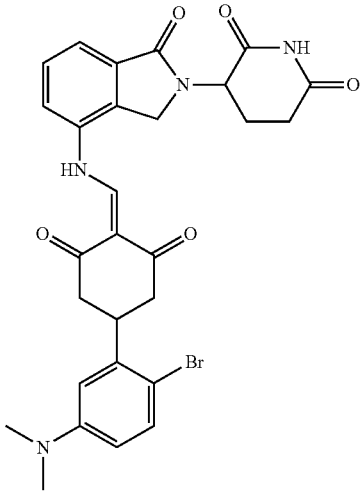 [SMILES: CN(C)c1ccc(Br)c(C2CC(=O)C(=CNc3cccc4c3CN(C3CCC(=O)NC3=O)C4=O)C(=O)C2)c1] | MS: 579.4 (M + 1) |
| 32 | 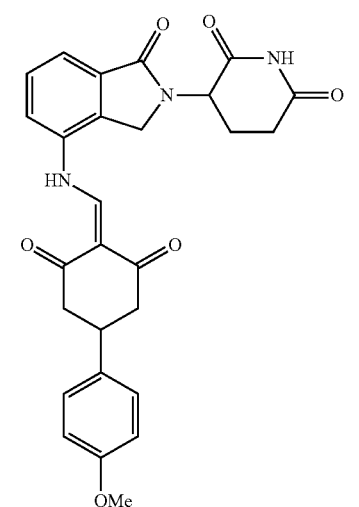 | MS: 488.5 (M + 1) |

TABLE 1-continued
| Compound | Structure | ¹HNMR, MS (m/z) |
|---|---|---|
| 33 | 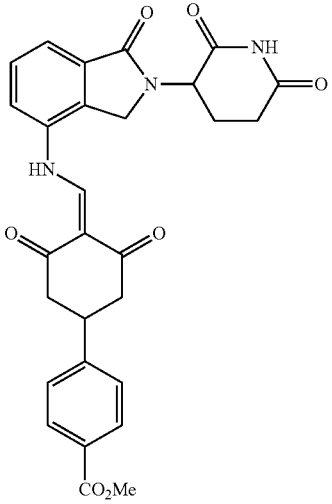 | MS: 516.4 (M + 1) |
| 34 | 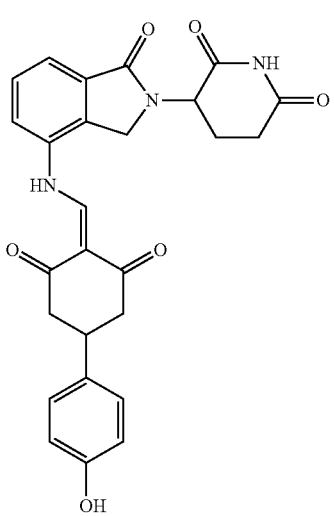 [SMILES: COc1ccc(C2CC(=O)C(=CNc3cccc4c3CN(C3CCC(=O)NC3=O)C4=O)C(=O)C2)cc1] | MS: 474.3 (M + 1) |
| 35 | 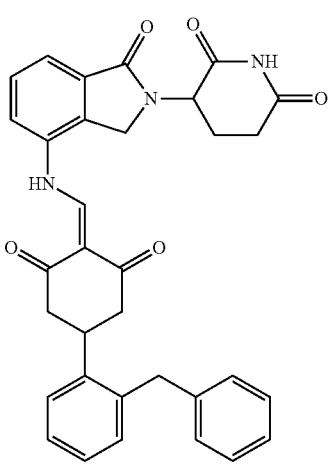 [SMILES: O=C1CCC(N2Cc3c(NC=C4C(=O)CC(c5ccccc5Cc5ccccc5)CC4=O)cccc3C2=O)C(=O)N1] | MS: 548.4 (M + 1) |

TABLE 1-continued
| Compound | Structure | ¹HNMR, MS (m/z) |
|---|---|---|
| 36 | 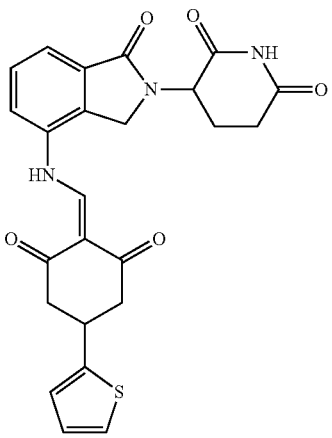 [SMILES: O=C1CCC(N2Cc3c(NC=C4C(=O)CC(c5cccs5)CC4=O)cccc3C2=O)C(=O)N1] | MS: 464.2 (M + 1) |
| 37 | 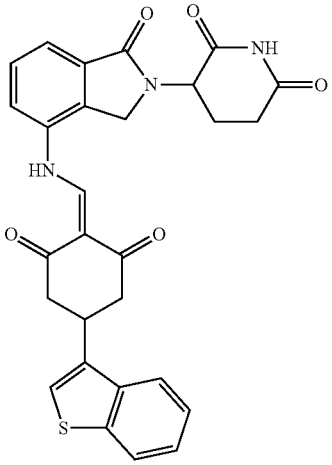 [SMILES: O=C1CCC(N2Cc3c(NC=C4C(=O)CC(c5csc6ccccc56)CC4=O)cccc3C2=O)C(=O)N1] | MS: 514.3 (M + 1) |
| 38 | 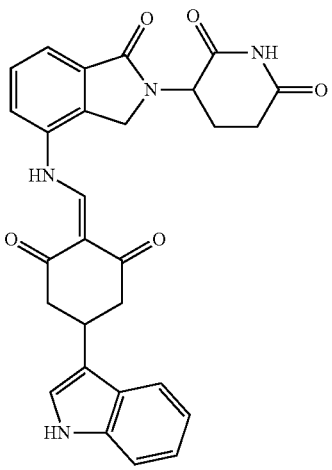 [SMILES: O=C1CCC(N2Cc3c(NC=C4C(=O)CC(c5c[nH]c6ccccc56)CC4=O)cccc3C2=O)C(=O)N1] | MS: 497.3 (M + 1) |

TABLE 1-continued
| Compound | Structure | ¹HNMR, MS (m/z) |
|---|---|---|
| 39 | 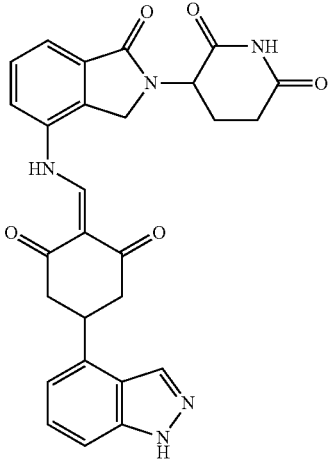 [SMILES: O=C1CCC(N2Cc3c(NC=C4C(=O)CC(c5cccc6[nH]ncc56)CC4=O)cccc3C2=O)C(=O)N1] | MS: 498.3 (M + 1). |
| 40 | 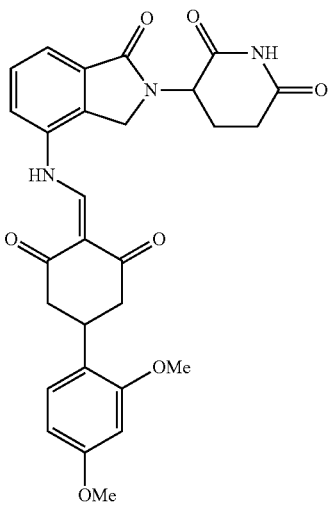 [SMILES: COc1ccc(C2CC(=O)C(=CNc3cccc4c3CN(C3CCC(=O)NC3=O)C4=O)C(=O)C2)c(OC)c1] | MS: 518.3 (M + 1). |
| 41 | 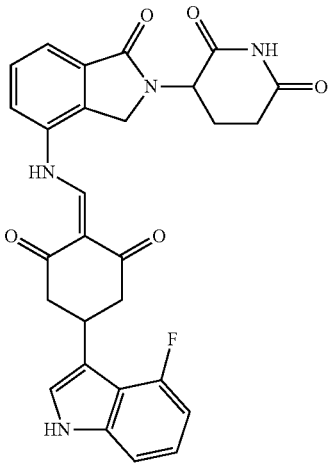 [SMILES: O=C1CCC(N2Cc3c(NC=C4C(=O)CC(c5c[nH]c6cccc(F)c56)CC4=O)cccc3C2=O)C(=O)N1] | MS: 515.4 (M + 1). |

TABLE 1-continued

| Compound | Structure | ¹HNMR, MS (m/z) |
|---|---|---|
| 110 | 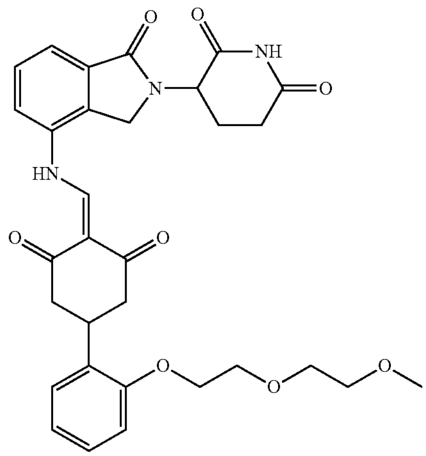 [SMILES: COCCOCCOc1ccccc1C1CC(=O)C(=CNc2cccc3c2CN(C2CCC(=O)NC2=O)C3=O)C(=O)C1] | MS: 576.4 (M + 1). |
| 111 | 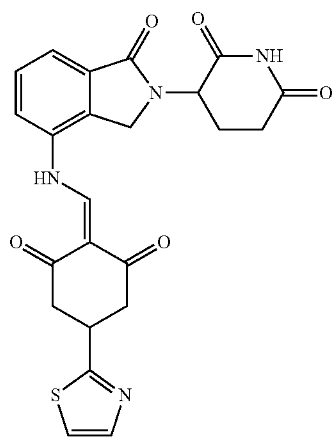 [SMILES: O=C1CCC(N2Cc3c(NC=C4C(=O)CC(c5nccs5)CC4=O)cccc3C2=O)C(=O)N1] | MS: 465.3 (M + 1). |
| 112 | 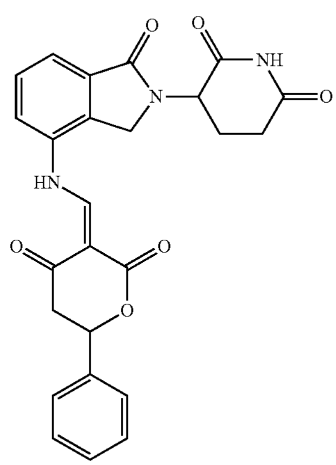 [SMILES: O=C1CCC(N2Cc3c(N/C=C4\C(=O)CC(c5ccccc5)OC4=O)cccc3C2=O)C(=O)N1] | MS: 460.3 (M + 1). |

TABLE 1-continued
| Compound | Structure | ¹HNMR, MS (m/z) |
|---|---|---|
| 113 | 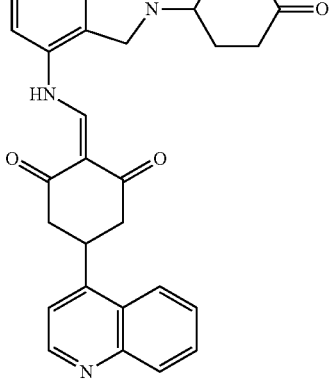 | MS: 508.4 (M + 1). |
| 114 | 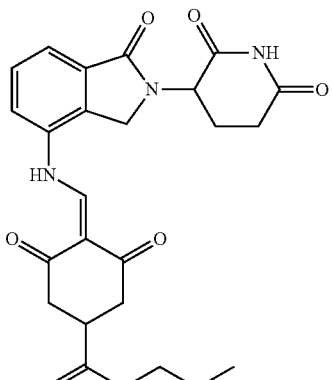 | MS: 467.4 (M + 1). |
| 115 | 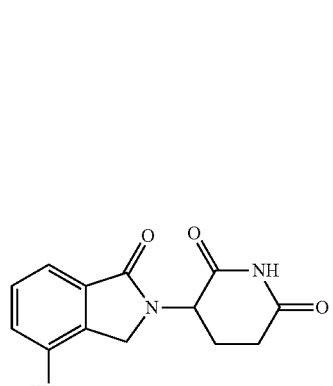 | MS: 460.3 (M + 1). |

TABLE 1-continued
| Compound | Structure | ¹HNMR, MS (m/z) |
|---|---|---|
| 116 | 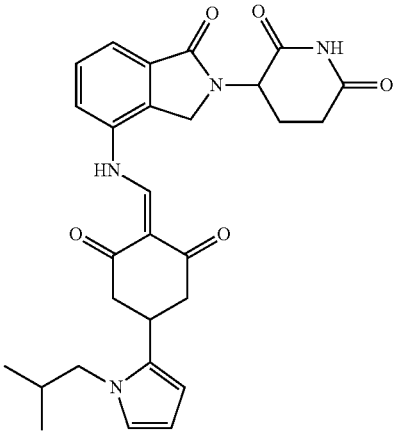 [SMILES: CC(C)Cn1cccc1C1CC(=O)C(=CNc2cccc3c2CN(C2CCC(=O)NC2=O)C3=O)C(=O)C1] | MS: 503.4 (M + 1). |
| 117 | 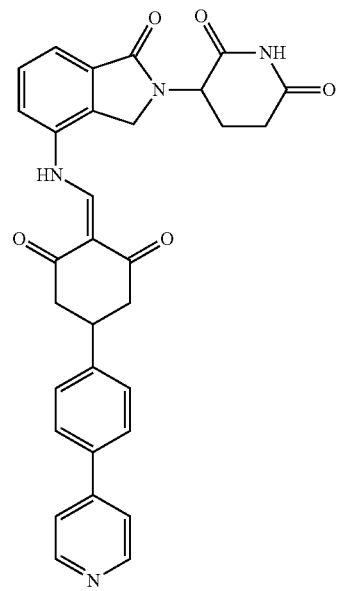 [SMILES: O=C1CCC(N2Cc3c(NC=C4C(=O)CC(c5ccc(-c6ccncc6)cc5)CC4=O)cccc3C2=O)C(=O)N1] | MS: 535.3 (M + 1). |
| 118 | 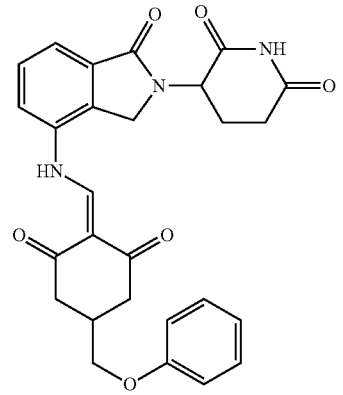 [SMILES: O=C1CCC(N2Cc3c(NC=C4C(=O)CC(COc5ccccc5)CC4=O)cccc3C2=O)C(=O)N1] | MS: 488.3 (M + 1). |

TABLE 1-continued

| Compound | Structure | ¹HNMR, MS (m/z) |
|---|---|---|
| 119 | 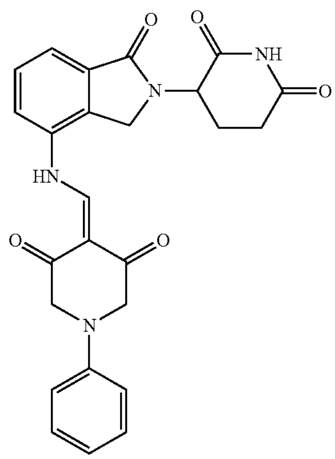 | MS: 459.3 (M + 1). |
| 120 | 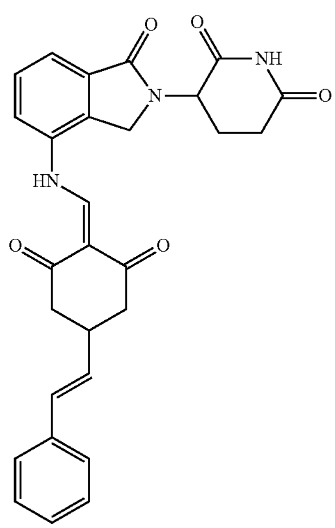 [SMILES: O=C1CCC(N2Cc3c(NC=C4C(=O)CC(/C=C/c5ccccc5)CC4=O)cccc3C2=O)C(=O)N1] | MS: 484.3 (M + 1). |
| 121 | 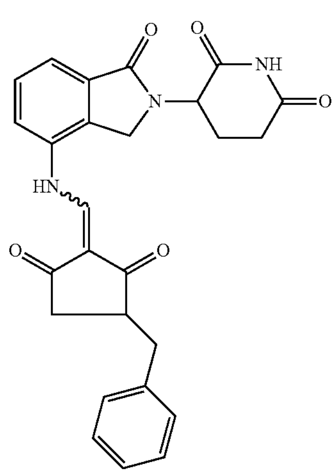 [SMILES: O=C1CCC(N2Cc3c(NC=C4C(=O)CC(Cc5ccccc5)C4=O)cccc3C2=O)C(=O)N1] | MS: 458.3 (M + 1). |

TABLE 1-continued

| Compound | Structure | ¹HNMR, MS (m/z) |
|---|---|---|
| 124 | 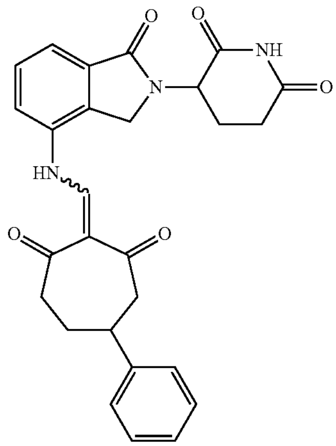 [SMILES: O=C1CCC(N2Cc3c(NC=C4C(=O)CCC(c5ccccc5)CC4=O)cccc3C2=O)C(=O)N1] | MS: 472.3 (M + 1). |
| 126 | 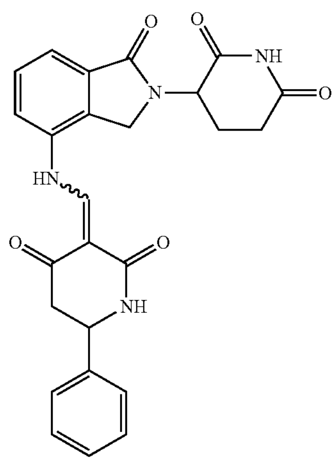 [SMILES: O=C1CCC(N2Cc3c(NC=C4C(=O)CC(c5ccccc5)NC4=O)cccc3C2=O)C(=O)N1] | MS: 459.4 (M + 1). |
| 127 | 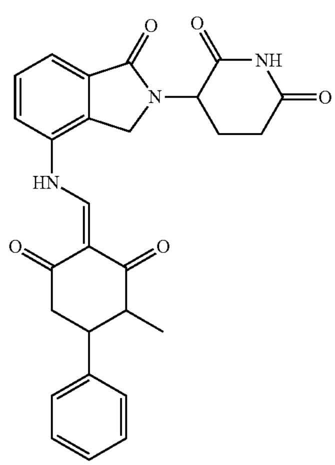 [SMILES: CC1C(=O)/C(=C/Nc2cccc3c2CN(C2CCC(=O)NC2=O)C3=O)C(=O)CC1c1ccccc1] | MS: 472.3 (M + 1). |

TABLE 1-continued
| Compound | Structure | ¹HNMR, MS (m/z) |
|---|---|---|
| 128 | 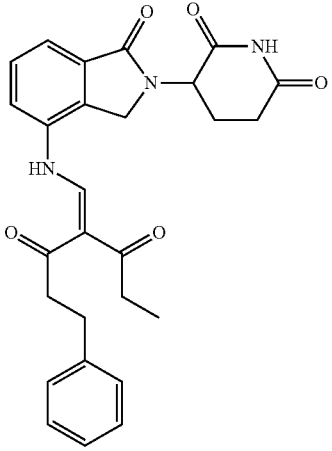 [SMILES: CCC(=O)/C(=C/Nc1cccc2c1CN(C1CCC(=O)NC1=O)C2=O)C(=O)CCc1ccccc1] | MS: 474.3 (M + 1). |
| 130 | 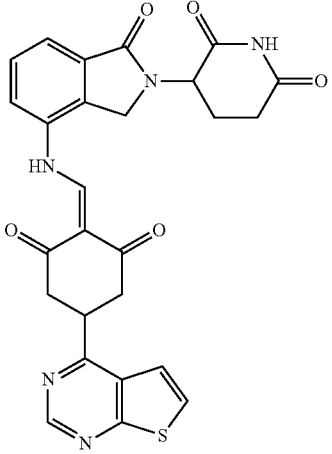 [SMILES: O=C1CCC(N2Cc3c(NC=C4C(=O)CC(c5ncnc6sccc56)CC4=O)cccc3C2=O)C(=O)N1] | MS: 516.3 (M + 1). |
| 131 | 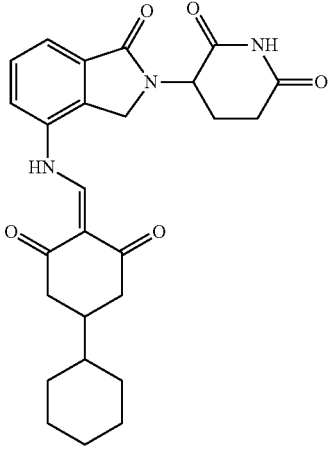 [SMILES: O=C1CCC(N2Cc3c(NC=C4C(=O)CC(C5CCCCC5)CC4=O)cccc3C2=O)C(=O)N1] | MS: 464.3 (M + 1). |

TABLE 1-continued

| Compound | Structure | ¹HNMR, MS (m/z) |
|---|---|---|
| 132 | 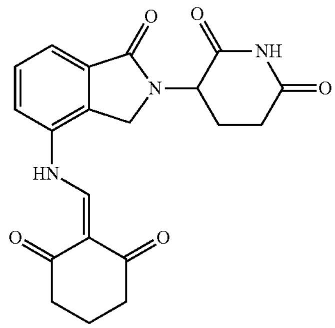 [SMILES: O=C1CCC(N2Cc3c(NC=C4C(=O)CCCC4=O)cccc3C2=O)C(=O)N1] | MS: 382.3 (M + 1). |
| 134 | 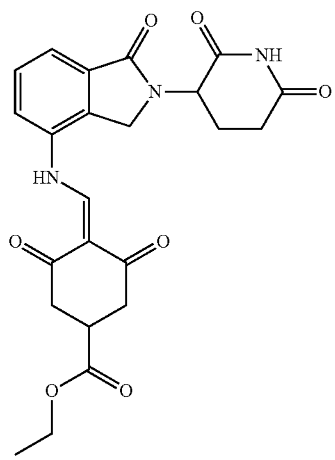 [SMILES: CCOC(=O)C1CC(=O)C(=CNc2cccc3c2CN(C2CCC(=O)NC2=O)C3=O)C(=O)C1] | MS: 454.4 (M + 1). |
| 135 | 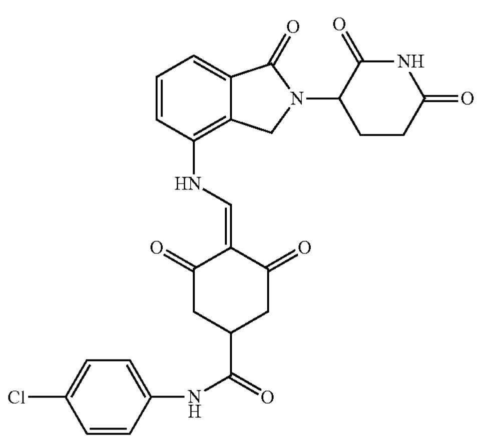 [SMILES: O=C1CCC(N2Cc3c(NC=C4C(=O)CC(C(=O)Nc5ccc(Cl)cc5)CC4=O)cccc3C2=O)C(=O)N1] | MS: 535.3 (M + 1). |

TABLE 1-continued

| Compound | Structure | ¹HNMR, MS (m/z) |
|---|---|---|
| 136 | 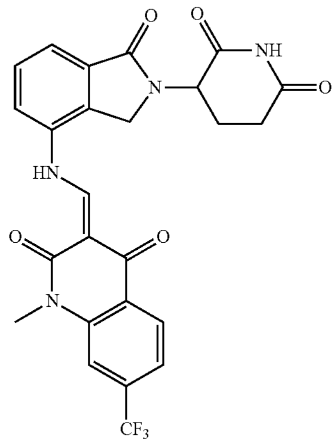 [SMILES: CN1C(=O)/C(=C\Nc2cccc3c2CN(C2CCC(=O)NC2=O)C3=O)C(=O)c2ccc(C(F)(F)F)cc21] | MS: 513.3 (M + 1). |
| 137 | 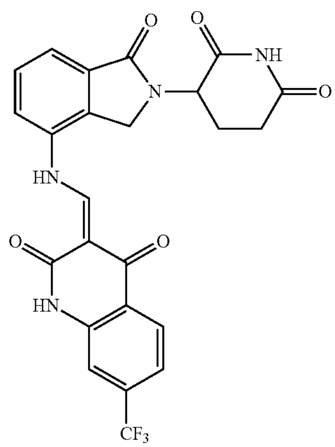 [SMILES: O=C1CCC(N2Cc3c(N/C=C4\C(=O)Nc5cc(C(F)(F)F)ccc5C4=O)cccc3C2=O)C(=O)N1] | MS: 499.2 (M + 1). |
| 138 | 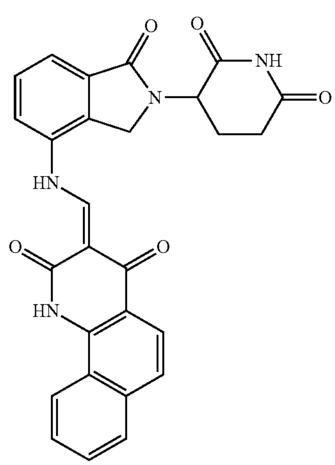 [SMILES: O=C1CCC(N2Cc3c(N/C=C4\C(=O)Nc5c(ccc6ccccc56)C4=O)cccc3C2=O)C(=O)N1] | MS: 481.3 (M + 1). |

TABLE 1-continued
| Compound | Structure | ¹HNMR, MS (m/z) |
|---|---|---|
| 139 | 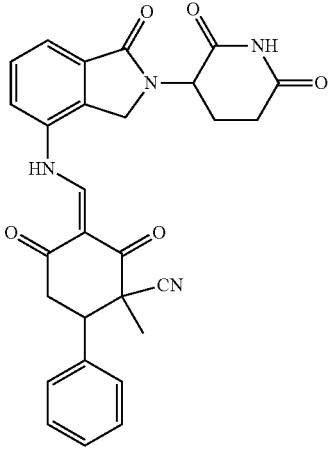 [SMILES: CC1(C#N)C(=O)/C(=C/Nc2cccc3c2CN(C2CCC(=O)NC2=O)C3=O)C(=O)CC1c1ccccc1] | MS: 497.3 (M + 1). |
| 140 | 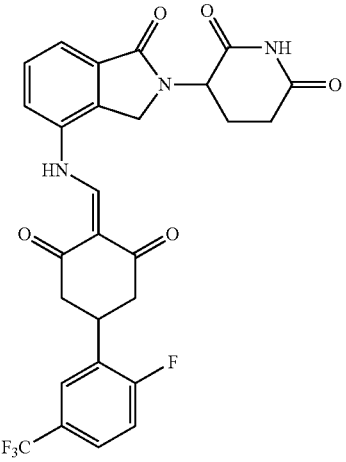 [SMILES: O=C1CCC(N2Cc3c(NC=C4C(=O)CC(c5cc(C(F)(F)F)ccc5F)CC4=O)cccc3C2=O)C(=O)N1] | MS: 544.3 (M + 1). |
| 141 | 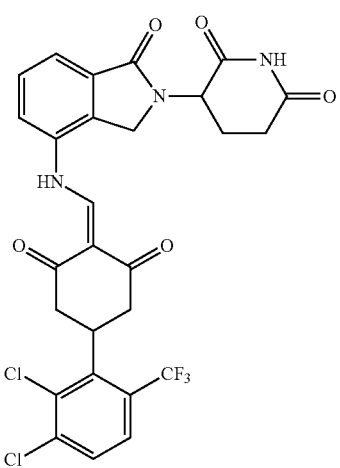 [SMILES: O=C1CCC(N2Cc3c(NC=C4C(=O)CC(c5c(C(F)(F)F)ccc(Cl)c5Cl)CC4=O)cccc3C2=O)C(=O)N1] | MS: 594.2 (M + 1). |

TABLE 1-continued
| Compound | Structure | ¹HNMR, MS (m/z) |
|---|---|---|
| 142 | 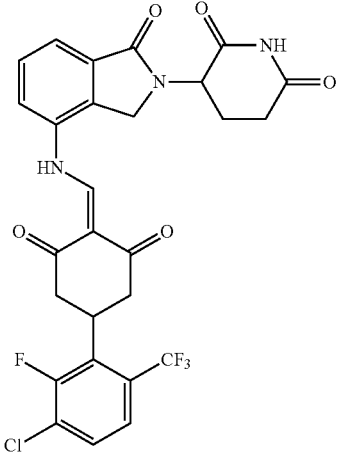 | MS: 578.3 (M + 1). |
| 143 | 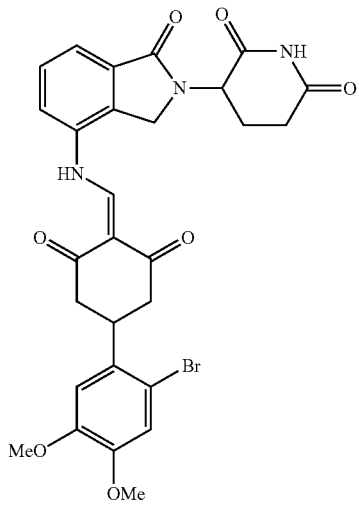 [SMILES: COc1cc(Br)c(C2CC(=O)C(=CNc3cccc4c3CN(C3CCC(=O)NC3=O)C4=O)C(=O)C2)cc1OC] | MS: 596.3 (M + 1). |
| 144 | 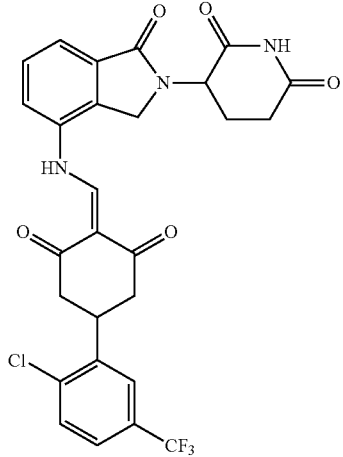 [SMILES: O=C1CCC(N2Cc3c(NC=C4C(=O)CC(c5cc(C(F)(F)F)ccc5Cl)CC4=O)cccc3C2=O)C(=O)N1] | MS: 560.3 (M + 1). |

TABLE 1-continued
| Compound | Structure | ¹HNMR, MS (m/z) |
|---|---|---|
| 145 | 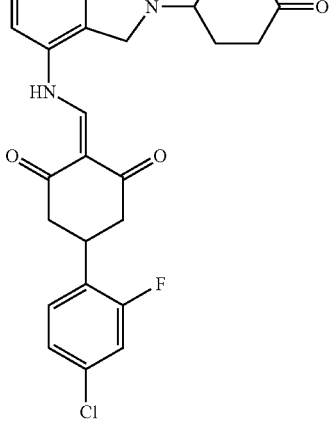 | MS: 510.3 (M + 1). |
| 146 | 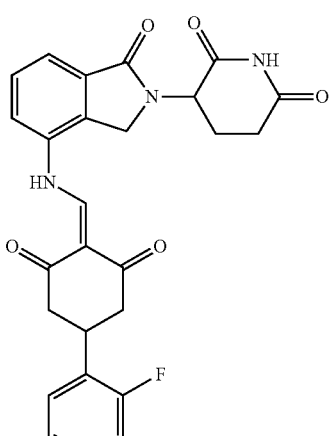 | MS: 510.3 (M + 1). |
| 147 | 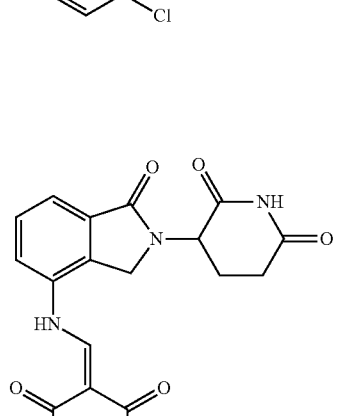 | .MS: 510.3 (M + 1). |

TABLE 1-continued
| Compound | Structure | ¹HNMR, MS (m/z) |
|---|---|---|
| 148 | 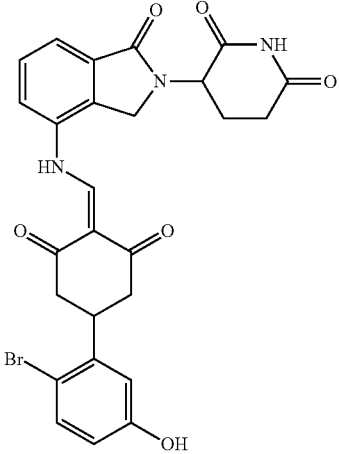 | MS: 552.2 (M + 1). |
| 149 | 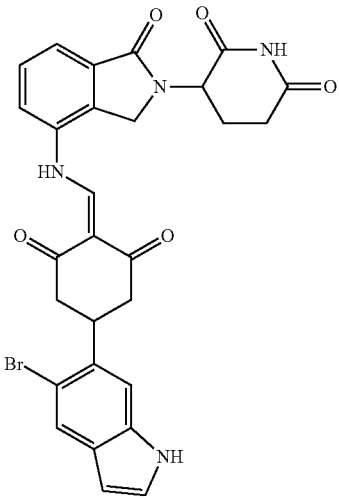 [SMILES: O=C1CCC(N2Cc3c(NC=C4C(=O)CC(c5cc6[nH]ccc6cc5Cl)CC4=O)cccc3C2=O)C(=O)N1] | MS: 575.2 (M + 1). |
| 150 | 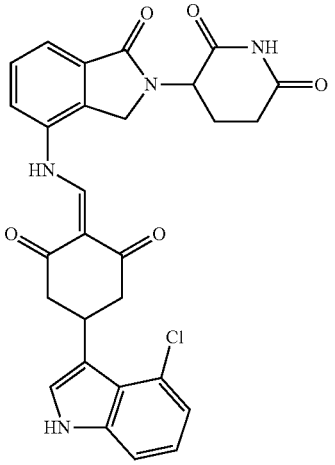 | MS: 531.3 (M + 1). |

TABLE 1-continued

| Compound | Structure | ¹HNMR, MS (m/z) |
|---|---|---|
| 151 | 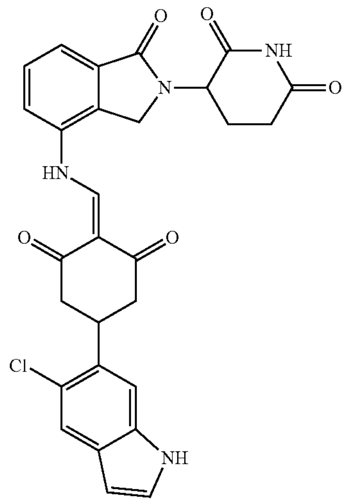 | .MS: 531.3 (M + 1). |
| 152 | 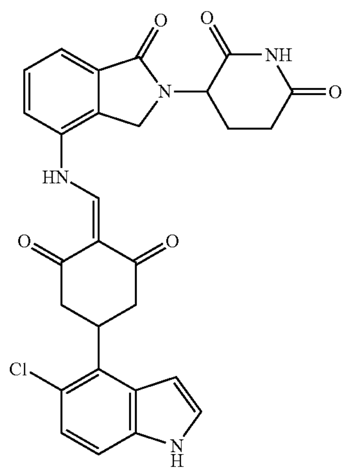 [SMILES: O=C1CCC(N2Cc3c(NC=C4C(=O)CC(c5c(Cl)ccc6[nH]ccc56)CC4=O)cccc3C2=O)C(=O)N1] | MS: 531.3 (M + 1). |
| 153 | 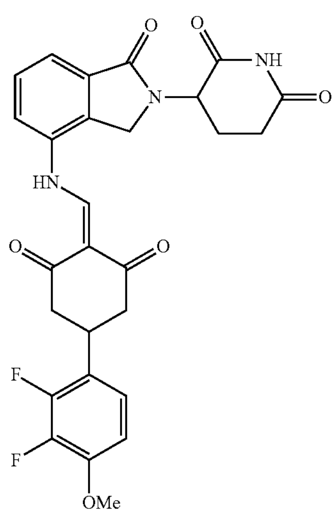 [SMILES: COc1ccc(C2CC(=O)C(=CNc3cccc4c3CN(C3CCC(=O)NC3=O)C4=O)C(=O)C2)c(F)c1F] | MS: 524.3 (M + 1). |

TABLE 1-continued
| Compound | Structure | ¹HNMR, MS (m/z) |
|---|---|---|
| 154 | 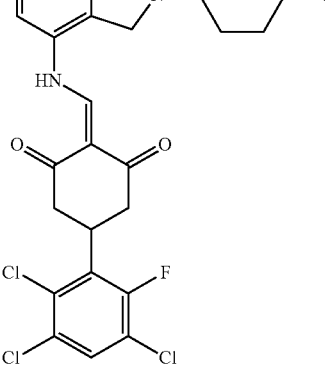 | MS: 578.2 (M + 1). |
| 155 | 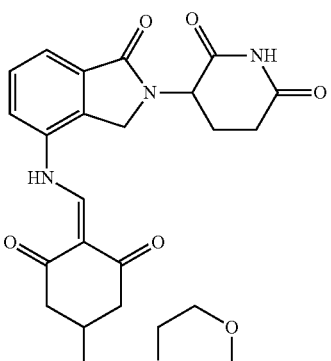 | MS: 543.4 (M + 1). |
| 156 | 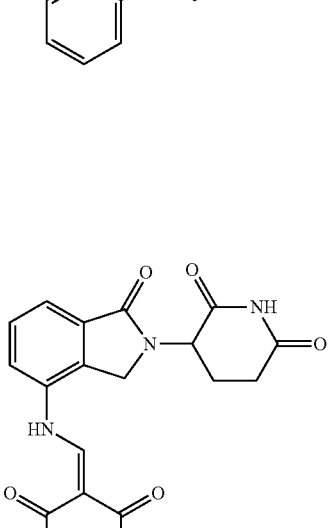 | MS: 515.4 (M + 1). |

Example 3: Synthesis of Compound 42

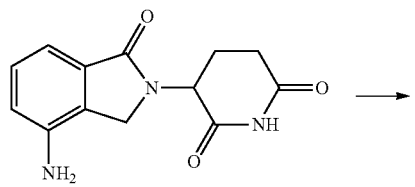

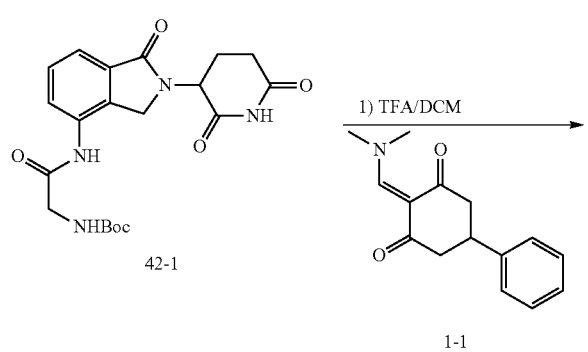

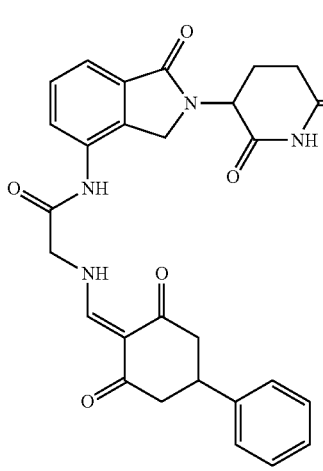

42

Step 1: N-Boc-glycine (405 mg, 2.31 mmol) was dissolved in dry DMF (10 ml). HATU (1.10 g, 2.9 mmol) and DIPEA (516 mg, 4 mmol) were added at room temperature, and stirred for 20 min. Then lenalidomide (500 mg, 1.93 mmol) was added and stirred for another 2 hrs until TLC showed the raw materials were completely reacted. The reaction solution was poured into water, and extracted with EtOAc. The organic phase was washed with water and brine, dried, and concentrated. The crude product was separated by column chromatography to afford the intermediate 42-1 (511 mg, 64%).

Step 2: The intermediate 42-1 (500 mg, 1.2 mmol) was dissolved in dichloromethane (DCM, 10 ml). Trifluoroacetic acid (TFA, 10 ml) was added and the reaction was stirred at room temperature for 1 hr, until TLC showed the reaction was complete. The TFA was distilled off under reduced pressure, and the crude product was dissolved in ethanol (30 ml). After dissolution, an appropriate amount of N,N-diisopropylethylamine (DIPEA) was added to adjust the pH to be basic. Then, the intermediate 1-1 (365 mg, 1.5 mmol) was added, and stirred at room temperature for 1 hr, until TLC showed that the reaction was almost complete. The reaction solution was poured into iced water, and a solid was precipitated out and filtered with suction. The filter cake was washed 3 times with ethanol and then 3 times with water, and dried to give the compound 42 (150 mg, 24.3%).

$^1$H NMR (400 MHz, DMSO-$d_6$) δ 11.07-10.89 (m, 2H), 10.11 (s, 1H), 8.13 (d, J=14.5 Hz, 1H), 7.82 (dd, J=7.0, 1.8 Hz, 1H), 7.59-7.44 (m, 2H), 7.42-7.13 (m, 5H), 5.15 (dd, J=13.3, 5.1 Hz, 1H), 4.52-4.26 (m, 4H), 3.31 (s, 1H), 3.00-2.50 (m, 6H), 2.41-2.21 (m, 1H), 2.10-1.98 (m, 1H). MS: 515.1 (M+1).

Example 4: Synthesis of Compounds 43-49, 54-57, 59-61, 64, 65, 93, 122-123, and 157-158

The synthesis method of the compounds 43-49, 54-57, 59-61, 64, 65, 93, 122-123, and 157-158 was the same as that for the compound 42. The details of these compounds are shown in Table 2:

TABLE 2
| Compound | Structure | ¹HNMR, MS (m/z) |
|---|---|---|
| 43 | 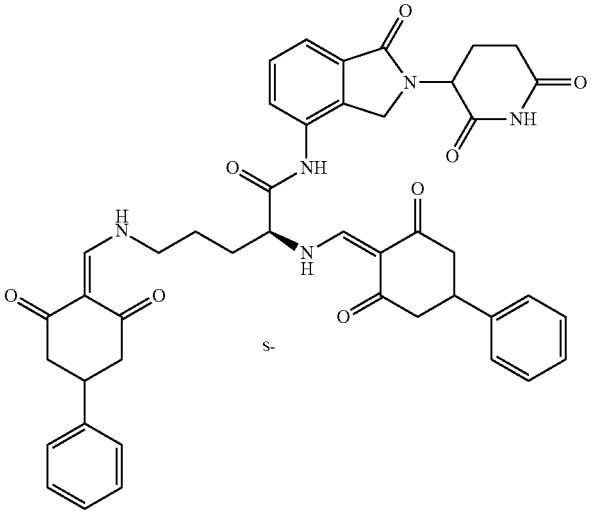 | ¹H NMR (400 MHz, DMSO-d$_6$) δ 11.40-11.24 (m, 1H), 11.01 (s, 1H), 10.98-10.86 (m, 1H), 10.29 (d, J = 11.9 Hz, 1H), 8.25 (d, J = 14.1 Hz, 1H), 8.12 (d, J = 14.6 Hz, 1H), 7.79 (dd, J = 16.2, 7.6 Hz, 1H), 7.61-7.46 (m, 2H), 7.29 (d, J = 5.2 Hz, 8H), 7.20 (s, 2H), 5.14 (d, J = 11.6 Hz, 1H), 4.66-4.49 (m, 1H), 4.48-4.28 (m, 2H), 3.51 (d, J = 5.8 Hz, 2H), 3.29-2.51 (m, 12H), 2.41-2.31 (m, 1H), 1.95 (t, J = 35.7 Hz, 3H), 1.73-1.52 (m, 2H). MS: 770.8 (M + 1) |
| 44 | 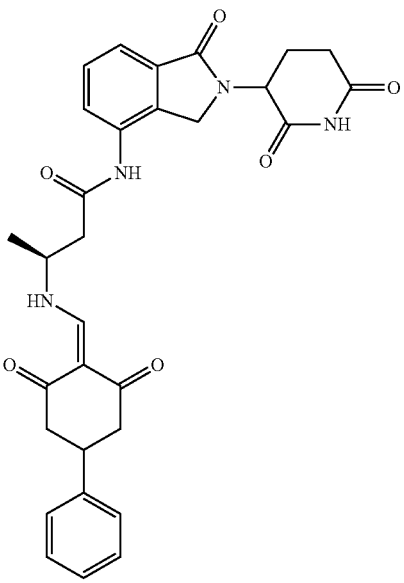 [SMILES: C[C@@H](CC(=O)Nc1cccc2c1CN(C1CCC(=O)NC1=O)C2=O)NC=C1C(=O)CC(c2ccccc2)CC1=O] | ¹H NMR (400 MHz, DMSO-d$_6$) δ 11.30-10.92 (m, 2H), 10.01 (d, J = 4.0 Hz, 1H), 8.21-8.07 (m, 1H), 7.75-7.65 (m, 1H), 7.51 (dd, J = 12.1, 7.6 Hz, 2H), 7.37-7.11 (m, 5H), 5.12 (d, J = 11.9 Hz, 1H), 4.31 (d, J = 3.8 Hz, 3H), 3.30-3.16 (m, 1H), 2.89 (d, J = 12.9 Hz, 1H), 2.75 (d, J = 5.8 Hz, 5H), 2.46-2.25 (m, 3H), 2.00 (s, 1H), 1.34 (d, J = 6.7 Hz, 3H). MS: 543.2 (M + 1). |

TABLE 2-continued
| Compound | Structure | ¹HNMR, MS (m/z) |
|---|---|---|
| 45 | 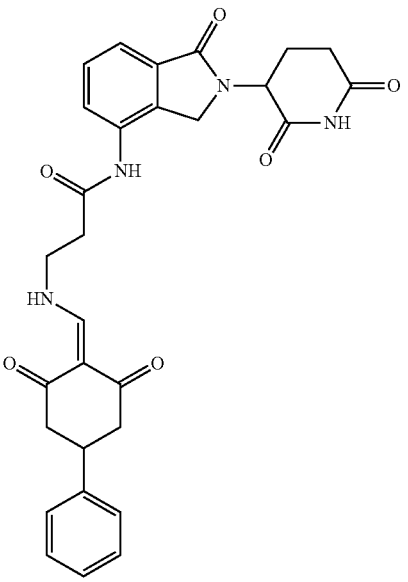 [SMILES: O=C1CCC(N2Cc3c(NC(=O)CCNC=C4C(=O)CC(c5ccccc5)CC4=O)cccc3C2=O)C(=O)N1] | ¹H NMR (400 MHz, DMSO-d₆) δ 11.11-10.98 (m, 2H), 10.05 (s, 1H), 8.15 (d, J = 14.4 Hz, 1H), 7.70 (d, J = 7.5 Hz, 1H), 7.55-7.45 (m, 2H), 7.34-7.14 (m, 4H), 7.19 (s, 1H), 5.13 (dd, J = 13.1, 5.2 Hz, 1H), 4.32 (dd, J = 36.8, 17.3 Hz, 2H), 3.75 (d, J = 6.0 Hz, 2H), 3.31-3.21 (m, 2H), 2.97-2.84 (m, 1H), 2.79-2.52 (m, 5H), 2.46-2.32 (m, 32H), 2.03-1.95 (m, 1H). MS: 529.2 (M + 1). |
| 46 | 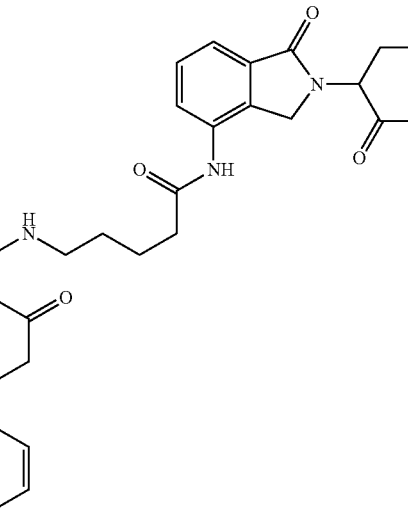 | ¹H NMR (400 MHz, DMSO-d₆) δ 11.03-10.87 (m, 2H), 9.81 (s, 1H), 8.15 (d, J = 14.5 Hz, 1H), 7.81 (dd, J = 7.0, 1.5 Hz, 1H), 7.58-7.43 (m, 2H), 7.40-7.15 (m, 5H), 5.14 (dd, J = 13.3, 5.0 Hz, 1H), 4.37 (q, J = 17.6 Hz, 2H), 3.51 (d, J = 6.0 Hz, 2H), 3.38-3.25 (m, 2H), 3.01-2.38 (m, 9H), 2.14-1.94 (m, 1H), 1.62 (d, J = 3.0 Hz, 4H). MS: 557.3 (M + 1). |
| 47 | 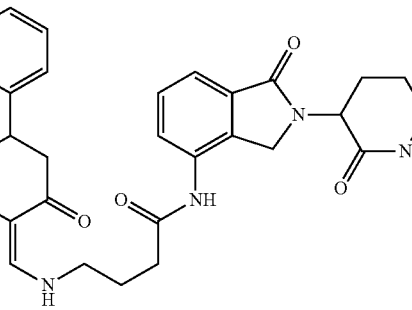 | ¹H NMR (400 MHz, DMSO-d₆) δ 11.08-10.89 (m, 2H), 9.86 (s, 1H), 8.14 (d, J = 14.6 Hz, 1H), 7.85 (dd, J = 7.0, 1.0 Hz, 1H), 7.50 (d, J = 6.9 Hz, 2H), 7.38-7.16 (m, 5H), 5.15 (dd, J = 13.3, 5.1 Hz, 1H), 4.38 (q, J = 17.5 Hz, 2H), 3.55-3.17 (m, 3H), 3.01-2.84 (m, 1H), 2.61 (d, J = 17.5 Hz, 3H), 2.49-2.30 (m, 3H), 2.13-1.83 (m, 3H), 1.34-1.17 (m, 2H). MS: 543.3 (M + 1). |

TABLE 2-continued
| Compound | Structure | ¹HNMR, MS (m/z) |
|---|---|---|
| 48 | 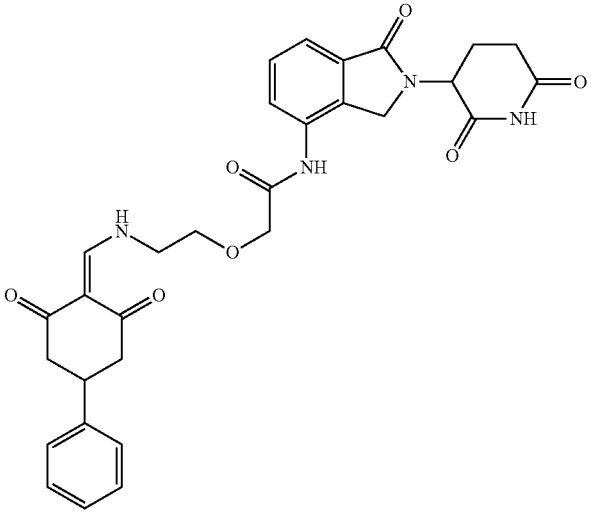 [SMILES: O=C1CCC(N2Cc3c(NC(=O)COCCNC=C4C(=O)CC(c5ccccc5)CC4=O)cccc3C2=O)C(=O)N1] | ¹H NMR (400 MHz, DMSO-d₆) δ 11.00 (d, J = 12.8 Hz, 2H), 9.72 (s, 1H), 8.17 (d, J = 14.5 Hz, 1H), 7.73 (dd, J = 7.6, 0.9 Hz, 1H), 7.60-7.44 (m, 2H), 7.30-7.20 (m, 5H), 5.12 (dd, J = 13.1, 5.1 Hz, 1H), 4.38 (q, J = 18.0 Hz, 2H), 4.14 (s, 2H), 3.71 (d, J = 2.1 Hz, 4H), 3.29-3.21 (m, 1H), 2.88-2.29 (m, 6H), 2.06-1.95 (m, 1H). MS: 559.2 (M + 1). |
| 49 | 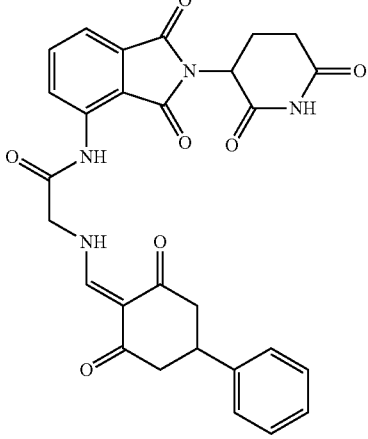 | ¹H NMR (400 MHz, DMSO-d₆) δ 11.93 (s, 1H), 11.49 (s, 1H), 10-58-10.50 (m, 1H), 8.45 (d, J = 7.2 Hz, 1H), 8.18 (d, J = 6.4 Hz, 1H), 7.59 (t, J = 7.9 Hz, 1H), 7.49 (dd, J = 7.9, 1.2 Hz, 1H), 7.35-7.16 (m, 5H), 5.01 (t, J = 6.0 Hz, 1H), 4.21 (d, J = 5.2 Hz, 2H), 3.39-3.22 (m, 1H), 2.73-2.41 (m, 6H), 2.17-1.98 (m, 2H). MS: 529.4 (M + 1). |
| 54 | 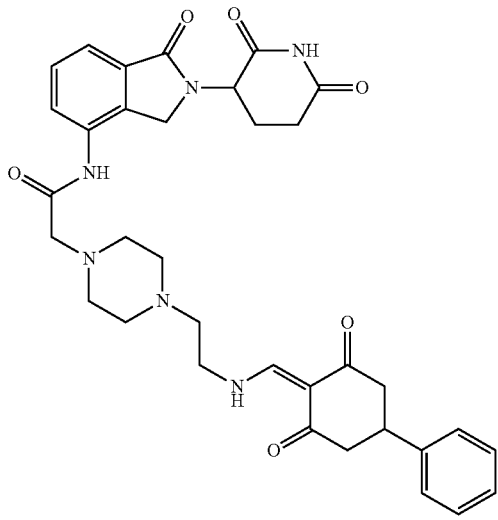 [SMILES: O=C1CCC(N2Cc3c(NC(=O)CN4CCN(CCNC=C5C(=O)CC(c6ccccc6)CC5=O)CC4)cccc3C2=O)C(=O)N1] | MS: 627.4 (M + 1). |

TABLE 2-continued
| Compound | Structure | ¹HNMR, MS (m/z) |
|---|---|---|
| 55 | 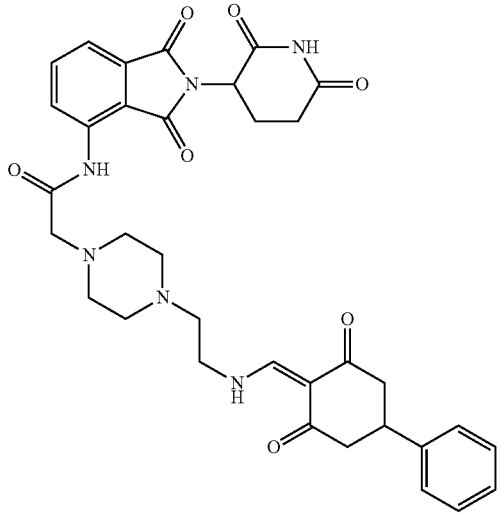 [SMILES: O=C1CCC(N2C(=O)c3cccc(NC(=O)CN4CCN(CCNC=C5C(=O)CC(c6ccccc6)CC5=O)CC4)c3C2=O)C(=O)N1] | MS: 641.4 (M + 1). |
| 56 | 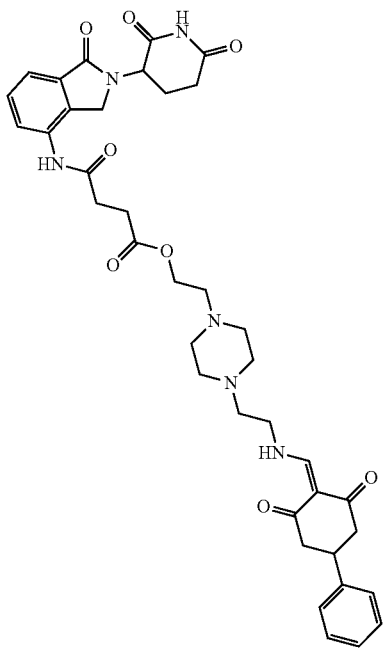 [SMILES: O=C1CCC(N2Cc3c(NC(=O)CCC(=O)OCCN4CCN(CCNC=C5C(=O)CC(c6ccccc6)CC5=O)CC4)cccc3C2=O)C(=O)N1] | MS: 713.5 (M + 1). |

TABLE 2-continued
| Compound | Structure | ¹HNMR, MS (m/z) |
|---|---|---|
| 57 | 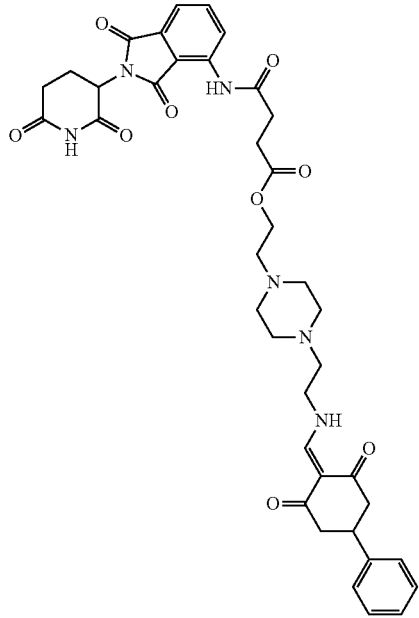 [SMILES: O=C1CCC(N2C(=O)c3cccc(NC(=O)CCC(=O)OCCN4CCN(CCNC=C5C(=O)CC(c6ccccc6)CC5=O)CC4)c3C2=O)C(=O)N1] | MS: 727.4 (M + 1). |
| 59 | 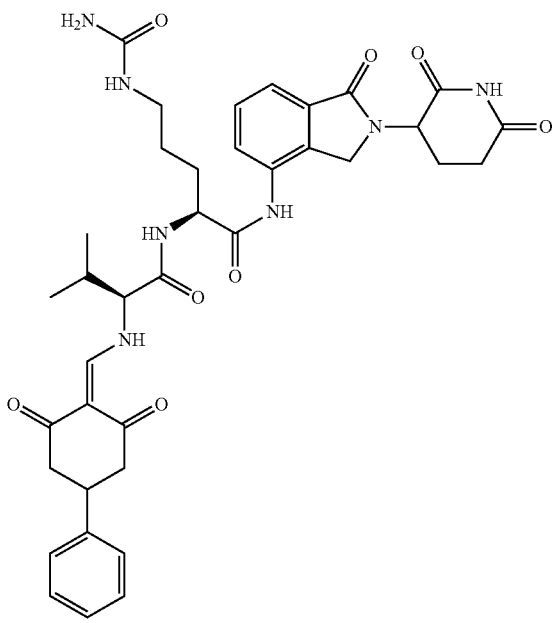 [SMILES: CC(C)[C@H](NC=C1C(=O)CC(c2ccccc2)CC1=O)C(=O)N[C@@H](CCCNC(N)=O)C(=O)Nc1cccc2c1CN(C1CCC(=O)NC1=O)C2=O] | MS: 714.5 (M + 1). |

TABLE 2-continued

| Compound | Structure | ¹HNMR, MS (m/z) |
|---|---|---|
| 60 | 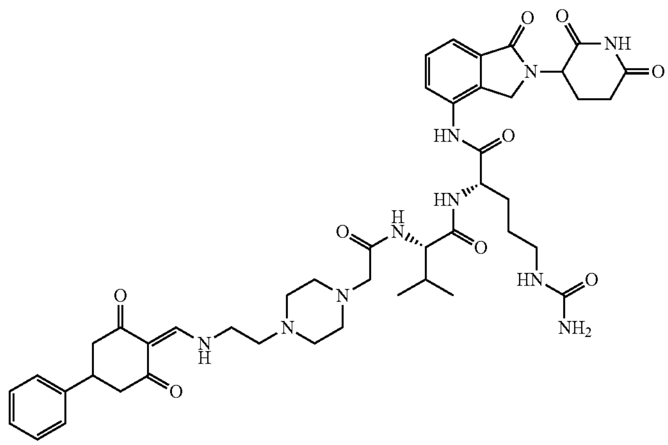 [SMILES: CC(C)[C@H](NC(=O)CN1CCN(CCNC=C2C(=O)CC(c3ccccc3)CC2=O)CC1)C(=O)N[C@@H](CCCNC(N)=O)C(=O)Nc1cccc2c1CN(C1CCC(=O)NC1=O)C2=O] | MS: 883.6 (M + 1). |
| 61 | 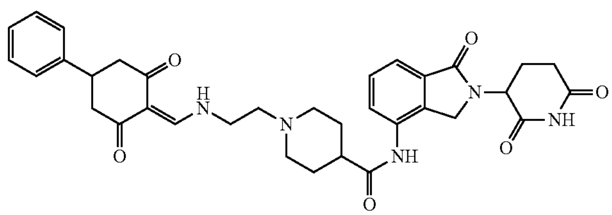 [SMILES: O=C1CCC(N2Cc3c(NC(=O)C4CCN(CCNC=C5C(=O)CC(c6ccccc6)CC5=O)CC4)cccc3C2=O)C(=O)N1] | MS: 612.4 (M + 1). |
| 64 | 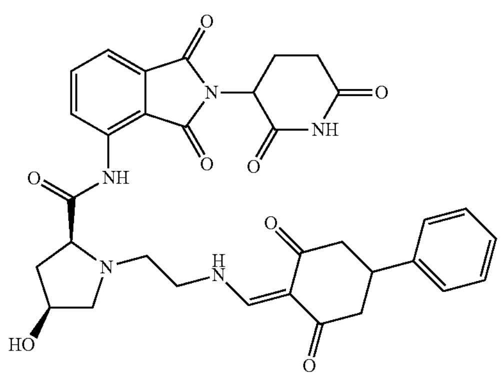 [SMILES: O=C1CCC(N2C(=O)c3cccc(NC(=O)[C@@H]4C[C@H](O)CN4CCNC=C4C(=O)CC(c5ccccc5)CC4=O)c3C2=O)C(=O)N1] | MS: 628.4 (M + 1). |
| 65 | 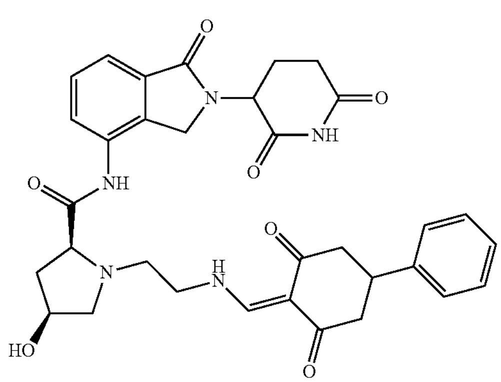 [SMILES: O=C1CCC(N2Cc3c(NC(=O)[C@@H]4C[C@H](O)CN4CCNC=C4C(=O)CC(c5ccccc5)CC4=O)cccc3C2=O)C(=O)N1] | MS: 614.4 (M + 1). |

TABLE 2-continued

| Compound | Structure | ¹HNMR, MS (m/z) |
|---|---|---|
| 93 | 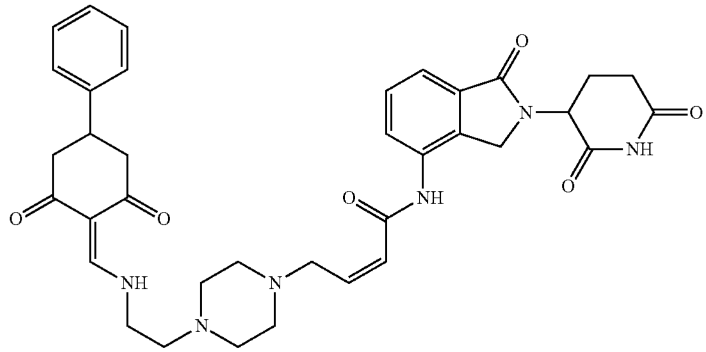 [SMILES: O=C(/C=C\CN1CCN(CCNC=C2C(=O)CC(c3ccccc3)CC2=O)CC1)Nc1cccc2c1CN(C1CCC(=O)NC1=O)C2=O] | MS: 653.5 (M + 1). |
| 122 | 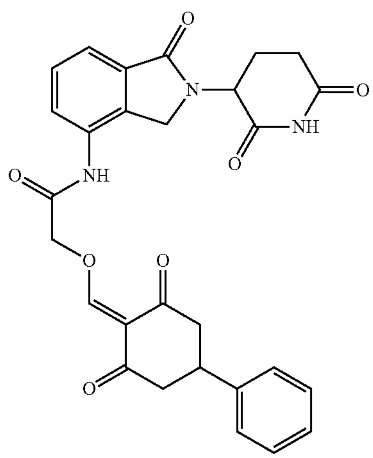 | MS: 530.3 (M + 1). |
| 123 | 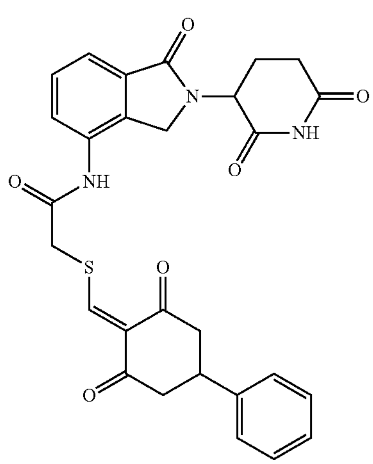 [SMILES: O=C1CCC(N2Cc3c(NC(=O)CSC=C4C(=O)CC(c5ccccc5)CC4=O)cccc3C2=O)C(=O)N1] | MS: 546.3 (M + 1). |

TABLE 2-continued
| Compound | Structure | $^1$HNMR, MS (m/z) |
|---|---|---|
| 157 | 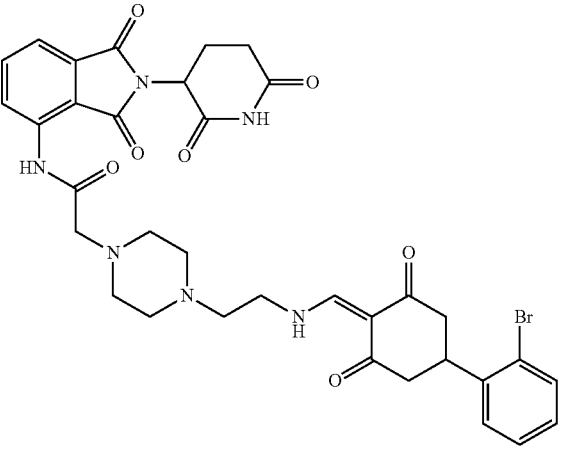 [SMILES: O=C1CCC(N2C(=O)c3cccc(NC(=O)CN4CCN(CCNC=C5C(=O)CC(c6ccccc6Br)CC5=O)CC4)c3C2=O)C(=O)N1] | $^1$H NMR (400 MHz, CDCl$_3$) δ 11.19 (s, 1H), 9.18 (s, 1H), 8.46 (s, 1H), 8.21 (d, J = 14.2 Hz, 1H), 7.72 (dd, J = 10.2, 7.9 Hz, 2H), 7.58 (d, J = 8.0 Hz, 1H), 7.50 (t, J = 7.8 Hz, 1H), 7.32 (t, J = 7.5 Hz, 1H), 7.24 (s, 1H), 7.12 (t, J = 7.6 Hz, 1H), 5.22 (dd, J = 13.2, 5.1 Hz, 1H), 4.44 (s, 2H), 3.83 (t, J = 11.7 Hz, 1H), 3.54 (d, J = 5.9 Hz, 2H), 3.49 (s, 1H), 3.21 (s, 2H), 2.96-2.54 (m, 15H), 2.44-2.32 (m, 1H), 2.25 (s, 1H). MS: 705.1 (M + 1). |
| 158 | 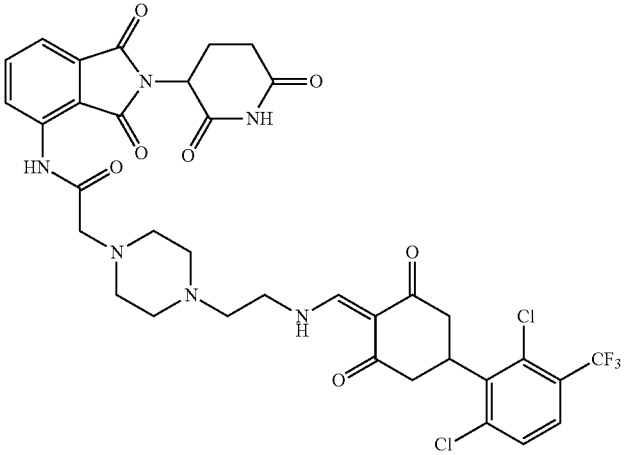 [SMILES: O=C1CCC(N2C(=O)c3cccc(NC(=O)CN4CCN(CCNC=C5C(=O)CC(c6c(Cl)ccc(C(F)(F)F)c6Cl)CC5=O)CC4)c3C2=O)C(=O)N1] | MS: 763.4 (M + 1). |
Example 5: Synthesis of Compound 50
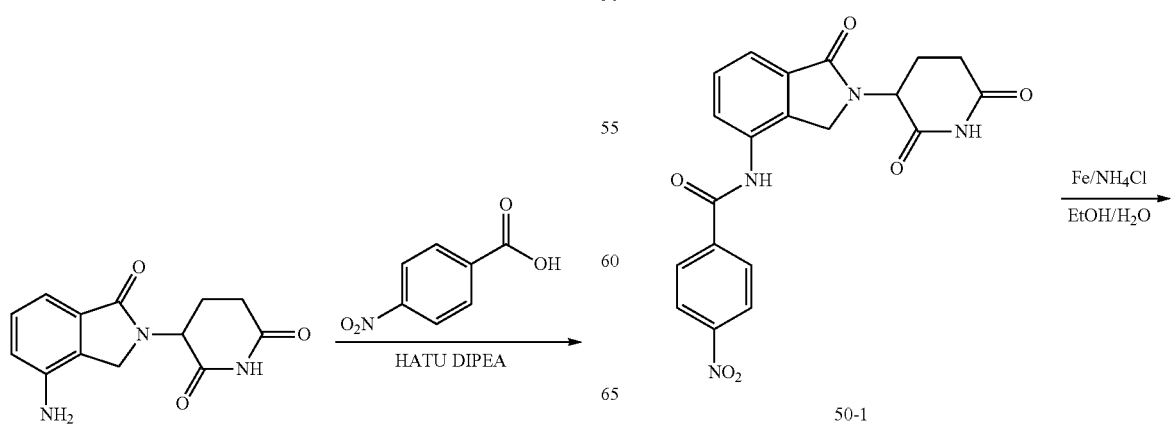

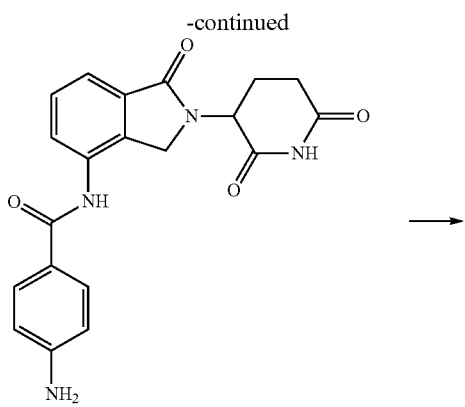

50-2

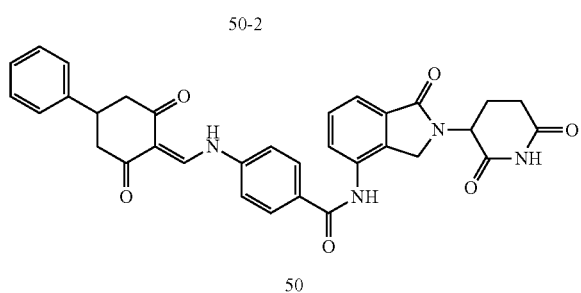

50

Step 1: The synthesis method was the same as that in Step 1 of Example 3.

Step 2: The intermediate 50-1 (500 mg, 1.22 mmol) was dissolved in ethanol (20 ml)/water (10 ml). Saturated ammonium chloride (3 mL) and reduced iron powder (560 mg, 10 mmol) were added and refluxed at 80° C. for 1 hr, until TLC showed the reaction was complete. The reaction solution was filtered through diatomaceous earth under sunction while hot. The filter cake was washed with EtOAc. The organic phase was separated, and the aqueous phase was extracted with EtOAc. The combined organic phase was washed with water and brine, dried, and concentrated. The crude product was separated by column chromatography to afford the intermediate 50-2 (200 mg, 43%).

Step 3: This step was the same as Step 2 in Example 1. Compound 50, $^1$H NMR (400 MHz, DMSO-$d_6$) δ 12.73 (d, J=13.5 Hz, 1H), 10.97 (s, 1H), 10.37 (s, 1H), 8.61 (d, J=13.5 Hz, 1H), 8.04 (d, J=8.5 Hz, 2H), 7.70 (t, J=8.3 Hz, 3H), 7.64-7.47 (m, 2H), 7.44-7.12 (m, 5H), 5.26-4.99 (m, 1H), 4.56-4.26 (m, 2H), 3.42 (s, 1H), 2.88 (ddd, J=40.5, 16.2, 11.3 Hz, 3H), 2.74-2.51 (m, 3H), 2.39 (d, J=13.0 Hz, 1H), 2.00 (s, 1H). MS: 577.3 (M+1).

Example 6: Synthesis of Compounds 51-53, 58, 62, 63, and 66

The synthesis method of the compounds 51-53, 58, 62, 63, and 66 was the same as that for the compound 50. The details of these compounds are shown in Table 3:

TABLE 3

| Compound | Structure | $^1$HNMR, MS (m/z) |
|---|---|---|
| 51 | 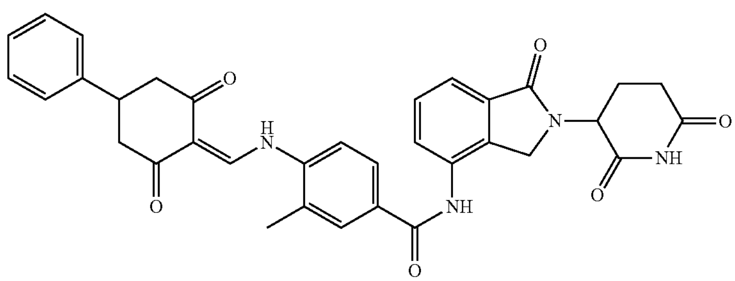 [SMILES: Cc1cc(C(=O)Nc2cccc3c2CN(C2CCC(=O)NC2=O)C3=O)ccc1NC=C1C(=O)CC(c2ccccc2)CC1=O] | $^1$H NMR (400 MHz, DMSO-$d_6$) δ 13.14 (d, J = 13.0 Hz, 1H), 10.98 (s, 1H), 10.36 (s, 1H), 8.70 (d, J = 13.0 Hz, 1H), 7.89 (dd, J = 37.8, 8.4 Hz, 3H), 7.74-7.51 (m, 3H), 7.41-7.15 (m, 5H), 5.13 (dd, J = 13.3, 5.0 Hz, 1H), 4.50-4.34 (m, 2H), 3.49-3.37 (m, 1H), 3.03-2.76 (m, 3H), 2.76-2.51 (m, 3H), 2.45-2.28 (m, 4H), 2.02-1.93 (m, 1H). MS: 591.3 (M + 1). |
| 52 | 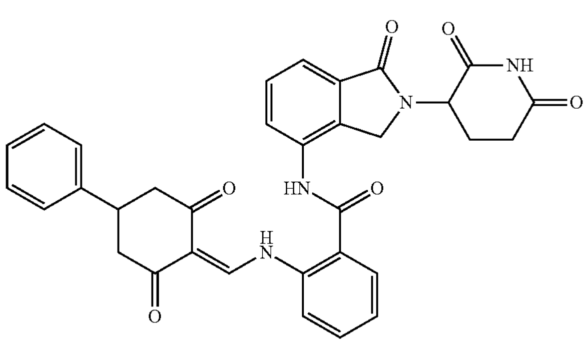 [SMILES: O=C1CCC(N2Cc3c(NC(=O)c4ccccc4NC=C4C(=O)CC(c5ccccc5)CC4=O)cccc3C2=O)C(=O)N1] | $^1$H NMR (400 MHz, DMSO-$d_6$) δ 13.49 (d, J = 13.6 Hz, 1H), 10.99 (s, 1H), 10.69 (s, 1H), 8.55 (d, J = 13.8 Hz, 1H), 7.96-7.53 (m, 6H), 7.48-7.15 (m, 6H), 5.23-5.07 (m, 1H), 4.60-4.37 (m, 2H), 3.47-3.33 (m, 1H), 2.79 (s, 3H), 2.65-2.51 (m, 3H), 2.44-2.33 (m, 1H), 2.10-1.93 (m, 1H). MS: 577.2 (M + 1). |

TABLE 3-continued

| Compound | Structure | ¹HNMR, MS (m/z) |
|---|---|---|
| 53 | 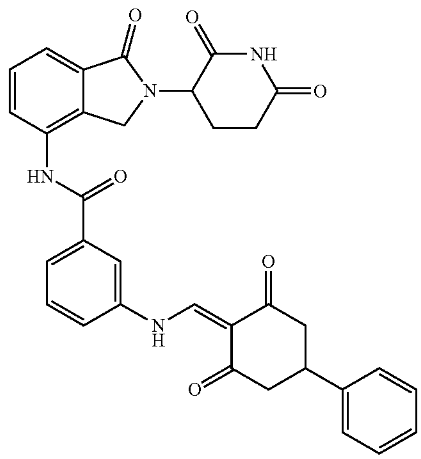 [SMILES: O=C1CCC(N2Cc3c(NC(=O)c4cccc(NC=C5C(=O)CC(c6ccccc6)CC5=O)c4)cccc3C2=O)C(=O)N1] | ¹H NMR (400 MHz, DMSO-d₆) δ 12.87-12.81 (m, 1H), 10.98 (s, 1H), 10.49 (s, 1H), 8.65 (d, J = 13.2 Hz, 1H), 8.11 (s, 1H), 7.84-7.53 (m, 6H), 7.41-7.23 (m, 5H), 5.14 (dd, J = 13.3, 5.0 Hz, 1H), 4.42 (t, J = 10.8 Hz, 2H), 3.48-3.36 (m, 1H), 2.87-2.53 (m, 6H), 2.39 (d, J = 12.9 Hz, 1H), 2.05-1.91 (m, 1H). MS: 577.2 (M + 1). |
| 58 | 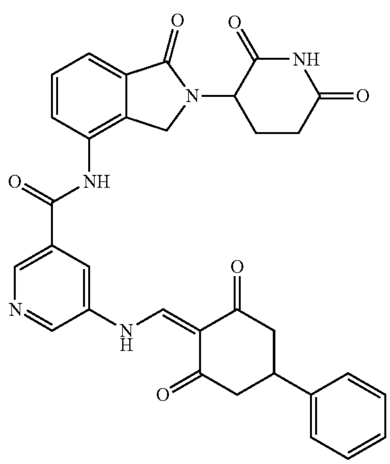 [SMILES: O=C1CCC(N2Cc3c(NC(=O)c4cncc(NC=C5C(=O)CC(c6ccccc6)CC5=O)c4)cccc3C2=O)C(=O)N1] | MS: 606.4 (M + 1). |
| 62 | 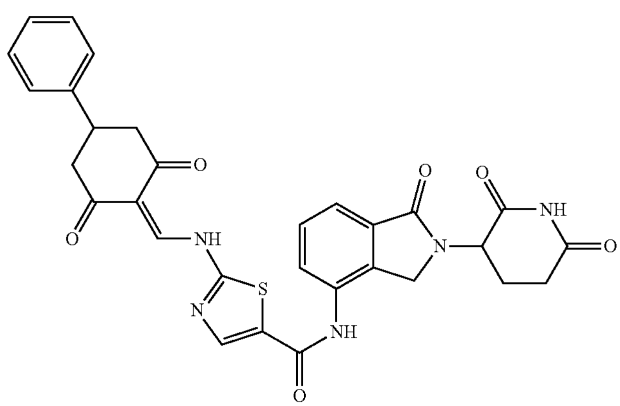 [SMILES: O=C1CCC(N2Cc3c(NC(=O)c4cnc(NC=C5C(=O)CC(c6ccccc6)CC5=O)s4)cccc3C2=O)C(=O)N1] | MS: 584.3 (M + 1). |

TABLE 3-continued
| Compound | Structure | ¹HNMR, MS (m/z) |
| --- | --- | --- |
| 63 | 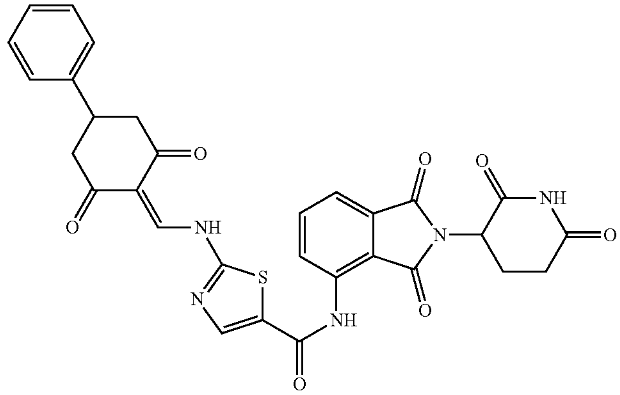 [SMILES: O=C1CCC(N2C(=O)c3cccc(NC(=O)c4cnc(NC=C5C(=O)CC(c6ccccc6)CC5=O)s4)c3C2=O)C(=O)N1] | MS: 598.3 (M + 1). |
| 66 | 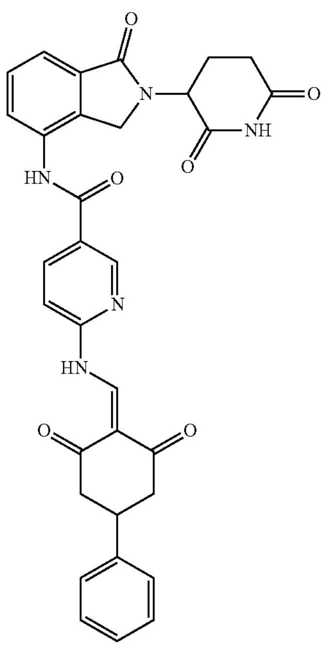 [SMILES: O=C1CCC(N2Cc3c(NC(=O)c4ccc(NC=C5C(=O)CC(c6ccccc6)CC5=O)nc4)cccc3C2=O)C(=O)N1] | ¹H NMR (400 MHz, DMSO-d₆) δ 12.51 (d, J = 4.0 Hz, 1H), 10.99 (d, J = 5.2 Hz, 1H), 10.47 (d, J = 1.4 Hz, 1H), 9.13 (d, J = 3.6 Hz, 1H), 8.99 (d, J = 3.0 Hz, 1H), 8.37 (d, J = 5.4 Hz, 1H), 7.75 (d, J = 1.8 Hz, 2H), 7.60 (d, J = 4.5 Hz, 2H), 7.45-7.07 (m, 5H), 5.16 (d, J = 7.2 Hz, 1H), 4.44 (d, J = 10.1 Hz, 2H), 3.40 (s, 2H), 3.07-2.78 (m, 4H), 2.67 (d, J = 10.8 Hz, 2H), 1.99 (d, J = 3.4 Hz, 1H). MS: 578.2 (M + 1). |
Example 7: Synthesis of Compound 73
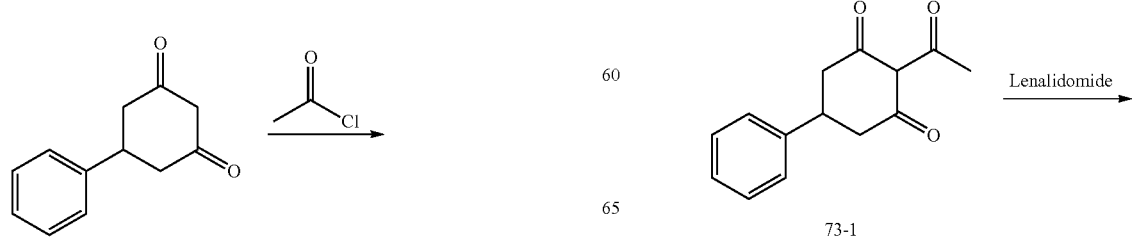
-continued

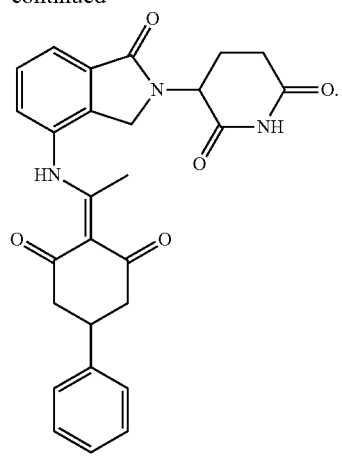

73

Step 1: 5-phenyl-1,3-cyclohexandione (10 g, 53.1 mmol), DIPEA (7.11 g, 55 mmol) and 4-dimethylaminopyridine (2.0 g, 16.4 mmol) were dissolved in 1,2-dichloroethane (140 ml). Acetyl chloride (4.32 g, 55 mmol) was slowly added dropwise at RT, and then reacted at 60° C. for 2 hrs, until TLC showed the reaction was complete. The reaction solution was poured into iced water, the organic layer was separated, and the aqueous phase was extracted with dichloromethane. The organic phase was washed with water and brine, dried, and concentrated. The crude product was separated by column chromatography to afford the intermediate 73-1 (7.31 g, yield 60%).

Step 2: The intermediate 73-1 (360 mg, 1.56 mmol) and lenalidomide (200 mg, 0.77 mmol) were dissolved in ethanol/chloroform (10 mL/10 mL), and reacted for 2 hrs under reflux by heating, until TLC showed the reaction was complete. The reaction solution was dried by rotation. The crude product was separated by column chromatography on silica gel to give the compound 73 (90 mg, 25%).

$^1$H NMR (400 MHz, DMSO_d6): δ 15.04 (s, 1H), 11.01 (s, 1H), 7.70-7.65 (m, 3H), 7.35-7.24 (m, 5H), 5.18-5.13 m, 1H), 4.40 (q, J=39.2 Hz, 2H), 2.90-2.86 (m, 3H), 2.67-2.51 (m, 3H), 2.48 (s, 3H), 2.46-2.40 (m, 1H), 2.01-1.95 (m, 1H). MS: 472.1 (M+1)

Example 8: Synthesis of Compounds 74-76

The synthesis method of the compounds 74-76 was the same as that for the compound 73. The details of these compounds are shown in Table 4.

TABLE 4

| Compound | Structure | $^1$HNMR, MS (m/z) |
|---|---|---|
| 74 | 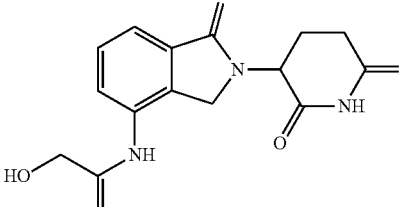 | $^1$H NMR (400 MHz, DMSO_d6): δ 11.90 (s, 1H), 10.99 (s, 1H), 7.75-7.64 (m, 3H), 7.34-7.32 (m, 4H), 7.24-7.21 (m, 1H), 5.33 (t, J = 6.4 Hz, 1H), 5.14 (dd, J = 12.8, 4.2 Hz, 1H), 4.50-4.34 (m, 4H), 3.36-3.34 (m, 1H), 2.93-2.83 (m, 3H), 2.69-2.54 (m, 3H), 2.45-2.38 (m, 1H). MS: 488.2 (M + 1). |
| 75 | 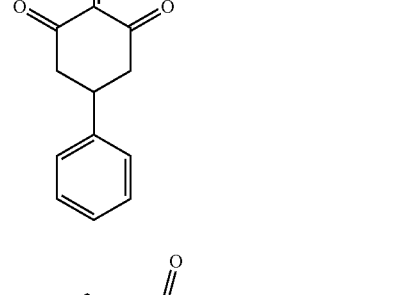 | $^1$H NMR (400 MHz, DMSO_d6): 14.52 (s, 1H), 11.02 (s, 1H), 7.47 (d, J = 8.0 Hz, 1H), 7.17-7.34 (m, 11H), 6.72 (d, J = 8.0 Hz, 1H), 5.12 (dd, J = 13.2, 4.2 Hz, 1H), 4.57-4.37 (m, 2H), 3.50-3.42 (m, 1H), 2.95-2.46 (m, 6H), 2.46-2.38 (m, 1H), 2.01-1.98 (m, 1H). MS: 534.2 (M + 1). |

TABLE 4-continued

| Compound | Structure | ¹HNMR, MS (m/z) |
|---|---|---|
| 76 | 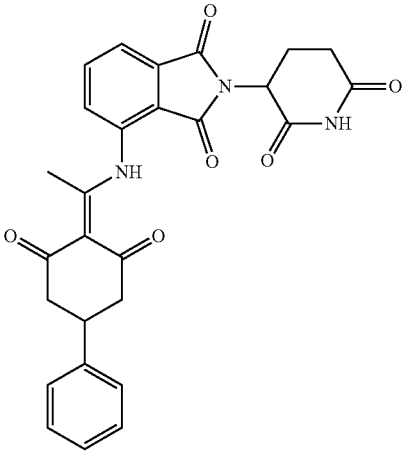 [SMILES: CC(Nc1cccc2c1C(=O)N(C1CCC(=O)NC1=O)C2=O)=C1C(=O)CC(c2ccccc2)CC1=O] | ¹H NMR (400 MHz, DMSO-d$_6$) δ 12.64 (s, 1H), 11.97 (s, 1H), 7.64 (t, J = 7.8 Hz, 1H), 7.36-7.12 (m, 7H), 5.05 (t, J = 5.9 Hz, 1H), 3.44-3.37 (m, 1H), 2.74-2.47 (m, 9H), 2.49 (s, 3H), 2.16-1.97 (m, 2H). MS: 486.3 (M + 1). |

Example 9: Synthesis of Compound 77

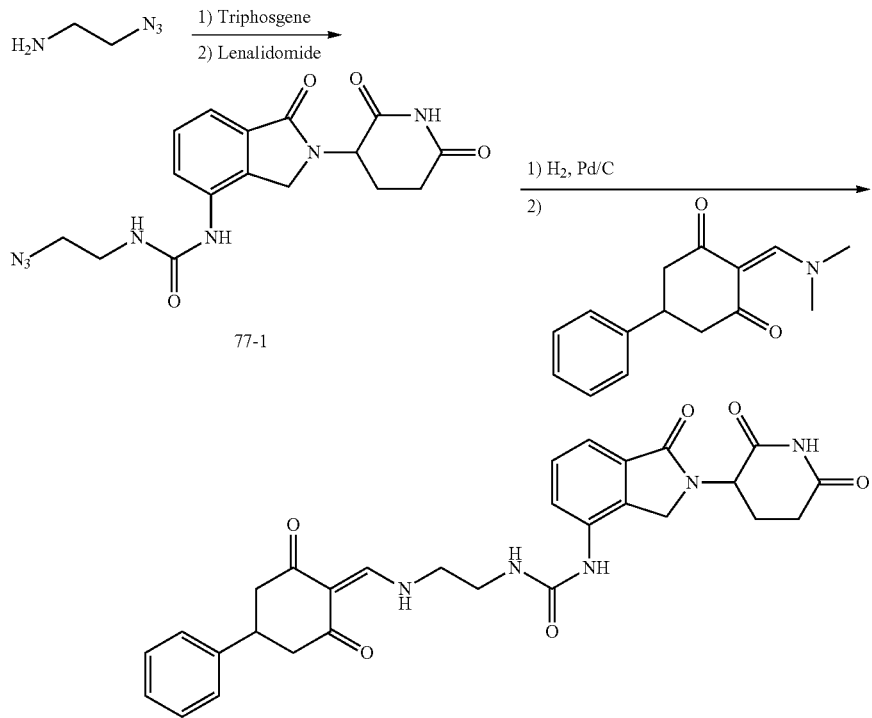

Step 1: Triphosgene (1.14 g, 3.84 mmol) was dissolved in dichloromethane (20 ml). After cooling to −10° C., 2-azidoethylamine (1.0 g, 11.61 mmol) was slowly added dropwise, and stirred at −10° C. for half an hour. Then, TEA (2.34 g, 23 mmol) was added and reacted for an additional 1 hr. The reaction solution was slowly added dropwise to a solution of lenalidomide (2.0 g, 7.7 mmol) in N,N-dimethylacetamide (20 ml), and then reacted at 65° C. for 1 hr. The reaction solution was poured into iced water, the aqueous phase was extracted with EtOAc, and the organic phase was washed with water and brine, dried and concentrated. The crude product was separated by column chromatography to afford the intermediate 77-1 (2.01 g, 70%).

Step 2: The intermediate 77-1 (2.0 g, 5.38 mmol) was dissolved in ethanol (50 ml), and then 10% Pd/C (200 mg) was added, and stirred for 1 hr while hydrogen was introduced at RT, until TLC showed the reaction was complete. The Pd/C was filtered off. Then, the intermediate 1-1 (423 mg, 1.74 mmol) was added, and stirred for another 1 hr at room temperature. A solid was precipitated out, which was filtered under suction, washed 3 times with ethanol and dried to give the compound 77 (533 mg, 68%).

¹H NMR (400 MHz, DMSO_d6): δ 11.02-10.89 (m, 2H), 8.41 (s, 1H), 8.06 (d, J=16.0 Hz, 1H), 7.93 (d, J=8.4 Hz, 1H), 7.42-7.20 (m, 7H), 6.50 (br, 1H), 5.14 (dd, J=13.2, 4.8 Hz, 1H), 4.30 (q, J=13.2 Hz, 2H), 3.56 (br, 2H), 3.37 (br, 1H), 3.25-3.16 (m, 2H), 2.96-2.87 (m, 1H), 2.75-2.57 (m, 4H), 2.46-2.30 (m, 1H). MS: 544.2 (M+1).
Example 10: Synthesis of Compounds 71, 72, and 78-90
The synthesis method of the compounds 71, 72, and 78-90 was the same as that for the compound 77. The details of these compounds are shown in Table 5.
TABLE 5
| Compound | Structure | ¹HNMR, MS (m/z) |
|---|---|---|
| 71 | 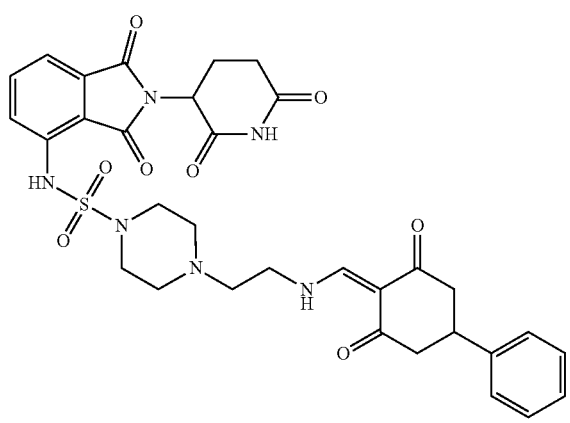 [SMILES: O=C1CCC(N2C(=O)c3cccc(NS(=O)(=O)N4CCN(CCNC=C5C(=O)CC(c6ccccc6)CC5=O)CC4)c3C2=O)C(=O)N1] | MS: 663.2 (M + 1). |
| 72 | 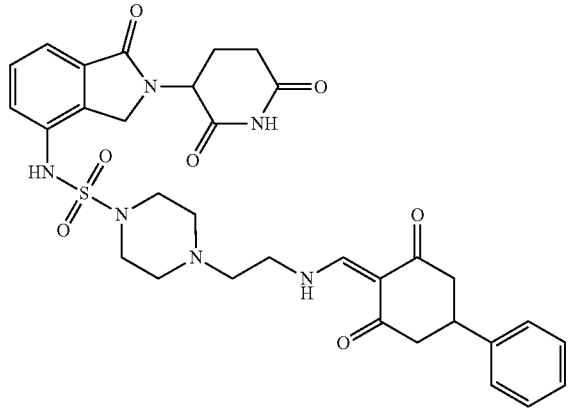 [SMILES: O=C1CCC(N2Cc3c(NS(=O)(=O)N4CCN(CCNC=C5C(=O)CC(c6ccccc6)CC5=O)CC4)cccc3C2=O)C(=O)N1] | MS: 649.3 (M + 1). |
| 78 | 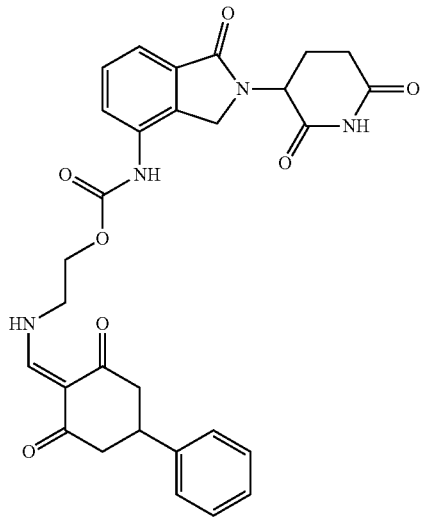 [SMILES: O=C1CCC(N2Cc3c(NC(=O)OCCNC=C4C(=O)CC(c5ccccc5)CC4=O)cccc3C2=O)C(=O)N1] | ¹H NMR (400 MHz, DMSO_d6): δ 11.00 (br, 2H), 9.68 (s, 1H), 8.13 (d, J = 14.0 Hz, 1H), 7.70-7.20 (m, 8H), 5.12 (br, 1H), 4.40-3.75 (m, 6H), 3.27-3.21 (m, 2H), 2.95-2.55 (m, 3H), 2.38-2.27 (m, 2H), 1.97 (br, 2H). MS: 545.1 (M + 1). |

TABLE 5-continued
| Compound | Structure | ¹HNMR, MS (m/z) |
|---|---|---|
| 79 | 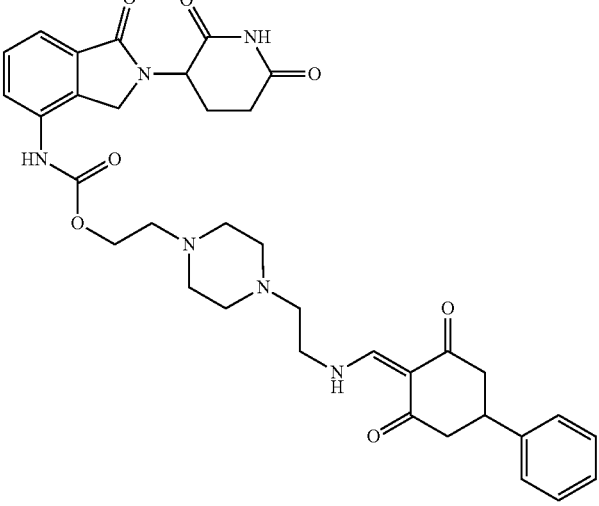 | ¹H NMR (400 MHz, DMSO-d$_6$) δ 11.00 (s, 2H), 9.58 (s, 1H), 8.11 (d, J = 14.9 Hz, 1H), 7.74 (s, 1H), 7.54-7.12 (m, 6H), 5.74 (s, 1H), 5.12 (s, 1H), 4.53-4.09 (m, 4H), 3.56 (s, 2H), 2.89 (s, 1H), 2.48 (s, 16H), 2.31 (s, 2H), 2.01 (s, 1H). MS: 657.3 (M + 1). |
| 80 | 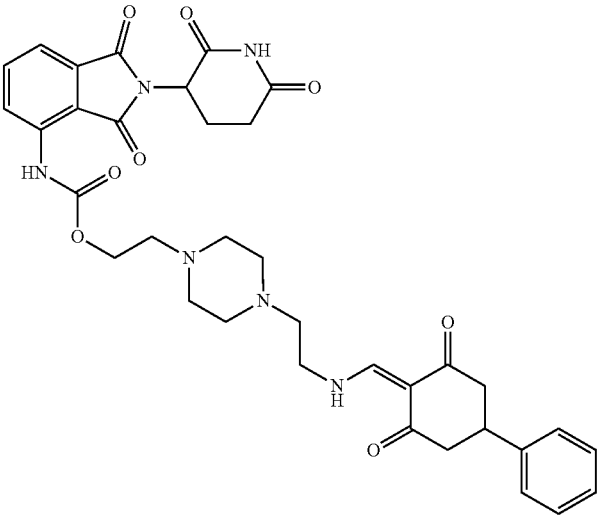 [SMILES: O=C1CCC(N2C(=O)c3cccc(NC(=O)OCCN4CCN(CCNC=C5C(=O)CC(c6ccccc6)CC5=O)CC4)c3C2=O)C(=O)N1] | MS: 671.5 (M + 1) |
| 81 | 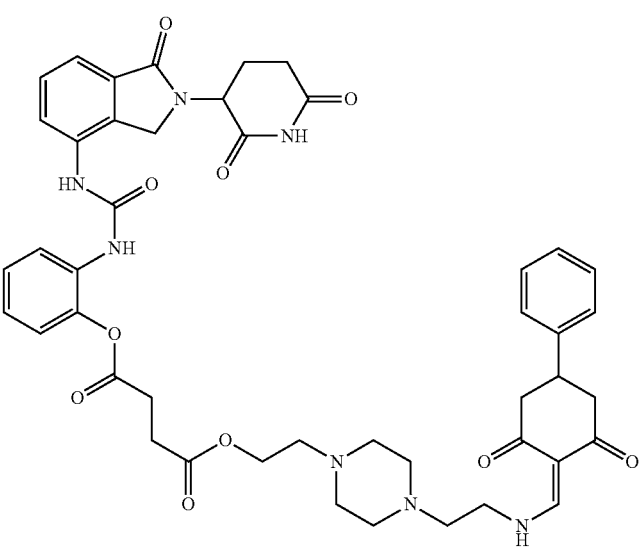 [SMILES: O=C1CCC(N2Cc3c(NC(=O)Nc4ccccc4OC(=O)CCC(=O)OCCN4CCN(CCNC=C5C(=O)CC(c6ccccc6)CC5=O)CC4)cccc3C2=O)C(=O)N1] | MS: 848.5 (M + 1). |

TABLE 5-continued

| Compound | Structure | ¹HNMR, MS (m/z) |
|---|---|---|
| 82 | 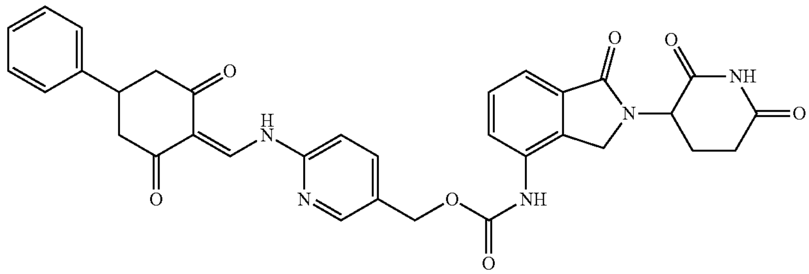 [SMILES: O=C1CCC(N2Cc3c(NC(=O)OCc4ccc(NC=C5C(=O)CC(c6ccccc6)CC5=O)nc4)cccc3C2=O)C(=O)N1] | MS: 608.3 (M + 1). |
| 83 | 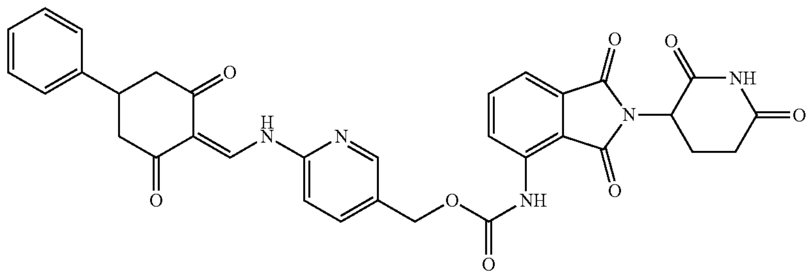 [SMILES: O=C1CCC(N2C(=O)c3cccc(NC(=O)OCc4ccc(NC=C5C(=O)CC(c6ccccc6)CC5=O)nc4)c3C2=O)C(=O)N1] | MS: 622.4 (M + 1). |
| 84 | 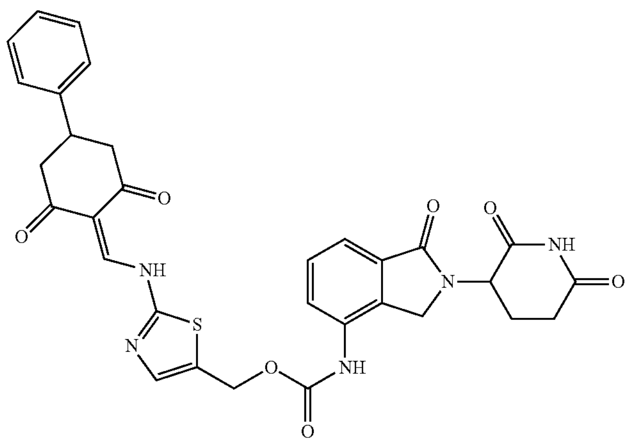 [SMILES: O=C1CCC(N2Cc3c(NC(=O)OCc4cnc(NC=C5C(=O)CC(c6ccccc6)CC5=O)s4)cccc3C2=O)C(=O)N1] | MS: 614.3 (M + 1) |
| 85 | 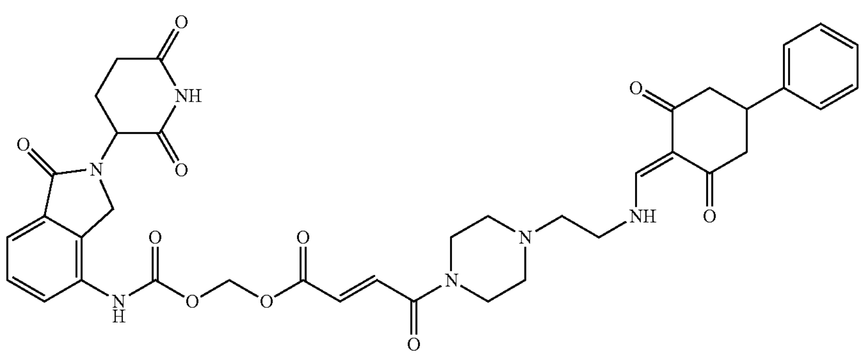 [SMILES: O=C1CCC(N2Cc3c(NC(=O)OCOC(=O)/C=C/C(=O)N4CCN(CCNC=C5C(=O)CC(c6ccccc6)CC5=O)CC4)cccc3C2=O)C(=O)N1] | MS: 741.5 (M + 1). |

TABLE 5-continued
| Compound | Structure | ¹HNMR, MS (m/z) |
|---|---|---|
| 86 | 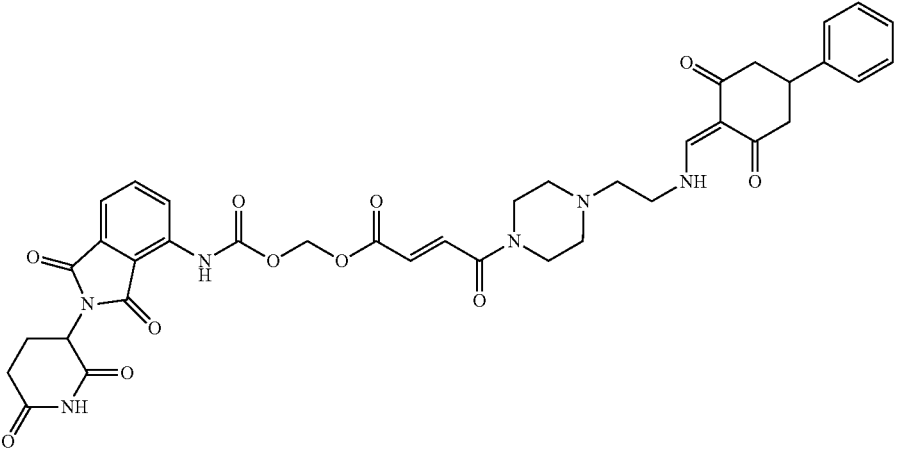 [SMILES: O=C1CCC(N2C(=O)c3cccc(NC(=O)OCOC(=O)/C=C/C(=O)N4CCN(CCNC=C5C(=O)CC(c6ccccc6)CC5=O)CC4)c3C2=O)C(=O)N1] | MS: 755.4 (M + 1). |
| 87 | 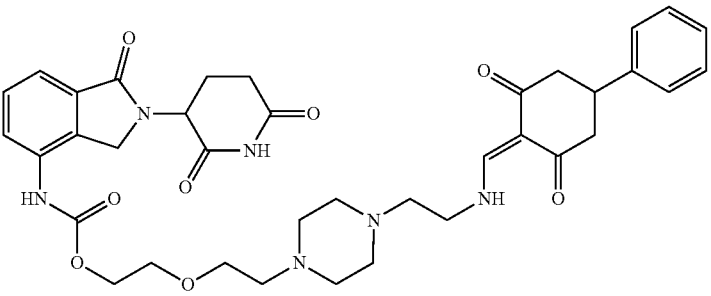 [SMILES: O=C1CCC(N2Cc3c(NC(=O)OCCOCCN4CCN(CCNC=C5C(=O)CC(c6ccccc6)CC5=O)CC4)cccc3C2=O)C(=O)N1] | MS: 701.5 (M + 1). |
| 88 | 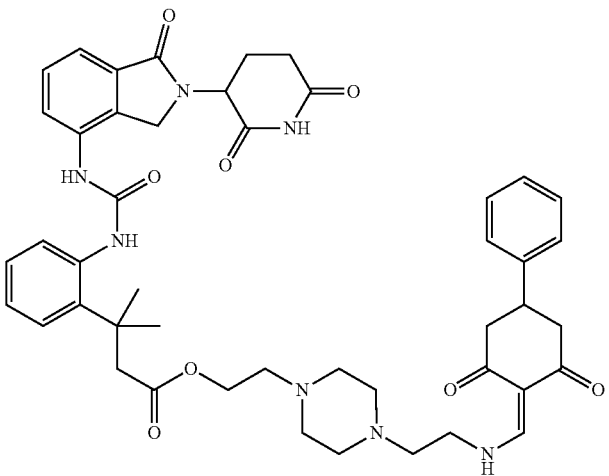 | MS: 833.5 (M + 1). |

TABLE 5-continued
| Compound | Structure | ¹HNMR, MS (m/z) |
|---|---|---|
| 89 | 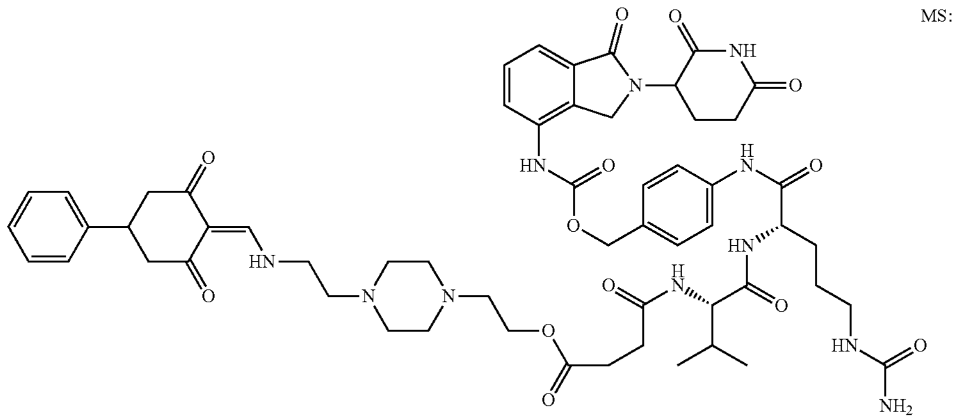 | MS: 1118.7 (M + 1). |
| 90 | 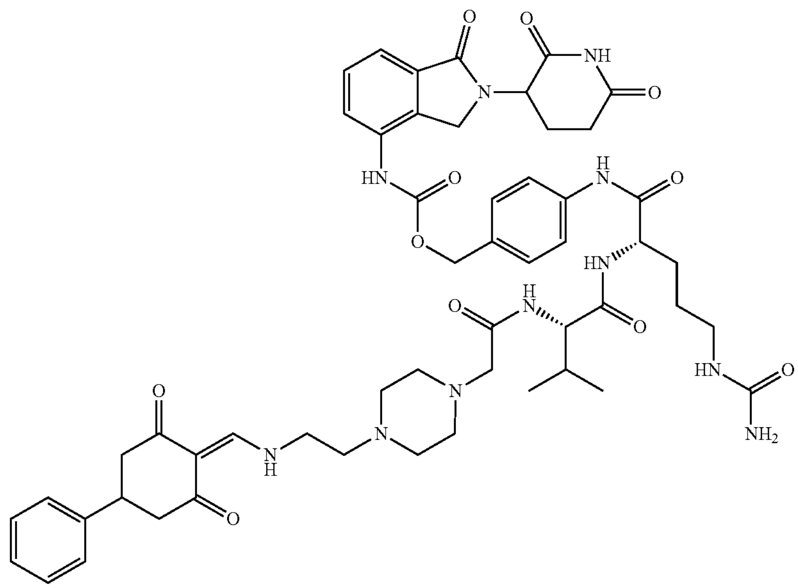 [SMILES: CC(C)[C@H](NC(=O)CN1CCN(CCNC=C2C(=O)CC(c3ccccc3)CC2=O)CC1)C(=O)N[C@@H](CCCNC(N)=O)C(=O)Nc1ccc(COC(=O)Nc2cccc3c2CN(C2CCC(=O)NC2=O)C3=O)cc1] | MS: 1032.6 (M + 1). |
Example 11: Synthesis of Compound 67
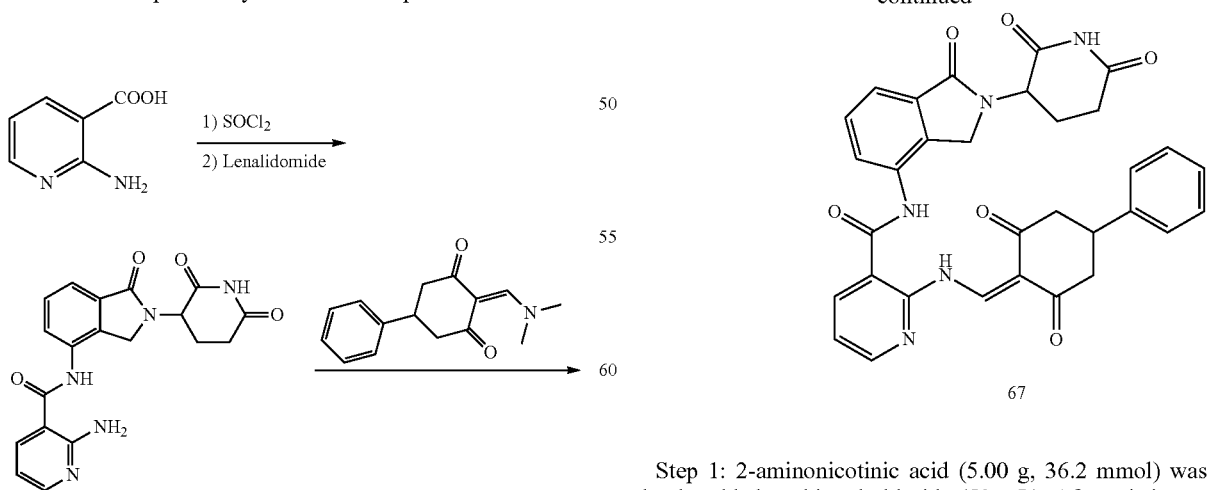
Step 1: 2-aminonicotinic acid (5.00 g, 36.2 mmol) was slowly added to thionyl chloride (50 mL). After stirring at 80° C. for 2 hrs, the thionyl chloride was directly removed under reduced pressure. At RT, The acyl chloride crude product was added in portions to a solution of lenalidomide (2.00 g, 7.72 mmol) and DIPEA (3.8 mL) in N,N-dimethylacetamide (20 mL), and the reaction solution was stirred at room temperature for 2 hrs. The reaction solution was poured into iced water, and extracted with ethyl acetate. The organic phase was washed with water and brine, dried, and concentrated. The crude product was separated by column chromatography to afford the intermediate 67-1 (620 mg, 21%).

Step 2: The intermediate 67-1 (200 mg, 0.526 mmol), the intermediate 1-1 (300 mg, 1.23 mmol) and acetic acid (60 mg, 1 mmol) were dissolved in methanol (20 mL)/dichloromethane (20 ml). The reaction solution was heated to 45° C. and reacted overnight. A solid was precipitated out, washed with ethanol and then with dichloromethane, and dried to obtain the compound 67 (32 mg, 10%).

$^1$H NMR (400 MHz, DMSO_d6): δ 13.63 (d, J=12.4 Hz, 1H), 10.99 (s, 1H), 10.80 (s, 1H), 9.24 (d, J=12.8 Hz, 1H), 8.64 (d, J=8.4 Hz, 1H), 8.41 (d, J=8.4 Hz, 1H), 7.73-7.60 (m, 3H), 7.48-7.44 (m, 1H), 7.32-7.21 (m, 6H), 5.20-5.14 (m, 1H), 4.58-4.40 (m, 2H), 3.44-3.36 (m, 2H), 2.92-2.80 (m, 3H), 2.67-2.63 (m, 3H), 2.04-1.98 (m, 1H). MS: 578.2 (M+1).

Example 12: Synthesis of Compound 91

Step 1: 1-(2-azidoethyl)piperazine (0.93 g, 6.0 mmol) was dissolved in tetrahydrofuran (20 mL), succinic anhydride (0.5 g, 5.0 mmol) was added and stirred for 3 hrs at room temperature until the raw materials were detected to disappear by TLC. The reaction solution was concentrated to obtain the intermediate 91-1 (1.46 g, crude) which was directly used in the next step.

Step 2: The intermediate 91-1 (1.46 g, crude), DIPEA (1.6 mL, 10.0 mmol), and lenalidomide (1.00 g, 3.86 mmol) were dissolved in dry DMF (20 mL), and then HATU (2.8 g, 7.5 mmol) was added and stirred overnight at RT. The reaction solution was poured into iced water, and extracted with EtOAc. The organic phase was washed with water and brine, dried and concentrated. The crude product was separated by column chromatography to afford the intermediate 91-2 (615 mg, 32%).

Step 3: The synthesis method was the same as that in Step 2 of Example 10.

Compound 91, $^1$H NMR (400 MHz, CD$_3$OD): δ 8.27 (s, 1H), 7.71 (d, J=8.0 Hz, 1H), 7.65 (d, J=8.0 Hz, 1H), 7.51 (t, J=8.0 Hz, 1H), 7.32-7.22 (m, 5H), 5.18 (q, J=8.0 Hz, 1H), 4.47 (d, J=3.2 Hz, 1H), 3.63-3.59 (m, 6H), 3.39-3.34 (m, 1H), 2.80-2.49 (m, 17H), 2.21-2.18 (m, 1H). MS: 669.2 (M+1).

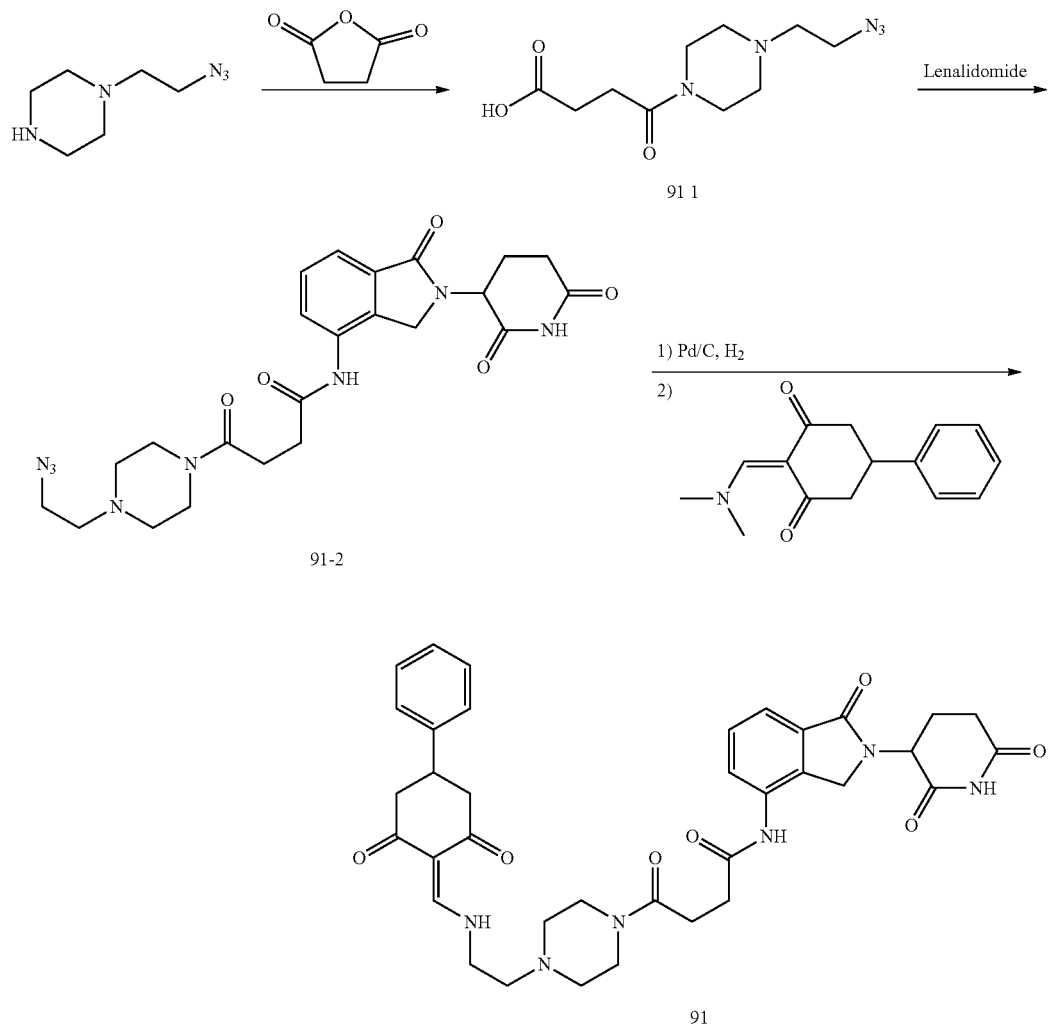

Example 13: Synthesis of Compound 92

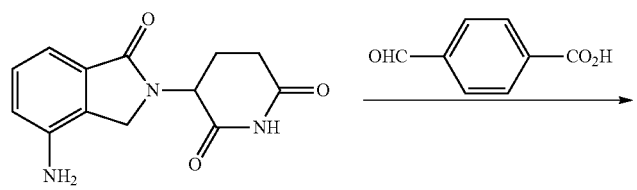

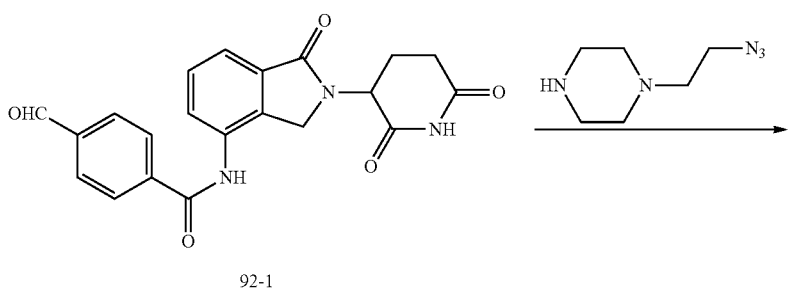

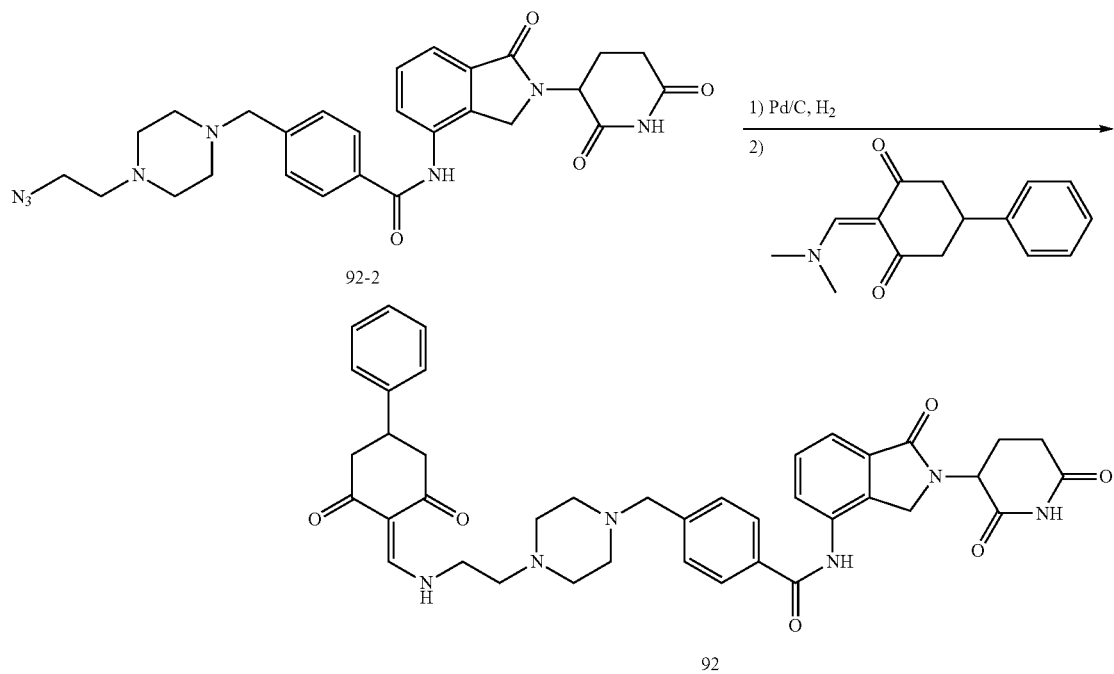

Step 1: 4-formyl benzoic acid (1.50 g, 10.0 mmol), DIPEA (3.87 g, 30.0 mmol), and lenalidomide (2.10 g, 8.1 mmol) were dissolved in dry DMF (20 mL), and then HATU (5.70 g, 15.0 mmol) was added and stirred overnight at RT. The reaction solution was poured into iced water, and extracted with ethyl acetate. The organic phase was washed with water and brine, dried and concentrated. The crude product was separated by column chromatography to afford the intermediate 92-1 (613 mg, 20%).

Step 2: The intermediate 92-1 (400 mg, 1.02 mmol) 1-(2-azidoethyl)piperazine (174 mg, 1.13 mmol), and acetic acid (90 mg, 1.5 mmol) were dissolved in dichloromethane (50 mL)/methanol (10 mL), and stirred at room temperature for half an hour. Sodium cyanoborohydride (126 mg, 2.04 mmol) was added, and continuously stirred overnight at room temperature. The reaction solution was poured into iced water, and extracted with dichloromethane. The organic phase was washed with water and brine, dried and concentrated. The crude product was separated by column chromatography to afford the intermediate 92-2 (140 mg, 26%).

Step 3: The synthesis method was same as that in Step 2 of Example 12.

Compound 92, $^1$H NMR (400 MHz, CD$_3$OD): δ8.24 (s, 1H), 7.96 (d, J=8.0 Hz, 1H), 7.74-7.67 (m, 2H), 7.61-7.50 (m, 3H), 7.31-7.21 (m, 5H), 5.17-5.13 (m, 1H), 4.54 (s, 2H), 3.68 (s, 2H), 3.61-3.58 (m, 2H), 3.36-3.39 (m, 1H), 2.85-2.59 (m, 17H) 2.21-2.19 (m, 1H). MS: 703.3 (M+1).

Example 14: Synthesis of Compound 94

The synthesis of the compound 94 was the same as that for the compound 92. The details of the compound are shown in Table 6 below.

TABLE 6

| Compound | Structure | MS (m/z) |
|---|---|---|
| 94 | 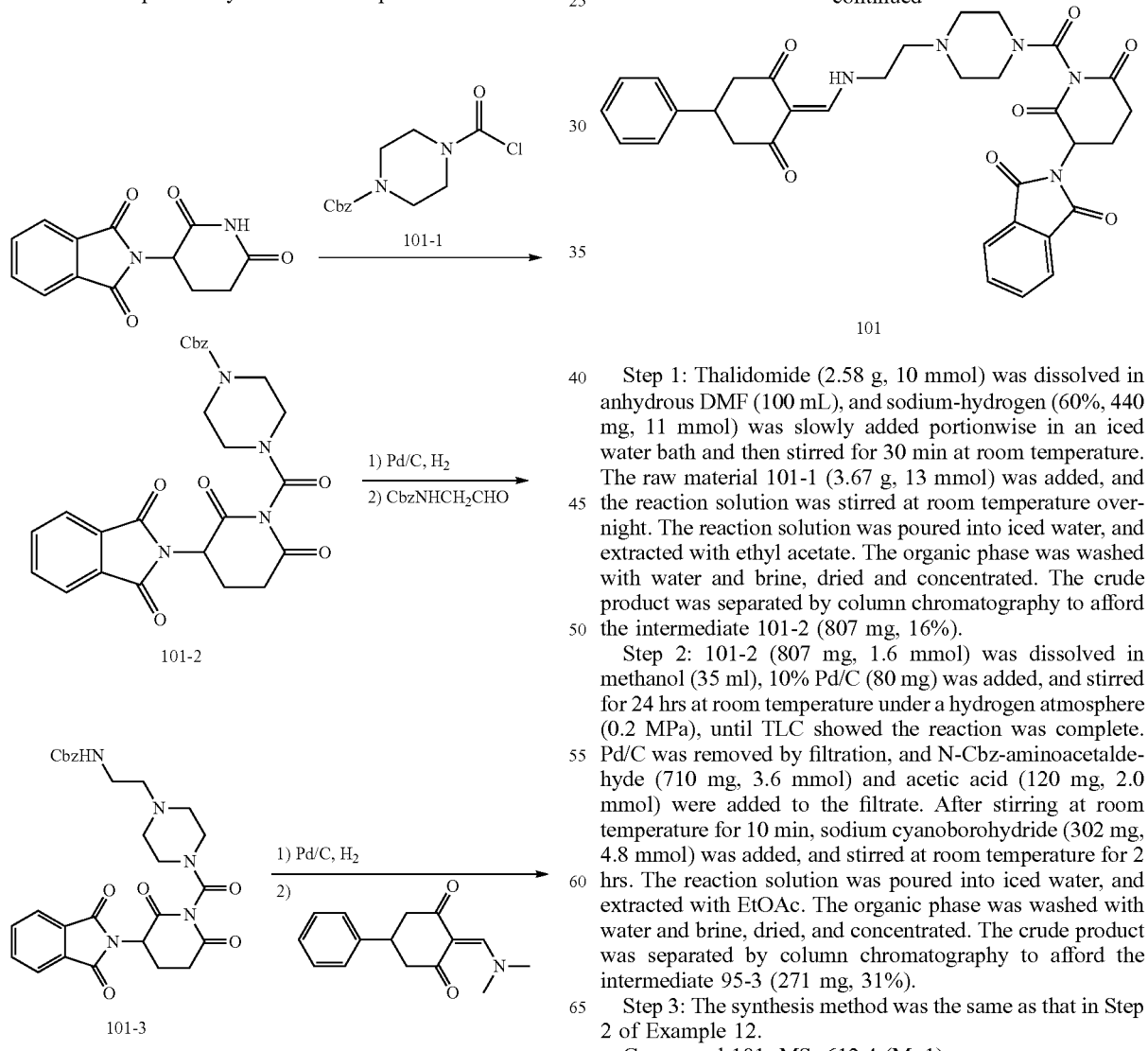 | MS: 717.4 (M + 1) |

Example 15: Synthesis of Compound 101

Step 1: Thalidomide (2.58 g, 10 mmol) was dissolved in anhydrous DMF (100 mL), and sodium-hydrogen (60%, 440 mg, 11 mmol) was slowly added portionwise in an iced water bath and then stirred for 30 min at room temperature. The raw material 101-1 (3.67 g, 13 mmol) was added, and the reaction solution was stirred at room temperature overnight. The reaction solution was poured into iced water, and extracted with ethyl acetate. The organic phase was washed with water and brine, dried and concentrated. The crude product was separated by column chromatography to afford the intermediate 101-2 (807 mg, 16%).

Step 2: 101-2 (807 mg, 1.6 mmol) was dissolved in methanol (35 ml), 10% Pd/C (80 mg) was added, and stirred for 24 hrs at room temperature under a hydrogen atmosphere (0.2 MPa), until TLC showed the reaction was complete. Pd/C was removed by filtration, and N-Cbz-aminoacetaldehyde (710 mg, 3.6 mmol) and acetic acid (120 mg, 2.0 mmol) were added to the filtrate. After stirring at room temperature for 10 min, sodium cyanoborohydride (302 mg, 4.8 mmol) was added, and stirred at room temperature for 2 hrs. The reaction solution was poured into iced water, and extracted with EtOAc. The organic phase was washed with water and brine, dried, and concentrated. The crude product was separated by column chromatography to afford the intermediate 95-3 (271 mg, 31%).

Step 3: The synthesis method was the same as that in Step 2 of Example 12.

Compound 101: MS: 612.4 (M+1).

Example 16: Synthesis of Compounds 100, 102, and 103
The synthesis method of compounds 100, 102, and 103 was the same as that for the compound 101. The details of these compounds are shown in Table 7.
TABLE 7
| Compound | Structure | MS (m/z) |
|---|---|---|
| 100 | 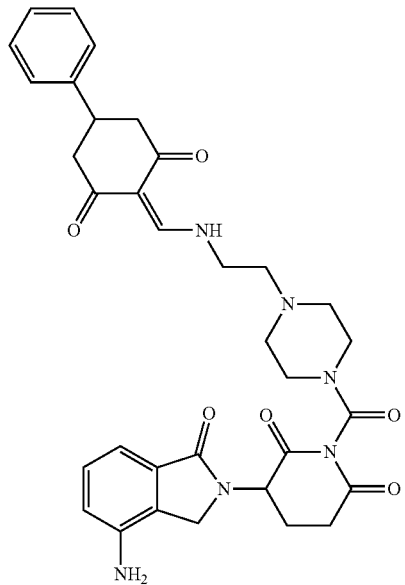 [SMILES: Nc1cccc2c1CN(C1CCC(=O)N(C(=O)N3CCN(CCNC=C4C(=O)CC(c5ccccc5)CC4=O)CC3)C1=O)C2=O] | MS: 613.5 (M + 1) |
| 102 | 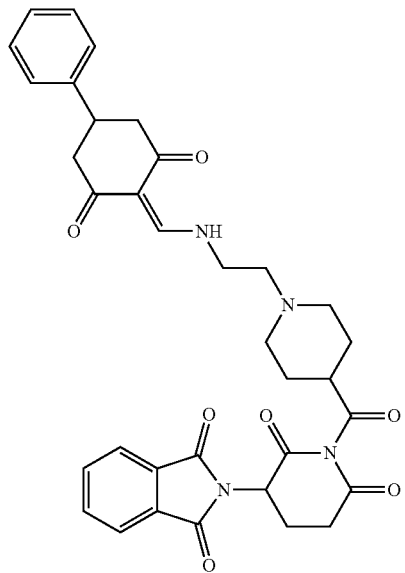 [SMILES: O=C1CC(c2ccccc2)CC(=O)C1=CNCCN1CCC(C(=O)N2C(=O)CCC(N3C(=O)c4ccccc4C3=O)C2=O)CC1] | MS: 611.4 (M + 1) |

TABLE 7-continued
| Compound | Structure | MS (m/z) |
|---|---|---|
| 103 | 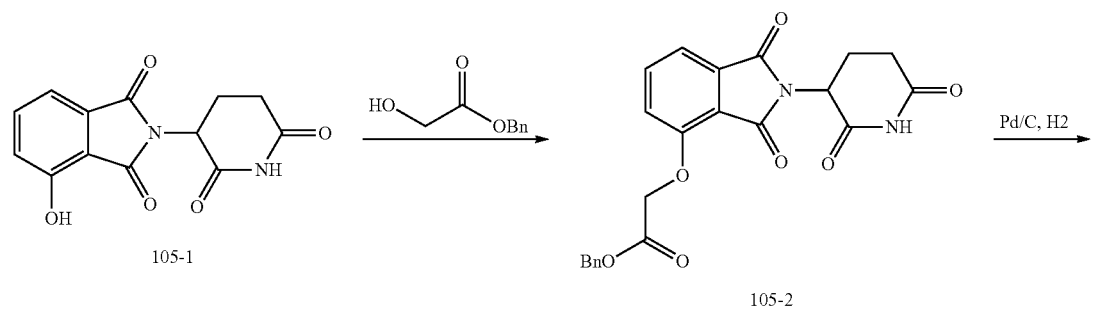 | MS: 656.4 (M + 1) |
Example 17: Synthesis of Compound 105
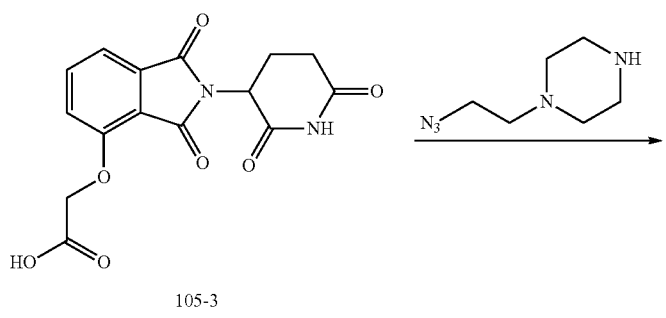

-continued

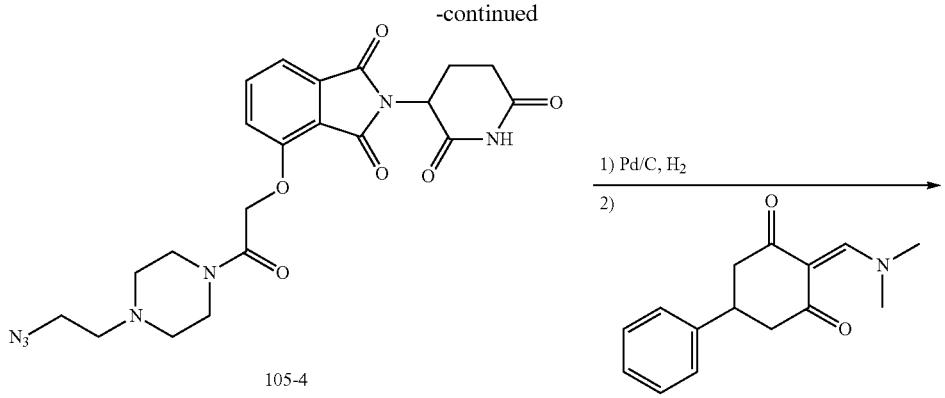

105-4

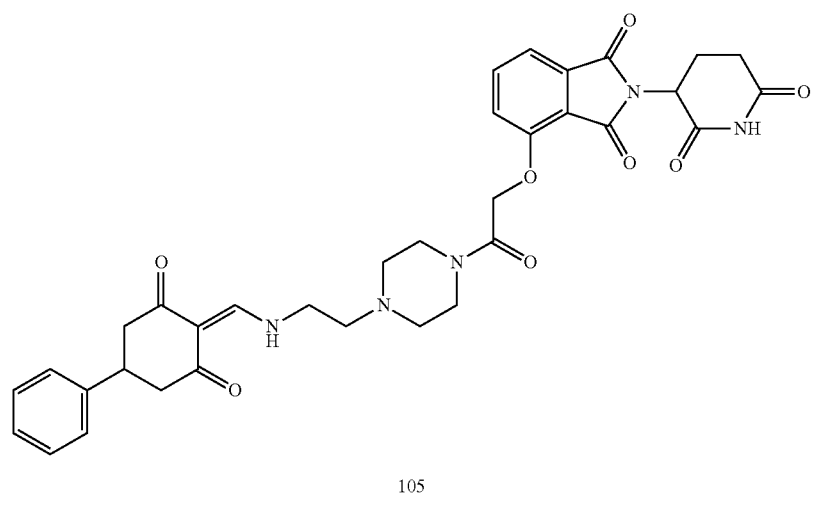

105

Step 1: The raw materials 105-1 (4.414 g, 16.10 mmol), triphenylphosphine (6.33 g, 24.13 mmol) and benzyl hydroxyacetate (2.51 mL, 17.7 mmol) were dissolved in anhydrous tetrahydrofuran (180 mL), and diisopropyl azodicarboxylate (3.49 mL, 17.7 mmol) was slowly added at 0° C. After stirring for 5 min, the reaction solution was slowly warmed to room temperature and stirred overnight. The reaction solution was poured into iced water, and extracted with dichloromethane. The organic phase was washed with water and brine, dried, and concentrated. The crude product was separated by column chromatography to afford the intermediate 105-2 (4.1 g, 60%).

Step 2: The intermediate 105-2 (4.1 g, 9.71 mmol) was dissolved in 5:2 ethyl acetate/dichloromethane (200 mL). 10% Pd/C (460 mg) was added, and the reaction solution was stirred for 3 hrs under a hydrogen atmosphere, until TLC showed the reaction was complete. Methanol (200 mL) was added, and heated to reflux to dissolve the product. Pd/C was removed by filtration, and the filtrate was washed with hot methanol. The organic phase was concentrated to give the intermediate 105-3 (3.23 g, 100%).

Step 3: The intermediate 105-3 (1.0 g, 3.0 mmol), 1-(2-azidoethyl)piperazine (620 mg, 4.0 mmol), and DIPEA (1.03 g, 8.0 mmol) were dissolved in anhydrous DMF (25 mL). HATU (1.9 g, 5.0 mmol) was added at RT, and the reaction solution was stirred overnight. The reaction solution was poured into iced water, and extracted with EtOAc. The organic phase was washed with water and brine, dried, and concentrated. The crude product was separated by column chromatography to afford the intermediate 105-4 (720 mg, 51%).

Step 4: The synthesis method was the same as that in the Step 2 of Example 10.

Compound 105: MS: 642.4 (M+1).

Example 18: Synthesis of Compounds 104, and 106

The synthesis method of the compounds 104 and 106 was the same as that for the compound 105. The details of these compounds are shown in Table 8:

TABLE 8

| compound | Structure | MS (m/z) |
|---|---|---|
| 104 | 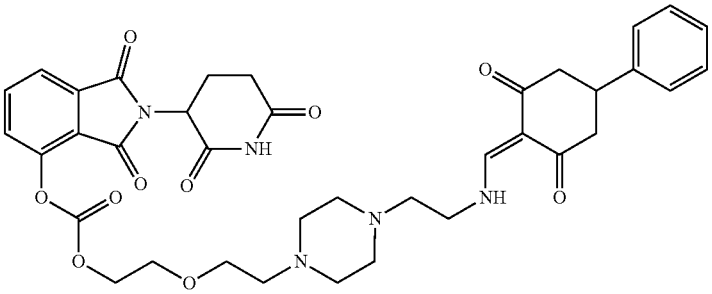 [SMILES: O=C1CCC(N2C(=O)c3cccc(OC(=O)OCCOCCN4CCN(CCNC=C5C(=O)CC(c6ccccc6)CC5=O)CC4)c3C2=O)C(=O)N1] | MS: 716.4 (M + 1) |
| 106 | 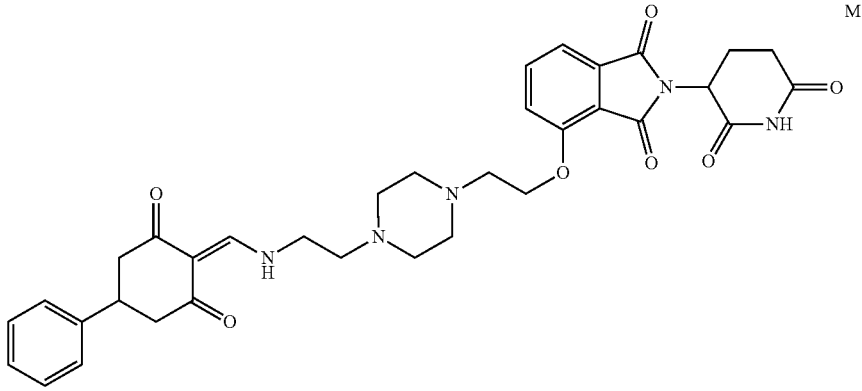 | MS: 628.4 (M + 1) |

Example 19: Synthesis of Compound 108

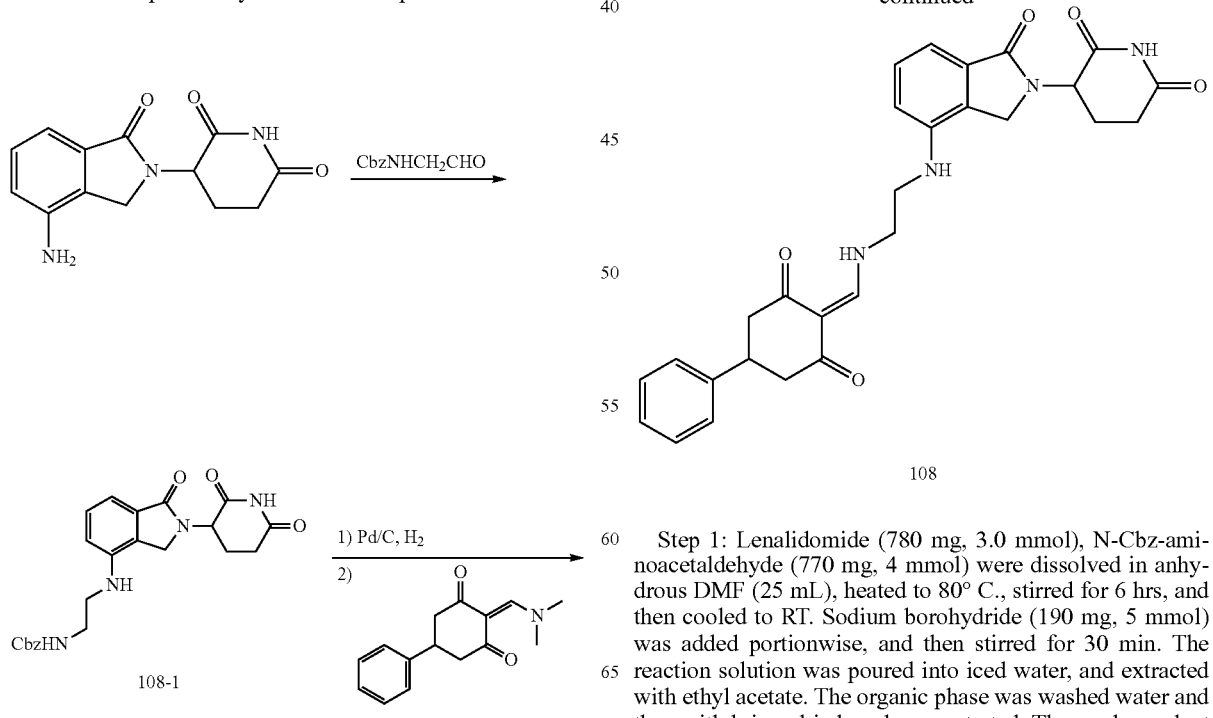

Step 1: Lenalidomide (780 mg, 3.0 mmol), N-Cbz-aminoacetaldehyde (770 mg, 4 mmol) were dissolved in anhydrous DMF (25 mL), heated to 80° C., stirred for 6 hrs, and then cooled to RT. Sodium borohydride (190 mg, 5 mmol) was added portionwise, and then stirred for 30 min. The reaction solution was poured into iced water, and extracted with ethyl acetate. The organic phase was washed water and then with brine, dried, and concentrated. The crude product was separated by column chromatography to afford the intermediate 108-2 (360 mg, 27%).
Step 2: The synthesis method was the same as that in Step 2 of Example 10.
Compound 108, MS: 501.3 (M+1).
Example 20: Synthesis of Compounds 107, and 133
The synthesis method of the compounds 107 and 133 was the same as that for the compound 108. The details of these compounds are shown in Table 9:
TABLE 9
| Compound | Structure | MS (m/z) |
| --- | --- | --- |
| 107 | 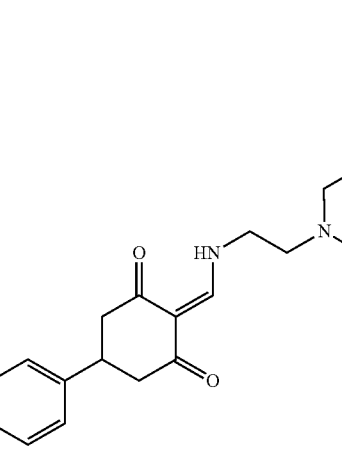 | MS: 613.5 (M + 1) |
| 133 | 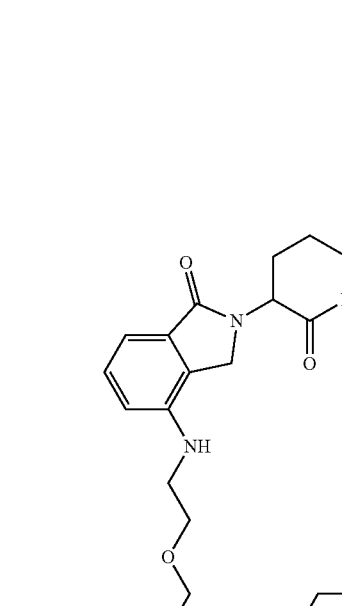 | MS: 745.5 (M + 1) |

Example 21: Synthesis of Compound 109

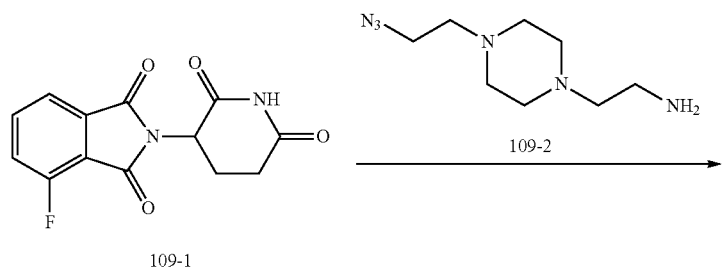

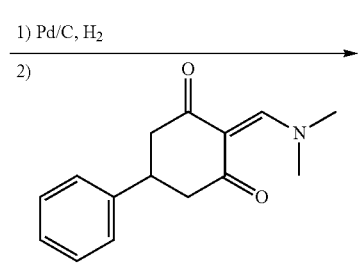

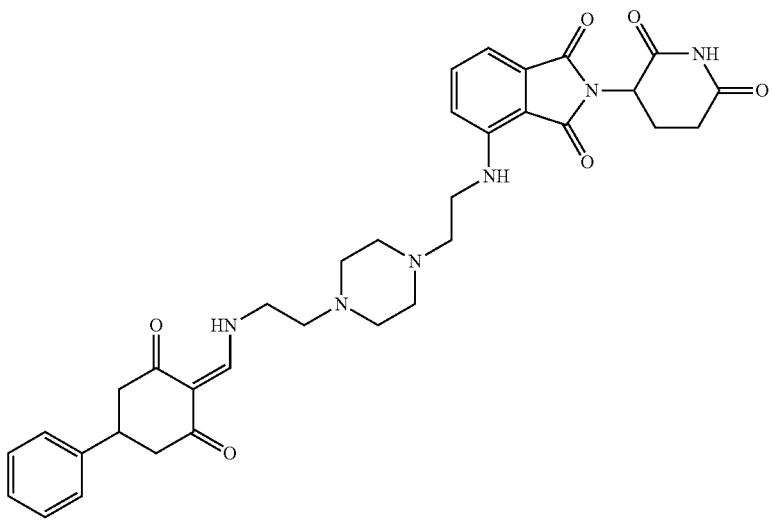

Step 1: The raw material 109-1 (830 mg, 3 mmol), the raw material 109-2 (1.0 g, 5 mmol), and DIPEA (775 mg, 6 mmol) were dissolved in anhydrous NMP (20 ml), heated to 90° C. and reacted overnight. The reaction solution was poured into iced water, and extracted with EtOAc. The organic phase was washed with water and then with brine, dried and concentrated. The crude product was separated by column chromatography to afford the intermediate 109-3 (340 mg, 25%)

Step 2: The synthesis method was the same as that in Step 2 of Example 10.

Compound 109, MS: 627.5 (M+1).

Example 22: Synthesis of Compound 125

The synthesis method of the compound 125 was the same as that for the compound 109. The details of the compound are shown in Table 10.

TABLE 10

| Compound | Structure | MS (m/z) |
|---|---|---|
| 125 | 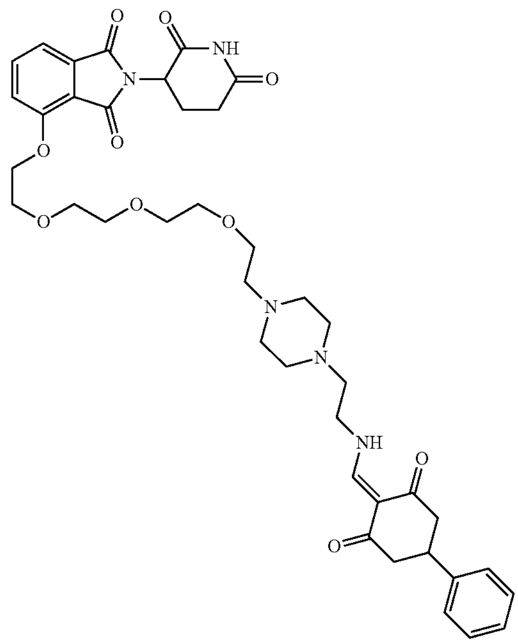 [SMILES: O=C1CCC(N2C(=O)c3cccc(OCCOCCOCCOCCN4CCN(CCNC=C5C(=O)CC(c6ccccc6)CC5=O)CC4)c3C2=O)C(=O)N1] | MS: 760.5 (M + 1) |

Example 23: Molecular Level Experiments of Targeting LC3B of Example Compounds 1-67, 71-94, and 100-158 or their Salts By constructing a prokaryotic expression system, the LC3B protein was successfully expressed and purified, and a preliminary screening and verification platform was established using fluorescence polarization experiments to determine the activity of purchased and synthesized small compound libraries. The recombinant protein GST-LC3B (final concentration 180 nM) (SEQ ID NO: 1) and N-terminal FITC-labeled peptide (SEQ ID NO: 2, final concentration 18 nM) were placed in the FP buffer (50 mM HEPES pH 7.5, 0.1 mg/ml BSA and 1 mM DTT), to which a compound serially diluted with the FP buffer was added. Then the mixture was incubated at 25° C. in the dark. The fluorescence polarization value (PerkinElmer Envision, emission wavelength 480 nm; absorption wavelength 535 nm) was monitored, and the $IC_{50}$ value was calculated using the GraphPad Prism 6.0 program. The test results are shown in Table 11.

In table 11 the inhibitory activity data of the example compounds for LC3B is summarized (where 1 mM≥$IC_{50}$>100 μM, the compound is considered to be less active (+) for LC3B; where 15 μM<$IC_{50}$≤100 μM, the compound is considered to be moderately active for LC3B (+ +); where 3 μM<$IC_{50}$≤15 μM, the compound is considered to be highly active for LC3B (+++); and where $IC_{50}$≤3 μM, the compound is considered to be highly active for LC3B (++++)).

TABLE 11

| Compound | IC50 (μM) |
|---|---|
| 1 | +++ |
| 2 | +++ |
| 3 | ++++ |
| 4 | +++ |
| 5 | ++++ |
| 6 | ++++ |
| 7 | ++++ |
| 8 | +++ |
| 9 | +++ |
| 10 | +++ |
| 11 | ++++ |
| 12 | ++++ |
| 13 | ++++ |
| 14 | ++++ |
| 15 | ++++ |
| 16 | ++++ |
| 17 | ++++ |
| 18 | ++++ |
| 19 | ++++ |
| 20 | ++++ |
| 21 | ++++ |
| 22 | +++ |
| 23 | +++ |
| 24 | +++ |
| 25 | ++++ |
| 26 | ++++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | ++++ |
| 39 | ++++ |
| 40 | +++ |
| 41 | ++++ |
| 42 | + |

TABLE 11-continued

| Compound | IC50 (μM) |
|---|---|
| 43 | + |
| 44 | + |
| 45 | + |
| 46 | + |
| 47 | + |
| 48 | + |
| 49 | + |
| 50 | ++ |
| 51 | ++ |
| 52 | ++ |
| 53 | ++ |
| 54 | +++ |
| 55 | +++ |
| 56 | +++ |
| 57 | +++ |
| 58 | ++ |
| 59 | + |
| 60 | ++ |
| 61 | +++ |
| 62 | +++ |
| 63 | +++ |
| 64 | ++ |
| 65 | ++ |
| 66 | ++ |
| 67 | +++ |
| 71 | +++ |
| 72 | ++ |
| 73 | +++ |
| 74 | ++ |
| 75 | + |
| 76 | + |
| 77 | ++ |
| 78 | ++ |
| 79 | ++ |
| 80 | ++ |
| 81 | ++ |
| 82 | +++ |
| 83 | +++ |
| 84 | +++ |
| 85 | ++ |
| 86 | ++ |
| 87 | ++ |
| 88 | ++ |
| 89 | ++ |
| 90 | ++ |
| 91 | ++ |
| 92 | ++ |
| 93 | ++ |
| 94 | ++ |
| 100 | ++ |
| 101 | ++ |
| 102 | ++ |
| 103 | ++ |
| 104 | ++ |
| 105 | ++ |
| 106 | ++ |
| 107 | ++ |
| 108 | +++ |
| 109 | ++ |
| 110 | ++ |
| 111 | ++ |
| 112 | ++ |
| 113 | +++ |
| 114 | + |
| 115 | ++ |
| 116 | ++ |
| 117 | ++ |
| 118 | ++ |
| 119 | ++ |
| 120 | ++ |
| 121 | ++ |
| 122 | + |
| 123 | + |
| 124 | ++ |
| 125 | ++ |
| 126 | +++ |
| 127 | +++ |
| 128 | + |
| 129 | ++ |
| 130 | ++ |
| 131 | ++ |
| 132 | + |
| 133 | ++ |
| 134 | ++ |
| 135 | +++ |
| 136 | +++ |
| 137 | +++ |
| 138 | +++ |
| 139 | +++ |
| 140 | ++++ |
| 141 | ++++ |
| 142 | ++++ |
| 143 | ++++ |
| 144 | ++++ |
| 145 | ++++ |
| 146 | ++++ |
| 147 | ++++ |
| 148 | ++++ |
| 149 | ++++ |
| 150 | ++++ |
| 151 | ++++ |
| 152 | ++++ |
| 153 | ++++ |
| 154 | ++++ |
| 155 | ++++ |
| 156 | ++++ |
| 157 | ++++ |
| 158 | ++++ |

Example 24: Inhibition of Compounds 1-68, 71-94, and 100-158 or Salts Thereof on Proliferation of Tumor Cells The inhibitory effects of the compounds 1-68, 71-94, and 100-158 on proliferation of lymphoma, multiple myeloma, leukemia, lung cancer, breast cancer, pancreatic cancer and other tumor cells were investigated. For various cell lines, the corresponding complete medium was used, and culture was carried out in an incubator at 37° C. with 5% $CO_2$. The cells were counted, and inoculated into a 96-well plate at 2000-10000 cells/100 μl per well according to the cell volume and growth rate. The suspended cells were treated immediately, and the adherent cells were treated after adherence. The CellTiter-Glo method was used to detect the changes in cell viability 72 hours after the administration, and the cell survival rate at different concentrations was calculated by a formula: Survival rate (%)=(RLU of treatment well−RLU of blank well)/(RLU of control well−RLU of blank well)×100.

Method for expressing the inhibitory activity of the compounds against the proliferation of tumor cells: Evaluation was made based on the cell survival rate at a compound concentration of 50 μM. 60≤survival rate (%)<90 is considered to have low inhibitory activity against the proliferation of tumor cells (+); 30<survival rate (%)≤60 is considered to have moderate inhibitory activity against the proliferation of tumor cells (++); and survival rate (%)≤30 is considered to have high inhibitory activity against the proliferation of tumor cells (+++). The test results are shown in Table 12. The compounds of the present application have different degrees of inhibition on the aforementioned various tumor cells.

TABLE 12

Inhibitory activity of compounds 1-67, 71-94, and 100-158 or salts thereof against proliferation of tumor cells

| Compound | SU-DHL6 | RPMI-8226 | K562 | A549 | MDA-MB-453 | BxPC-3 |
|---|---|---|---|---|---|---|
| 1 | +++ | +++ | +++ | +++ | ++ | ++ |
| 2 | +++ | ++ | +++ | ++ | + | + |
| 3 | +++ | + | + | + | ++ | + |
| 4 | + | +++ | ++ | + | + | + |
| 5 | + | + | + | +++ | +++ | + |
| 6 | + | + | + | + | + | + |
| 7 | +++ | ++ | ++ | ++ | ++ | + |
| 8 | + | ++ | ++ | ++ | + | ++ |
| 9 | + | ++ | ++ | ++ | + | ++ |
| 10 | + | ++ | ++ | + | + | ++ |
| 11 | + | + | +++ | + | + | + |
| 12 | + | + | + | + | + | + |
| 13 | ++ | + | + | +++ | +++ | ++ |
| 14 | ++ | + | + | +++ | +++ | + |
| 15 | ++ | +++ | + | + | + | ++ |
| 16 | + | +++ | + | + | + | + |
| 17 | + | +++ | + | ++ | + | + |
| 18 | ++ | + | ++ | + | + | + |
| 19 | + | ++ | ++ | + | ++ | ++ |
| 20 | ++ | + | ++ | ++ | + | + |
| 21 | + | + | ++ | ++ | + | + |
| 22 | + | + | + | + | ++ | ++ |
| 23 | +++ | +++ | ++ | +++ | ++ | ++ |
| 24 | +++ | + | + | ++ | ++ | ++ |
| 25 | + | + | + | + | + | + |
| 26 | + | + | + | + | + | + |
| 27 | +++ | +++ | +++ | +++ | +++ | + |
| 28 | +++ | +++ | +++ | +++ | +++ | ++ |
| 29 | ++ | +++ | +++ | +++ | +++ | ++ |
| 30 | +++ | +++ | +++ | +++ | +++ | + |
| 31 | +++ | +++ | +++ | +++ | +++ | + |
| 32 | +++ | +++ | +++ | +++ | ++ | + |
| 33 | +++ | +++ | +++ | +++ | +++ | + |
| 34 | +++ | ++ | ++ | + | +++ | + |
| 35 | +++ | +++ | +++ | +++ | ++ | ++ |
| 36 | +++ | + | + | + | ++ | + |
| 37 | +++ | + | + | + | +++ | + |
| 38 | +++ | +++ | +++ | +++ | +++ | ++ |
| 39 | ++ | + | +++ | + | +++ | ++ |
| 40 | + | + | +++ | +++ | + | ++ |
| 41 | + | + | +++ | +++ | + | + |
| 42 | + | ++ | ++ | ++ | + | + |
| 43 | + | +++ | +++ | +++ | + | + |
| 44 | +++ | +++ | +++ | +++ | + | + |
| 45 | + | + | + | + | + | + |
| 46 | + | ++ | ++ | +++ | +++ | + |
| 47 | +++ | + | + | + | +++ | ++ |
| 48 | +++ | +++ | +++ | +++ | +++ | + |
| 49 | ++ | ++ | | ++ | ++ | + |
| 50 | +++ | ++ | + | + | + | + |
| 51 | + | +++ | + | + | + | + |
| 52 | + | +++ | +++ | ++ | ++ | + |
| 53 | +++ | +++ | +++ | +++ | ++ | + |
| 54 | +++ | ++ | +++ | +++ | ++ | + |
| 55 | +++ | ++ | + | +++ | ++ | + |
| 56 | +++ | + | + | +++ | +++ | + |
| 57 | +++ | + | + | + | + | + |
| 58 | ++ | + | + | + | + | + |
| 59 | +++ | +++ | +++ | +++ | + | ++ |
| 60 | ++ | +++ | + | | + | ++ |
| 61 | ++ | + | + | + | +++ | + |
| 62 | ++ | +++ | + | ++ | +++ | ++ |
| 63 | ++ | ++ | +++ | + | + | + |
| 64 | +++ | ++ | +++ | | +++ | + |
| 65 | +++ | +++ | +++ | +++ | +++ | + |
| 66 | +++ | + | +++ | +++ | ++ | + |
| 67 | +++ | +++ | +++ | +++ | ++ | + |
| 71 | +++ | +++ | +++ | +++ | +++ | + |
| 72 | +++ | + | +++ | + | + | + |
| 73 | +++ | + | +++ | +++ | + | + |
| 74 | + | + | + | + | + | + |
| 75 | +++ | +++ | +++ | +++ | +++ | + |
| 76 | +++ | +++ | +++ | +++ | | ++ |
| 77 | + | + | +++ | +++ | +++ | + |
| 78 | + | + | +++ | +++ | +++ | + |
| 79 | + | +++ | + | + | ++ | ++ |
| 80 | + | +++ | +++ | +++ | ++ | + |
| 81 | +++ | + | +++ | +++ | ++ | + |
| 82 | +++ | + | + | +++ | ++ | + |
| 83 | + | + | + | + | ++ | + |
| 84 | +++ | +++ | +++ | + | +++ | + |
| 85 | + | +++ | ++ | ++ | + | + |
| 86 | + | + | +++ | +++ | +++ | ++ |
| 87 | +++ | +++ | ++ | ++ | +++ | + |
| 88 | ++ | +++ | ++ | ++ | +++ | + |
| 89 | ++ | ++ | ++ | ++ | +++ | + |
| 90 | +++ | ++ | +++ | ++ | ++ | ++ |
| 91 | ++ | ++ | ++ | ++ | ++ | + |
| 92 | +++ | +++ | + | + | ++ | + |
| 93 | +++ | +++ | ++ | ++ | ++ | + |
| 94 | +++ | +++ | +++ | +++ | +++ | + |
| 100 | ++ | + | +++ | +++ | ++ | ++ |
| 101 | ++ | +++ | +++ | +++ | ++ | + |
| 102 | ++ | +++ | +++ | +++ | +++ | + |
| 103 | +++ | + | + | +++ | +++ | + |
| 104 | +++ | +++ | +++ | +++ | +++ | ++ |
| 105 | + | + | + | +++ | ++ | ++ |
| 106 | + | + | + | +++ | ++ | ++ |
| 107 | + | +++ | +++ | +++ | ++ | + |
| 108 | + | +++ | +++ | ++ | ++ | + |
| 109 | + | +++ | ++ | ++ | + | ++ |
| 110 | + | ++ | ++ | ++ | + | ++ |
| 111 | +++ | +++ | +++ | + | +++ | + |
| 112 | + | ++ | ++ | + | ++ | ++ |
| 113 | + | +++ | ++ | + | +++ | + |
| 114 | ++ | + | ++ | ++ | + | + |
| 115 | ++ | + | ++ | ++ | +++ | + |
| 116 | + | ++ | ++ | ++ | ++ | ++ |
| 117 | + | +++ | ++ | + | + | + |
| 118 | + | + | ++ | + | + | + |
| 119 | ++ | ++ | ++ | + | ++ | ++ |
| 120 | ++ | ++ | ++ | + | ++ | + |
| 121 | +++ | +++ | ++ | + | ++ | + |
| 122 | +++ | + | + | + | +++ | + |
| 123 | +++ | +++ | +++ | +++ | +++ | + |
| 124 | + | + | + | + | +++ | ++ |
| 125 | +++ | +++ | + | + | +++ | ++ |
| 126 | + | + | + | + | + | ++ |
| 127 | +++ | + | + | + | + | + |
| 128 | +++ | +++ | +++ | +++ | +++ | + |
| 129 | +++ | ++ | + | +++ | + | + |
| 130 | +++ | ++ | ++ | +++ | +++ | + |
| 131 | + | +++ | ++ | | +++ | + |
| 132 | +++ | +++ | ++ | + | + | ++ |
| 133 | + | + | ++ | + | + | ++ |
| 134 | + | + | + | + | +++ | ++ |
| 135 | ++ | ++ | ++ | +++ | +++ | + |
| 136 | + | +++ | ++ | | +++ | + |
| 137 | +++ | +++ | ++ | + | + | ++ |
| 138 | +++ | ++ | ++ | +++ | +++ | + |
| 139 | +++ | +++ | +++ | + | +++ | + |
| 140 | +++ | +++ | +++ | +++ | ++ | ++ |
| 141 | +++ | ++ | ++ | +++ | +++ | + |
| 142 | +++ | +++ | +++ | + | +++ | + |
| 143 | +++ | ++ | ++ | +++ | +++ | + |
| 144 | +++ | +++ | +++ | + | +++ | + |
| 145 | +++ | ++ | ++ | +++ | +++ | + |
| 146 | +++ | +++ | +++ | + | +++ | + |
| 147 | +++ | +++ | +++ | +++ | ++ | ++ |
| 148 | +++ | ++ | ++ | +++ | +++ | + |
| 149 | +++ | +++ | +++ | + | +++ | + |
| 150 | +++ | ++ | ++ | +++ | +++ | + |
| 151 | +++ | +++ | +++ | +++ | +++ | + |
| 152 | +++ | +++ | +++ | +++ | ++ | ++ |
| 153 | +++ | ++ | ++ | +++ | +++ | + |
| 154 | +++ | +++ | +++ | + | +++ | + |
| 155 | +++ | ++ | ++ | +++ | +++ | + |
| 156 | +++ | +++ | +++ | + | +++ | + |

TABLE 12-continued

Inhibitory activity of compounds 1-67, 71-94, and 100-158 or salts thereof against proliferation of tumor cells

| Compound | SU-DHL6 | RPMI-8226 | K562 | A549 | MDA-MB-453 | BxPC-3 |
|---|---|---|---|---|---|---|
| 157 | +++ | +++ | +++ | +++ | ++ | ++ |
| 158 | +++ | ++ | ++ | +++ | +++ | + |

Example 25: Pharmacodynamic Study of Compound 1 in a Mouse Model of Multiple Myeloma Xenograft Tumor The in-vivo anti-tumor efficacy of the compound 1, lenalidomide, dexamethasone and a combination of the compound 1 or lenalidomide with dexamethasone in human multiple myeloma RPMI8226 cell xenograft tumor model was evaluated.

The test animals were female CB17 SCID mice. Human RPMI8226 cells were cultured in RPMI1640 medium containing 10% heat-inactivated fetal bovine serum and 1% penicillin-streptomycin double antibody in an incubator with 5% $CO_2$ at 37° C. When the cells were in an exponential growth phase, the cells were harvested, counted, and subcutaneously inoculated into the right dorsal portion of each mouse. The mice were grouped and administered when the average tumor volume reached about 150 $mm^3$. Grouping method: the animals were weighed and measured for the tumor volume before administration, and grouped by block design according to the tumor volume. The dosage regimen is shown in Table 13.

Figure 2:
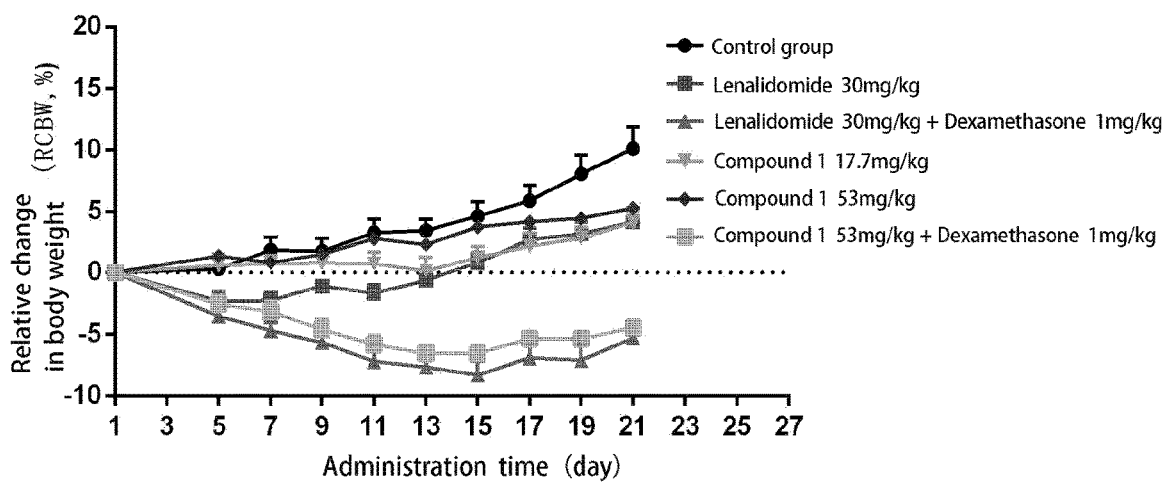
FIG. 2 shows the changes in body weight vs time of each group of mice in the in-vivo pharmacodynamic test in Example 25 of the present invention.
Figure 3:
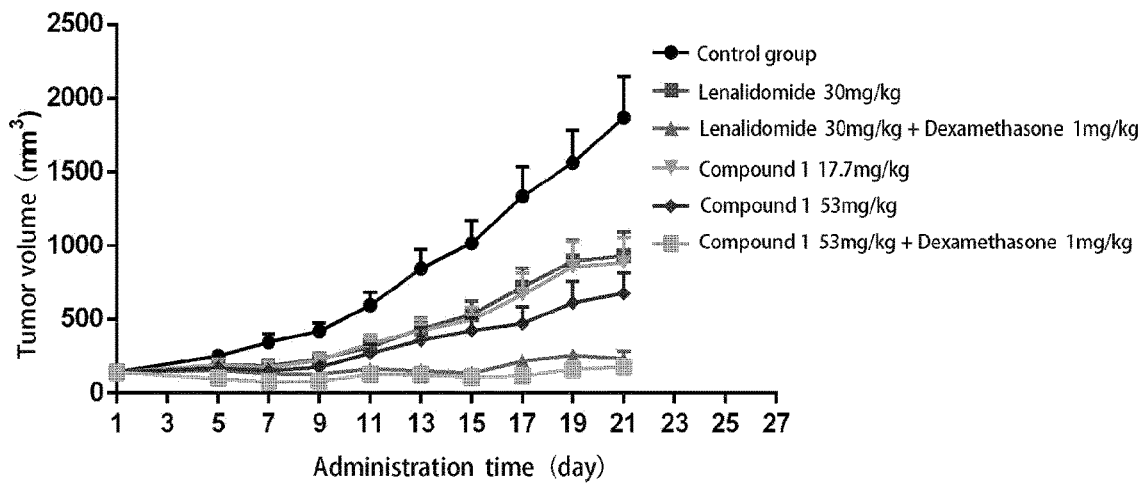
FIG. 3 shows the tumor volume vs time of each group of mice in the in-vivo pharmacodynamic test in Example 25 of the present invention.
Figure 4:
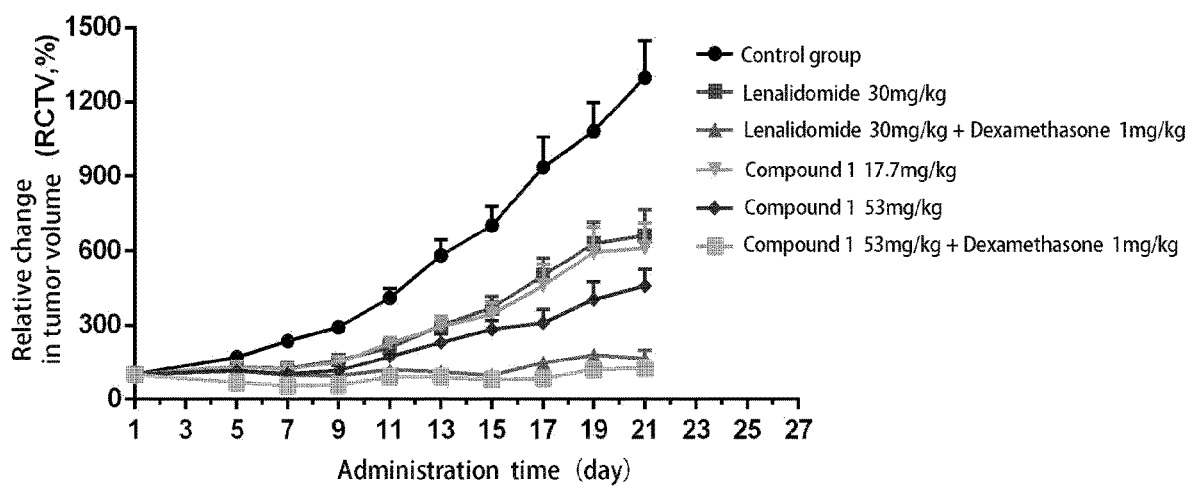
FIG. 4 shows the changes in tumor volume vs time of each group of mice in the in-vivo pharmacodynamic test in Example 25 of the present invention.

Whether the tumor growth could be inhibited, delayed or cured was investigated. The diameter of the tumor was measured by a vernier caliper. The tumor volume was calculated by a formula: V=0.5×a×$b^2$, in which a and b respectively represent the long diameter and short diameter of the tumor. The anti-tumor effect T/C (%) of the compound was evaluated by a formula: T/C %=$T_{RTV}$/$C_{RTV}$×100% ($T_{RTV}$: RTV of the treatment group; $C_{RTV}$: RTV of the negative control group). The relative tumor volume RTV was calculated by a formula: RTV=$V_t$/$V_0$, where $V_0$ is the measured tumor volume at the time of grouping and administration (i.e. day 0), and $V_t$ is the tumor volume at each measurement. T/C (%) reflects the inhibition rate on tumor growth. The therapeutic effect in terms of the tumor weight was evaluated with TGI %, which is calculated by a formula: Inhibition rate on tumor weight (TGI) %=(TWc−$TW_T$)/TWc×100%, in which TWc is the tumor weight in the control group, and $TW_T$ is the tumor weight in the treatment group. The weight of the mice bearing tumor in each group was recorded and analyzed, as shown in FIGS. 1 and 2 and Table 14, and the effect of the compound on the tumor volume of the mice bearing tumor is shown in FIGS. 3 and 4 and Table 15.

The results show that the compound 1 does not affect the body weight of tumor-bearing mice throughout the administration period (where the weight loss in the group treated with the compound 1 in combination with dexamethasone was attributed to dexamethasone). The compound 1 at a dosage of 17.7 mg/kg (1/3 of the molar dose of lenalidomide) has a tumor inhibition effect comparable to that of lenalidomide at a dosage of 30 mg/kg. When the compound 1 is administered at a dosage of 53 mg/kg (the same molar dose as lenalidomide), the anti-tumor effect is significantly higher than lenalidomide. Moreover, when used in combination with dexamethasone, the compound 1 also shows a stronger tumor inhibition effect than lenalidomide. Therefore, the compound 1 has significant in-vivo anti-tumor efficacy in human multiple myeloma RPMI8226 cell xenograft tumor model, and is more potent than the commercially available drug lenalidomide.

TABLE 13

Experimental animal grouping and dosage regimen for in-vivo pharmacodynamic test

| Group | | Number of mice | Dosage (mg/kg) | Route of administration | Administration frequency |
|---|---|---|---|---|---|
| 1 | Control group | 8 | — | p.o | QD × 21 |
| 2 | Lenalidomide | 8 | 30 | p.o | QD × 21 |
| 3 | Lenalidomide | 8 | 30 | p.o | QD × 21 |
|   | Dexamethasone |   | 1.0 | i.p | QD × 21 |
| 4 | Compound 1 | 8 | 17.7 | p.o | QD × 21 |
| 5 | Compound 1 | 8 | 53 | p.o | QD × 21 |
| 6 | Compound 1 | 8 | 53 | p.o | QD × 21 |
|   | Dexamethasone |   | 1.0 | i.p | QD × 21 | p.o: oral administration
i.p: intraperitoneal injection

TABLE 14

Body weight of tumor-bearing mice in each group ($\bar{x}$ ± SEM)

| Group | Number of animals | Average body weight (g) | | Average RCBW* (%)/end of the treatment Day 21 |
|---|---|---|---|---|
| | | Start of the treatment Day 1 | End of the treatment Day 21 | |
| Control group p.o. | 8 | 20.84 ± 0.41 | 22.96 ± 0.64 | 10.11 |
| Lenalidomide 30 mg/kg p.o. | 8 | 21.02 ± 0.23 | 21.90 ± 0.30 | 4.18 |
| Lenalidomide 30 mg/kg p.o + Dexamethasone 1 mg/kg i.p | 8 | 21.23 ± 0.34 | 20.08 ± 0.25 | −5.33 |
| Compound 1 17.7 mg/kg p.o | 8 | 21.60 ± 0.36 | 22.49 ± 0.39 | 4.13 |
| Compound 1 53 mg/kg p.o | 8 | 21.15 ± 0.36 | 22.25 ± 0.31 | 5.27 |
| Compound 1 53 mg/kg p.o + Dexamethasone 1 mg/kg i.p | 8 | 21.41 ± 0.32 | 20.46 ± 0.31 | −4.46 | p.o: oral administration
i.p: intraperitoneal injection
Note:
*The relative change in body weight (RCBW) reflects the animal's body weight affected by the drug. The time of the first administration is defined as the first day, and the RCBW (%) is calculated based on the weight on the first day of grouping and administration. Calculation formula: RCBW (%) = ((weight on some day of administration − weight on the first day of administration)/weight on the first day of administration) × 100%

TABLE 15

Effect of lest compound on tumor volume of RPMI8226 tumor-bearing mice

| Group | Number of animals | Average volume (mm3) | | #T/C % |
|---|---|---|---|---|
| | | Start of the treatment Day 1 | End of the treatment Day 21 | |
| Control group | 8 | 143.32 ± 15.02 | 1867.95 ± 278.66 | — |
| Lenalidomide 30 mg/kg | 8 | 140.44 ± 15.82 | 927.82 ± 164.85 | 49.67 |

TABLE 15-continued

Effect of lest compound on tumor volume of RPMI8226 tumor-bearing mice

| Group | Number of animals | Average volume (mm3) Start of the treatment Day 1 | Average volume (mm3) End of the treatment Day 21 | #T/C % |
|---|---|---|---|---|
| Lenalidomide 30 mg/kg + Dexamethasone 1 mg/kg | 8 | 141.35 ± 15.02 | 233.72 ± 47.47 | 12.51 |
| Compound 1 17.7 mg/kg | 8 | 141.27 ± 14.61 | 881.71 ± 175.49 | 47.20 |
| Compound 1 53 mg/kg | 8 | 142.38 ± 15.41 | 674.46 ± 137.82 | 36.11 |
| Compound 1 53 mg/kg + Dexamethasone 1 mg/kg | 8 | 141.54 ± 14.27 | 179.24 ± 48.35 | 9.60 |

Note:
T/C % = $T_{RTV}/C_{RTV}$ * 100% ($T_{RTV}$: RTV of the treatment group; $C_{RTV}$: RTV of the negative control group, RTV = $V_t/V_1$, where $V_1$ is the tumor volume meansured at the time of grouping and administration (i.e. day 1), and Vt is the tumor volume at each measurement.

What is claimed is:

1. A compound of General Formula (I) or a pharmaceutically acceptable salt thereof:

Ar-L(-X)$p$     (I)

wherein p is 1, 2 or 3;

Ar is an isoindolone-imide group represented by Formula (II):

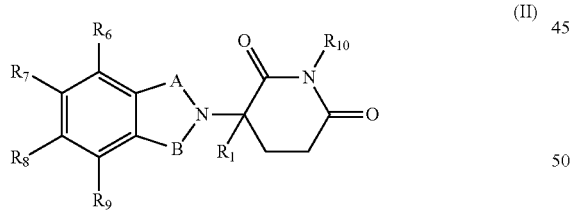

(II)

wherein one of A and B is C=O, and the other is C=O or $CH_2$;

$R_1$ is selected from hydrogen, deuterium, halo, and C1-C4 alkyl;

one of $R_6$, $R_7$, $R_8$ and $R_9$ is a divalent group selected from O, S, $SO_2$, and NH, which is attached to L or directly to X, and the remaining three of $R_6$, $R_7$, $R_8$ and $R_9$ are each independently selected from the group consisting of hydrogen, deuterium, halo, C1-C4 alkyl, unsubstituted or substituted phenyl, and unsubstituted or substituted 5-10 membered heteroaryl; and $R_{10}$ is hydrogen; or $R_6$, $R_7$, $R_8$ and $R_9$ are each independently selected from the group consisting of hydrogen, deuterium, halo, C1-C4 alkyl, unsubstituted or substituted phenyl, unsubstituted or substituted 5-10 membered heteroaryl, and $NR_{b1}R_{b'}$, in which $R_{b1}$ and $R_{b'}$ are each independently selected from the group consisting of hydrogen, C1-C4 alkyl, unsubstituted or substituted phenyl, and unsubstituted or substituted 5-10 membered heteroaryl; and $R_{10}$ is absent, and the nitrogen attached to $R_{10}$ is directly attached to L or X;

L is absent, or is a divalent, trivalent or tetravalent linking group, where when L is absent or is a divalent linking group, p is 1; when L is a trivalent linking group, p is 2; when L is a tetravalent linking group, p is 3; and when p is 2 or 3, the 2 or 3 Xs linked to L are the same or different; and X is a group represented by General Formula (III):

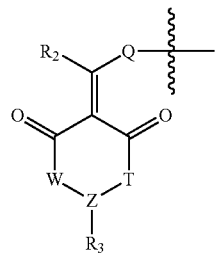

(III)

wherein $R_2$ is selected from hydrogen, deuterium, halo, C1-C6 alkyl, unsubstituted or substituted phenyl, and unsubstituted or substituted 5-10 membered heteroaryl;

W and T are each independently absent, —C($R_{a1}$)($R_{a1'}$)—, —C($R_{a1}$)($R_{a1'}$) C($R_{a2}$)($R_{a2'}$))—, —O—, —S— or —N$R_{a3}$—, where $R_{a1}$, $R_{a1'}$, $R_{a2}$, $R_{a2'}$ and $R_{a3}$ are each independently selected from the group consisting of hydrogen, deuterium, hydroxyl, amino, halo, CN, $CO_2R_{a4'}$, $CONR_{a5}R_{a5'}$, C1-C6 alkyl, C1-C10 heteroalkyl, C2-C4 alkenyl, C2-C4 alkynyl, unsubstituted or substituted —CONH—(C6-C10) aryl, unsubstituted or substituted —CH=CH—(C6-C10) aryl, unsubstituted or substituted C6-10 aryl, unsubstituted or substituted 5-10 membered heteroaryl, unsubstituted or substituted C3-10 cycloalkyl, unsubstituted or substituted 3-10 membered heterocycloalkyl, unsubstituted or substituted 3-7 membered heterocycloalkenyl, unsubstituted or substituted C6-C10 aryl-C1-C6 alkyl, unsubstituted or substituted C1-C6 alkyl-C6-C10 aryl, unsubstituted or substituted 5-10 membered heteroaryl-C1-C6 alkyl or unsubstituted or substituted C1-C6 alkyl-5-10 membered heteroaryl;

Z is selected from N, O or $CR_d$, in which $R_d$ is hydrogen, deuterium, halo, C1-C4 alkyl or C6-C12 aryl; and when Z is O, $R_3$ is absent;

$R_3$ is selected from the group consisting of hydrogen, deuterium, hydroxyl, amino, halo, CN, $CO_2R_{e1'}$, $CONR_{e2}R_{e2'}$, C1-C6 alkyl, C1-C10 heteroalkyl, C2-C4 alkenyl, C2-C4 alkynyl, —O(C6-C10) aryl, unsubstituted or substituted —S(C6-C10) aryl, unsubstituted or substituted —NH(C6-C10) aryl, unsubstituted or substituted —NHC(=O)(C6-C10) aryl, unsubstituted or substituted —CONH—(C6-C10) aryl, unsubstituted or substituted —CH=CH—(C6-C10) aryl, unsubstituted or substituted C6-10 aryl, unsubstituted or substituted 5-10 membered heteroaryl, unsubstituted or substituted C3-C10 cycloalkyl, unsubstituted or substituted 3-10 membered heterocycloalkyl, unsubstituted or substituted 3-7 membered heterocycloalkenyl, unsubstituted or substituted C6-C10 aryl-C1-C6 alkyl, unsubstituted or substituted C1-C6 alkyl-C6-C10 aryl, unsubstituted or substituted 5-10 membered heteroaryl-C1-C6 alkyl or unsubstituted or substituted C1-C6 alkyl-5-10 membered heteroaryl; and $R_3$ forms, together with the adjacent W and T, unsubstituted or substituted C6-C10 aryl, unsubstituted or substituted 5-10 membered heteroaryl, 5-10 membered cycloalkyl or 5-10 membered heterocycloalkyl, where $R_{e1}$, $R_{e1'}$ and $R_{e2'}$ are each independently hydrogen, hydroxyl, and C1-C6 alkyl; and Q is absent, O, N($R_f$), S or $SO_2$, where $R_f$ is selected from hydrogen or C1-C4 alkyl, where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl and C1-C6 hydroxyalkyl; and

represents the point of attachment.

2. The compound according to claim 1 or a pharmaceutically acceptable salt thereof, wherein Ar is a group represented by General Formula (IIa):

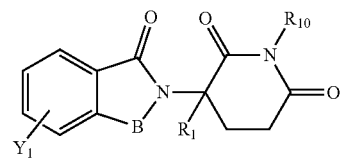

wherein

B is C=O or $CH_2$;

$R_1$ is selected from hydrogen, deuterium, halo, and C1-C4 alkyl;

$R_{10}$ is H, and $Y_1$ is NH or O, and is attached to L or directly to X; or $R_{10}$ is absent, and the N attached to $R_{10}$ is directly attached to L or X; and $Y_1$ is H, $NH_2$ or halo; or Ar is selected from the groups of:

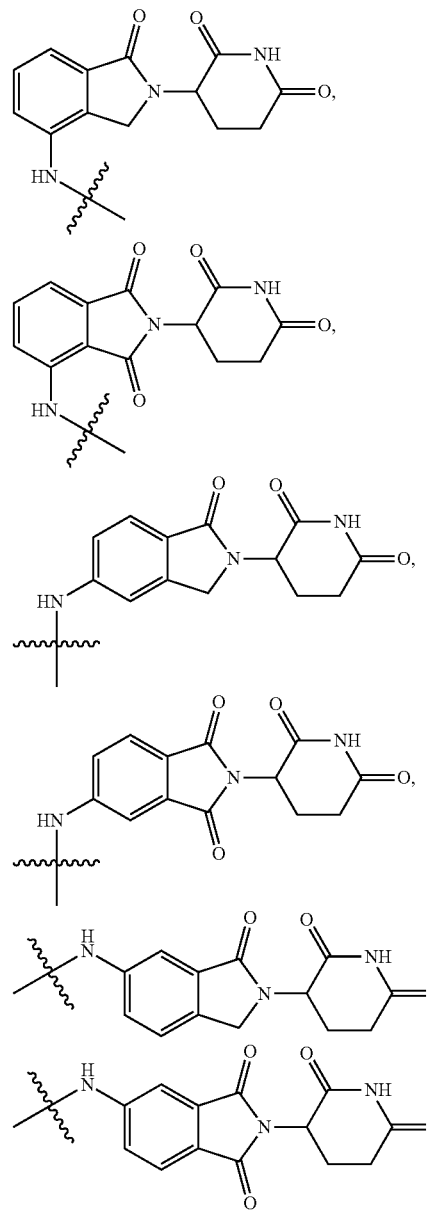

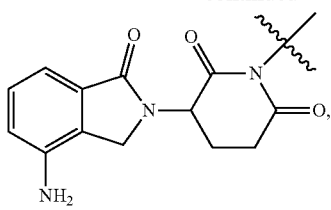

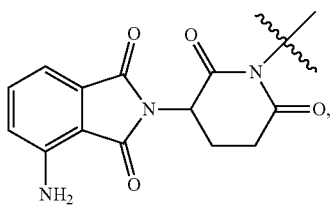

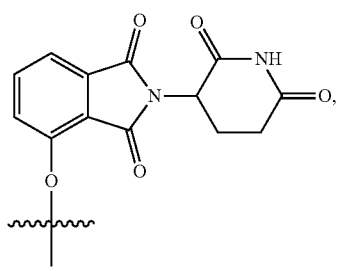

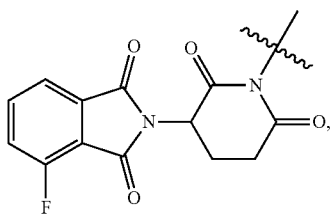

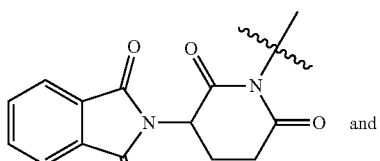 and

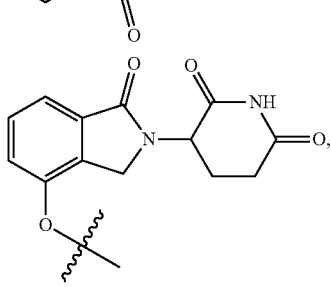

wherein

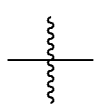

represents the point of attachment.

3. The compound or a pharmaceutically acceptable salt thereof as claimed in claim 1, wherein X is selected from the groups represented by General Formulas

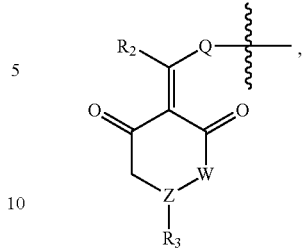

(IIIa)

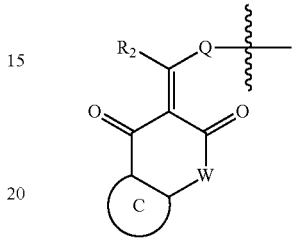

(IIIb)

where
$R_2$ is selected from hydrogen, deuterium, halo, C1-C4 alkyl, and unsubstituted or substituted phenyl;
Q is absent, or selected from NH and O;
W is selected from $CR_{g1}R_{g1'}$, O, and $NR_{g2}$, in which $R_{g1}$, $R_{g1'}$ and $R_{g2}$ are each independently hydrogen, C1-C6 alkyl, $CO_2R_{g3}$ or $CONR_{g4}R_{g4'}$; where $R_{g3}$, $R_{g4}$ and $R_{g4'}$ are each independently hydrogen or C1-C6 alkyl;
$R_3$ is selected from the group consisting of unsubstituted or substituted —CONH—(C6-C10) aryl, —$CO_2$—(C6-C10) aryl, unsubstituted or substituted —CH=CH—(C6-C10) aryl, unsubstituted or substituted C6-C10 aryl, unsubstituted or substituted 5-10 membered heteroaryl, unsubstituted or substituted C3-C10 cycloalkyl, unsubstituted or substituted 3-10 membered heterocycloalkyl, unsubstituted or substituted 3-7 membered heterocycloalkenyl, unsubstituted or substituted C1-C6 alkyl-C6-C10 aryl, unsubstituted or substituted —O(C6-C10) aryl, unsubstituted or substituted —S(C6-C10) aryl, unsubstituted or substituted —NH(C6-C10) aryl, unsubstituted or substituted —NHC(=O)(C6-C10) aryl, or unsubstituted or substituted C1-C6 alkyl-5-10 membered heteroaryl;
Z is selected from $CR_{e3}$ and N, in which $R_{e3}$ is selected from hydrogen, C1-C6 alkyl, C1-C10 heteroalkyl, C2-C4 alkenyl, C2-C4 alkynyl, and unsubstituted or substituted C6-10 aryl; and
the ring C is unsubstituted or substituted C6-C10 aryl, or unsubstituted or substituted 5-10 membered heteroaryl;
where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl and C1-C6 hydroxyl alkyl; and

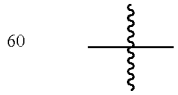

represents the point of attachment.

4. The compound or a pharmaceutically acceptable salt thereof as claimed in claim 1, wherein $R_3$ is selected from the groups of:

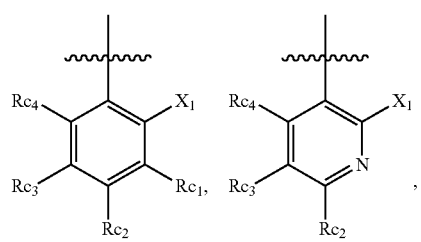
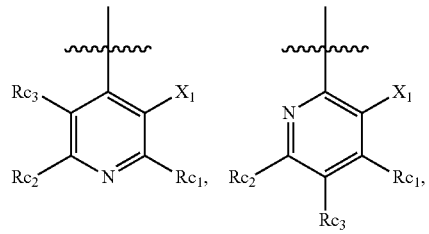
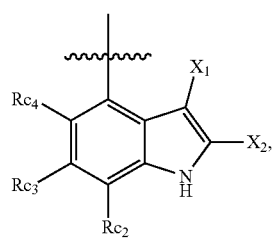
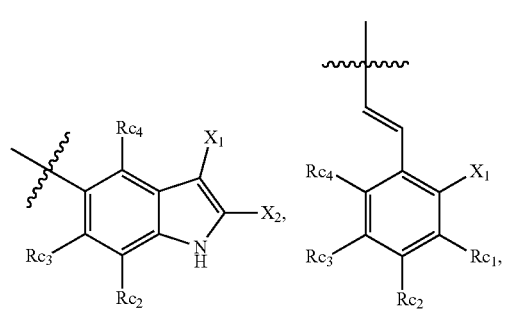
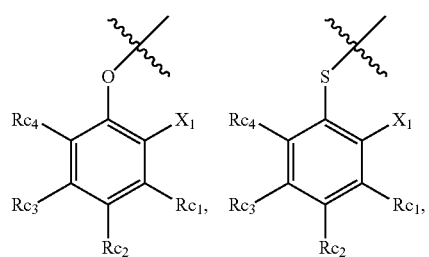
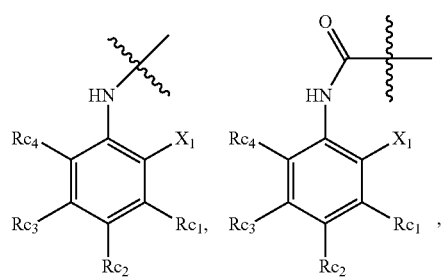
-continued
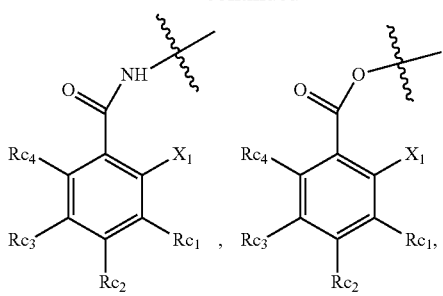
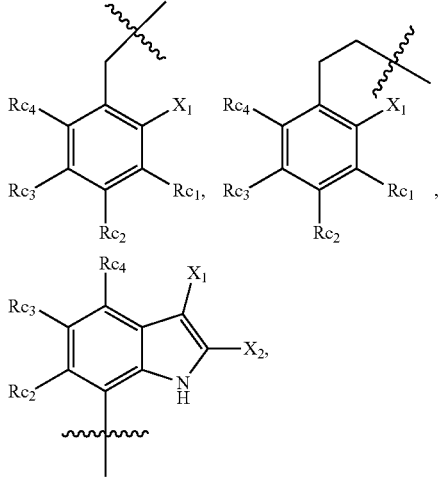
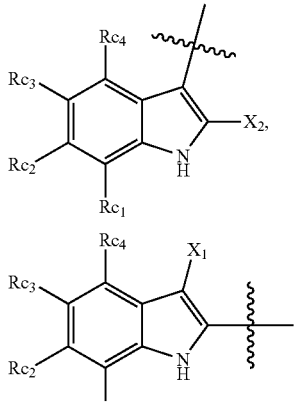
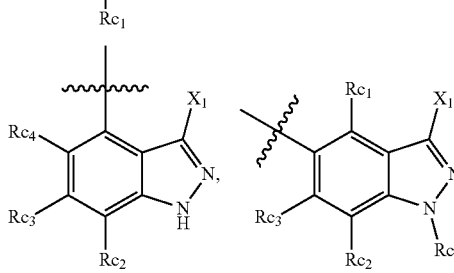
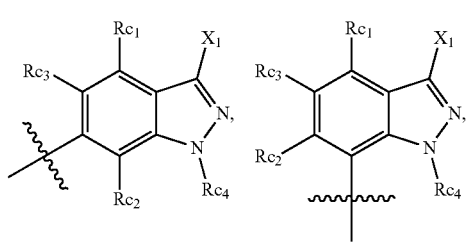

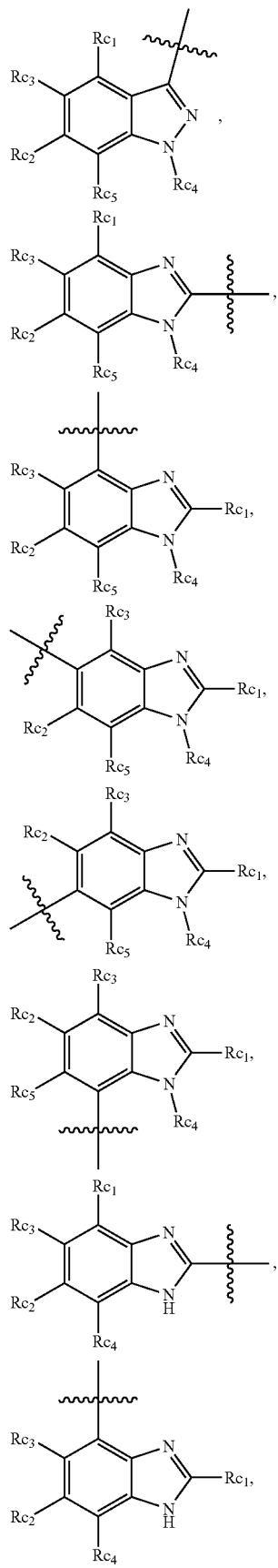
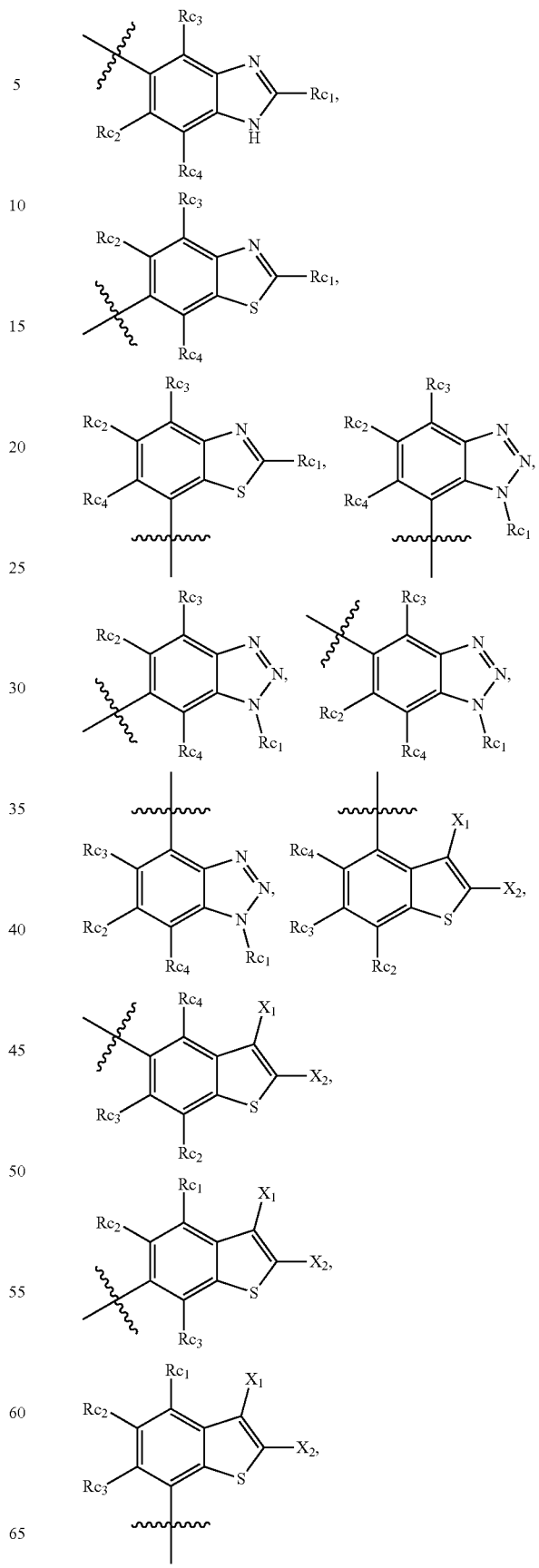

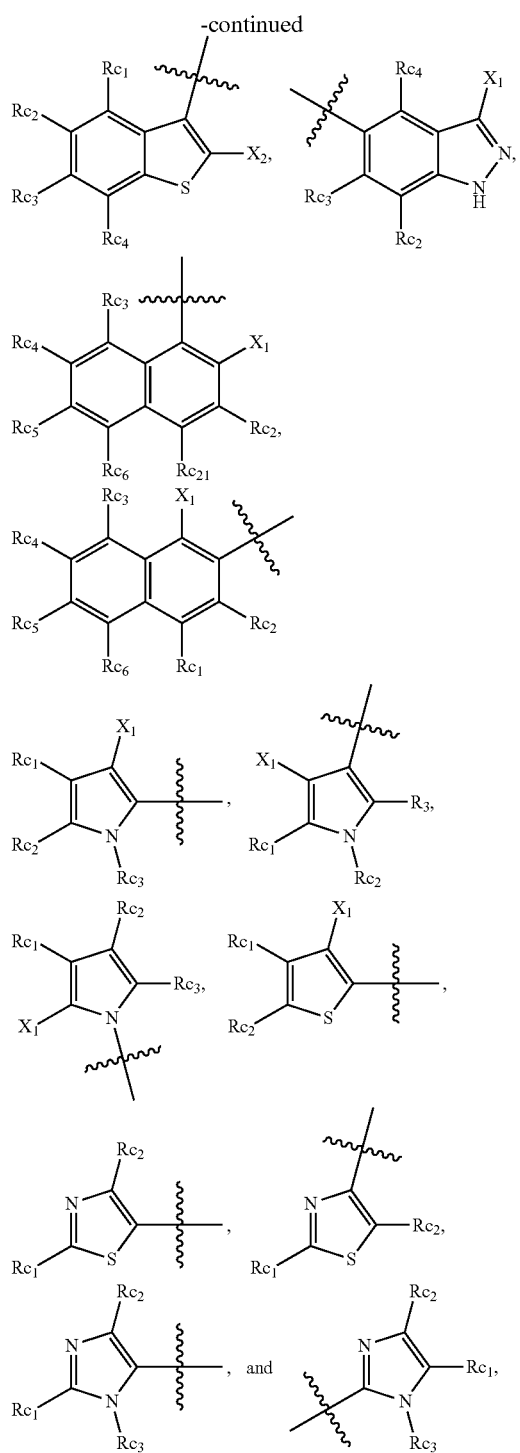

wherein
X₁ is hydrogen, halo or $CF_3$;
X₂ is hydrogen, halo or $CF_3$;
$R_{c1}$, $R_{c2}$, $R_{c3}$, $R_{c4}$, $R_{c5}$ and $R_{c6}$ are each independently selected from the group consisting of hydrogen, deuterium, hydroxyl, halo, cyano, nitro, formyl, $CO_2R_h$, $CONR_{h1}R_{h1'}$, $NR_{h2}R_{h2'}$, C1-C4 alkyl, C1-C10 heteroalkyl, C2-C4 alkenyl, C2-C4 alkynyl, unsubstituted or substituted C6-10 aryl, unsubstituted or substituted 5-10 membered heteroaryl, unsubstituted or substituted C3-C10 cycloalkyl, unsubstituted or substituted 3-10 membered heterocycloalkyl, unsubstituted or substituted 3-7 membered heterocycloalkenyl, unsubstituted or substituted C6-C10 aryl-C1-C6 alkyl, unsubstituted or substituted C1-C6 alkyl-C6-C10 aryl, unsubstituted or substituted 5-10 membered heteroaryl-C1-C6 alkyl, and unsubstituted or substituted C1-C6 alkyl-5-10 membered heteroaryl, in which $R_h$, $R_{h1}$, $R_{h1'}$, $R_{h2}$ and $R_{h2'}$ are each independently selected from hydrogen and C1-C4 alkyl; or $R_{c1}$ and $R_{c2}$, or $R_{c2}$ and $R_{c3}$, or $R_{c3}$ and $R_{c4}$, or $R_{c5}$ and $R_{c6}$ form, together with the ring atoms in the ring to which they are attached, unsubstituted or substituted C6-C10 aryl, or unsubstituted or substituted 5-10 membered heteroaryl, where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl, and C1-C6 hydroxyl alkyl; or R₃ is selected from the groups of:

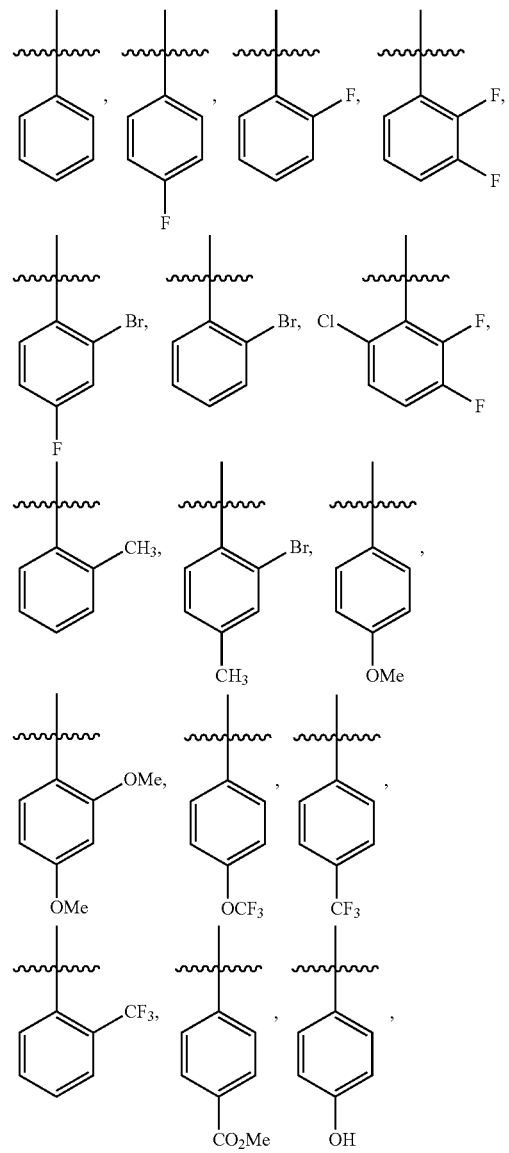

-continued
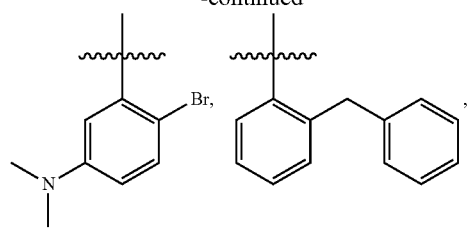
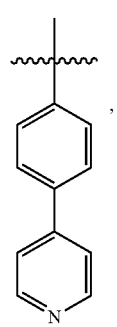
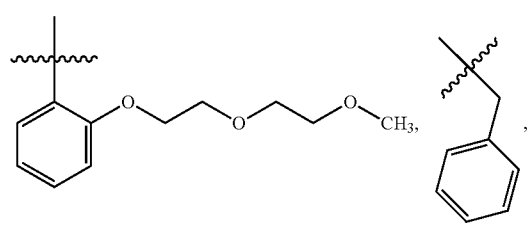
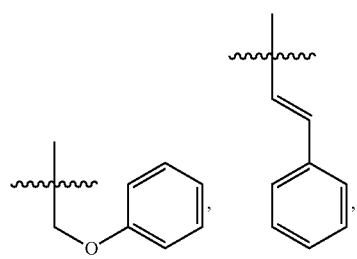
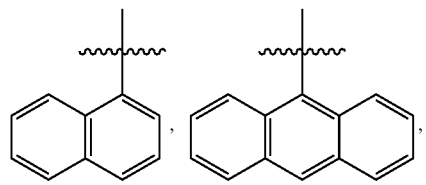
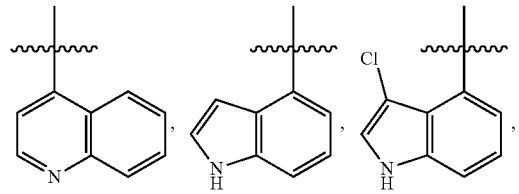
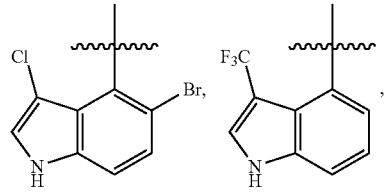
-continued
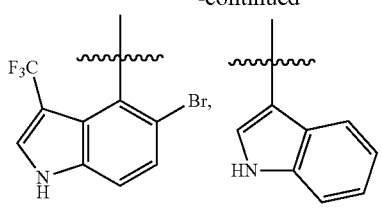
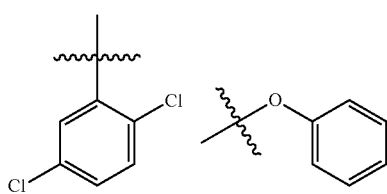
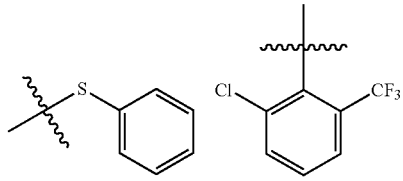
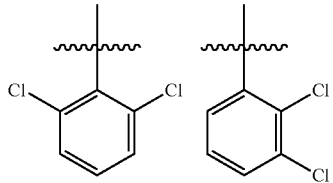
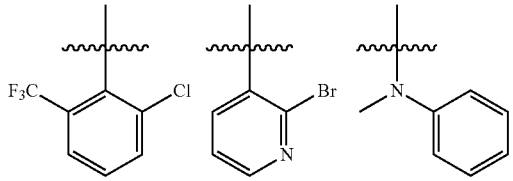
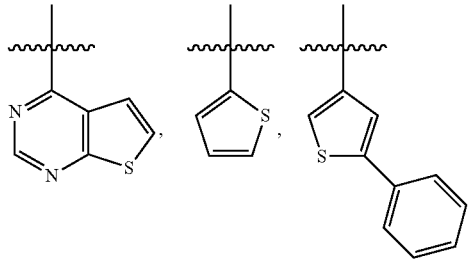
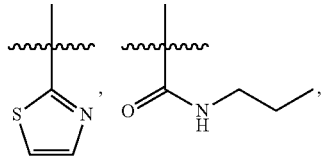
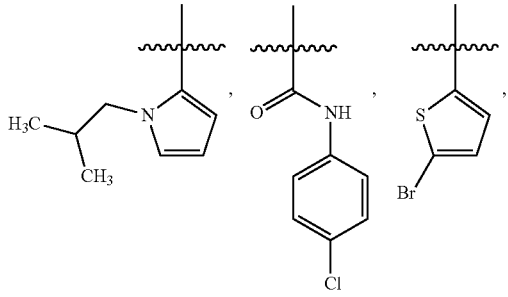

-continued
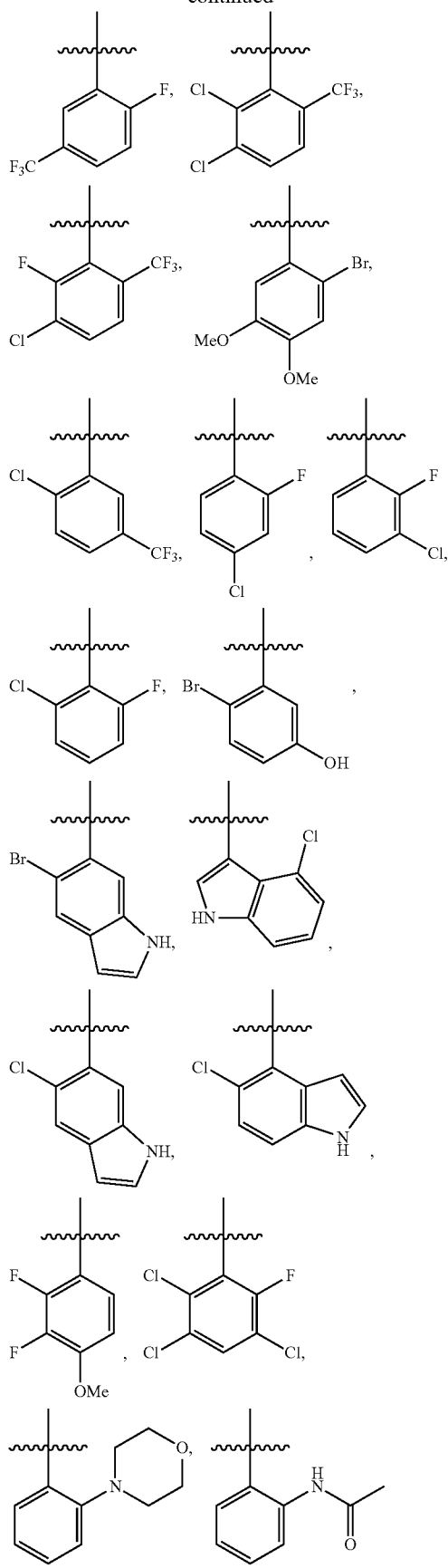
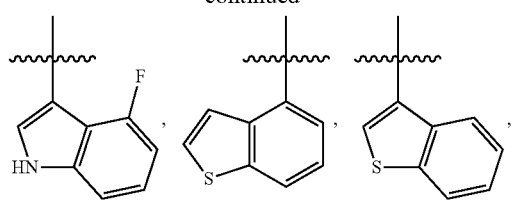
wherein
represents the point of attachment.
5. The compound or a pharmaceutically acceptable salt thereof as claimed in claim 1, wherein X is selected from the groups of:
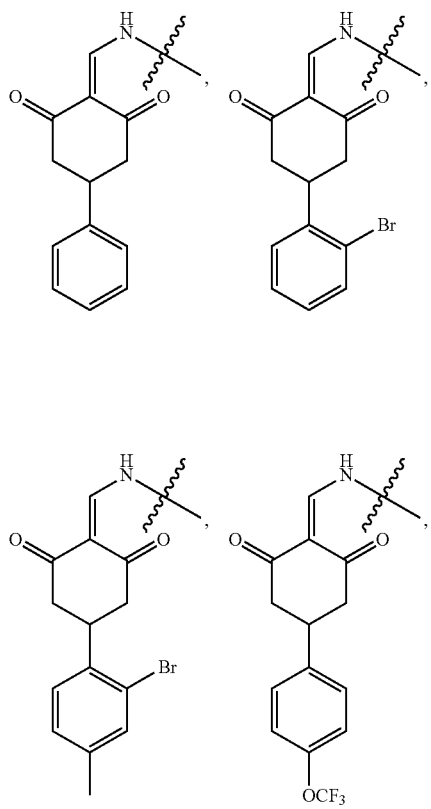

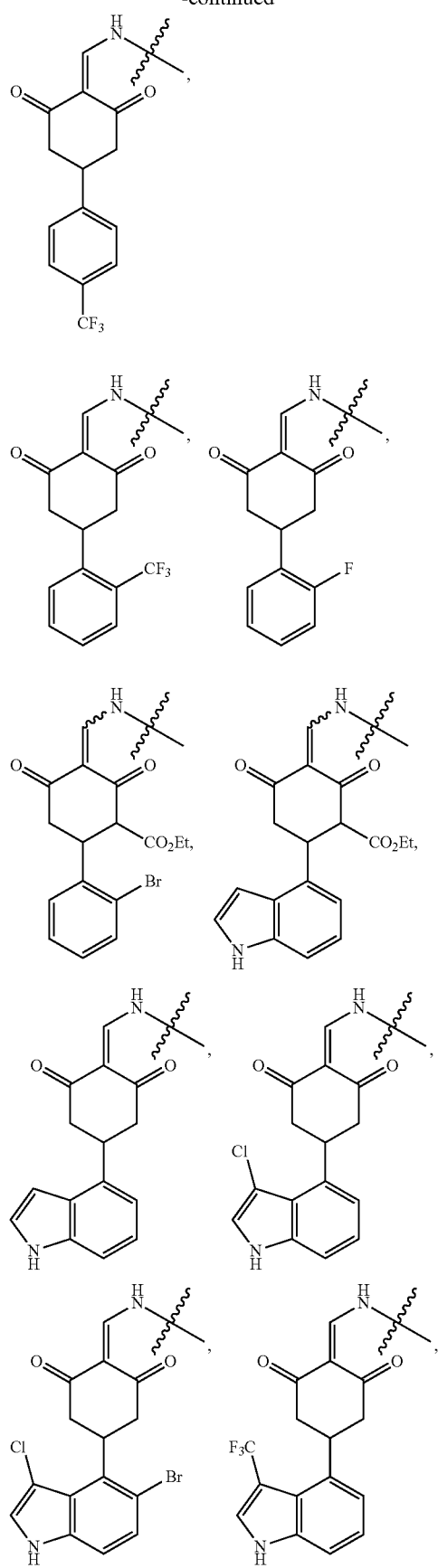
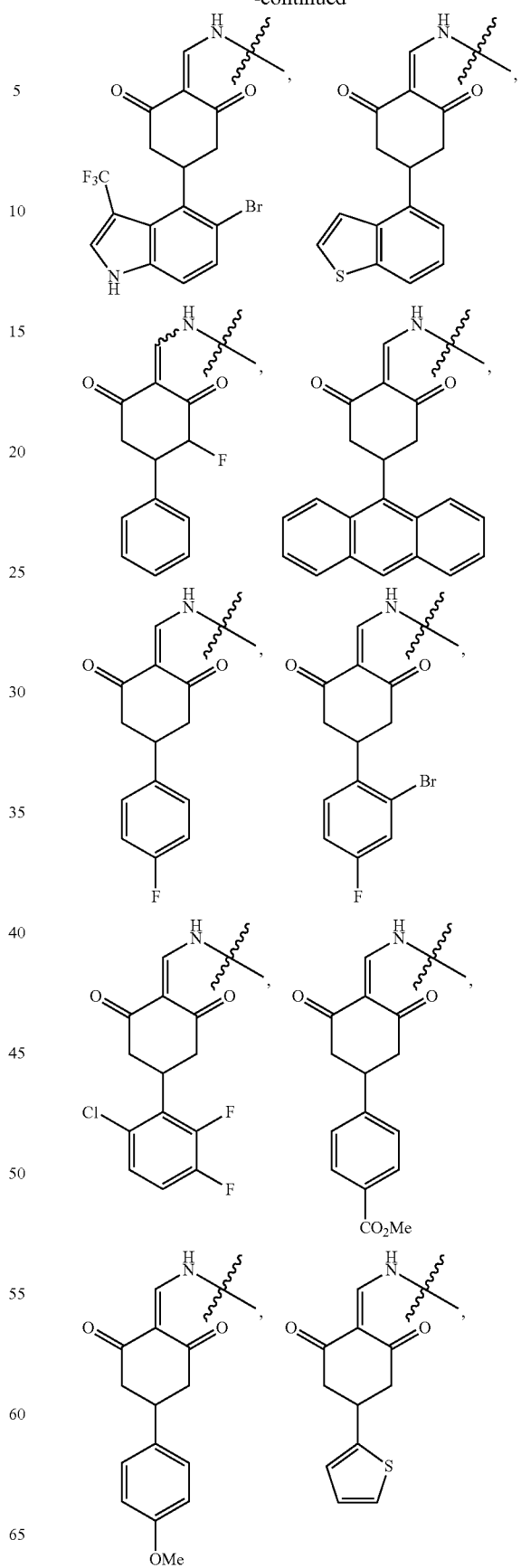

297
-continued
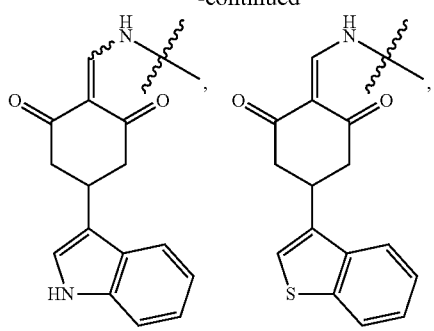
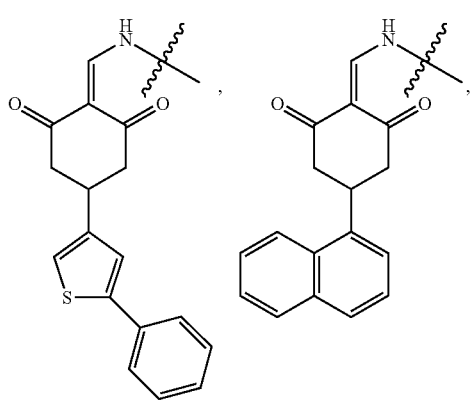
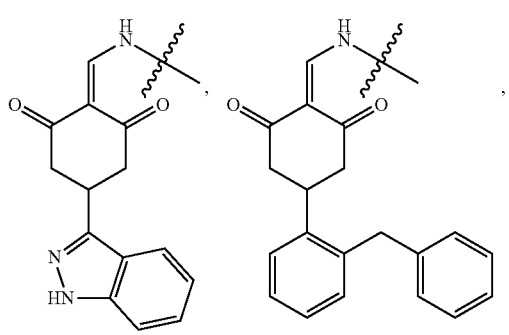
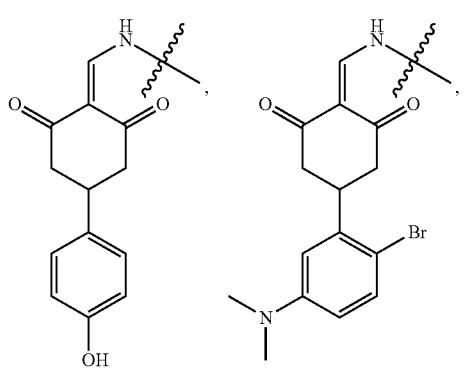
298
-continued
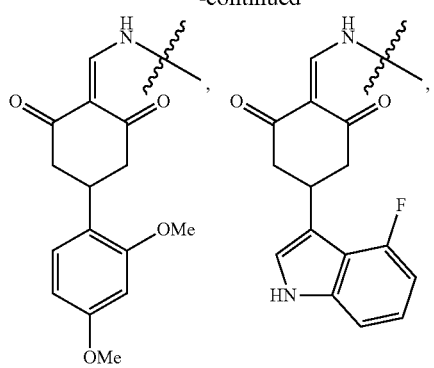
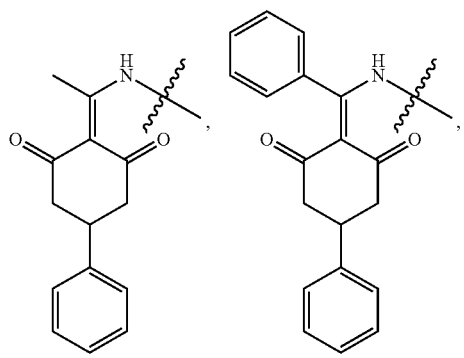
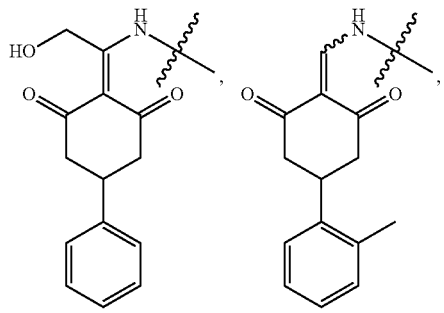
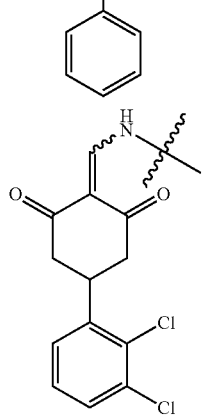
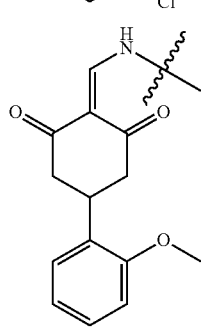

299
-continued
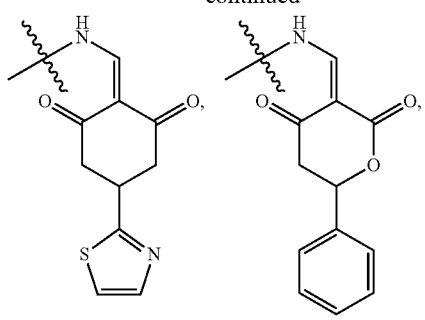
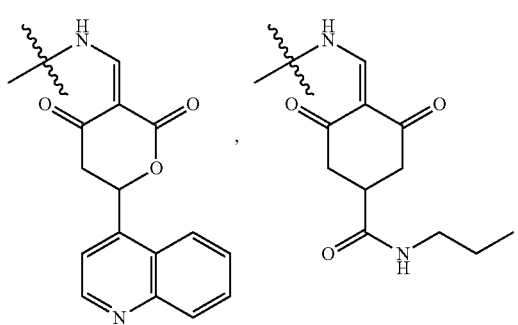
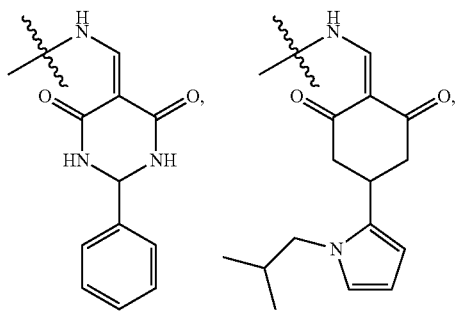
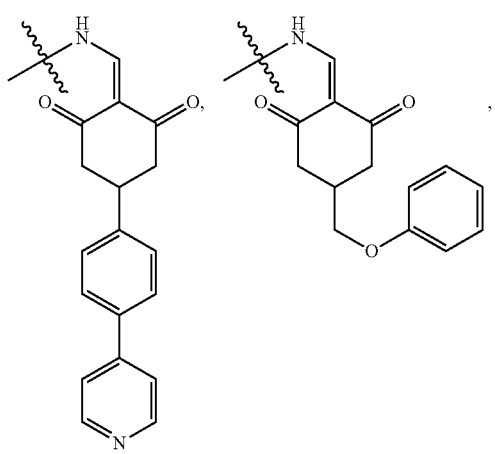
300
-continued
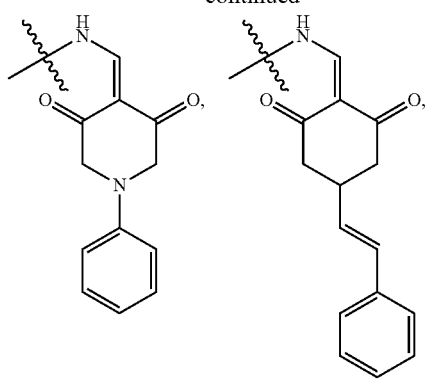
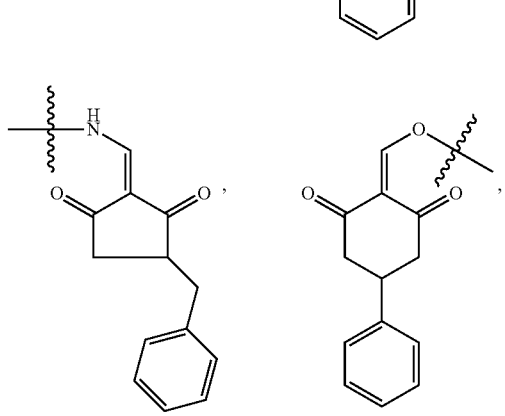
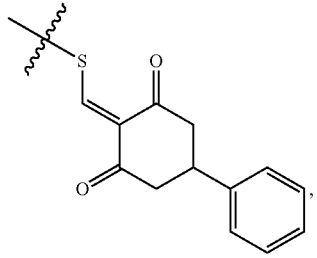
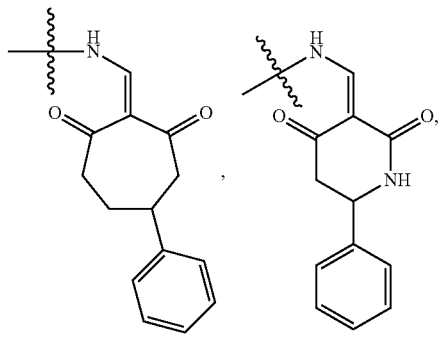
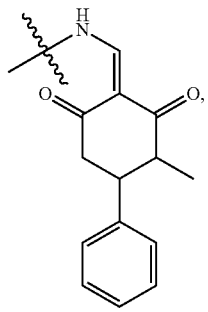

301
-continued
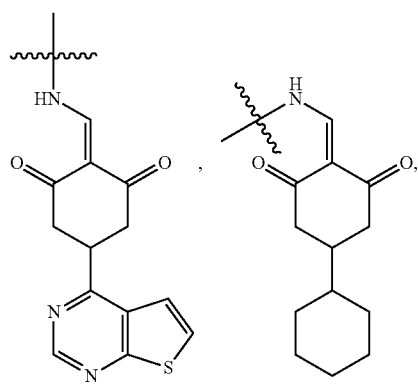
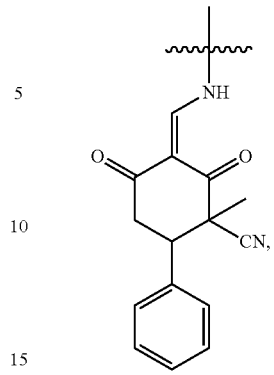
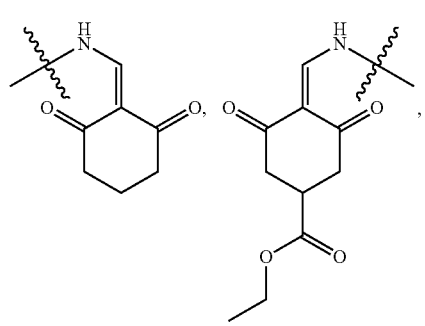
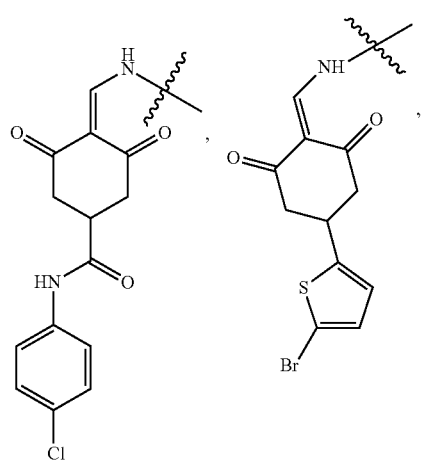
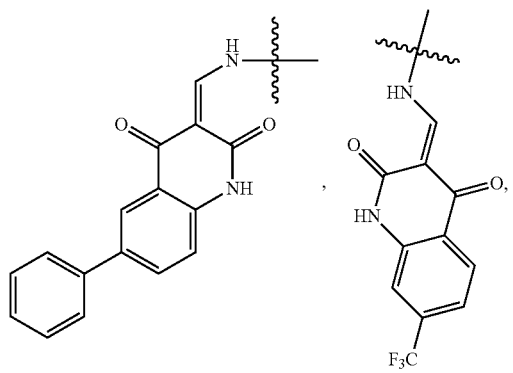
302
-continued
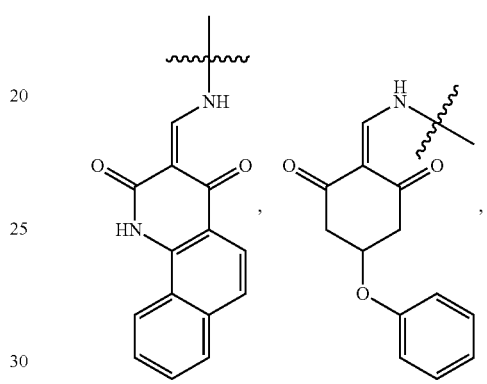
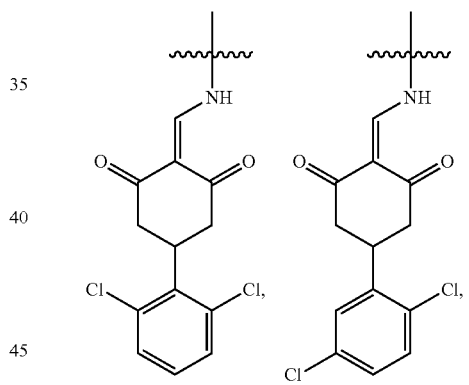
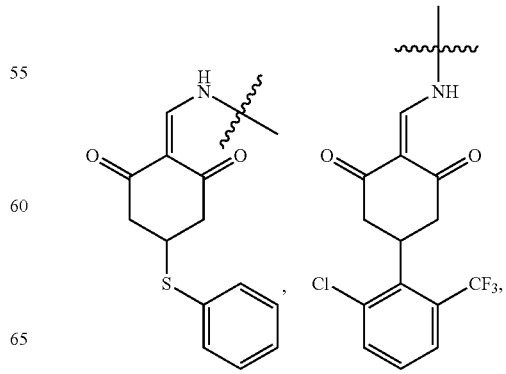

303
-continued
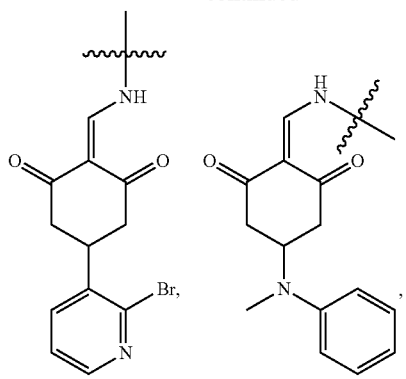
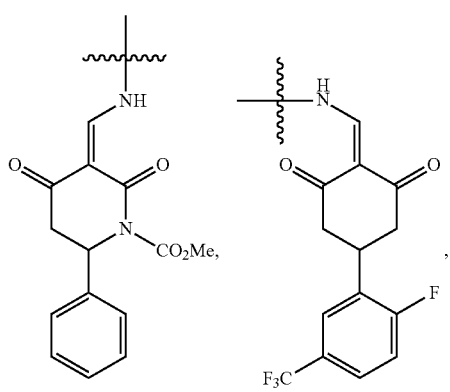
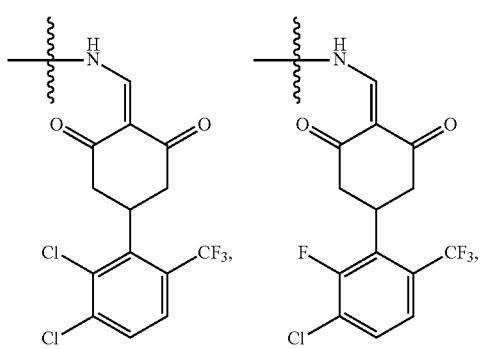
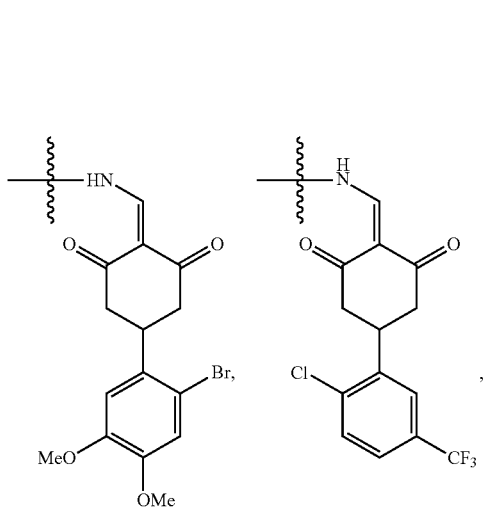
304
-continued
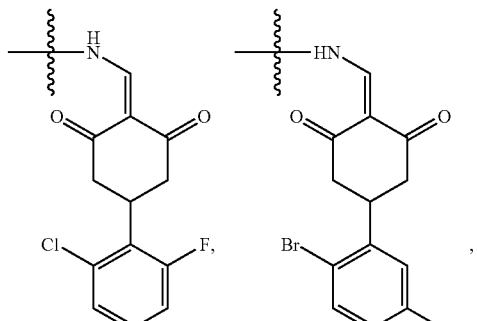
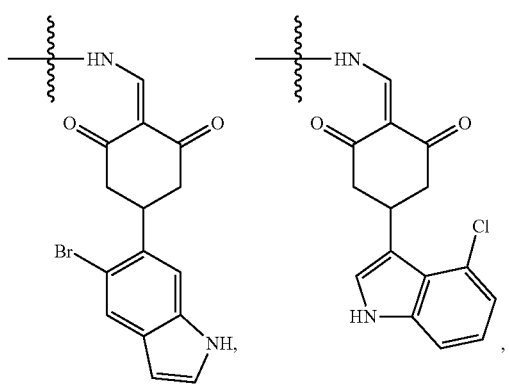
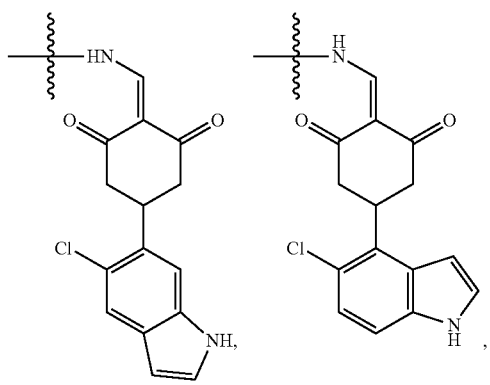

305
-continued

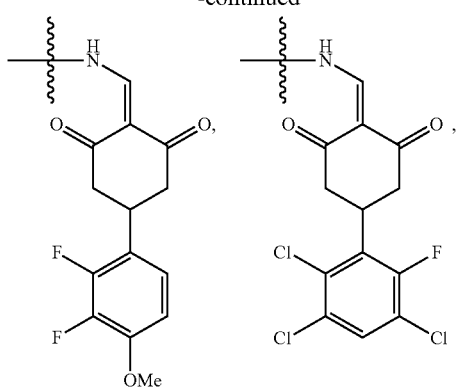

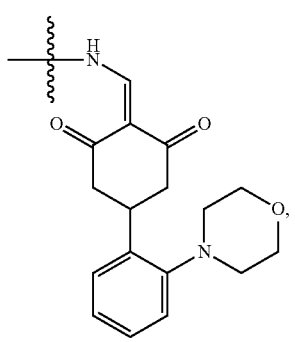

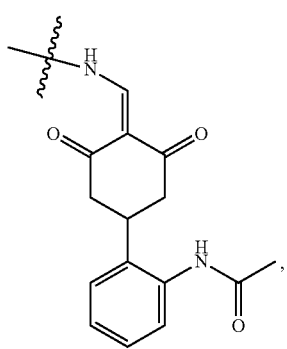

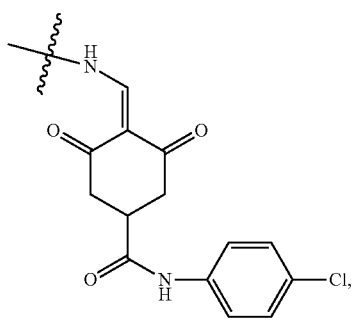

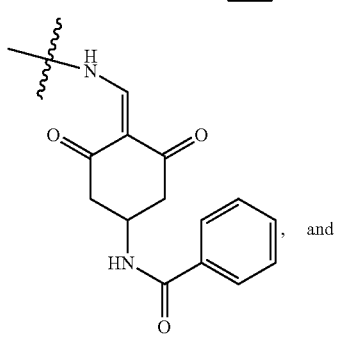

and

306
-continued

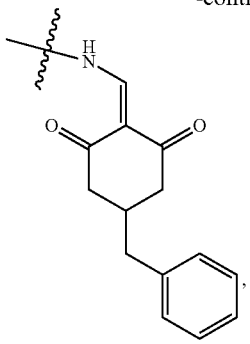

wherein

represents the point of attachment.

6. The compound or a pharmaceutically acceptable salt thereof as claimed in claim 1, wherein L is absent, or is a divalent group represented by General Formula (IV) or a trivalent group represented by General Formula (V):

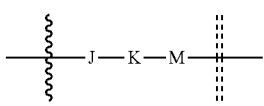  (IV)

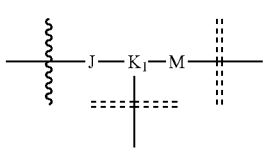  (V)

wherein

J and M are each independently absent, $NR_i$, O, S, $SO_2$, C(=O) or C(=S), in which $R_i$ is 11 hydrogen, C1-C4 alkyl or C6-C10 aryl;

K is absent, C1-C10 alkylene, C3-C10 cycloalkylene, C1-C6 heteroalkylene, C2-C6 alkenylene, C2-C6 alkynylene, unsubstituted or substituted C6-C10 arylene, unsubstituted or substituted 5-10 membered heteroarylene, unsubstituted or substituted C3-C8 cycloalkylene, unsubstituted or substituted 3-10 membered non-aromatic heterocyclylene, peptidylene consisting of 2 to 8 identical or different amino acids, or any combination of two, three, or four identical or different groups thereof; and $K_1$ is a bivalent group, selected from the group consisting of C1-C10 alkyl, C3-C10 cycloalkyl, C1-C6 heteroalkyl, C2-C6 alkenyl, C2-C6 alkynyl, unsubstituted or substituted C6-C10 aryl, unsubstituted or substituted 5-10 membered heteroaryl, unsubstituted or substituted C3-C8 cycloalkyl, unsubstituted or substituted 3-10 membered non-aromatic heterocyclyl, peptidyl consisting of 2 to 8 identical or different amino acids, and any combination of two, three, or four identical or different groups thereof, where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl, and C1-C6 hydroxyl alkyl;

preferably, the divalent and trivalent groups represented by General Formulas (IV) and (V) are selected from the following groups or any combinations of identical or different groups thereof:

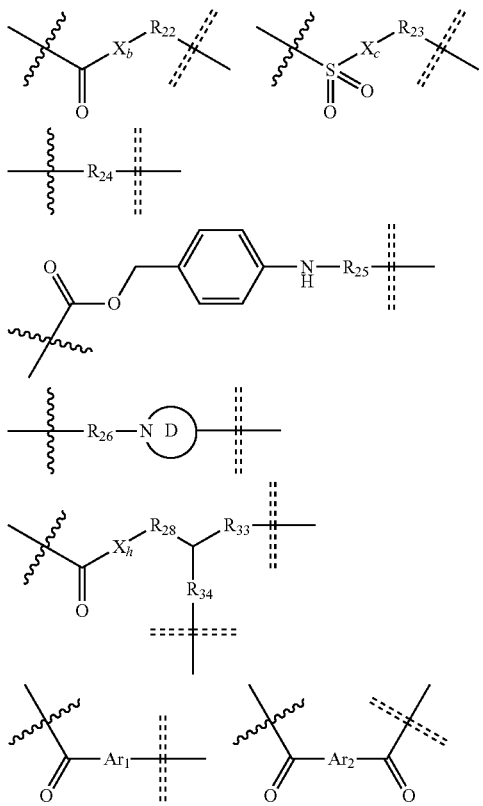

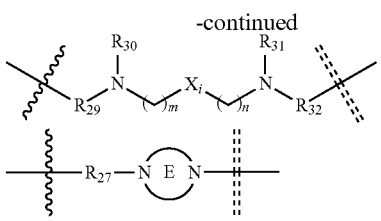

wherein m and n are each independently 0, 1, 2, 3, 4 or 5;
$X_b$, $X_c$, $X_h$ and $X_i$ are each independently absent, O, S or NH;
$R_{22}$, $R_{23}$, $R_{24}$, $R_{25}$, $R_{26}$, $R_{27}$, $R_{29}$, $R_{32}$, $R_{33}$ and $R_{34}$ are each independently absent, C1-C10 alkylene, C3-C10 cycloalkylene, C1-C6 heteroalkylene, C2-C6 alkenylene, C2-C6 alkynylene, unsubstituted or substituted C6-C10 arylene, unsubstituted or substituted 5-10 membered heteroaryl ene, unsubstituted or substituted C3-C8 cycloalkylene, unsubstituted or substituted 3-10 membered non-aromatic heterocyclylene, or any combination of two, three, or four identical or different groups thereof;
$R_{30}$ and $R_{31}$ are each independently H, C1-C10 alkyl, C3-C10 cycloalkyl, C1-C6 heteroalkyl, C2-C6 alkenyl, C2-C6 alkynyl, unsubstituted or substituted C6-C10 aryl, unsubstituted or substituted 5-10 membered heteroaryl, unsubstituted or substituted C3-C8 cycloalkyl, unsubstituted or substituted 3-10 membered non-aromatic heterocyclyl, or any combination of two, three, or four identical or different groups thereof;
An and $Ar_2$ are each independently unsubstituted or substituted C6-C10 arylene, or unsubstituted or substituted 5-10 membered heteroarylene; and
the rings D and E are each independently unsubstituted or substituted 3-10 membered nitrogen-containing heterocyclic ring,
where "unsubstituted or substituted" indicates that the group is unsubstituted or substituted with one or more substituents selected from hydroxyl, amino, cyano, nitro, carboxyl, halo, C1-C6 alkyl, C1-C6 haloalkyl or C1-C6 hydroxyalkyl; and
preferably, the divalent and trivalent groups represented by General Formulas IV and V are selected from the groups of:

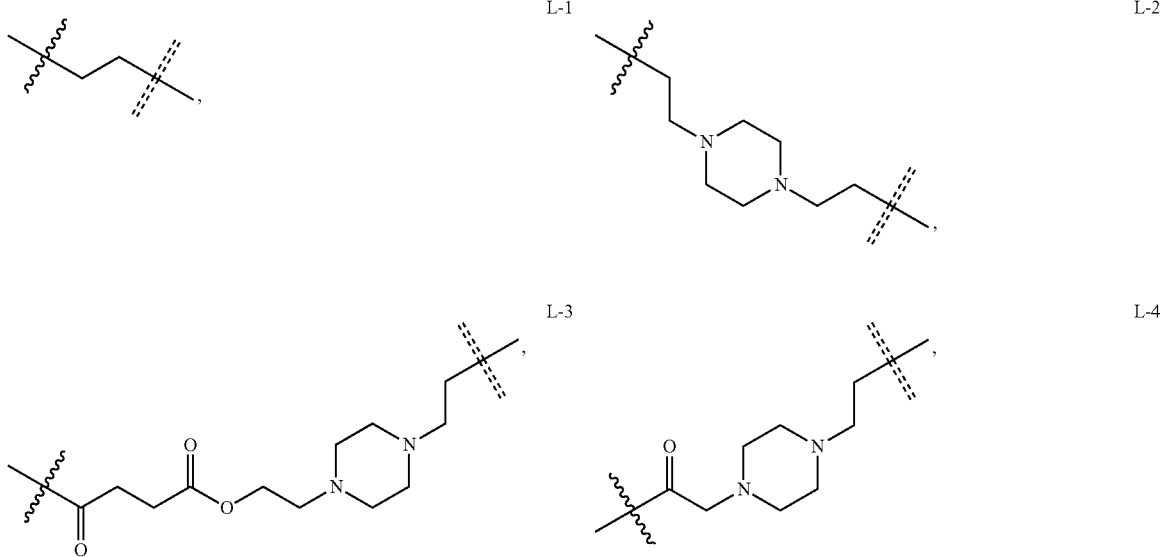

-continued
| L-5 | L-6 |
|---|---|
| 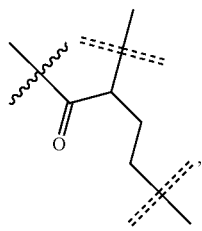 | 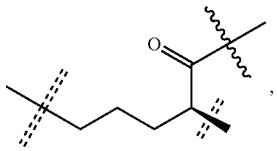 |
| L-7 | L-8 |
| 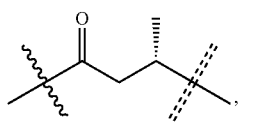 | 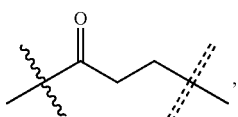 |
| L-9 | L-10 |
| 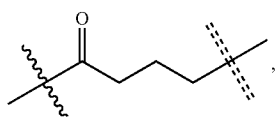 | 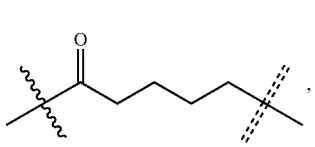 |
| L-11 | L-12 |
| 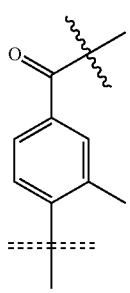 | 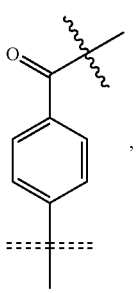 |
| L-13 | L-14 |
| 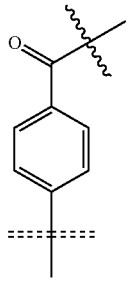 | 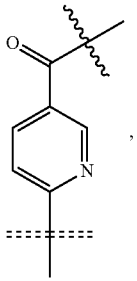 |
| L-15 | L-16 |
| 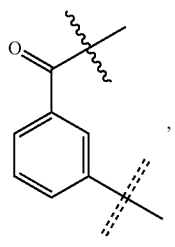 | 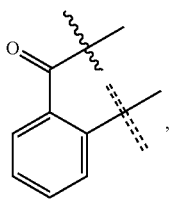 |
| L-17 | L-18 |
| 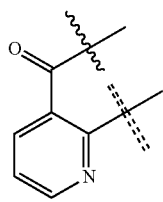 | 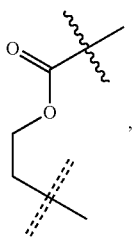 |

-continued
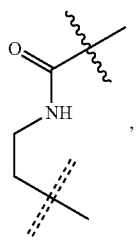
L-19
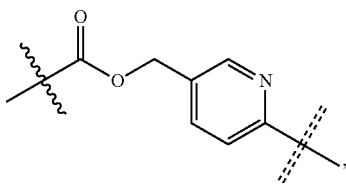
L-20
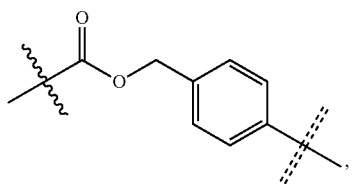
L-21
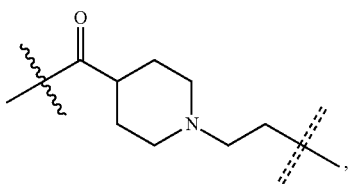
L-22
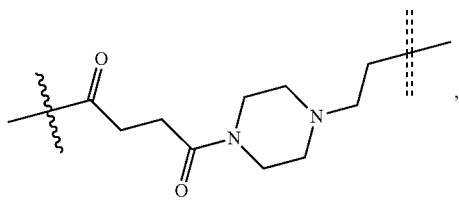
L-23
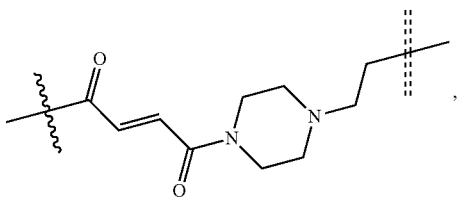
L-24
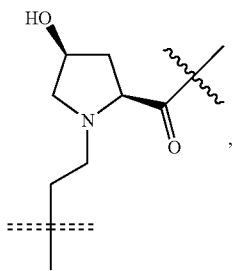
L-25
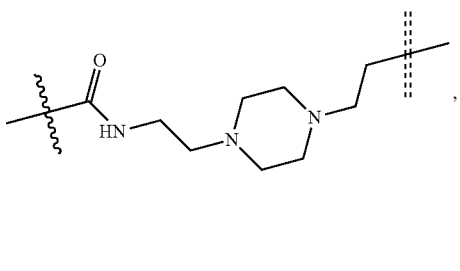
L-26
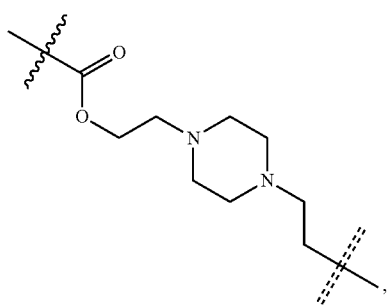
L-27
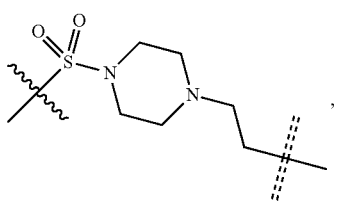
L-28
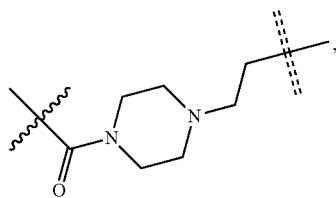
L-30
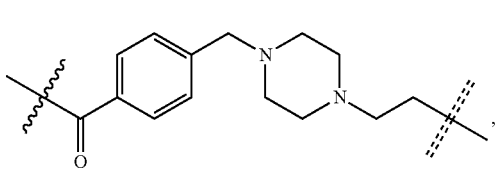
L-40

-continued
L-41
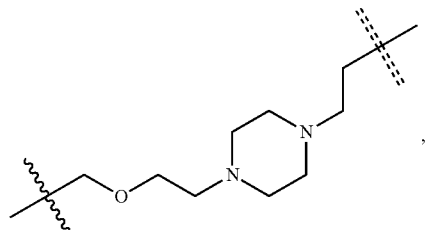
L-42
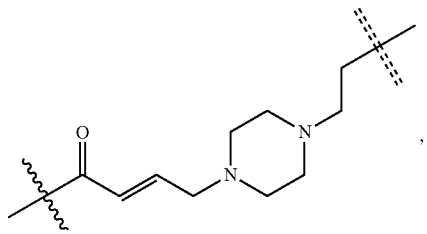
L-43
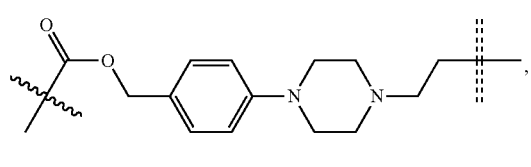
L-44
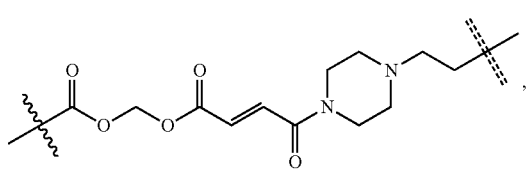
L-46
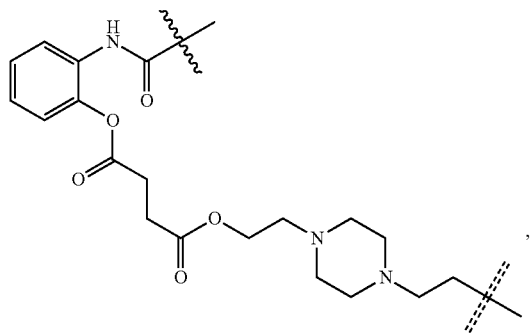
L-47
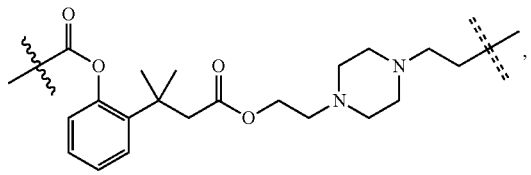
L-48
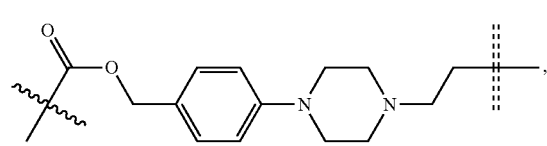
L-49
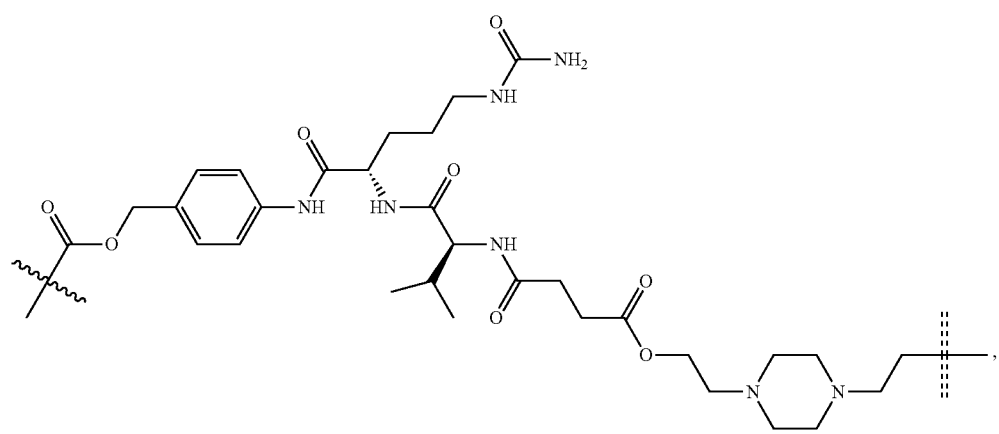

L-50
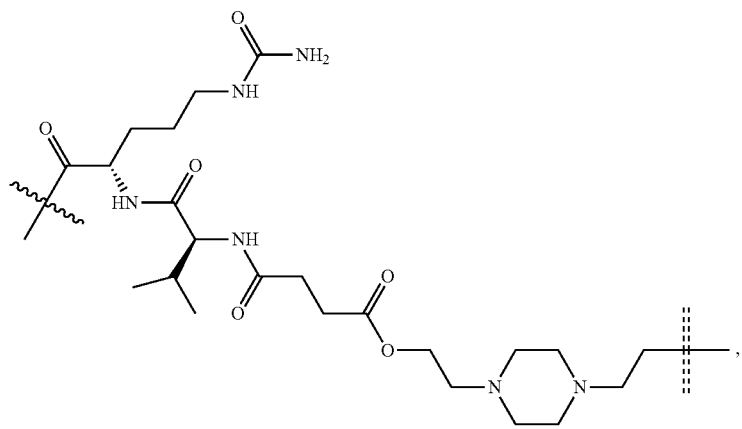
L-51
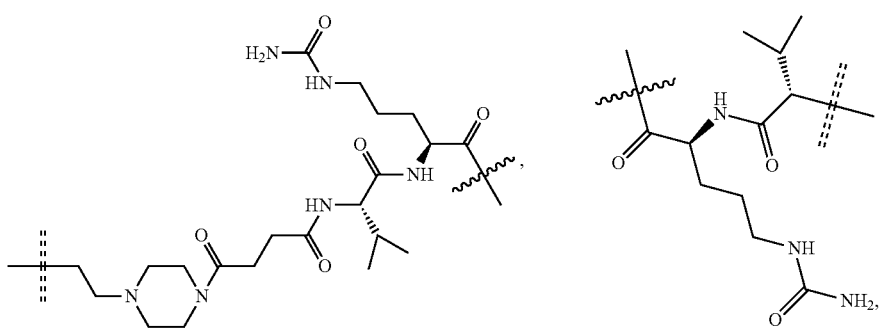
L-52
L-53 L-54
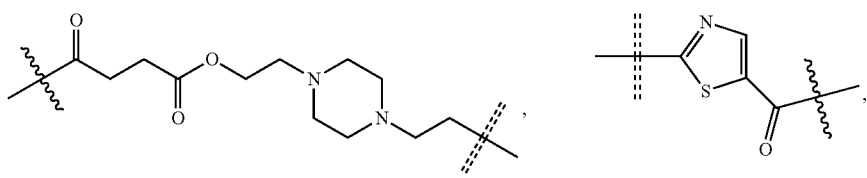
L-55 L-56
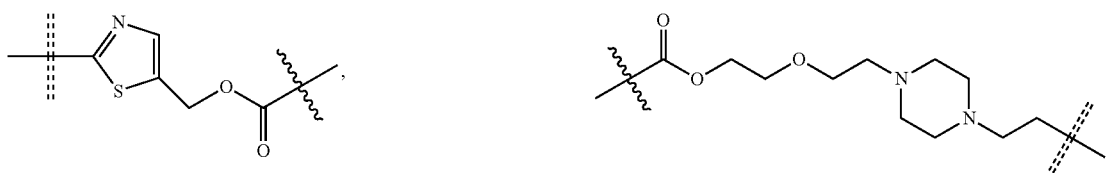
L-57 L-58
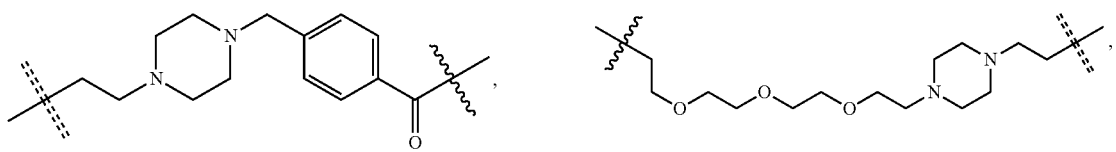
L-59 L-60

-continued
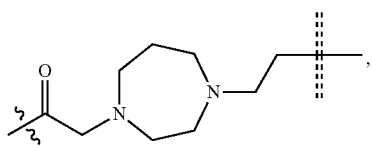 L-61
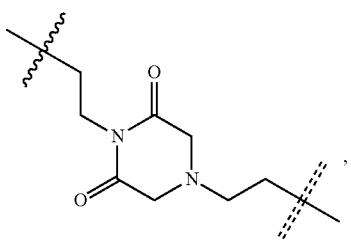 L-62
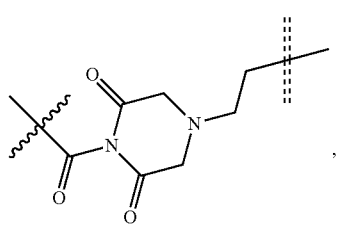 L-63
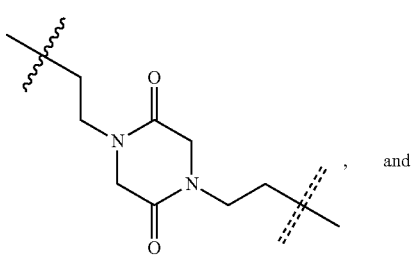 L-64, and
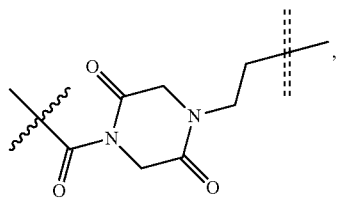 L-65
wherein the group is attached to Ar at the end
and to the fragment X at the end
7. The compound or a pharmaceutically acceptable salt thereof as claimed in claim 1, wherein the compound is selected from the compounds of General Formulas (VI), (VII), (VIII), (IX), (X) and (XI):
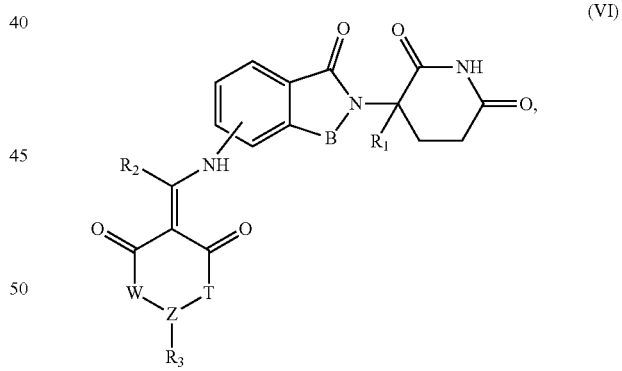 (VI)
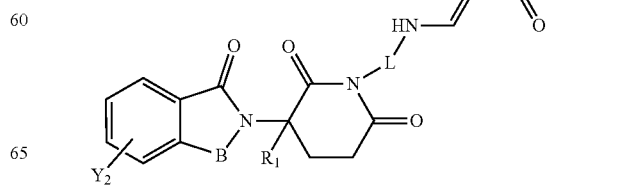 (VII)

(VIII)
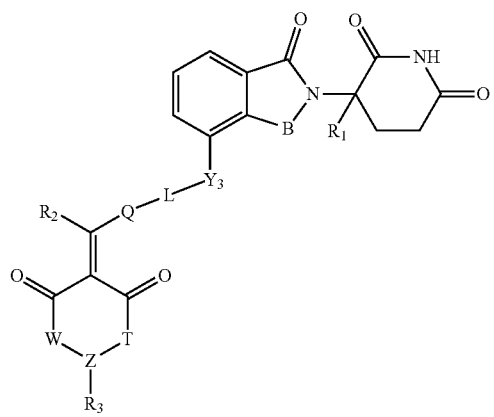
(X)
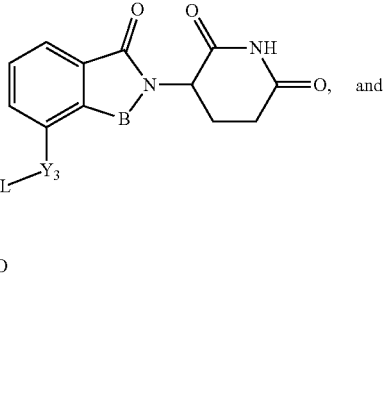
, and
(IX)
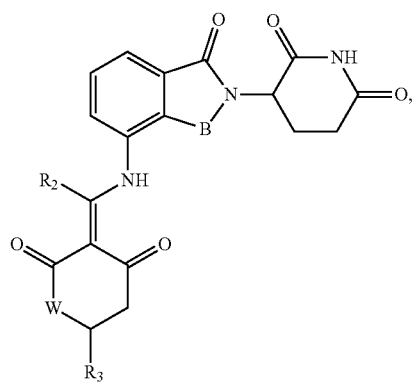
(XI)
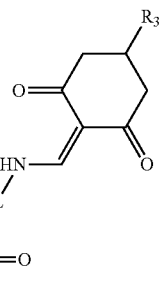
wherein A, B, Ra, R$_2$, R$_3$, Q, L, W, T, and Z are as defined in corresponding claims;
Y$_2$ is H, NH$_2$ or halo; and
Y$_3$ is NH or O.
8. The compound or a pharmaceutically acceptable salt thereof as claimed in claim 1, wherein the compound is selected from:
| Compound |
|---|
| 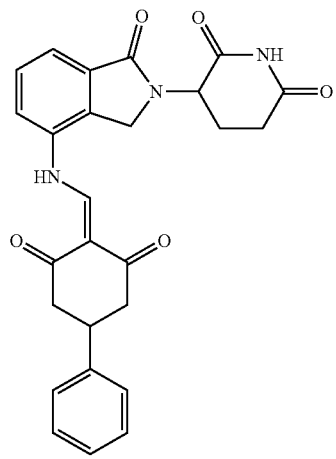    1 |

| Compound | |
|---|---|
| 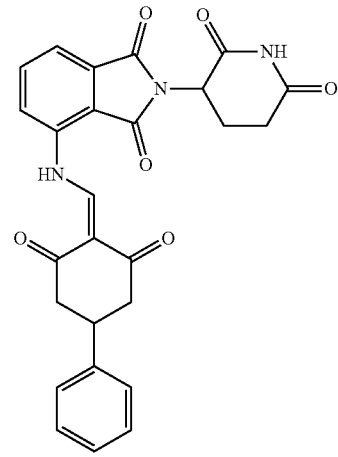 [SMILES: O=C1CCC(N2C(=O)c3cccc(NC=C4C(=O)CC(c5ccccc5)CC4=O)c3C2=O)C(=O)N1] | 2 |
| 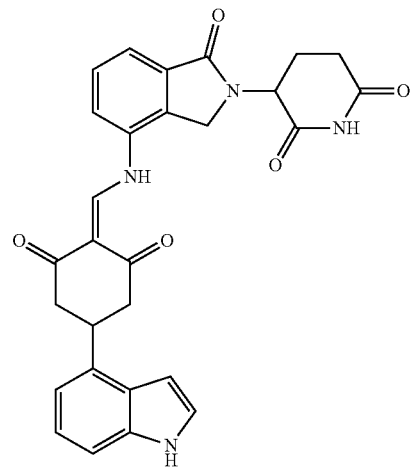 [SMILES: O=C1CCC(N2Cc3c(NC=C4C(=O)CC(c5cccc6[nH]ccc56)CC4=O)cccc3C2=O)C(=O)N1] | 3 |
| 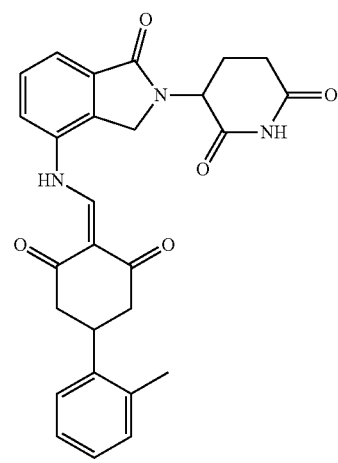 [SMILES: Cc1ccccc1C1CC(=O)C(=CNc2cccc3c2CN(C2CCC(=O)NC2=O)C3=O)C(=O)C1] | 4 |

-continued
| Compound | |
|---|---|
| 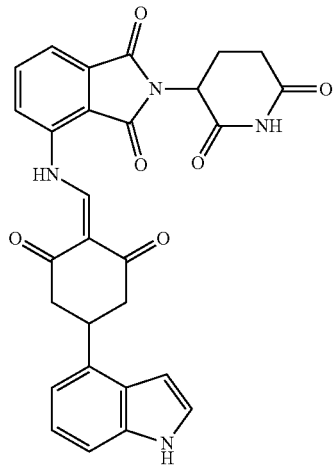 [SMILES: O=C1CCC(N2C(=O)c3cccc(NC=C4C(=O)CC(c5cccc6[nH]ccc56)CC4=O)c3C2=O)C(=O)N1] | 5 |
| 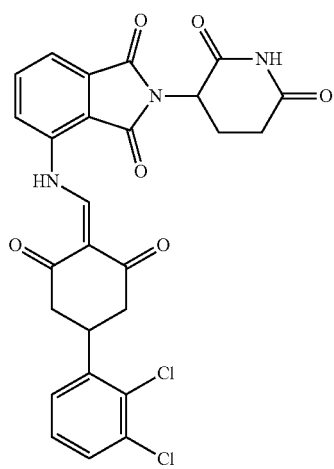 [SMILES: O=C1CCC(N2C(=O)c3cccc(NC=C4C(=O)CC(c5cccc(Cl)c5Cl)CC4=O)c3C2=O)C(=O)N1] | 6 |
| 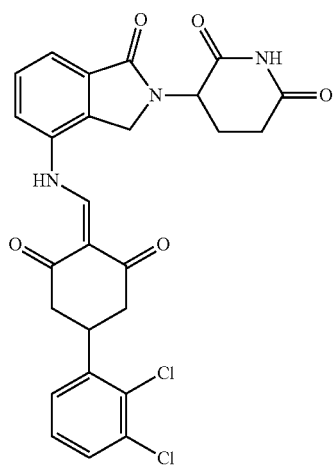 [SMILES: O=C1CCC(N2Cc3c(NC=C4C(=O)CC(c5cccc(Cl)c5Cl)CC4=O)cccc3C2=O)C(=O)N1] | 7 |

-continued
| Compound |
|---|
| 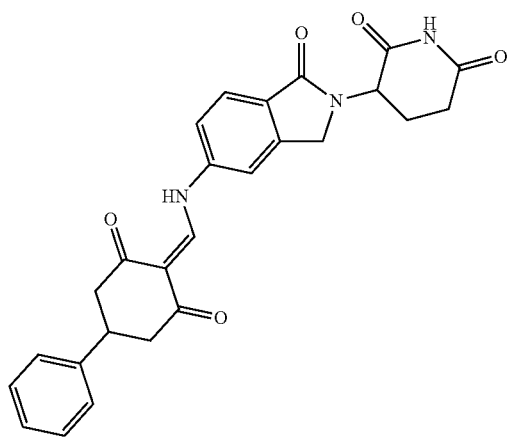 [SMILES: O=C1CCC(N2Cc3cc(NC=C4C(=O)CC(c5ccccc5)CC4=O)ccc3C2=O)C(=O)N1] 8 |
| 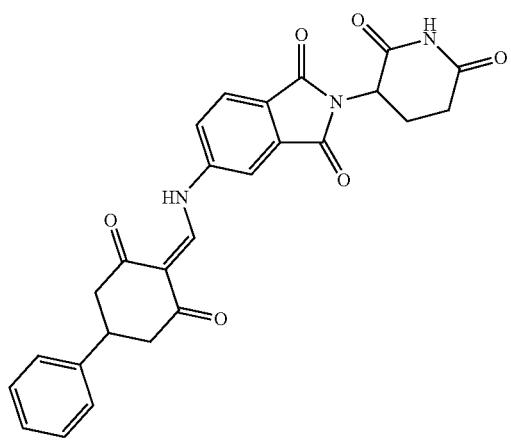 [SMILES: O=C1CCC(N2C(=O)c3ccc(NC=C4C(=O)CC(c5ccccc5)CC4=O)cc3C2=O)C(=O)N1] 9 |
| 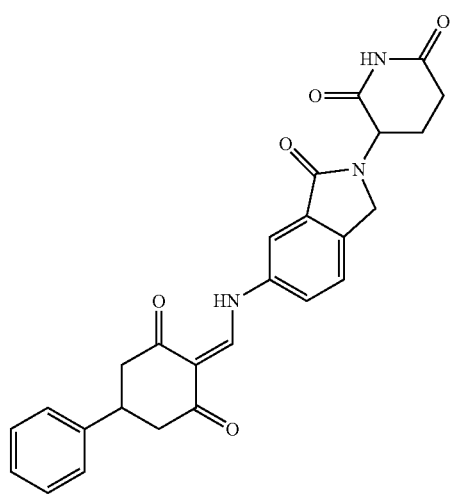 [SMILES: O=C1CCC(N2Cc3ccc(NC=C4C(=O)CC(c5ccccc5)CC4=O)cc3C2=O)C(=O)N1] 10 |

| Compound | |
|---|---|
| 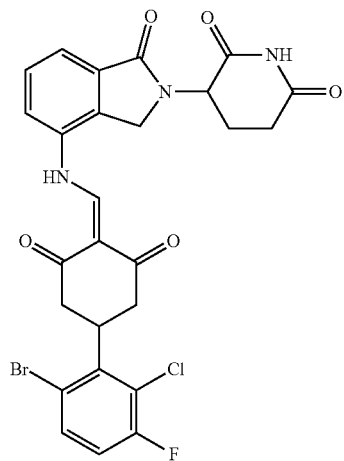 | 11 |
| 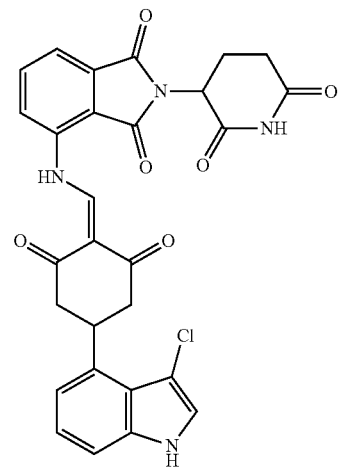 [SMILES: O=C1CCC(N2C(=O)c3cccc(NC=C4C(=O)CC(c5cccc6[nH]cc(Cl)c56)CC4=O)c3C2=O)C(=O)N1] | 12 |
| 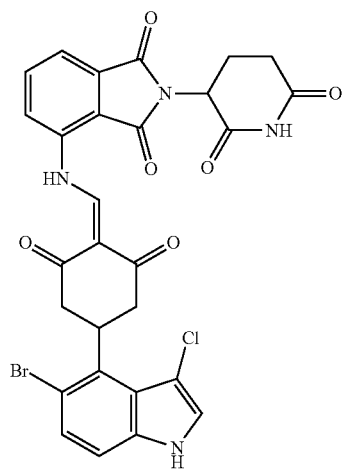 [SMILES: O=C1CCC(N2C(=O)c3cccc(NC=C4C(=O)CC(c5c(Br)ccc6[nH]cc(Cl)c56)CC4=O)c3C2=O)C(=O)N1] | 13 |

| Compound | |
|---|---|
| 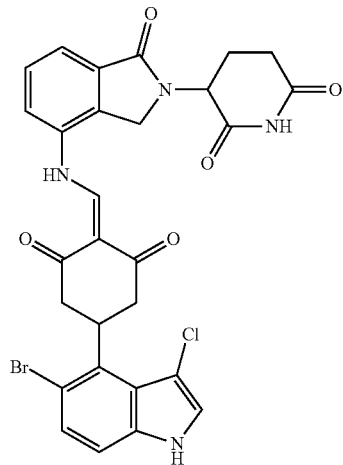 [SMILES: O=C1CCC(N2Cc3c(NC=C4C(=O)CC(c5c(Br)ccc6[nH]cc(Cl)c56)CC4=O)cccc3C2=O)C(=O)N1] | 14 |
| 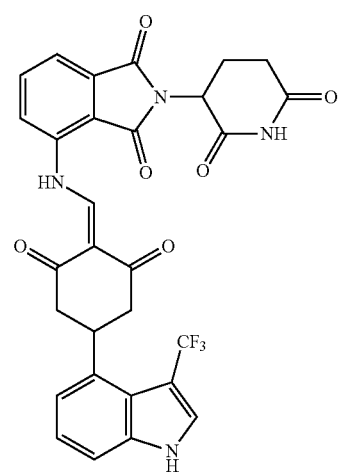 [SMILES: O=C1CCC(N2C(=O)c3cccc(NC=C4C(=O)CC(c5cccc6[nH]cc(C(F)(F)F)c56)CC4=O)c3C2=O)C(=O)N1] | 15 |
| 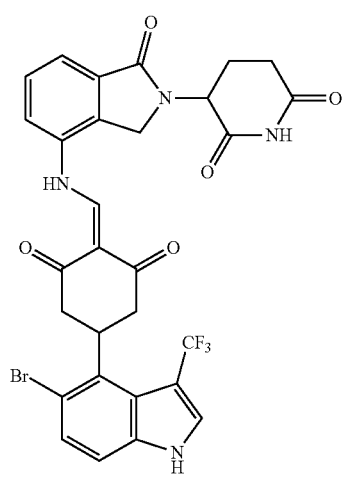 [SMILES: O=C1CCC(N2Cc3c(NC=C4C(=O)CC(c5c(Br)ccc6[nH]cc(C(F)(F)F)c56)CC4=O)cccc3C2=O)C(=O)N1] | 16 |

-continued
| Compound | |
|---|---|
| 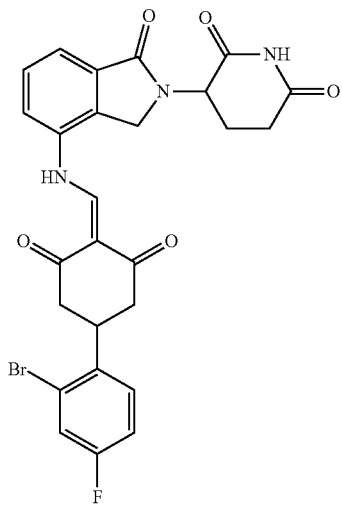 | 17 |
| 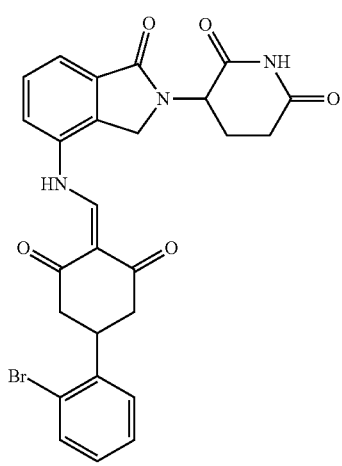 | 18 |
| 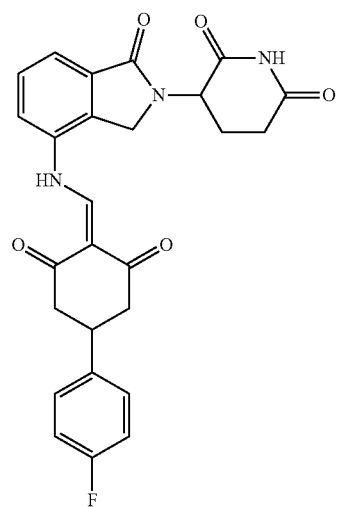 [SMILES: O=C1CCC(N2Cc3c(NC=C4C(=O)CC(c5ccc(F)cc5)CC4=O)cccc3C2=O)C(=O)N1] | 19 |

| Compound | |
|---|---|
| 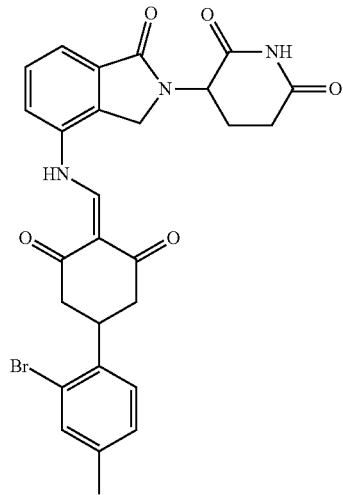 | 20 |
| 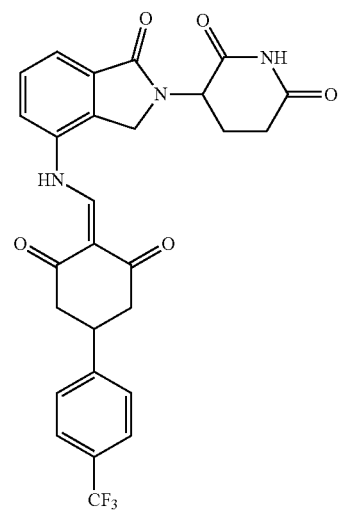 [SMILES: O=C1CCC(N2Cc3c(NC=C4C(=O)CC(c5ccc(C(F)(F)F)cc5)CC4=O)cccc3C2=O)C(=O)N1] | 21 |
| 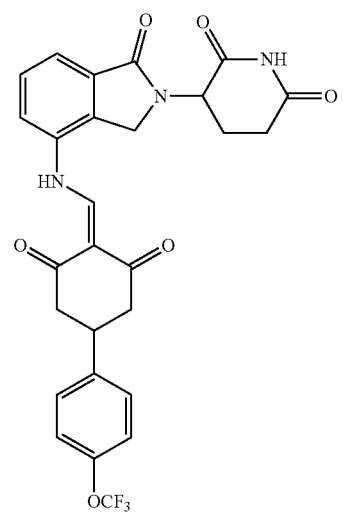 [SMILES: O=C1CCC(N2Cc3c(NC=C4C(=O)CC(c5ccc(OC(F)(F)F)cc5)CC4=O)cccc3C2=O)C(=O)N1] | 22 |

| Compound | |
|---|---|
| 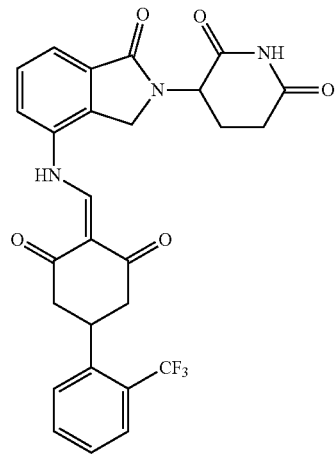 [SMILES: O=C1CCC(N2Cc3c(NC=C4C(=O)CC(c5ccccc5C(F)(F)F)CC4=O)cccc3C2=O)C(=O)N1] | 23 |
| 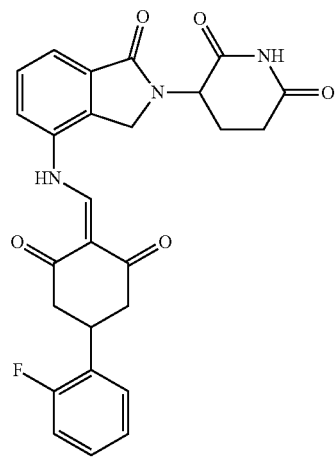 [SMILES: O=C1CCC(N2Cc3c(NC=C4C(=O)CC(c5ccccc5F)CC4=O)cccc3C2=O)C(=O)N1] | 24 |
| 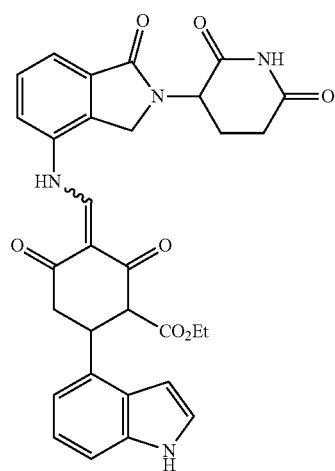 [SMILES: CCOC(=O)C1C(=O)C(=CNc2cccc3c2CN(C2CCC(=O)NC2=O)C3=O)C(=O)CC1c1cccc2[nH]ccc12] | 25 |

| Compound | |
|---|---|
| 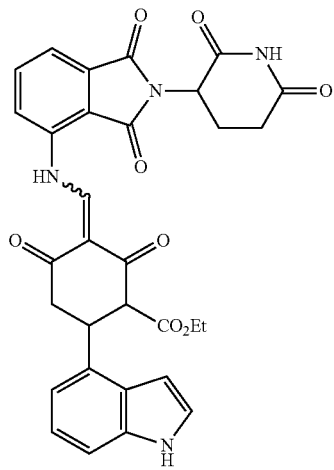 [SMILES: CCOC(=O)C1C(=O)C(=CNc2cccc3c2C(=O)N(C2CCC(=O)NC2=O)C3=O)C(=O)CC1c1cccc2[nH]ccc12] | 26 |
| 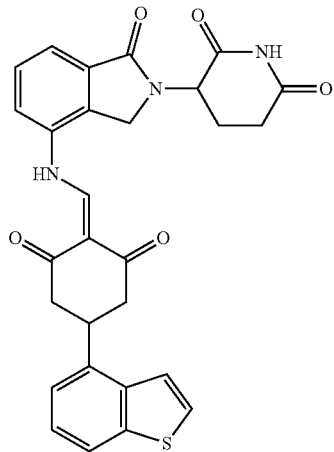 [SMILES: O=C1CCC(N2Cc3c(NC=C4C(=O)CC(c5cccc6sccc56)CC4=O)cccc3C2=O)C(=O)N1] | 27 |
| 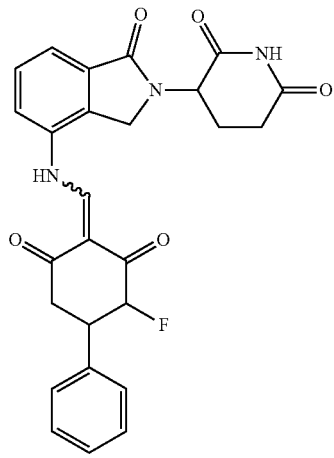 [SMILES: O=C1CCC(N2Cc3c(NC=C4C(=O)CC(c5ccccc5)C(F)C4=O)cccc3C2=O)C(=O)N1] | 28 |

| Compound | |
|---|---|
| 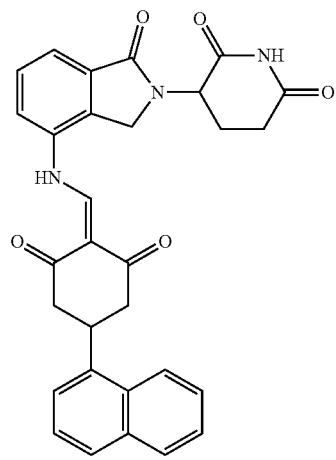 [SMILES: O=C1CCC(N2Cc3c(NC=C4C(=O)CC(c5cccc6ccccc56)CC4=O)cccc3C2=O)C(=O)N1] | 29 |
| 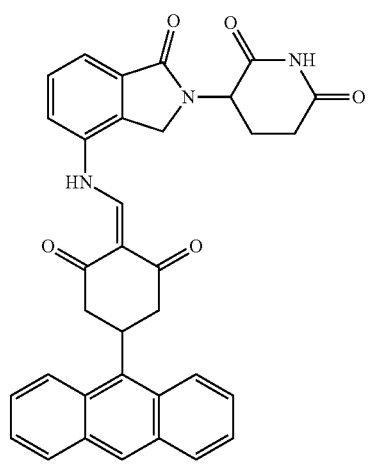 [SMILES: O=C1CCC(N2Cc3c(NC=C4C(=O)CC(c5c6ccccc6cc6ccccc56)CC4=O)cccc3C2=O)C(=O)N1] | 30 |
| 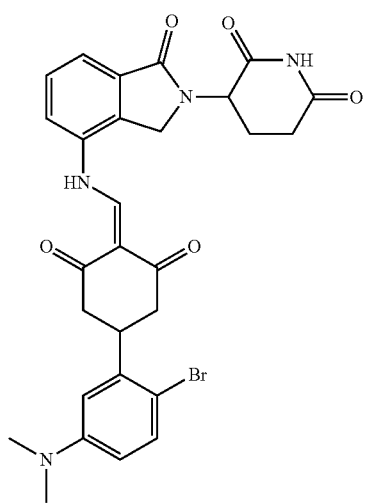 [SMILES: CN(C)c1ccc(Br)c(C2CC(=O)C(=CNc3cccc4c3CN(C3CCC(=O)NC3=O)C4=O)C(=O)C2)c1] | 31 |

-continued
| Compound | |
|---|---|
| 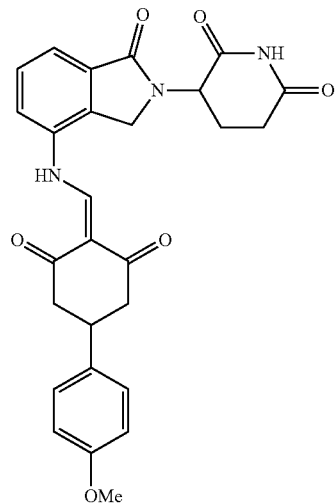 | 32 |
| 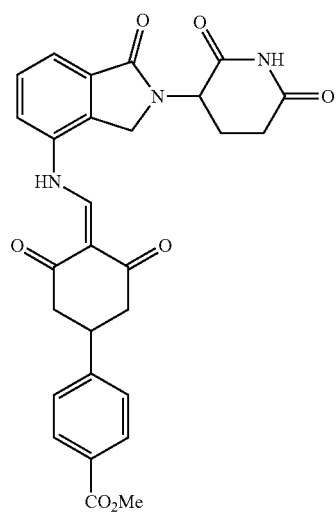 [SMILES: COC(=O)c1ccc(C2CC(=O)C(=CNc3cccc4c3CN(C3CCC(=O)NC3=O)C4=O)C(=O)C2)cc1] | 33 |
| 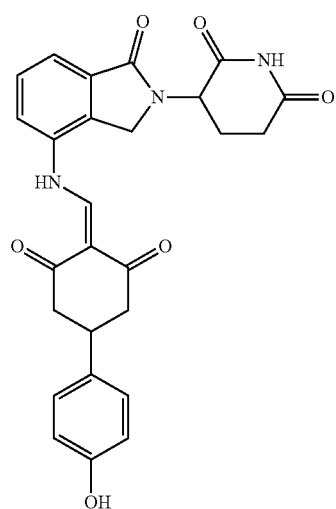 [SMILES: O=C1CCC(N2Cc3c(NC=C4C(=O)CC(c5ccc(O)cc5)CC4=O)cccc3C2=O)C(=O)N1] | 34 |

| Compound | |
|---|---|
| 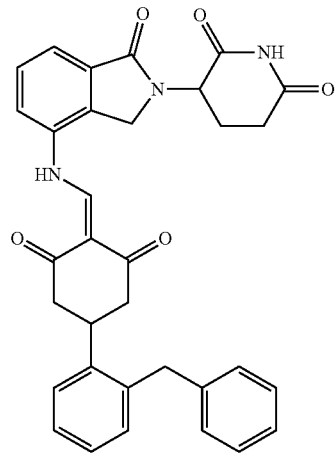 [SMILES: O=C1CCC(N2Cc3c(NC=C4C(=O)CC(c5ccccc5Cc5ccccc5)CC4=O)cccc3C2=O)C(=O)N1] | 35 |
| 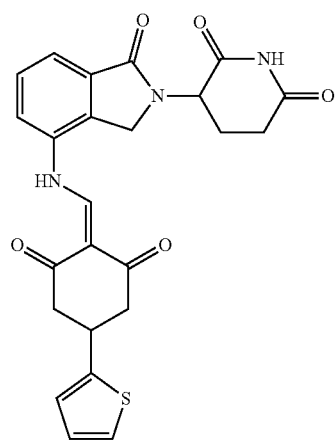 [SMILES: O=C1CCC(N2Cc3c(NC=C4C(=O)CC(c5cccs5)CC4=O)cccc3C2=O)C(=O)N1] | 36 |
| 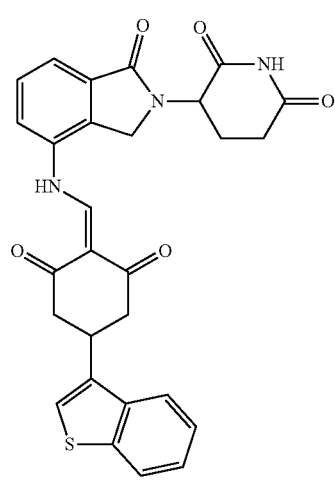 [SMILES: O=C1CCC(N2Cc3c(NC=C4C(=O)CC(c5csc6ccccc56)CC4=O)cccc3C2=O)C(=O)N1] | 37 |

| Compound | |
|---|---|
| (structure) | 38 |
| (structure) | 39 |
| (structure) | 40 |

-continued
| Compound | |
|---|---|
| 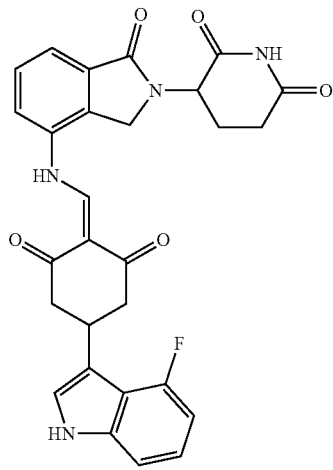 [SMILES: O=C1CCC(N2Cc3c(NC=C4C(=O)CC(c5c[nH]c6cccc(F)c56)CC4=O)cccc3C2=O)C(=O)N1] | 41 |
| 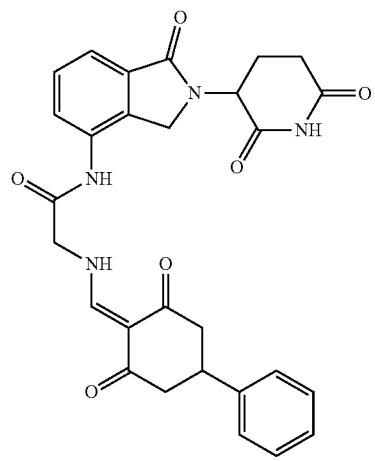 [SMILES: O=C1CCC(N2Cc3c(NC(=O)CNC=C4C(=O)CC(c5ccccc5)CC4=O)cccc3C2=O)C(=O)N1] | 42 |
| 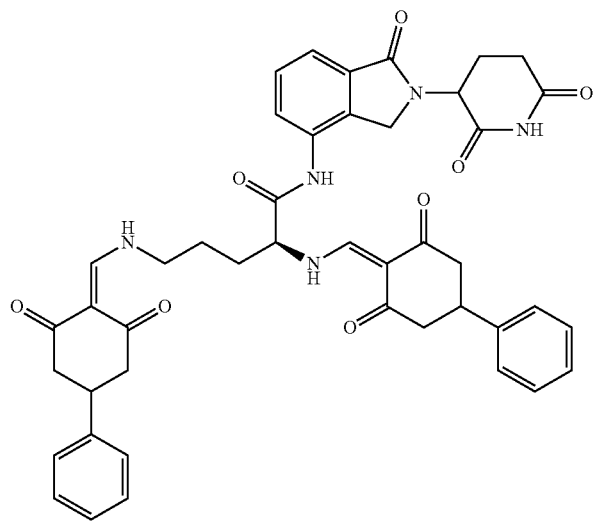 [SMILES: O=C1CCC(N2Cc3c(NC(=O)[C@H](CCCNC=C4C(=O)CC(c5ccccc5)CC4=O)NC=C4C(=O)CC(c5ccccc5)CC4=O)cccc3C2=O)C(=O)N1] | 43 |

| Compound |
|---|
| 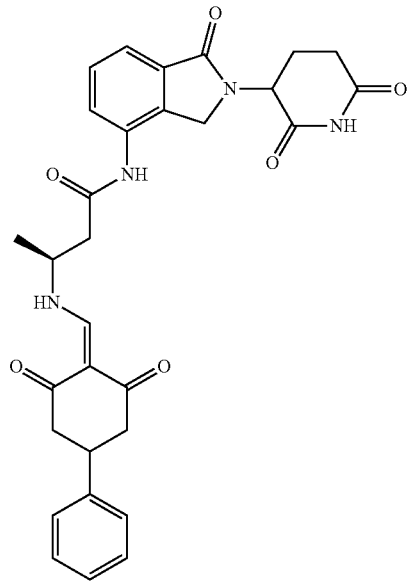 [SMILES: C[C@@H](CC(=O)Nc1cccc2c1CN(C1CCC(=O)NC1=O)C2=O)NC=C1C(=O)CC(c2ccccc2)CC1=O] 44 |
| 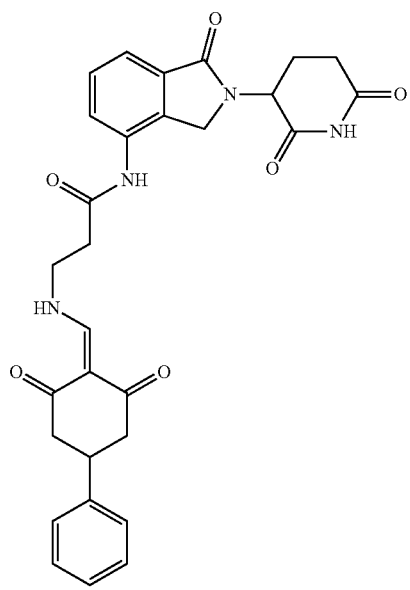 [SMILES: O=C1CCC(N2Cc3c(NC(=O)CCNC=C4C(=O)CC(c5ccccc5)CC4=O)cccc3C2=O)C(=O)N1] 45 |

| Compound | |
|---|---|
| 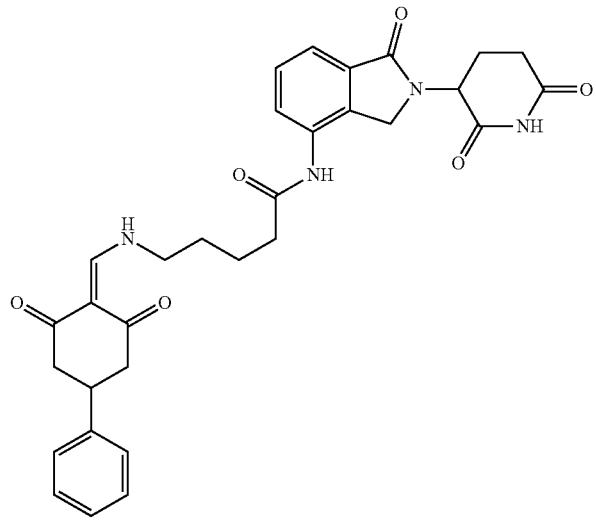 [SMILES: O=C1CCC(N2Cc3c(NC(=O)CCCCNC=C4C(=O)CC(c5ccccc5)CC4=O)cccc3C2=O)C(=O)N1] | 46 |
| 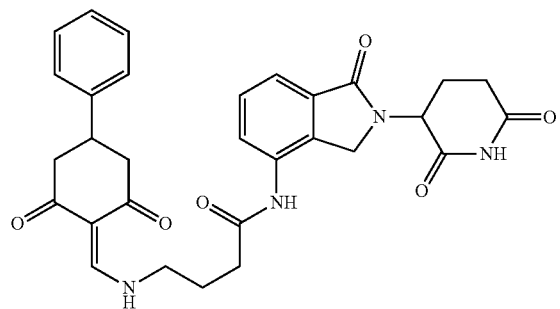 [SMILES: O=C1CCC(N2Cc3c(NC(=O)CCCNC=C4C(=O)CC(c5ccccc5)CC4=O)cccc3C2=O)C(=O)N1] | 47 |
| 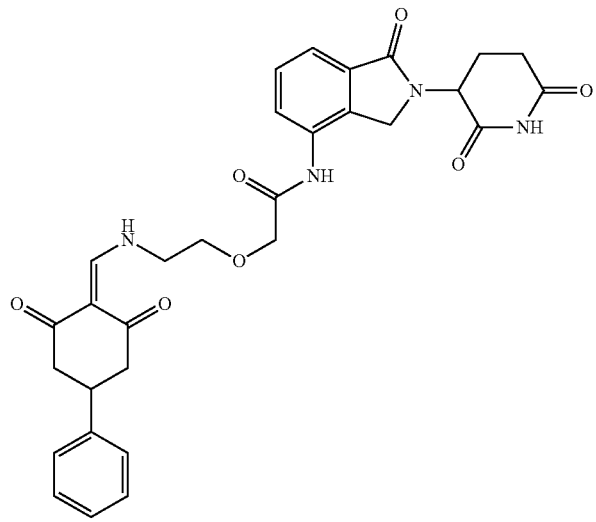 [SMILES: O=C1CCC(N2Cc3c(NC(=O)COCCNC=C4C(=O)CC(c5ccccc5)CC4=O)cccc3C2=O)C(=O)N1] | 48 |

| Compound |
|---|
| 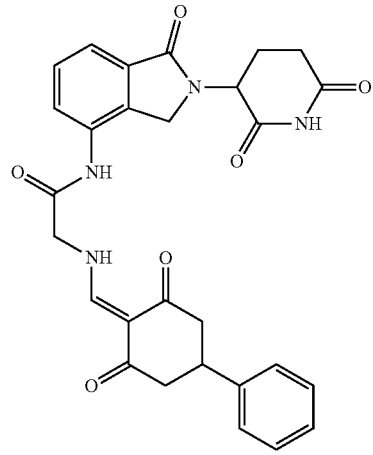 [SMILES: O=C1CCC(N2Cc3c(NC(=O)CNC=C4C(=O)CC(c5ccccc5)CC4=O)cccc3C2=O)C(=O)N1] 49 |
| 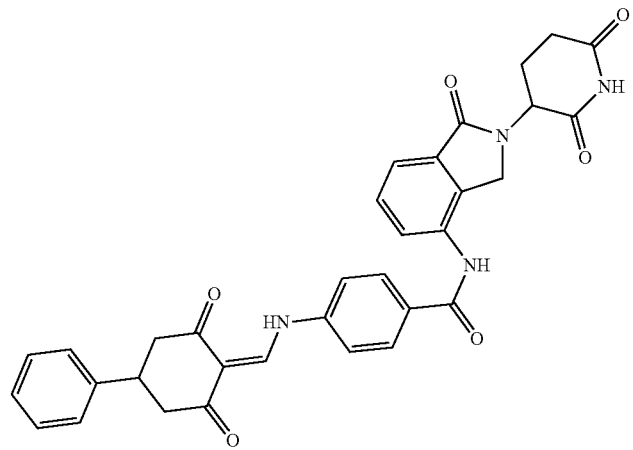 [SMILES: O=C1CCC(N2Cc3c(NC(=O)c4ccc(NC=C5C(=O)CC(c6ccccc6)CC5=O)cc4)cccc3C2=O)C(=O)N1] 50 |
| 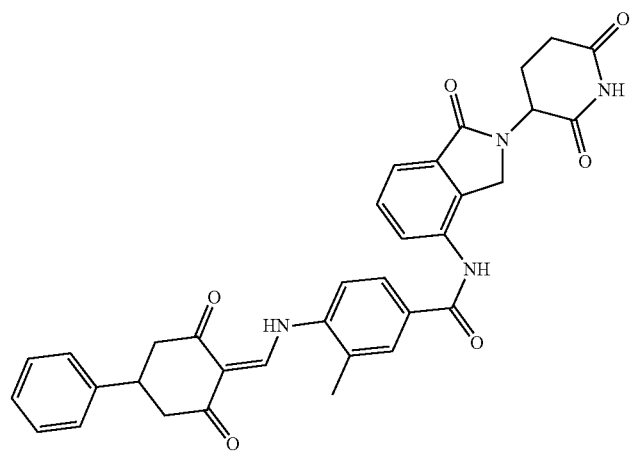 [SMILES: Cc1cc(C(=O)Nc2cccc3c2CN(C2CCC(=O)NC2=O)C3=O)ccc1NC=C1C(=O)CC(c2ccccc2)CC1=O] 51 |

-continued
| Compound |
|---|
| 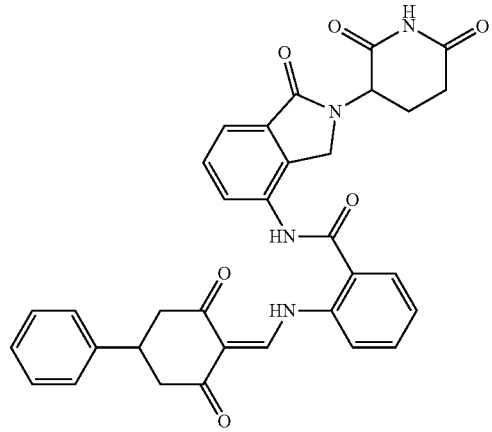 [SMILES: O=C1CCC(N2Cc3c(NC(=O)c4ccccc4NC=C4C(=O)CC(c5ccccc5)CC4=O)cccc3C2=O)C(=O)N1] 52 |
| 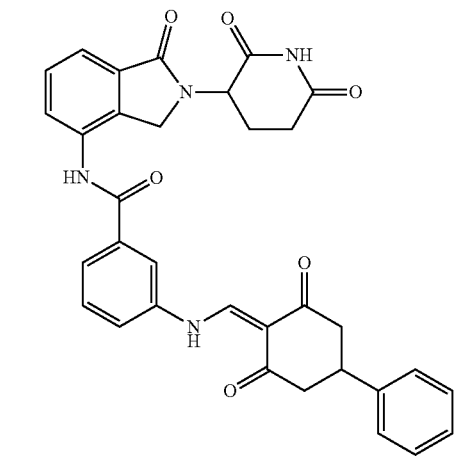 [SMILES: O=C1CCC(N2Cc3c(NC(=O)c4cccc(NC=C5C(=O)CC(c6ccccc6)CC5=O)c4)cccc3C2=O)C(=O)N1] 53 |
| 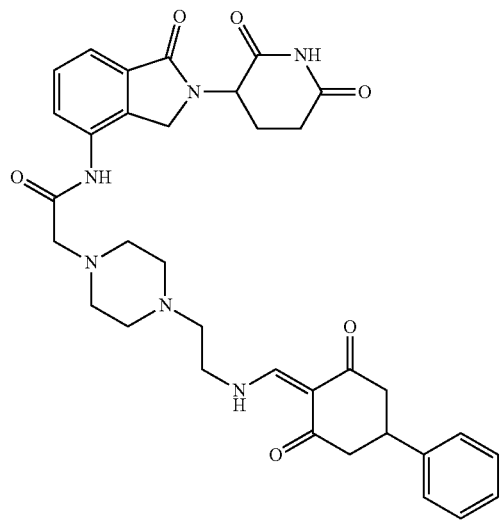 [SMILES: O=C1CCC(N2Cc3c(NC(=O)CN4CCN(CCNC=C5C(=O)CC(c6ccccc6)CC5=O)CC4)cccc3C2=O)C(=O)N1] 54 |

| Compound |
|---|
| 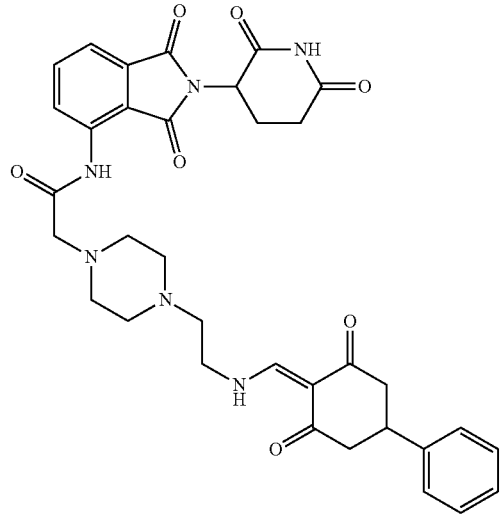 [SMILES: O=C1CCC(N2C(=O)c3cccc(NC(=O)CN4CCN(CCNC=C5C(=O)CC(c6ccccc6)CC5=O)CC4)c3C2=O)C(=O)N1] 55 |
| 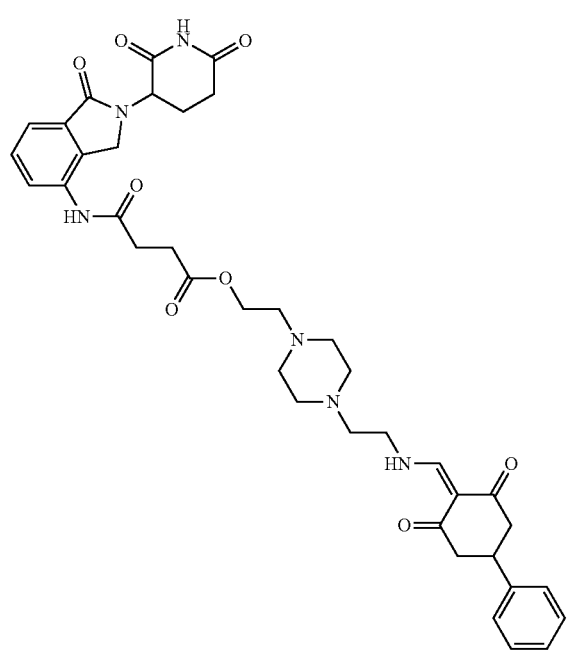 [SMILES: O=C1CCC(N2Cc3c(NC(=O)CCC(=O)OCCN4CCN(CCNC=C5C(=O)CC(c6ccccc6)CC5=O)CC4)cccc3C2=O)C(=O)N1] 56 |

| Compound | |
|---|---|
| 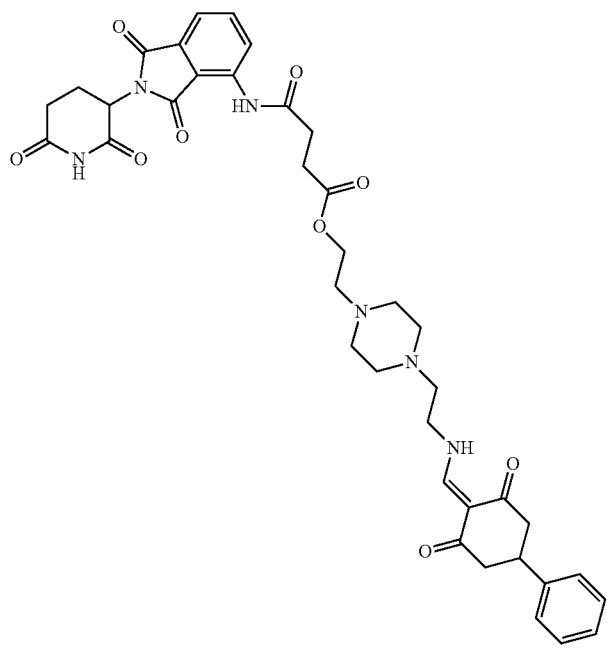 [SMILES: O=C1CCC(N2C(=O)c3cccc(NC(=O)CCC(=O)OCCN4CCN(CCNC=C5C(=O)CC(c6ccccc6)CC5=O)CC4)c3C2=O)C(=O)N1] | 57 |
| 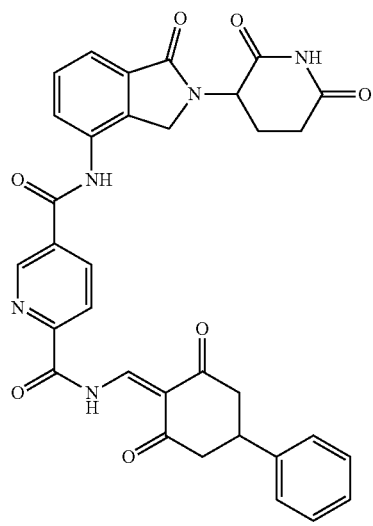 [SMILES: O=C1CCC(N2Cc3c(NC(=O)c4ccc(C(=O)NC=C5C(=O)CC(c6ccccc6)CC5=O)nc4)cccc3C2=O)C(=O)N1] | 58 |

| Compound | |
|---|---|
| 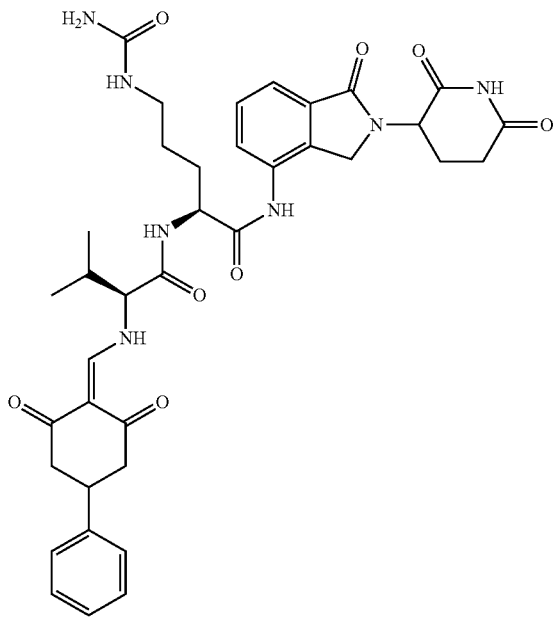 [SMILES: CC(C)[C@H](NC=C1C(=O)CC(c2ccccc2)CC1=O)C(=O)N[C@@H](CCCNC(N)=O)C(=O)Nc1cccc2c1CN(C1CCC(=O)NC1=O)C2=O] | 59 |
| 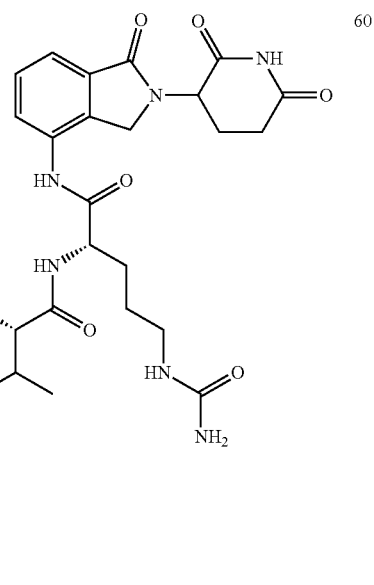 | 60 |

-continued
| Compound |
|---|
| 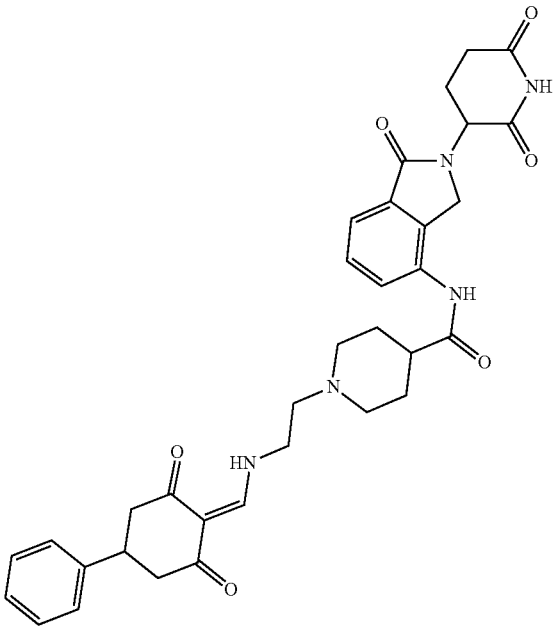 [SMILES: O=C1CCC(N2Cc3c(NC(=O)C4CCN(CCNC=C5C(=O)CC(c6ccccc6)CC5=O)CC4)cccc3C2=O)C(=O)N1] 61 |
| 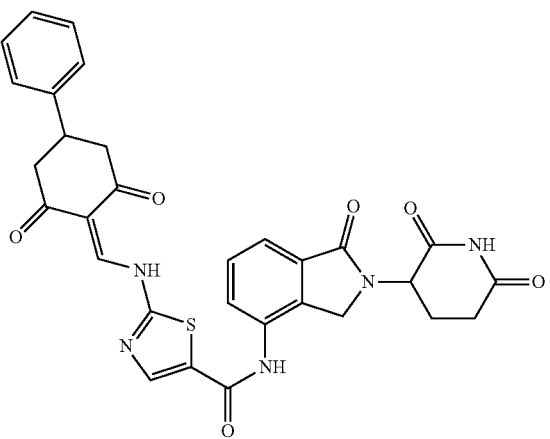 [SMILES: O=C1CCC(N2Cc3c(NC(=O)c4cnc(NC=C5C(=O)CC(c6ccccc6)CC5=O)s4)cccc3C2=O)C(=O)N1] 62 |
| 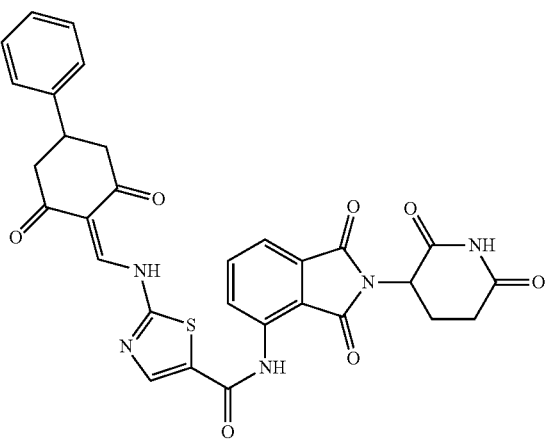 [SMILES: O=C1CCC(N2C(=O)c3cccc(NC(=O)c4cnc(NC=C5C(=O)CC(c6ccccc6)CC5=O)s4)c3C2=O)C(=O)N1] 63 |

| Compound | |
|---|---|
| 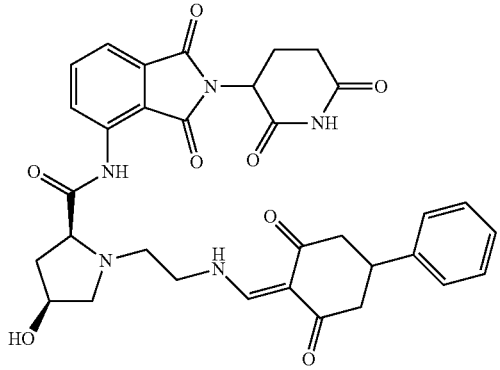 [SMILES: O=C1CCC(N2C(=O)c3cccc(NC(=O)[C@@H]4C[C@H](O)CN4CCNC=C4C(=O)CC(c5ccccc5)CC4=O)c3C2=O)C(=O)N1] | 64 |
| 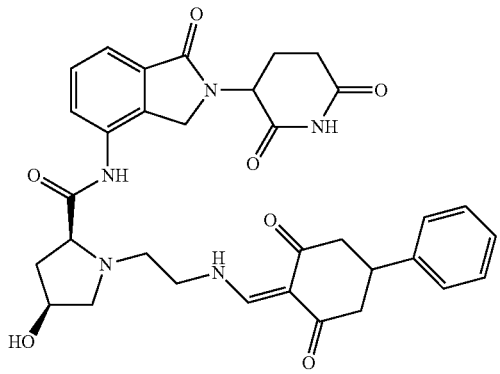 [SMILES: O=C1CCC(N2Cc3c(NC(=O)[C@@H]4C[C@H](O)CN4CCNC=C4C(=O)CC(c5ccccc5)CC4=O)cccc3C2=O)C(=O)N1] | 65 |
| 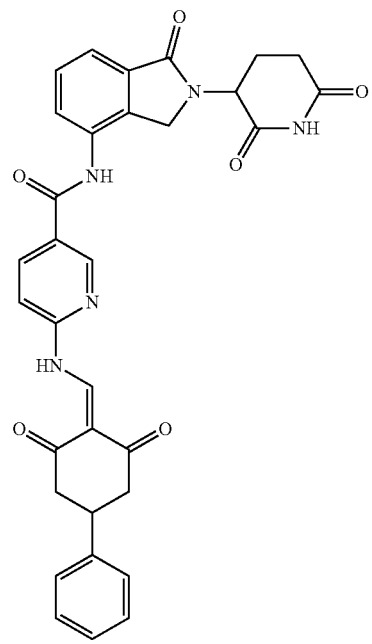 [SMILES: O=C1CCC(N2Cc3c(NC(=O)c4ccc(NC=C5C(=O)CC(c6ccccc6)CC5=O)nc4)cccc3C2=O)C(=O)N1] | 66 |

| Compound | |
|---|---|
| 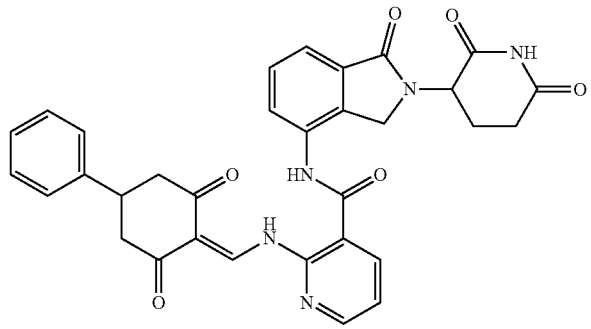 [SMILES: O=C1CCC(N2Cc3c(NC(=O)c4cccnc4NC=C4C(=O)CC(c5ccccc5)CC4=O)cccc3C2=O)C(=O)N1] | 67 |
| 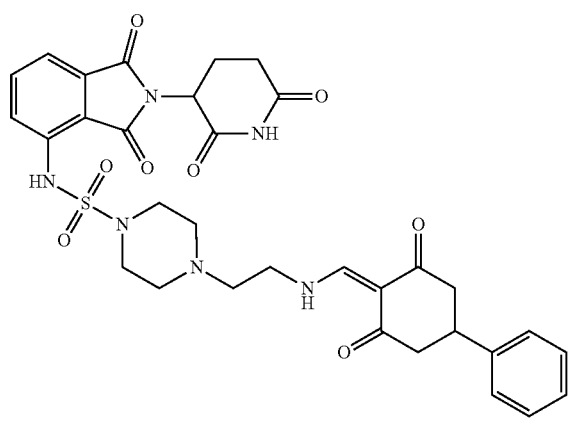 [SMILES: O=C1CCC(N2C(=O)c3cccc(NS(=O)(=O)N4CCN(CCNC=C5C(=O)CC(c6ccccc6)CC5=O)CC4)c3C2=O)C(=O)N1] | 71 |
| 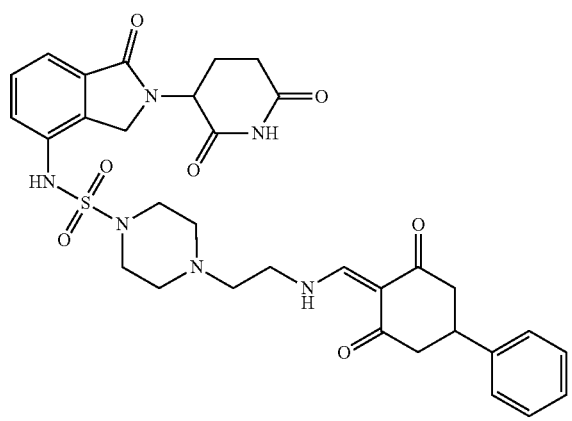 [SMILES: O=C1CCC(N2Cc3c(NS(=O)(=O)N4CCN(CCNC=C5C(=O)CC(c6ccccc6)CC5=O)CC4)cccc3C2=O)C(=O)N1] | 72 |

| Compound | |
|---|---|
| 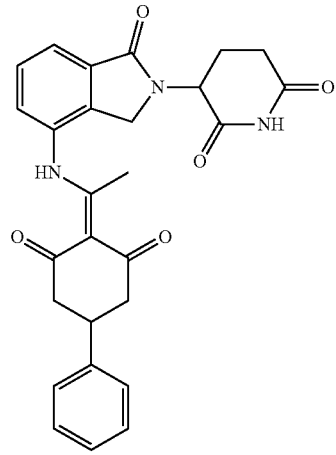 [SMILES: CC(Nc1cccc2c1CN(C1CCC(=O)NC1=O)C2=O)=C1C(=O)CC(c2ccccc2)CC1=O] | 73 |
| 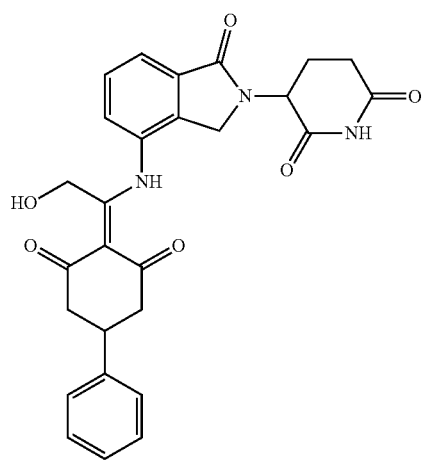 [SMILES: O=C1CCC(N2Cc3c(NC(CO)=C4C(=O)CC(c5ccccc5)CC4=O)cccc3C2=O)C(=O)N1] | 74 |
| 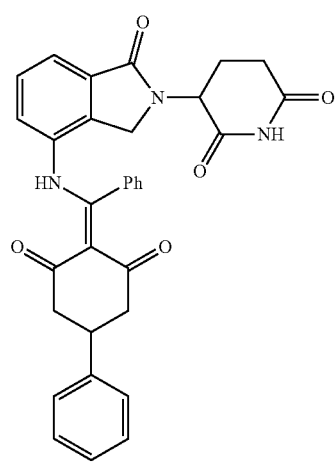 [SMILES: O=C1CCC(N2Cc3c(NC(=C4C(=O)CC(c5ccccc5)CC4=O)c4ccccc4)cccc3C2=O)C(=O)N1] | 75 |

| Compound |
|---|
| 76 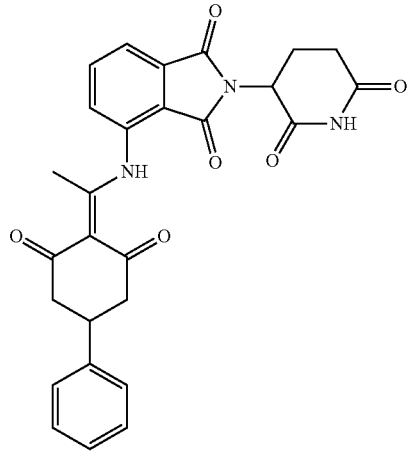 [SMILES: CC(Nc1cccc2c1C(=O)N(C1CCC(=O)NC1=O)C2=O)=C1C(=O)CC(c2ccccc2)CC1=O] |
| 77 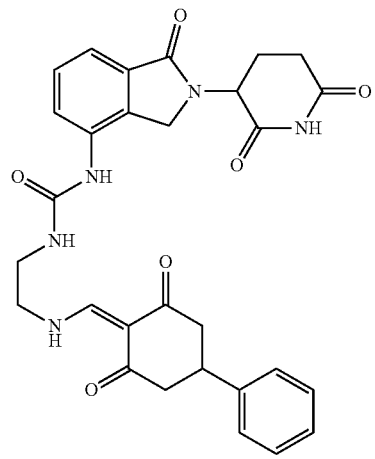 [SMILES: O=C1CCC(N2Cc3c(NC(=O)NCCNC=C4C(=O)CC(c5ccccc5)CC4=O)cccc3C2=O)C(=O)N1] |
| 78 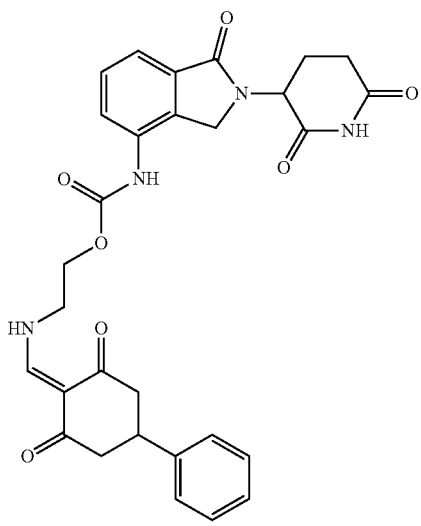 [SMILES: O=C1CCC(N2Cc3c(NC(=O)OCCNC=C4C(=O)CC(c5ccccc5)CC4=O)cccc3C2=O)C(=O)N1] |

-continued
| Compound | |
|---|---|
| 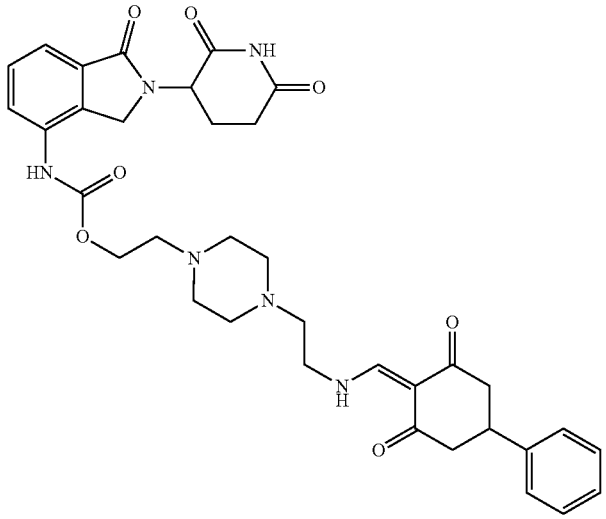 [SMILES: O=C1CCC(N2Cc3c(NC(=O)OCCN4CCN(CCNC=C5C(=O)CC(c6ccccc6)CC5=O)CC4)cccc3C2=O)C(=O)N1] | 79 |
| 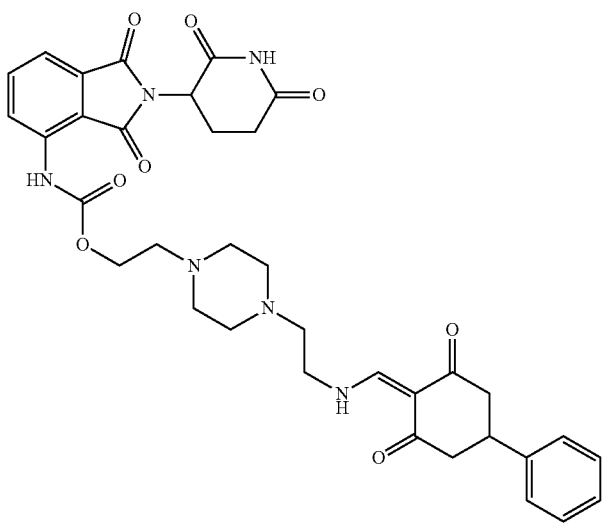 [SMILES: O=C1CCC(N2C(=O)c3cccc(NC(=O)OCCN4CCN(CCNC=C5C(=O)CC(c6ccccc6)CC5=O)CC4)c3C2=O)C(=O)N1] | 80 |
| 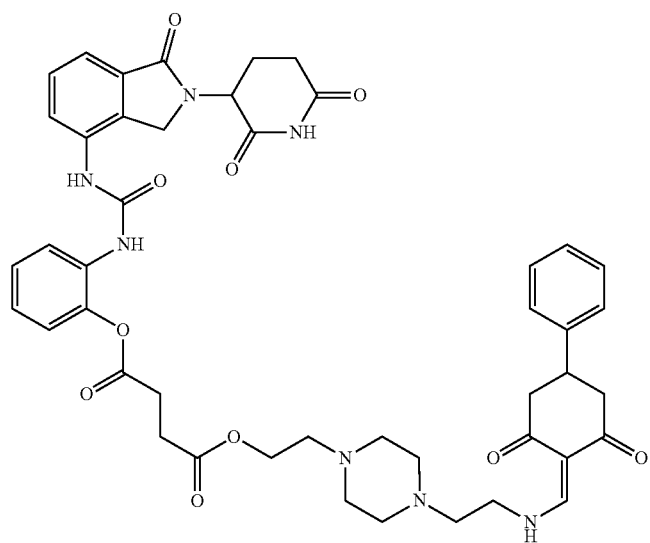 [SMILES: O=C1CCC(N2Cc3c(NC(=O)Nc4ccccc4OC(=O)CCC(=O)OCCN4CCN(CCNC=C5C(=O)CC(c6ccccc6)CC5=O)CC4)cccc3C2=O)C(=O)N1] | 81 |

| Compound |
|---|
| 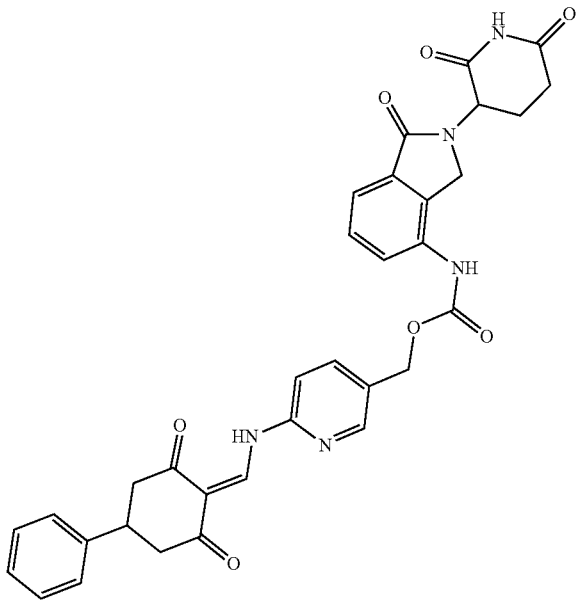 [SMILES: O=C1CCC(N2Cc3c(NC(=O)OCc4ccc(NC=C5C(=O)CC(c6ccccc6)CC5=O)nc4)cccc3C2=O)C(=O)N1] 82 |
| 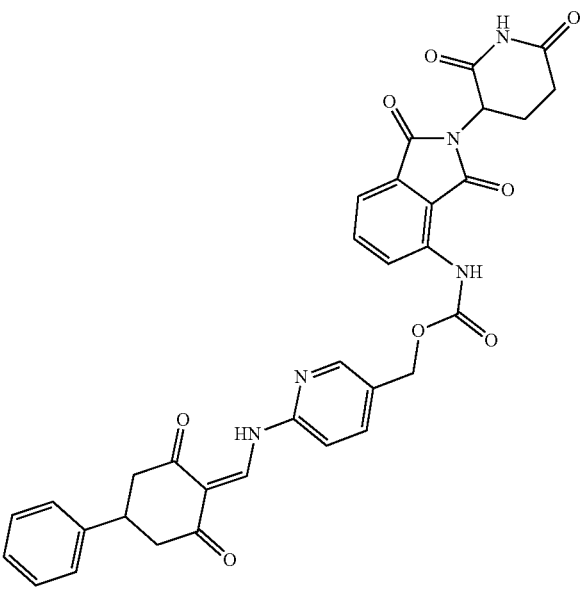 [SMILES: O=C1CCC(N2C(=O)c3cccc(NC(=O)OCc4ccc(NC=C5C(=O)CC(c6ccccc6)CC5=O)nc4)c3C2=O)C(=O)N1] 83 |
| 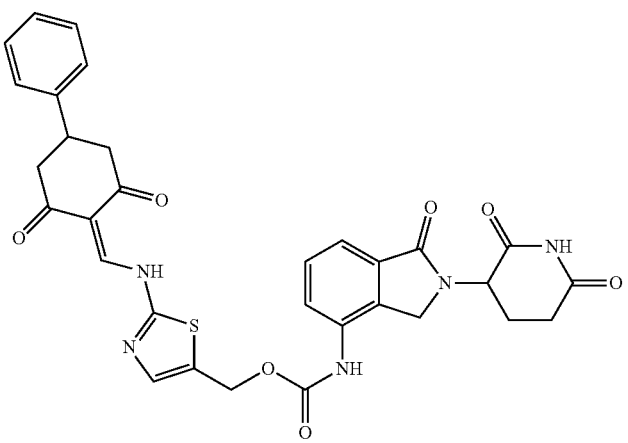 [SMILES: O=C1CCC(N2Cc3c(NC(=O)OCc4cnc(NC=C5C(=O)CC(c6ccccc6)CC5=O)s4)cccc3C2=O)C(=O)N1] 84 |

| Compound |
|---|
| 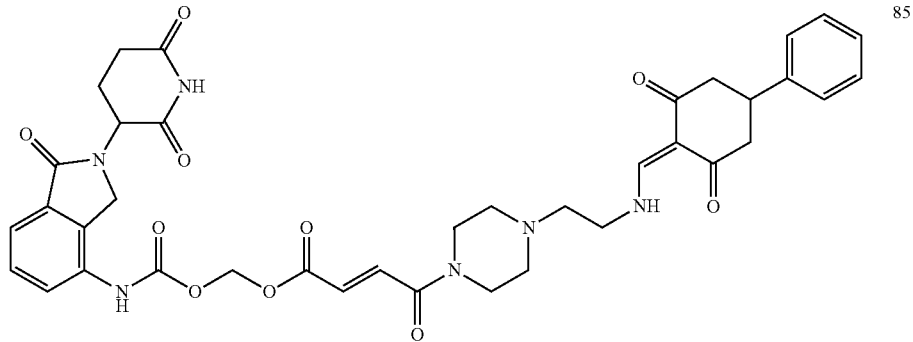 85 |
| 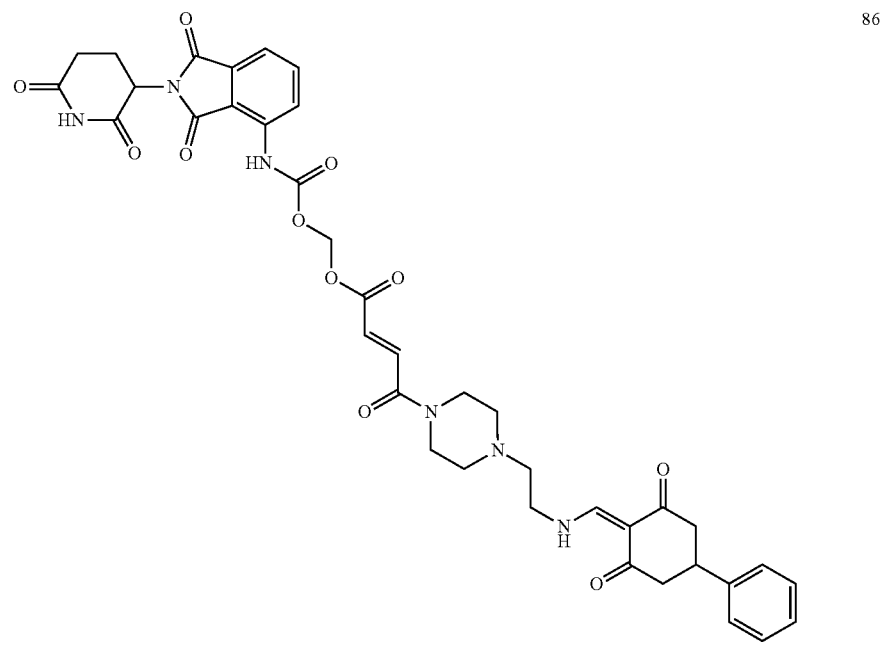 86 |
| 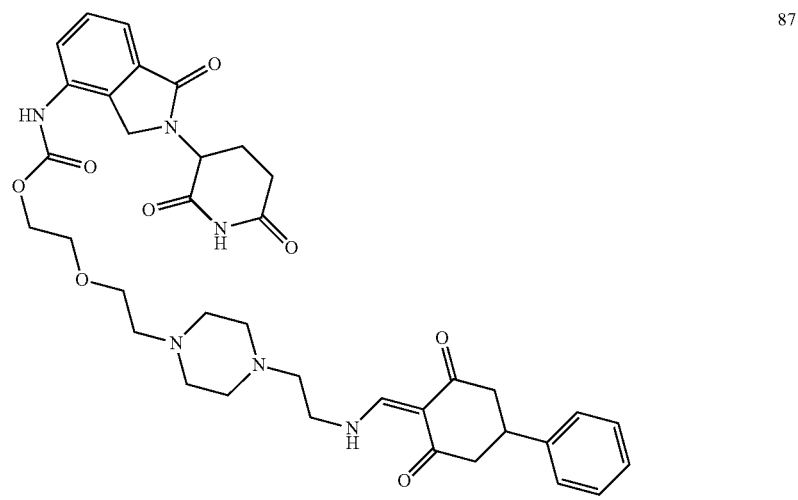 87 |

| Compound |
|---|
| 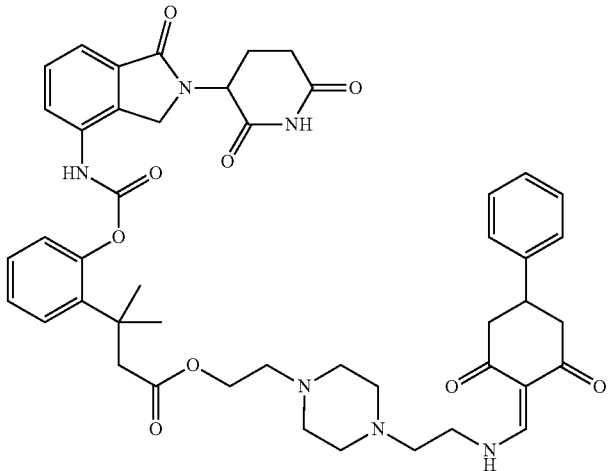 [SMILES: CC(C)(CC(=O)OCCN1CCN(CCNC=C2C(=O)CC(c3ccccc3)CC2=O)CC1)c1ccccc1OC(=O)Nc1cccc2c1CN(C1CCC(=O)NC1=O)C2=O] 88 |
| 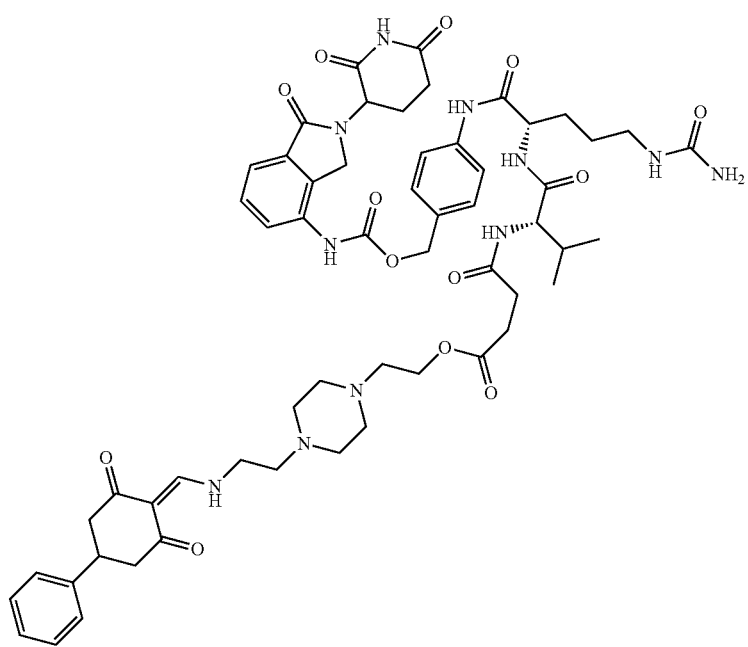 [SMILES: CC(C)[C@H](NC(=O)CCC(=O)OCCN1CCN(CCNC=C2C(=O)CC(c3ccccc3)CC2=O)CC1)C(=O)N[C@@H](CCCNC(N)=O)C(=O)Nc1ccc(COC(=O)Nc2cccc3c2CN(C2CCC(=O)NC2=O)C3=O)cc1] 89 |

-continued
| Compound | |
|---|---|
| 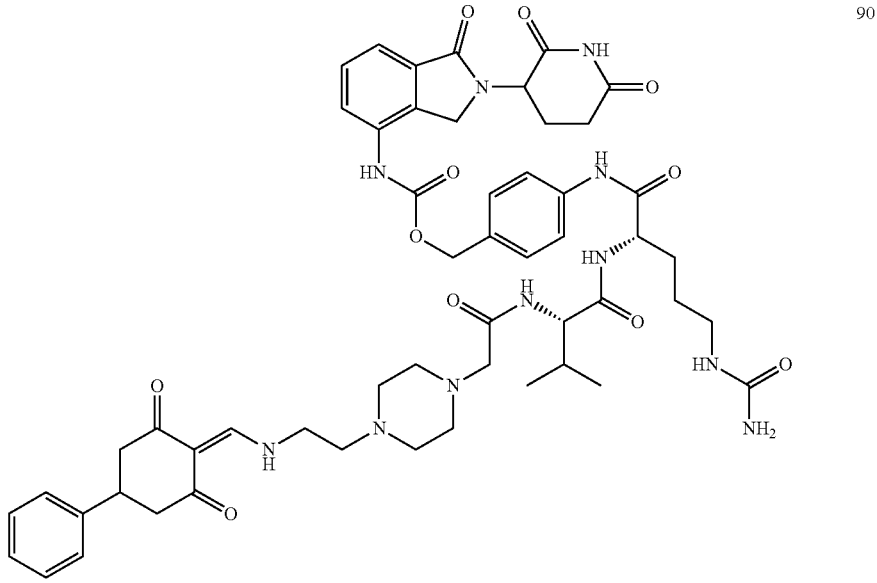 | 90 |
| 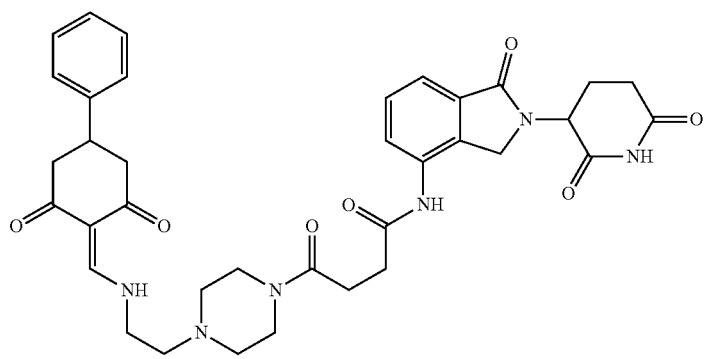 [SMILES: O=C1CCC(N2Cc3c(NC(=O)CCC(=O)N4CCN(CCNC=C5C(=O)CC(c6ccccc6)CC5=O)CC4)cccc3C2=O)C(=O)N1] | 91 |
| 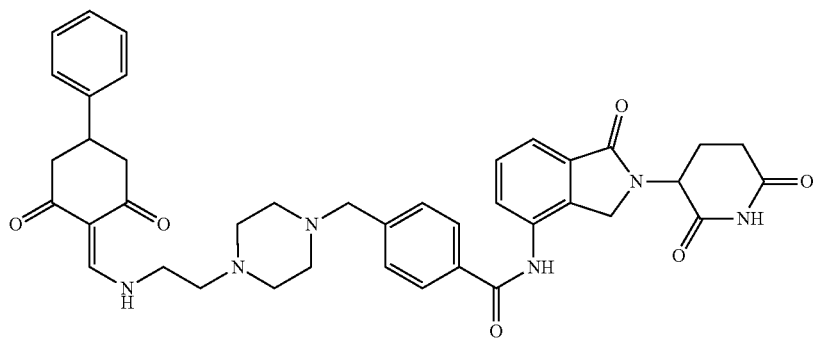 [SMILES: O=C1CCC(N2Cc3c(NC(=O)c4ccc(CN5CCN(CCNC=C6C(=O)CC(c7ccccc7)CC6=O)CC5)cc4)cccc3C2=O)C(=O)N1] | 92 |

-continued
| Compound |
|---|
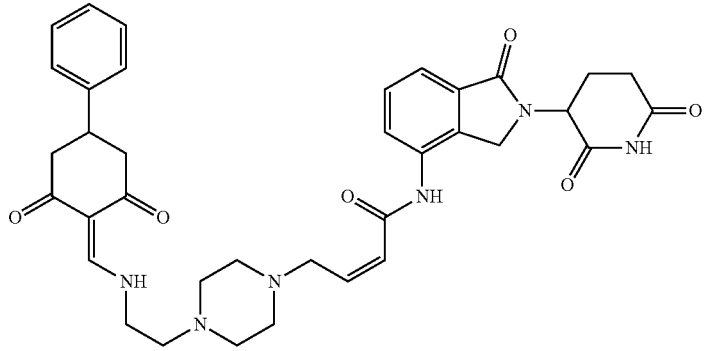 [SMILES: O=C(/C=C\CN1CCN(CCNC=C2C(=O)CC(c3ccccc3)CC2=O)CC1)Nc1cccc2c1CN(C1CCC(=O)NC1=O)C2=O]
93
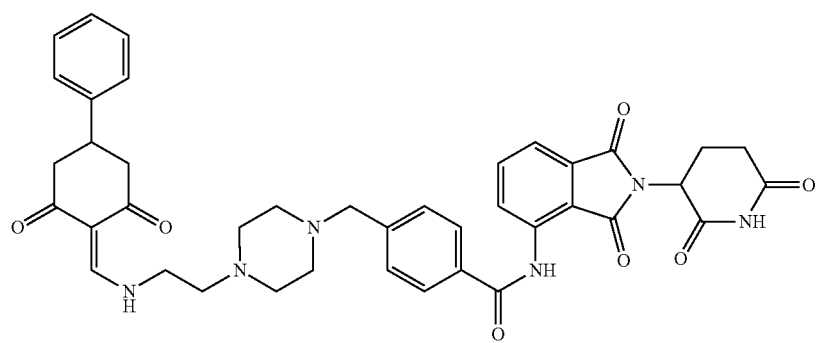 [SMILES: O=C1CCC(N2C(=O)c3cccc(NC(=O)c4ccc(CN5CCN(CCNC=C6C(=O)CC(c7ccccc7)CC6=O)CC5)cc4)c3C2=O)C(=O)N1]
94
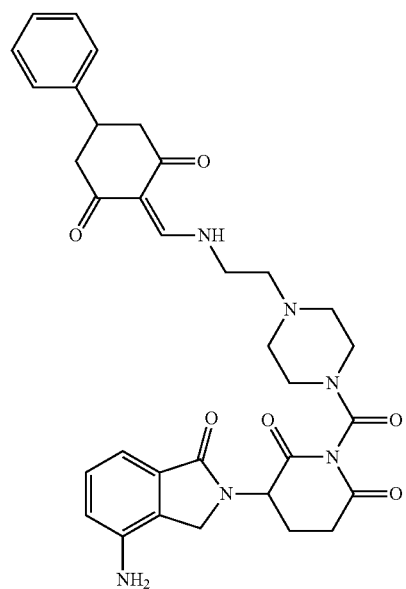 [SMILES: Nc1cccc2c1CN(C1CCC(=O)N(C(=O)N3CCN(CCNC=C4C(=O)CC(c5ccccc5)CC4=O)CC3)C1=O)C2=O]
100

-continued
| Compound |
|---|
| 101 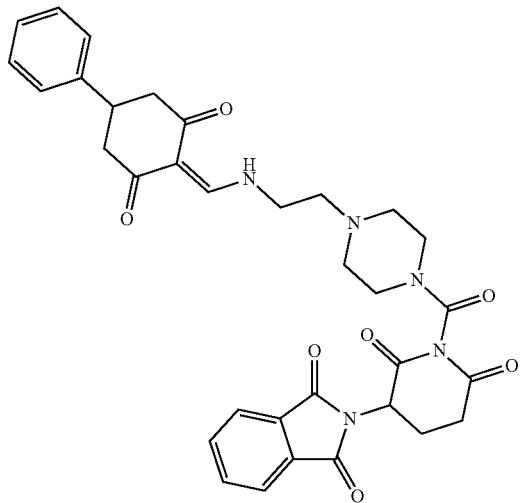 [SMILES: O=C1CC(c2ccccc2)CC(=O)C1=CNCCN1CCN(C(=O)N2C(=O)CCC(N3C(=O)c4ccccc4C3=O)C2=O)CC1] |
| 102 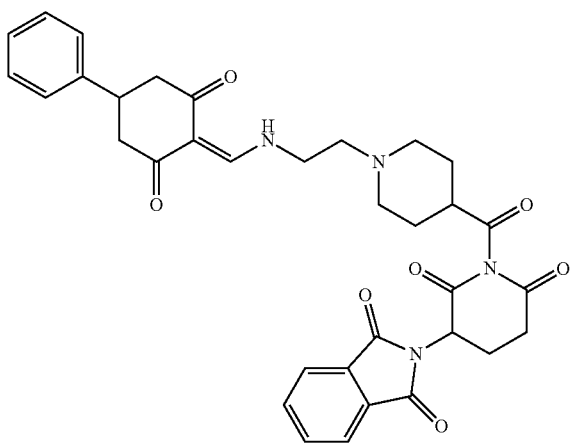 [SMILES: O=C1CC(c2ccccc2)CC(=O)C1=CNCCN1CCC(C(=O)N2C(=O)CCC(N3C(=O)c4ccccc4C3=O)C2=O)CC1] |
| 103 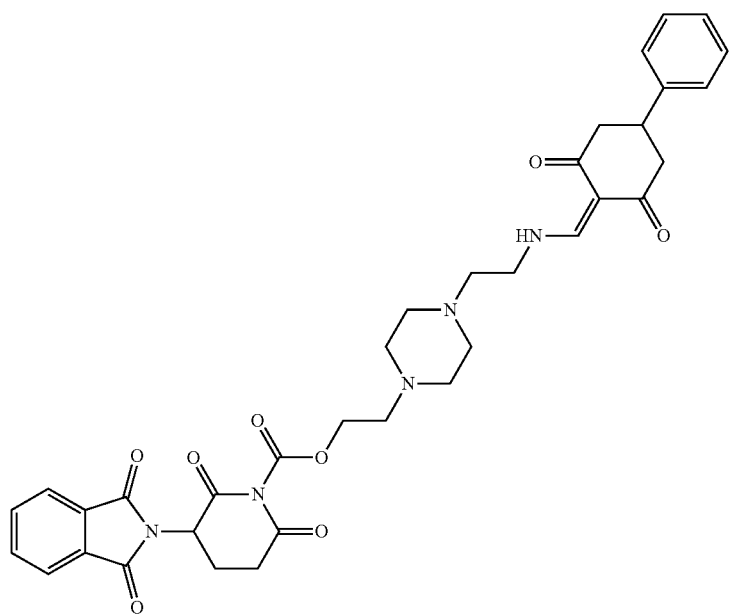 [SMILES: O=C1CC(c2ccccc2)CC(=O)C1=CNCCN1CCN(CCOC(=O)N2C(=O)CCC(N3C(=O)c4ccccc4C3=O)C2=O)CC1] |

| Compound |
|---|
| 104 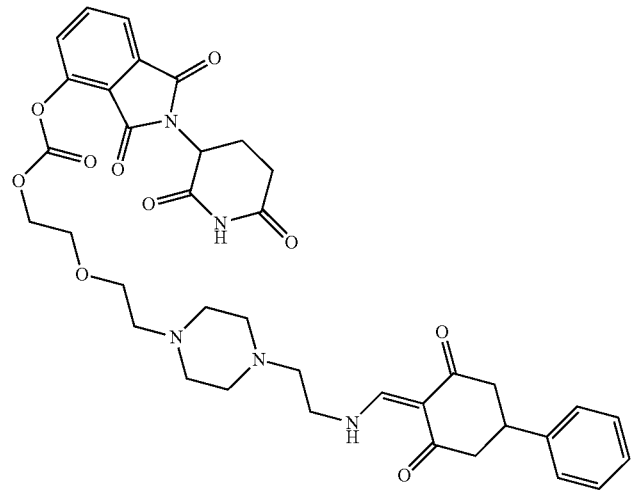 [SMILES: O=C1CCC(N2C(=O)c3cccc(OC(=O)OCCOCCN4CCN(CCNC=C5C(=O)CC(c6ccccc6)CC5=O)CC4)c3C2=O)C(=O)N1] |
| 105 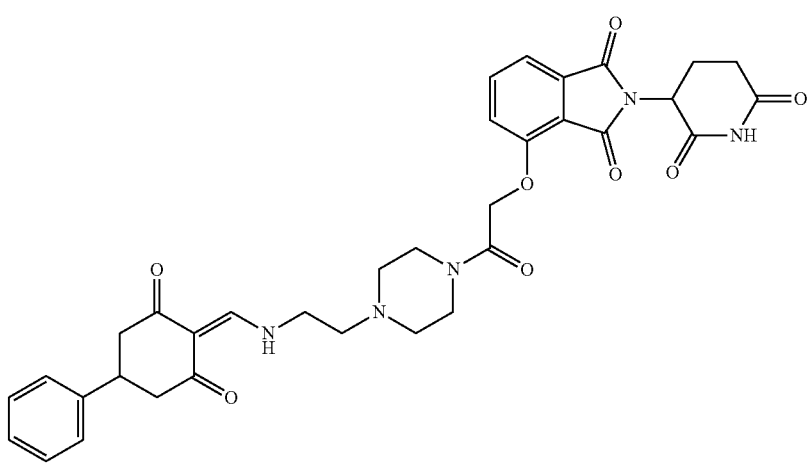 [SMILES: O=C1CCC(N2C(=O)c3cccc(OCC(=O)N4CCN(CCNC=C5C(=O)CC(c6ccccc6)CC5=O)CC4)c3C2=O)C(=O)N1] |
| 106 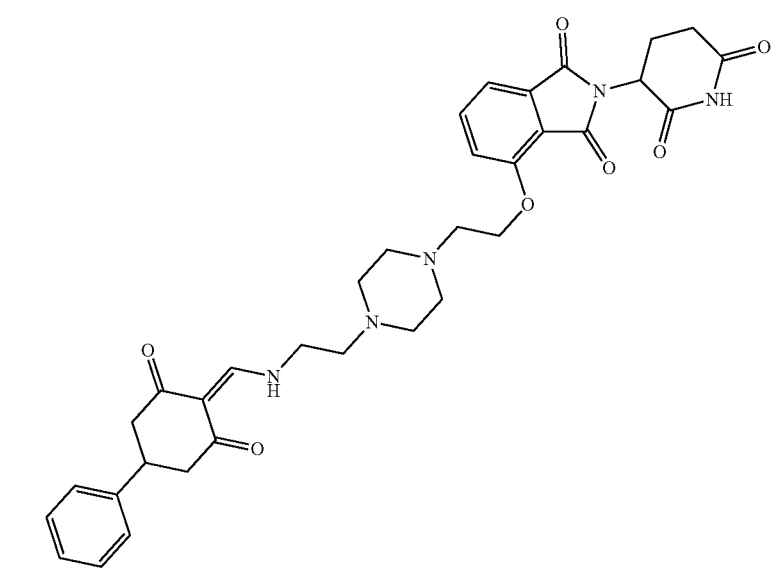 [SMILES: O=C1CCC(N2C(=O)c3cccc(OCCN4CCN(CCNC=C5C(=O)CC(c6ccccc6)CC5=O)CC4)c3C2=O)C(=O)N1] |

| Compound |
|---|
| 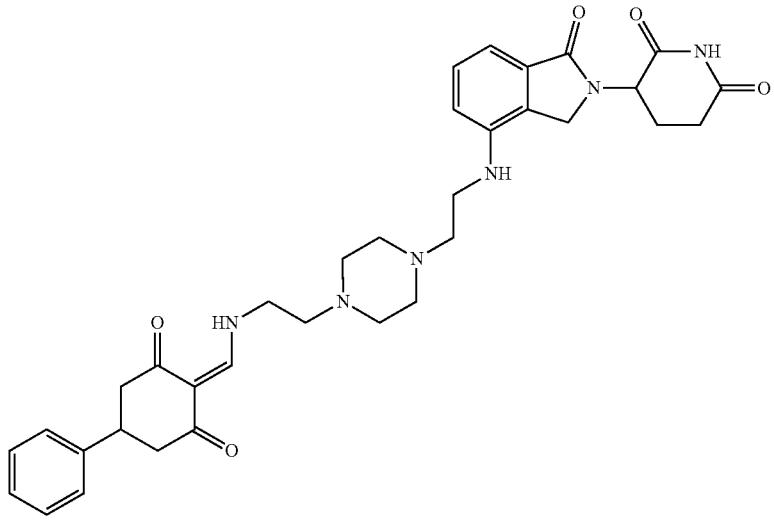 [SMILES: O=C1CCC(N2Cc3c(NCCN4CCN(CCNC=C5C(=O)CC(c6ccccc6)CC5=O)CC4)cccc3C2=O)C(=O)N1] 107 |
| 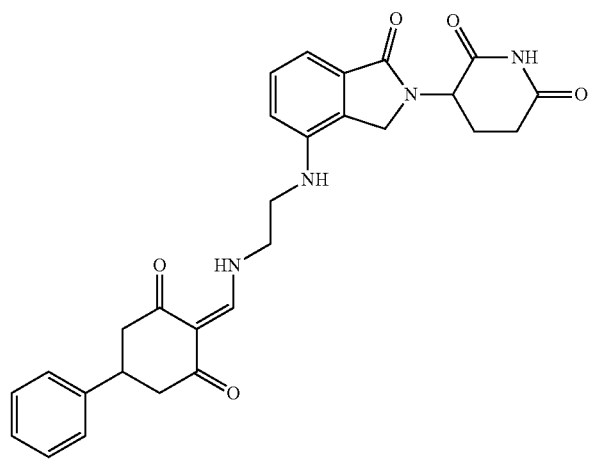 [SMILES: O=C1CCC(N2Cc3c(NCCNC=C4C(=O)CC(c5ccccc5)CC4=O)cccc3C2=O)C(=O)N1] 108 |
| 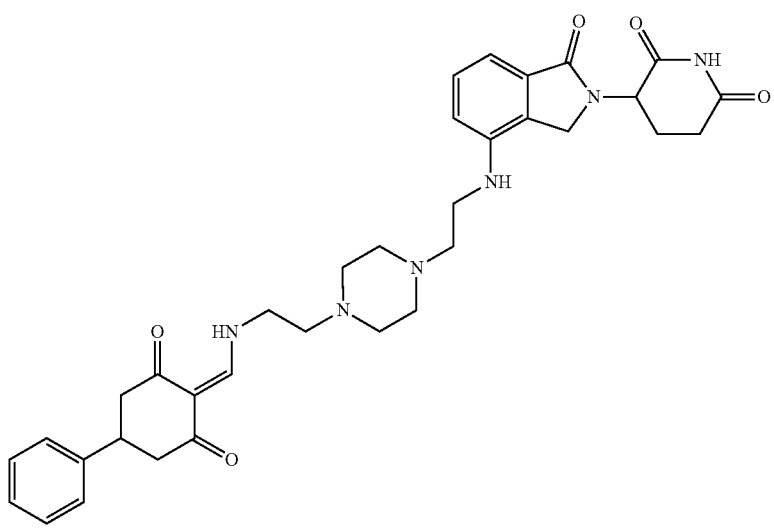 [SMILES: O=C1CCC(N2Cc3c(NCCN4CCN(CCNC=C5C(=O)CC(c6ccccc6)CC5=O)CC4)cccc3C2=O)C(=O)N1] 109 |

| Compound | |
|---|---|
| 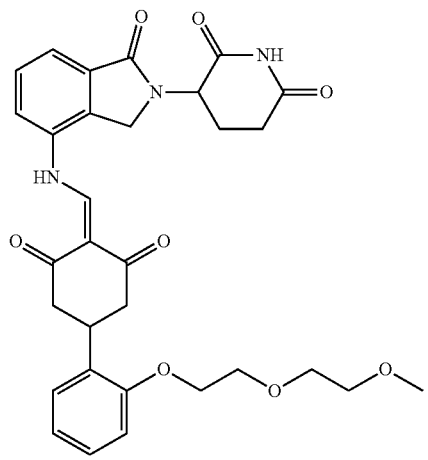 [SMILES: COCCOCCOc1ccccc1C1CC(=O)C(=CNc2cccc3c2CN(C2CCC(=O)NC2=O)C3=O)C(=O)C1] | 110 |
| 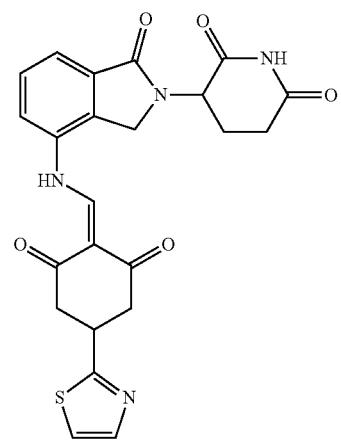 [SMILES: O=C1CCC(N2Cc3c(NC=C4C(=O)CC(c5nccs5)CC4=O)cccc3C2=O)C(=O)N1] | 111 |
| 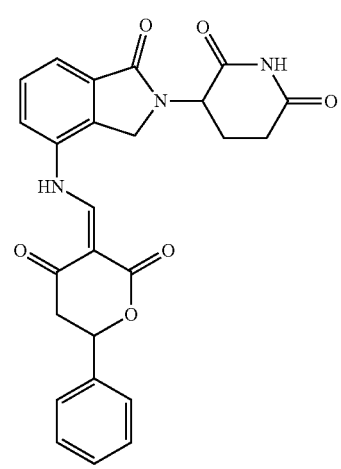 | 112 |

| Compound | |
|---|---|
| 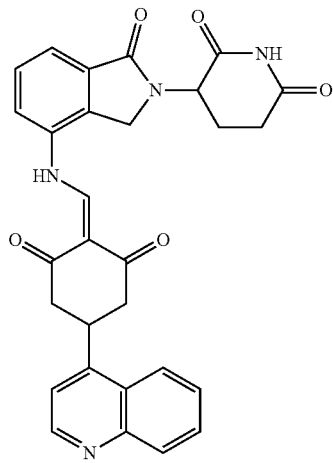 [SMILES: O=C1CCC(N2Cc3c(NC=C4C(=O)CC(c5ccnc6ccccc56)CC4=O)cccc3C2=O)C(=O)N1] | 113 |
| 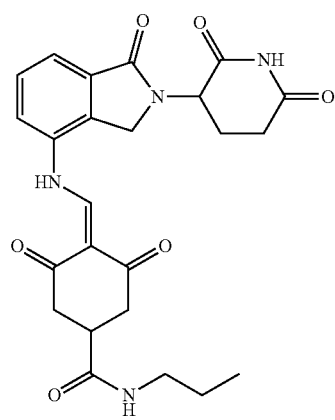 [SMILES: CCCNC(=O)C1CC(=O)C(=CNc2cccc3c2CN(C2CCC(=O)NC2=O)C3=O)C(=O)C1] | 114 |
| 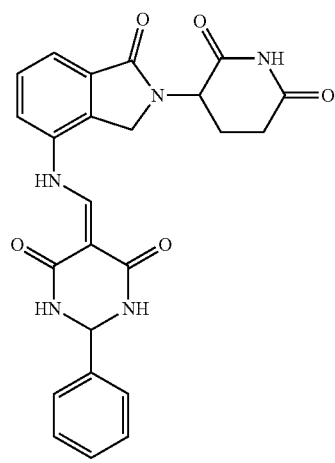 [SMILES: O=C1CCC(N2Cc3c(NC=C4C(=O)NC(c5ccccc5)NC4=O)cccc3C2=O)C(=O)N1] | 115 |

| Compound | |
|---|---|
| 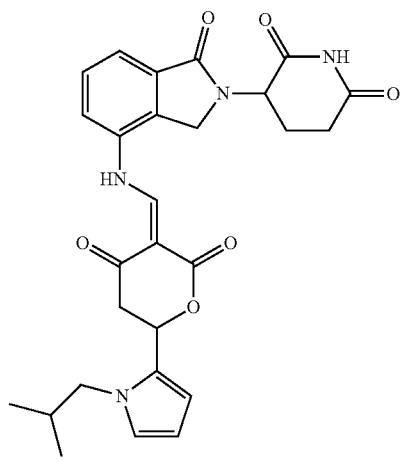 [SMILES: CC(C)Cn1cccc1C1CC(=O)/C(=C\Nc2cccc3c2CN(C2CCC(=O)NC2=O)C3=O)C(=O)O1] | 116 |
| 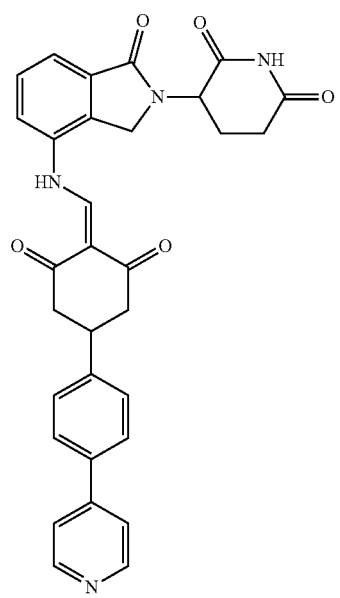 [SMILES: O=C1CCC(N2Cc3c(NC=C4C(=O)CC(c5ccc(-c6ccncc6)cc5)CC4=O)cccc3C2=O)C(=O)N1] | 117 |
| 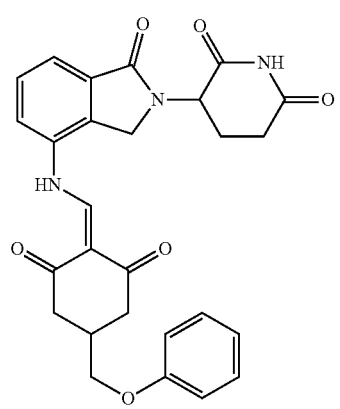 [SMILES: O=C1CCC(N2Cc3c(NC=C4C(=O)CC(COc5ccccc5)CC4=O)cccc3C2=O)C(=O)N1] | 118 |

-continued
| Compound | |
|---|---|
| 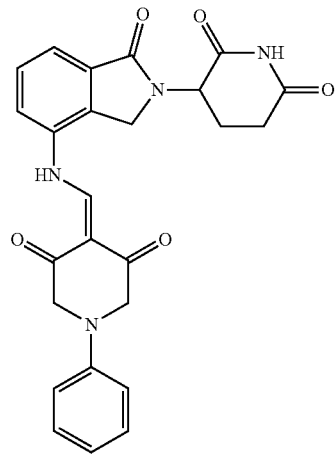 | 119 |
| 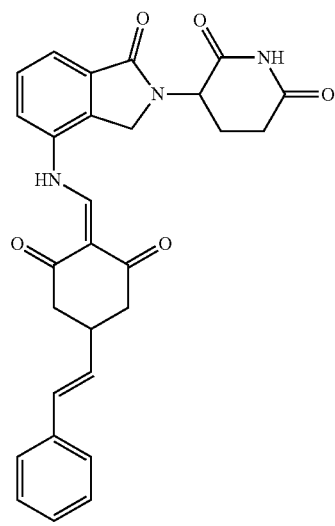 [SMILES: O=C1CCC(N2Cc3c(NC=C4C(=O)CC(/C=C/c5ccccc5)CC4=O)cccc3C2=O)C(=O)N1] | 120 |
| 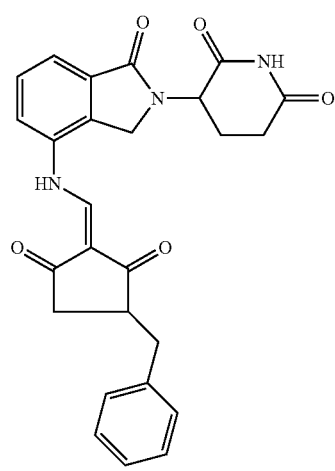 [SMILES: O=C1CCC(N2Cc3c(N/C=C4\C(=O)CC(Cc5ccccc5)C4=O)cccc3C2=O)C(=O)N1] | 121 |

| Compound | |
|---|---|
| 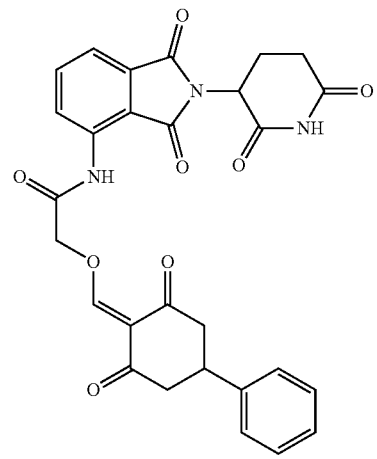 [SMILES: O=C1CCC(N2C(=O)c3cccc(NC(=O)COC=C4C(=O)CC(c5ccccc5)CC4=O)c3C2=O)C(=O)N1] | 122 |
| 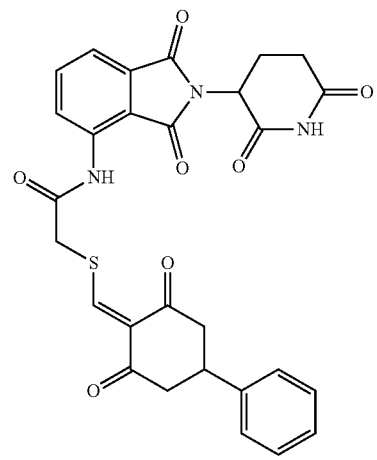 | 123 |
| 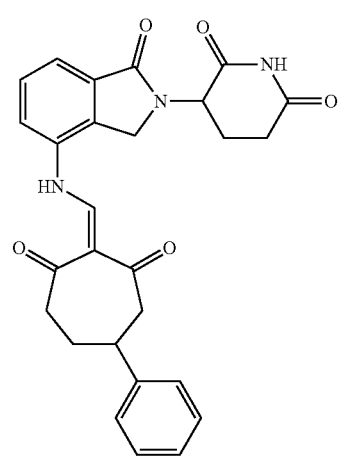 [SMILES: O=C1CCC(N2Cc3c(N/C=C4\C(=O)CCC(c5ccccc5)CC4=O)cccc3C2=O)C(=O)N1] | 124 |

-continued
| Compound |
|---|
| 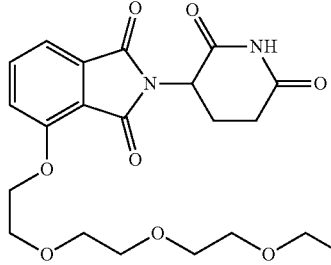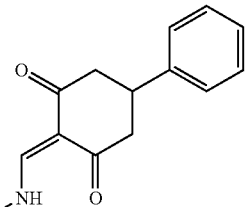 125 |
| 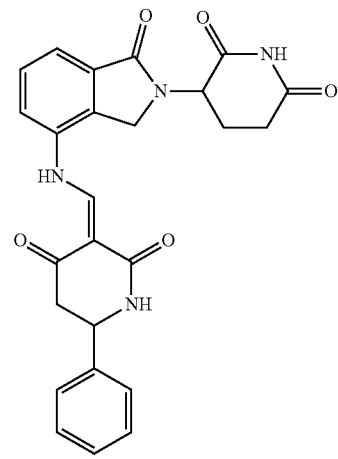 [SMILES: O=C1CCC(N2Cc3c(N/C=C4\C(=O)CC(c5ccccc5)NC4=O)cccc3C2=O)C(=O)N1] 126 |
| 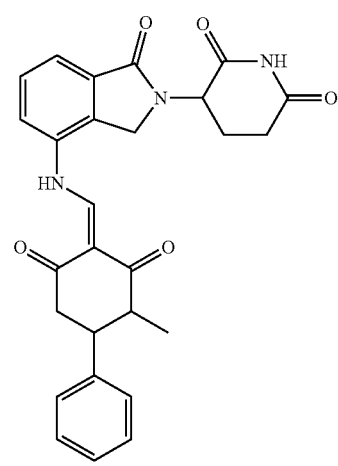 [SMILES: CC1C(=O)/C(=C/Nc2cccc3c2CN(C2CCC(=O)NC2=O)C3=O)C(=O)CC1c1ccccc1] 127 |

| Compound | |
|---|---|
| 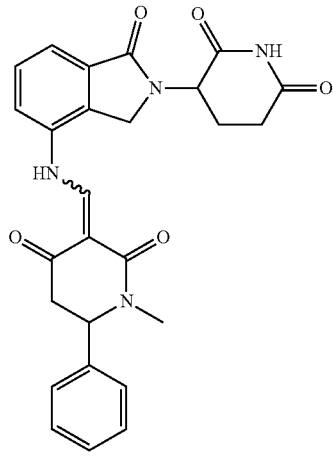 [SMILES: CN1C(=O)C(=CNc2cccc3c2CN(C2CCC(=O)NC2=O)C3=O)C(=O)CC1c1ccccc1] | 128 |
| 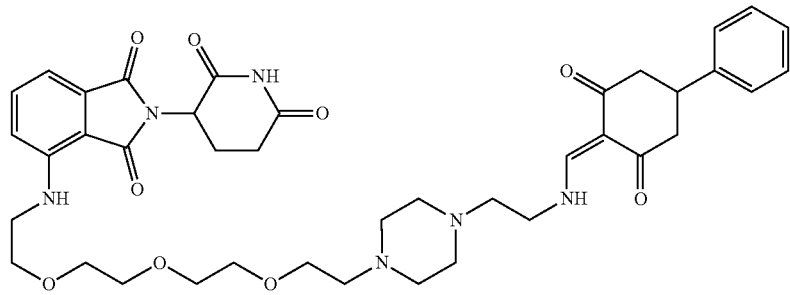 [SMILES: O=C1CCC(N2C(=O)c3cccc(NCCOCCOCCOCCN4CCN(CCNC=C5C(=O)CC(c6ccccc6)CC5=O)CC4)c3C2=O)C(=O)N1] | 129 |
| 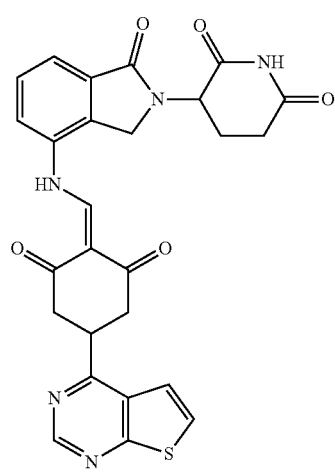 [SMILES: O=C1CCC(N2Cc3c(NC=C4C(=O)CC(c5ncnc6sccc56)CC4=O)cccc3C2=O)C(=O)N1] | 130 |

| Compound | |
|---|---|
| 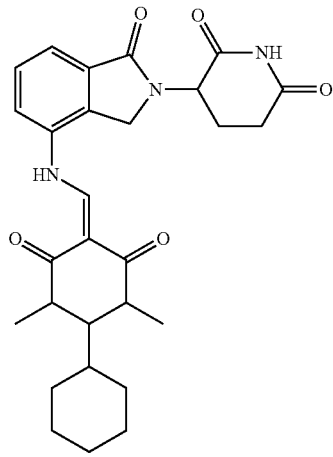 [SMILES: CC1C(=O)C(=CNc2cccc3c2CN(C2CCC(=O)NC2=O)C3=O)C(=O)C(C)C1C1CCCCC1] | 131 |
| 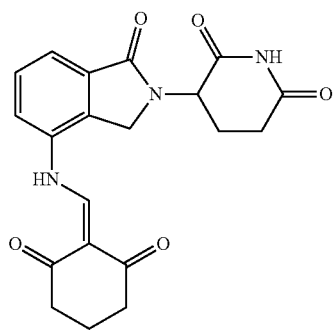 [SMILES: O=C1CCC(N2Cc3c(NC=C4C(=O)CCCC4=O)cccc3C2=O)C(=O)N1] | 132 |
| 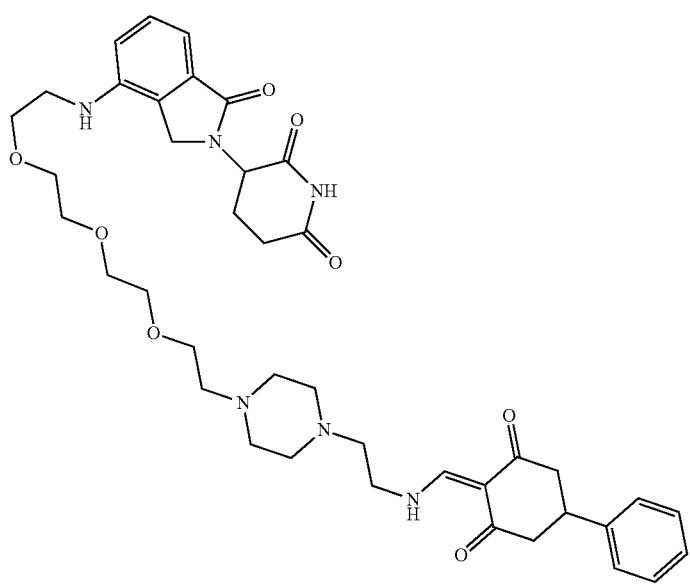 [SMILES: O=C1CCC(N2Cc3c(NCCOCCOCCOCCN4CCN(CCNC=C5C(=O)CC(c6ccccc6)CC5=O)CC4)cccc3C2=O)C(=O)N1] | 133 |

| Compound | |
|---|---|
| 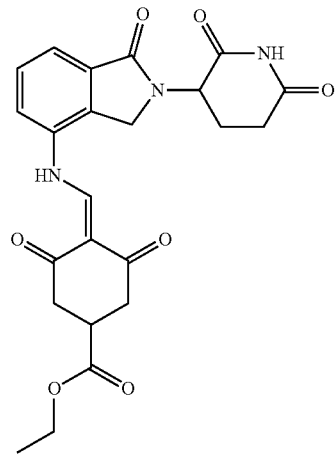 [SMILES: CCOC(=O)C1CC(=O)C(=CNc2cccc3c2CN(C2CCC(=O)NC2=O)C3=O)C(=O)C1] | 134 |
| 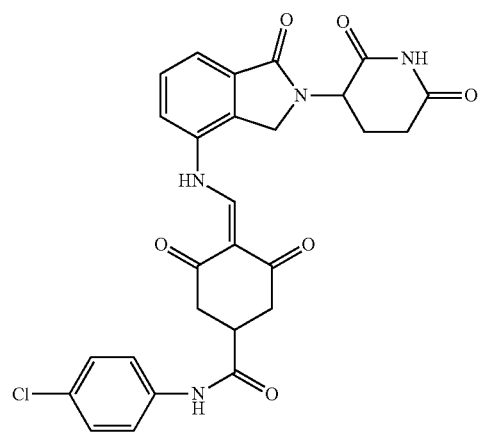 [SMILES: O=C1CCC(N2Cc3c(NC=C4C(=O)CC(C(=O)Nc5ccc(Cl)cc5)CC4=O)cccc3C2=O)C(=O)N1] | 135 |
| 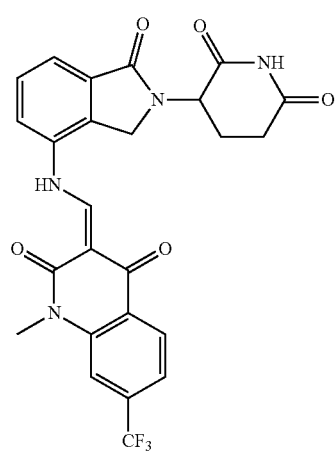 [SMILES: CN1C(=O)/C(=C\Nc2cccc3c2CN(C2CCC(=O)NC2=O)C3=O)C(=O)c2ccc(C(F)(F)F)cc21] | 136 |

-continued
| Compound | |
|---|---|
| 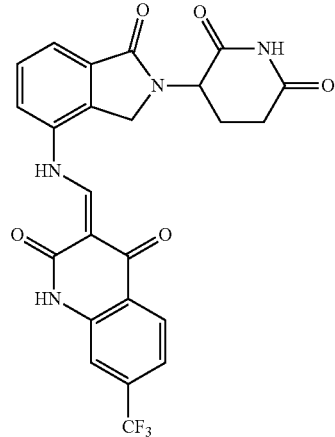 [SMILES: O=C1CCC(N2Cc3c(N/C=C4\C(=O)Nc5cc(C(F)(F)F)ccc5C4=O)cccc3C2=O)C(=O)N1] | 137 |
| 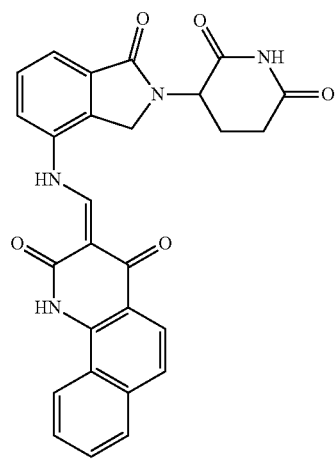 [SMILES: O=C1CCC(N2Cc3c(N/C=C4\C(=O)Nc5c(ccc6ccccc56)C4=O)cccc3C2=O)C(=O)N1] | 138 |
| 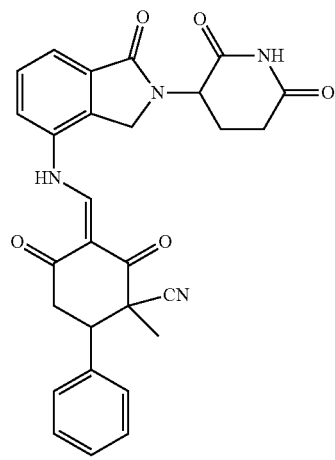 [SMILES: CC1(C#N)C(=O)/C(=C/Nc2cccc3c2CN(C2CCC(=O)NC2=O)C3=O)C(=O)CC1c1ccccc1] | 139 |

-continued
| Compound | |
|---|---|
| 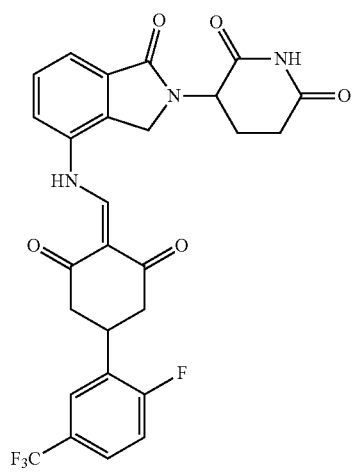 [SMILES: O=C1CCC(N2Cc3c(NC=C4C(=O)CC(c5cc(C(F)(F)F)ccc5F)CC4=O)cccc3C2=O)C(=O)N1] | 140 |
| 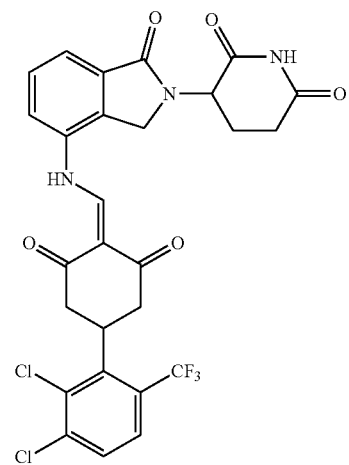 | 141 |
| 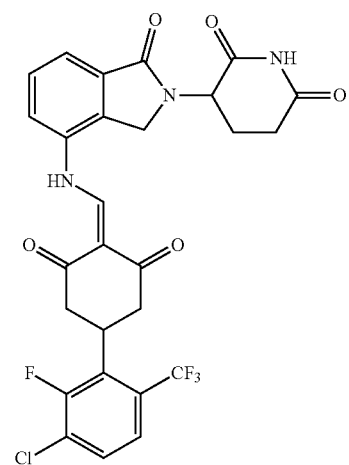 [SMILES: O=C1CCC(N2Cc3c(NC=C4C(=O)CC(c5c(C(F)(F)F)ccc(Cl)c5F)CC4=O)cccc3C2=O)C(=O)N1] | 142 |

|Compound|
|---|
| 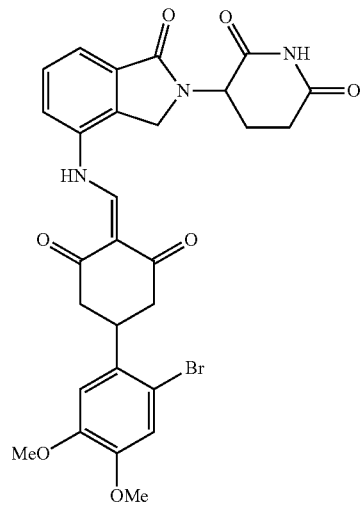 [SMILES: COc1cc(Br)c(C2CC(=O)C(=CNc3cccc4c3CN(C3CCC(=O)NC3=O)C4=O)C(=O)C2)cc1OC] 143 |
| 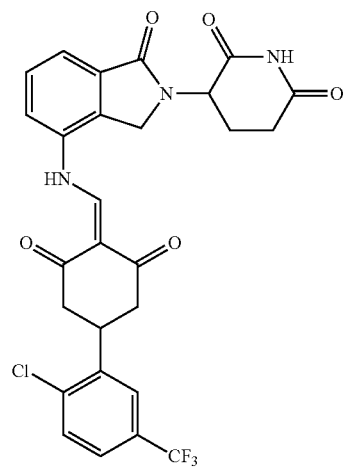 [SMILES: O=C1CCC(N2Cc3c(NC=C4C(=O)CC(c5cc(C(F)(F)F)ccc5Cl)CC4=O)cccc3C2=O)C(=O)N1] 144 |
| 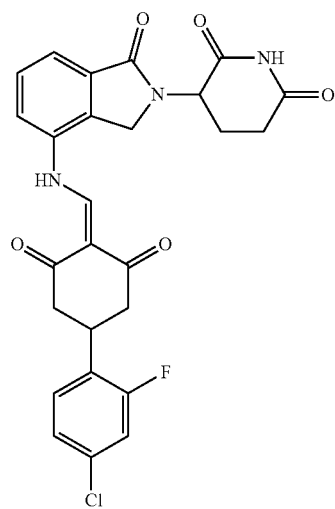 [SMILES: O=C1CCC(N2Cc3c(NC=C4C(=O)CC(c5ccc(Cl)cc5F)CC4=O)cccc3C2=O)C(=O)N1] 145 |

| Compound |
|---|
| 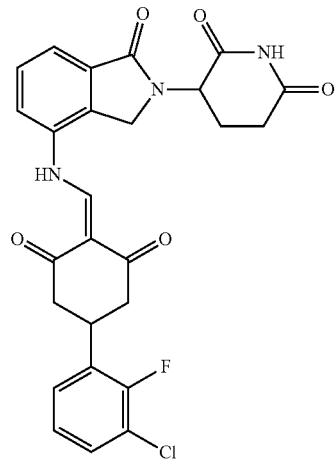 [SMILES: O=C1CCC(N2Cc3c(NC=C4C(=O)CC(c5cccc(Cl)c5F)CC4=O)cccc3C2=O)C(=O)N1] 146 |
| 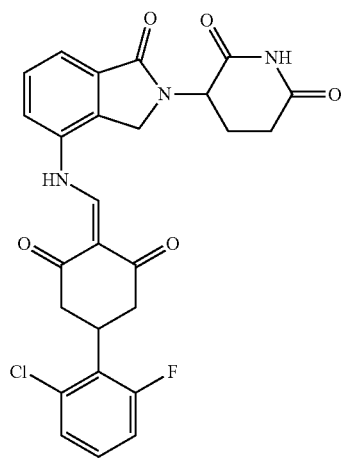 [SMILES: O=C1CCC(N2Cc3c(NC=C4C(=O)CC(c5c(F)cccc5Cl)CC4=O)cccc3C2=O)C(=O)N1] 147 |
| 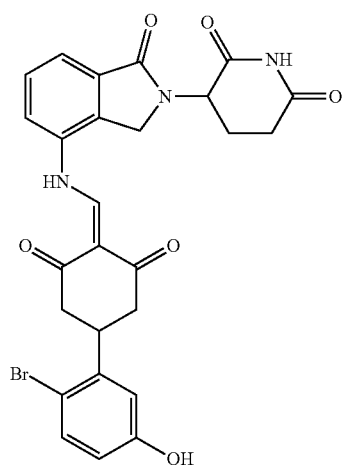 148 |

| Compound | |
|---|---|
| 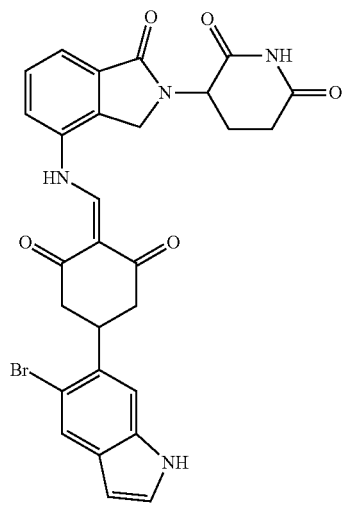 | 149 |
| 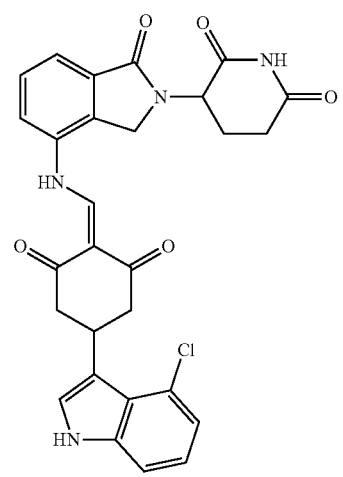 | 150 |
| 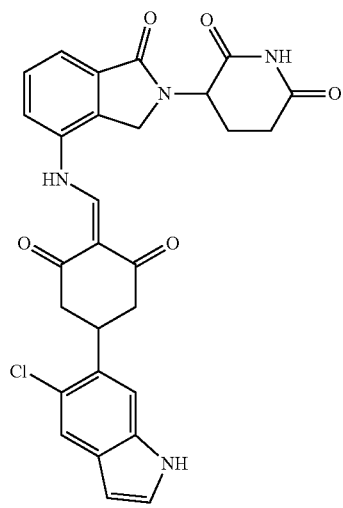 [SMILES: O=C1CCC(N2Cc3c(NC=C4C(=O)CC(c5cc6[nH]ccc6cc5Cl)CC4=O)cccc3C2=O)C(=O)N1] | 151 |

| Compound | |
|---|---|
| (structure) | 152 |
| (structure) | 153 |
| (structure) | 154 |

| Compound |
|---|
| 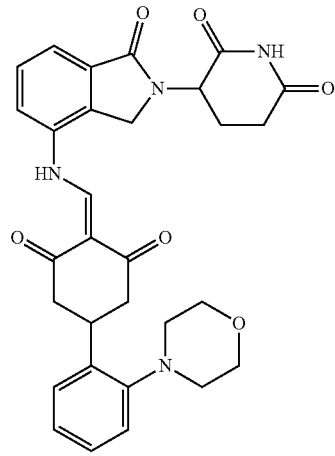 [SMILES: O=C1CCC(N2Cc3c(NC=C4C(=O)CC(c5ccccc5N5CCOCC5)CC4=O)cccc3C2=O)C(=O)N1] 155 |
| 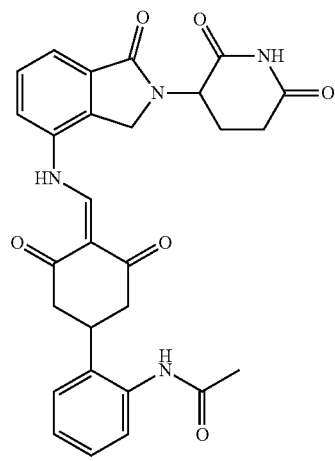 [SMILES: CC(=O)Nc1ccccc1C1CC(=O)C(=CNc2cccc3c2CN(C2CCC(=O)NC2=O)C3=O)C(=O)C1] 156 |
| 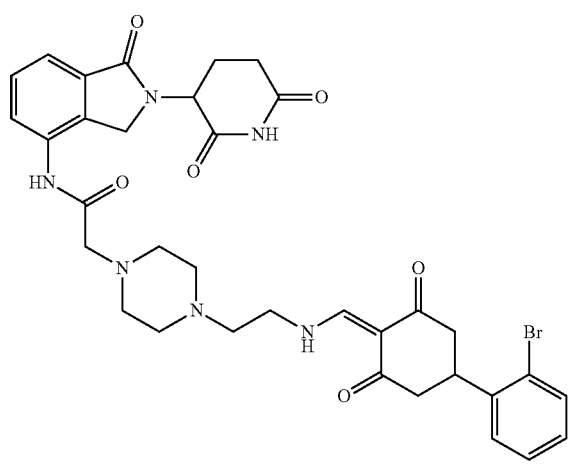 [SMILES: O=C1CCC(N2Cc3c(NC(=O)CN4CCN(CCNC=C5C(=O)CC(c6ccccc6Br)CC5=O)CC4)cccc3C2=O)C(=O)N1] 157 |

-continued
| Compound | |
|---|---|
| 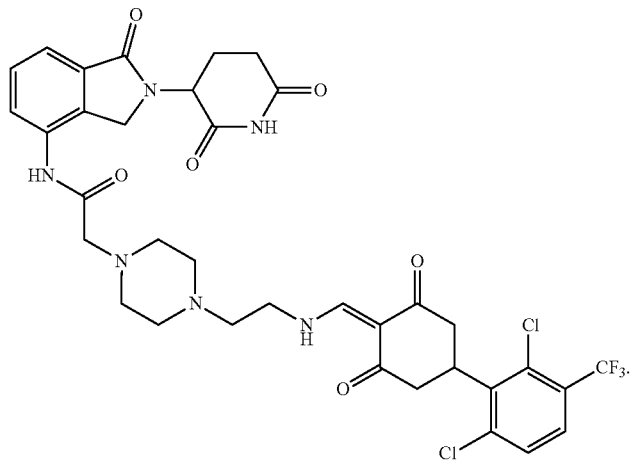 [SMILES: O=C1CCC(N2Cc3c(NC(=O)CN4CCN(CCNC=C5C(=O)CC(c6c(Cl)ccc(C(F)(F)F)c6Cl)CC5=O)CC4)cccc3C2=O)C(=O)N1] | 158 |
9. A pharmaceutical composition, comprising the compound or a pharmaceutically acceptable salt thereof as claimed in claim 1, and optionally a pharmaceutically acceptable excipient.
* * * * *